(12) United States Patent
Marlow et al.

(10) Patent No.: US 7,517,994 B2
(45) Date of Patent: Apr. 14, 2009

(54) HETEROCYCLIC INHIBITORS OF MEK AND METHODS OF USE THEREOF

(75) Inventors: Allison L. Marlow, Louisville, CO (US); Eli Wallace, Lyons, CO (US); Jeongbeob Seo, Broomfield, CO (US); Joseph P. Lyssikatos, Superior, CO (US); Hong Woon Yang, Superior, CO (US); James Blake, Longmont, CO (US)

(73) Assignee: Array Biopharma Inc., Boulder, CO (US)

( * ) Notice: Subject to any disclaimer, the term of this patent is extended or adjusted under 35 U.S.C. 154(b) by 502 days.

(21) Appl. No.: 11/132,164

(22) Filed: May 18, 2005

(65) Prior Publication Data

US 2005/0256123 A1     Nov. 17, 2005

Related U.S. Application Data

(63) Continuation-in-part of application No. 10/992,612, filed on Nov. 18, 2004.

(60) Provisional application No. 60/523,270, filed on Nov. 19, 2003.

(51) Int. Cl.

| C07D 211/76 | (2006.01) |
|---|---|
| C07D 211/86 | (2006.01) |
| C07D 213/74 | (2006.01) |
| C07D 213/75 | (2006.01) |
| C07D 237/04 | (2006.01) |
| C07D 413/06 | (2006.01) |
| C07D 413/14 | (2006.01) |
| C07D 237/12 | (2006.01) |
| C07D 487/06 | (2006.01) |
| C07D 401/06 | (2006.01) |
| C07D 401/14 | (2006.01) |
| C07D 403/06 | (2006.01) |
| C07D 405/06 | (2006.01) |
| C07D 409/06 | (2006.01) |
| C07D 411/06 | (2006.01) |
| C07D 419/06 | (2006.01) |
| C07D 221/04 | (2006.01) |
| C07D 213/22 | (2006.01) |
| C07D 213/26 | (2006.01) |
| A61K 31/501 | (2006.01) |
| A61K 31/4412 | (2006.01) |
| A61P 35/00 | (2006.01) |
| C07D 417/06 | (2006.01) |

(52) U.S. Cl. ............... 546/291; 544/239; 544/124; 544/405; 544/238; 544/333; 544/224; 544/236; 514/252.01; 514/247; 514/349; 546/274.1; 546/258; 546/269.4; 546/268.4; 546/272.4; 546/268.7; 546/183

(58) Field of Classification Search ............... 546/297, 546/291

See application file for complete search history.

(56) References Cited

U.S. PATENT DOCUMENTS

| 5,231,094 | A | 7/1993 | Bru-Magniez et al. |
|---|---|---|---|
| 5,525,625 | A | 6/1996 | Bridges et al. |
| 6,310,060 | B1 | 10/2001 | Barrett et al. |
| 6,469,004 | B1 | 10/2002 | Barrett et al. |
| 6,506,798 | B1 | 1/2003 | Barrett et al. |
| 7,211,562 | B2 | 5/2007 | Rosen et al. |
| 2003/0004193 | A1 | 1/2003 | Barrett et al. |
| 2003/0045521 | A1 | 3/2003 | Tecle |
| 2003/0078428 | A1 | 4/2003 | Barrett et al. |
| 2003/0092748 | A1 | 5/2003 | Barrett et al. |
| 2003/0195183 | A1 | 10/2003 | Zhilov |
| 2003/0216460 | A1 | 11/2003 | Wallace et al. |
| 2003/0232869 | A1 | 12/2003 | Wallace et al. |
| 2004/0116710 | A1 | 6/2004 | Wallace et al. |
| 2005/0026964 | A1 | 2/2005 | Black et al. |

FOREIGN PATENT DOCUMENTS

| GB | 1373314 | 11/1974 |
|---|---|---|
| WO | WO 96/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |

| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/44166 A1 | 6/2002 |
| WO | WO03/076405 A1 | 9/2003 |
| WO | WO 03/077855 A2 | 9/2003 |
| WO | WO 03/077914 A1 | 9/2003 |
| WO | WO2005/000818 A1 | 1/2005 |
| WO | WO 2005/123692 A1 | 12/2005 |

OTHER PUBLICATIONS

M-C- Viaud, et al. "Acylation of Oxazolo[4,5-b]pyridin-2(3H)-ones, 2-Phenyloxazolo[4,5-b]pyridines and Pyrrolo[2,3-b]pyridin-2(2H)-ones"; Tetrahedron; 1997, pp. 5159-5168; vol. 53, No. 14; Elsevier Science Ltd.

Moreau, et al. "Synthesis and Anticonvulsant Properties of Triazolo- and Imidazopyridazinyl Carboxamides and Carboxylic Acids"; Bioorganic & Medicinal Chemistry; 1998; pp. 983-991; vol. 6; Elsevier Science Ltd.

Bachman "Further Studies of Aminobenzacrfidines"; Journal of Organic Chemistry; 1948; pp. 89-96; vol. 13.

Gotthardt, "Synthesis and Physical Properties of First 3,3-Bridged Bis- and Tris(1,3-Thiazolium-4-Olates) as well as one of 5,5-Bridged Bis-(1,3-Thiazolium4-Olate) and its Conversion into 3,3-(1,4-Phenylene)bisA2(1eta)-Pyridinone", Chemische Berichte, vol. 120, No. 6, 1987, pp. 1017-1022.

Potts et al., "Mesoionic Compounds, XXXII. Cycloaddition Reactions of the Anhydro-4-Hydroxythiazolium Hydroxide System With Olefinic Dipolarophiles", Journal of Organic Chemistry, 39(25) 3631-40.

Potts et al., "Mesoionic Compounds. XXXI. Preparation and Cycloaddition Reactions of the Anhyydro-4-Hydroxythiazolium Hydroxide System with Acetylenic Dipolarophiles", Jounral of Organic Chemistry, 39(25) 3627-30.

Ried et al., "Reactions with Cyclobutenediones. XXIX. Structure and Reactions of Phenycyclobutenedione-Enamine 1:1 Addition Compounds", Justus Liebigs Annalen Der Chemie, 1972, 762, 1-12.

Ried et al., "Reactions of Cyclobutenediones. XX. Synthesis and Reactivity of p-Substituted Phenylcyclobutenediones", Chemische Berichte, 1971, 104(8), 2622-8.

Konykhova, N.A. et al., "Unusual Reaction of Enhydrazines With Oxalyl Chloride", Chemistry of Heterocyclic Compounds, 2001, 647-648, 37(5), New York, NY, USA.

Schober, Bernt D. et al., "Pyridazines With Heteroatom Substituents in Positions 3 and 5. 6. SN Reactions in Position 5 of 2-aryl-5-hydroxypyridazin-3(2H)-ones", Journal of Heterocyclic Chemistry, 1990, 471-477, 27(3).

European Search Report corresponding to European Patent Application No. 04811727.9-1211, dated Dec. 12, 2006.

*Primary Examiner*—Mark L. Berch
*Assistant Examiner*—Cecilia M Jaisle
(74) *Attorney, Agent, or Firm*—Hogan & Hartson LLP

(57) ABSTRACT

Disclosed are compounds of the Formula I

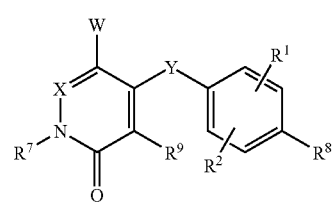

and pharmaceutically acceptable salts and prodrugs thereof, wherein $R^1$, $R^2$, $R^7$, $R^8$ and $R^9$, W, X and Y are as defined in the specification. Such compounds are MEK inhibitors and useful in the treatment of hyperproliferative diseases, such as cancer and inflammation, in mammals, and inflammatory conditions. Also disclosed are methods of using such compounds in the treatment of hyperproliferative diseases in mammals and pharmaceutical compositions containing such compounds.

1 Claim, 37 Drawing Sheets

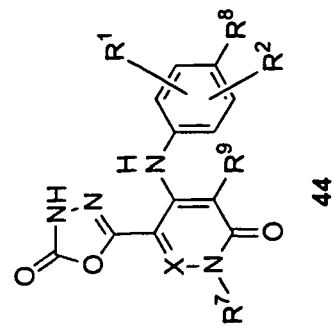
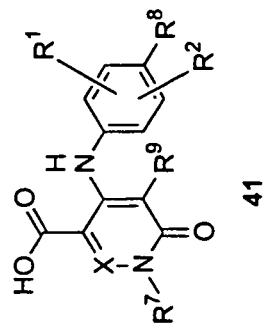
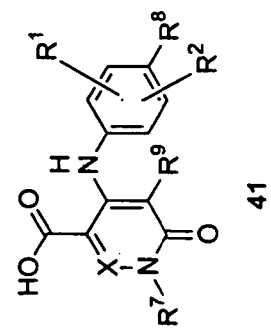

$R^9$ = aryl, heteroaryl, alkyl, cycloalkyl, alkenyl, alkynyl, amino or anilinyl

61

1. Pd coupling (2. when $R^9$ = alkenyl or alkynyl: reduction, if desired)

where $R^1, R^2, R^8 \neq$ Br, I

79

HETEROCYCLIC INHIBITORS OF MEK AND METHODS OF USE THEREOF

CROSS-REFERENCE TO RELATED APPLICATIONS

This application is a Continuation-in-Part of U.S. patent application Ser. No. 10/992,612, filed Nov. 18, 2004, which application claims the benefit of U.S. Provisional Application Ser. No. 60/523,270, filed Nov. 19, 2003, each of which is incorporated herein by reference in its entirety.

BACKGROUND OF THE INVENTION

1. Field of the Invention

This invention relates to a series of novel heterocyclic compounds that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

2. Description of the State of the Art

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology*, 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology*, 2001, 332, 417-431). Phosphorylated ERK dimerizes and then translocates to the nucleus where it accumulates (Khokhlatchev et al., *Cell*, 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell*, 2000, 6, 1343-1354). Overall, treatment of cells with growth factors leads to the activation of ERK1 and 2 which results in proliferation and, in some cases, differentiation (Lewis et al., *Adv. Cancer Res.*, 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science*, 1993, 260, 1834-1837). Recently, bRaf mutations have been identified in more than 60% of malignant melanoma (Davies, H. et al., *Nature*, 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene*, 1999, 18, 813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine*, 1999, 5 (7), 810-816; Trachet et al., AACR Apr. 6-10, 2002, Poster #5426; Tecle, H., IBC $2^{nd}$ International Conference of Protein Kinases, Sep. 9-10, 2002), block static allodynia in animals (WO 01/05390) and inhibit growth of acute myeloid leukemia cells (Milella et al., *J. Clin. Invest.*, 2001, 108 (6), 851-859).

Small molecule inhibitors of MEK have been disclosed, including in U.S. Patent Publication Nos. 2003/0232869, 2004/0116710, and 2003/0216460, and U.S. patent application Ser. Nos. 10/654,580 and 10/929,295, each of which is hereby incorporated by reference. At least fifteen additional patent applications have appeared in the last several years. See, for example: U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

SUMMARY OF THE INVENTION

This invention provides novel heterocyclic compounds, and pharmaceutically acceptable salts and prodrugs thereof which are useful in the treatment of hyperproliferative diseases. Specifically, one embodiment of the present invention relates to MEK inhibitors of Formulas I-V:

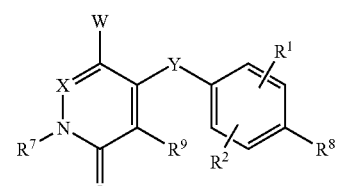

I

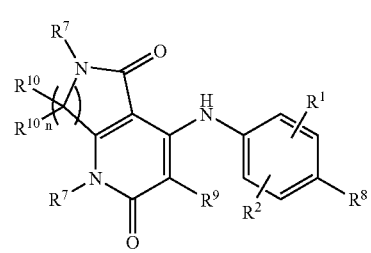

II

-continued

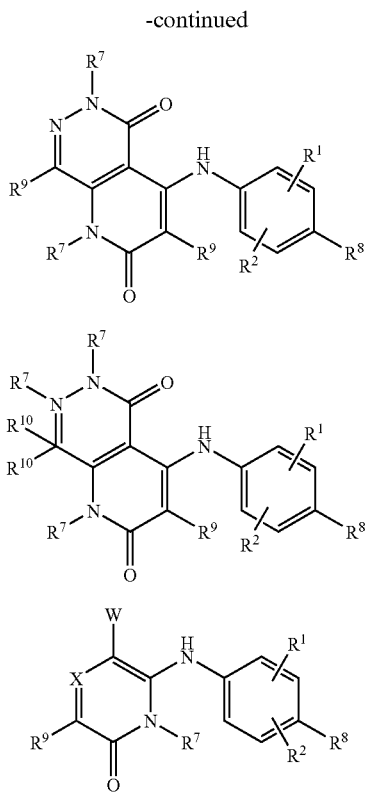

and tautomers, metabolites, resolved enantiomers, diastereomers, solvates and pharmaceutically acceptable salts and prodrugs thereof, wherein:

X is N or $CR^{10}$;

Y is $NR^3$, O, S, S(O), $S(O)_2$, C(O) or $CH_2$;

$R^1$, $R^2$, $R^8$, and $R^9$ are independently hydrogen, hydroxy, halogen, cyano, nitro, trifluoromethyl, difluoromethyl, fluoromethyl, fluoromethoxy, difluoromethoxy, trifluoromethoxy, azido, $-SR^{11}$, $-OR^3$, $-C(O)R^3$, $-C(O)OR^3$, $-NR^4C(O)OR^6$, $-OC(O)R^3$, $-NR^4SO_2R^6$, $-SO_2NR^3R^4$, $-NR^4C(O)R^3$, $-C(O)NR^3R^4$, $-NR^5C(O)NR^3R^4$, $-NR^5C(NCN)NR^3R^4$, $-NR^3R^4$, $C_1-C_{10}$ alkyl, $C_2-C_{10}$ alkenyl, $C_2-C_{10}$ alkynyl, $C_3-C_{10}$ cycloalkyl, $C_3-C_{10}$ cycloalkylalkyl, $-S(O)_j(C_1-C_6$ alkyl), $-S(O)_j(CR^4R^5)_m$-aryl, aryl, arylalkyl, heteroaryl, heteroarylalkyl, heterocyclyl, heterocyclylalkyl, $-O(CR^4R^5)_m$-aryl, $-NR^4(CR^4R^5)_m$-aryl, $-O(CR^4R^5)_m$-heteroaryl, $-NR^4(CR^4R^5)_m$-heteroaryl, $-O(CR^4R^5)_m$-heterocyclyl or $-NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, $-NR^4SO_2R^6$, $-SO_2NR^3R^4$, $-C(O)R^3$, $-C(O)OR^3$, $-OC(O)R^3$, $-NR^4C(O)OR^6$, $-NR^4C(O)R^3$, $-C(O)NR^3R^4$, $-NR^3R^4$, $-NR^5C(O)NR^3R^4$, $-NR^5C(NCN)NR^3R^4$, $-OR^3$, aryl, heteroaryl, arylalkyl, heteroarylalkyl, heterocyclyl and heterocyclylalkyl, and wherein said aryl, heteroaryl, arylalkyl, heteroarylalkyl, heterocyclyl or heterocyclylalkyl rings are optionally substituted independently with one or more groups selected from halogen, hydroxyl, cyano, nitro, azido, fluoromethyl, difluoromethyl, trifluoromethyl, $C_1-C_4$ alkyl, $C_2-C_4$ alkenyl, $C_2-C_4$ alkynyl, $C_3-C_6$ cycloalkyl, $C_3-C_6$ heterocycloalkyl, $NR^3R^4$ and $OR^3$;

$R^7$ is hydrogen, trifluoromethyl, $C_1-C_{10}$ alkyl, $C_2-C_{10}$ alkenyl, $C_2-C_{10}$ alkynyl, $C_3-C_{10}$ cycloalkyl, $C_3-C_{10}$ cycloalkylalkyl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, difluoromethoxy, trifluoromethoxy, azido, $-NR^{11}SO_2R^4$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, $C_1-C_{10}$ alkyl, $C_2-C_{10}$ alkenyl, $C_2-C_{10}$ alkynyl, $C_3-C_{10}$ cycloalkyl, aryl, heteroaryl, arylalkyl, heteroarylalkyl, heterocyclyl and heterocyclylalkyl, and wherein said aryl, heteroaryl, arylalkyl, heteroarylalkyl, heterocyclyl or heterocyclylalkyl rings are optionally substituted independently with one or more groups selected from halogen, hydroxyl, cyano, nitro, azido, fluoromethyl, difluoromethyl, trifluoromethyl, $C_1-C_4$ alkyl, $C_2-C_4$ alkenyl, $C_2-C_4$ alkynyl, $C_3-C_6$ cycloalkyl, $C_3-C_6$ heterocycloalkyl, $NR^3R^4$ and $OR^3$;

$R^3$ is hydrogen, trifluoromethyl, $C_1-C_{10}$ alkyl, $C_2-C_{10}$ alkenyl, $C_2-C_{10}$ alkynyl, $C_3-C_{10}$ cycloalkyl, $C_3-C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl and heterocyclylalkyl;

or $R^3$ and $R^4$ together with the atom to which they are attached form a 4 to 10 membered heteroaryl or heterocyclic ring, wherein said heteroaryl and heterocyclic rings are optionally substituted independently with one or more groups independently selected from halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl and heterocyclylalkyl;

$R^4$ and $R^5$ independently are hydrogen or $C_1-C_6$ alkyl, or $R^4$ and $R^5$ together with the atom to which they are attached form a 4 to 10 membered carbocyclic ring, wherein said alkyl and carbocyclic ring are optionally substituted independently with one or more groups independently selected from halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $-OR^{11}$, aryl, heteroaryl, arylalkyl, heteroarylalkyl, heterocyclyl, and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl and heterocyclylalkyl;

wherein in Formulas I and V, $R^{10}$ is hydrogen, hydroxy, halogen, cyano, nitro, trifluoromethyl, difluoromethoxy, trifluoromethoxy, azido, —$SR^{11}$, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, and wherein said aryl, heteroaryl, arylalkyl, heteroarylalkyl, heterocyclyl or heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

and wherein in Formulas II and IV, each $R^{10}$ is independently hydrogen, cyano, nitro, trifluoromethyl, difluoromethoxy, trifluoromethoxy, azido, —$C(O)R^3$, —$C(O)OR^3$, —$SO_2NR^3R^4$, —$C(O)NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl and heterocyclylalkyl, and wherein said aryl, heteroaryl, arylalkyl, heteroarylalkyl, heterocyclyl or heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^{11}$, $R^{12}$ and $R^{13}$ independently are hydrogen, lower alkyl, lower alkenyl, aryl and arylalkyl, and $R^{14}$ is lower alkyl, lower alkenyl, aryl and arylalkyl, or any two of $R^{11}$, $R^{12}$, $R^{13}$ and $R^{14}$ together with the atom to which they are attached form a 4 to 10 membered heteroaryl or heterocyclic ring, wherein said alkyl, alkenyl, aryl, arylalkyl, heteroaryl ring and heterocyclic ring are optionally substituted independently with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —$C(O)OR^3$, —$C(O)NR^3R^4$, —$C(O)NR^4OR^3$, —$C(O)R^4OR^3$, —$C(O)NR^4SO_2R^3$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$ or $CR^3OR^3$ wherein any of said heteroaryl, heterocyclyl, —$C(O)OR^3$, —$C(O)NR^3R^4$, —$C(O)NR^4OR^3$, —$C(O)R^4OR^3$, —$C(O)NR^4SO_2R^3$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$ and $CR^3OR^3$ are optionally substituted independently with one or more groups independently selected from halogen, cyano, nitro, azido, —$NR^3R^4$, —$OR^3$, $C_1$-$C_{10}$ alkyl, $C_2$-$C_{10}$ alkenyl, $C_2$-$C_{10}$ alkynyl, cycloalkyl and heterocycloalkyl, wherein any of said $C_1$-$C_{10}$ alkyl, $C_2$-$C_{10}$ alkenyl, $C_2$-$C_{10}$ alkynyl, cycloalkyl and heterocycloalkyl are optionally substituted independently with 1 or more groups independently selected from —$NR^3R^4$ and —$OR^3$;

m is 0, 1, 2, 3, 4 or 5; and j is 0, 1 or 2.

In a further aspect, the present invention provides compositions that inhibit MEK comprising one or more compounds of Formulas I-V.

The invention also provides methods of making the compounds of Formulas I-V.

In a further aspect the present invention provides a method of using the compounds of this invention as a medicament to treat diseases or medical conditions mediated by MEK. For example, this invention provides a method for treatment of a hyperproliferative disorder or an inflammatory condition in a mammal comprising administrating to said mammal one or more compounds of Formula I-V or a pharmaceutically acceptable salt or prodrug thereof in an amount effective to treat said hyperproliferative disorder.

In a further aspect the present invention provides treating or preventing an MEK-mediated condition, comprising administering to a human or animal in need thereof a pharmaceutical composition comprising a compound of Formula I-V or a pharmaceutically-acceptable salt or in vivo cleavable prodrug thereof in an amount effective to treat or prevent said MEK-mediated condition.

The inventive compounds may further be used advantageously in combination with other known therapeutic agents.

The invention also relates to pharmaceutical compositions that inhibit MEK, comprising an effective amount of a compound selected from compounds of Formulas I-V or pharmaceutically acceptable prodrugs, pharmaceutically active metabolites, or pharmaceutically acceptable salts thereof.

An additional aspect of the invention is the use of a compound of Formula I, Formula II, Formula III, Formula IV or Formula V in the preparation of a medicament for the treatment or prevention of a disease or medical condition mediated by MEK in a warm-blooded animal, preferably a mammal, more preferably a human, suffering from such disorder.

More particularly, the invention includes the use of a compound of the invention in the preparation of a medicament for the treatment or prevention of a hyperproliferative disorder or an inflammatory condition in a mammal.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
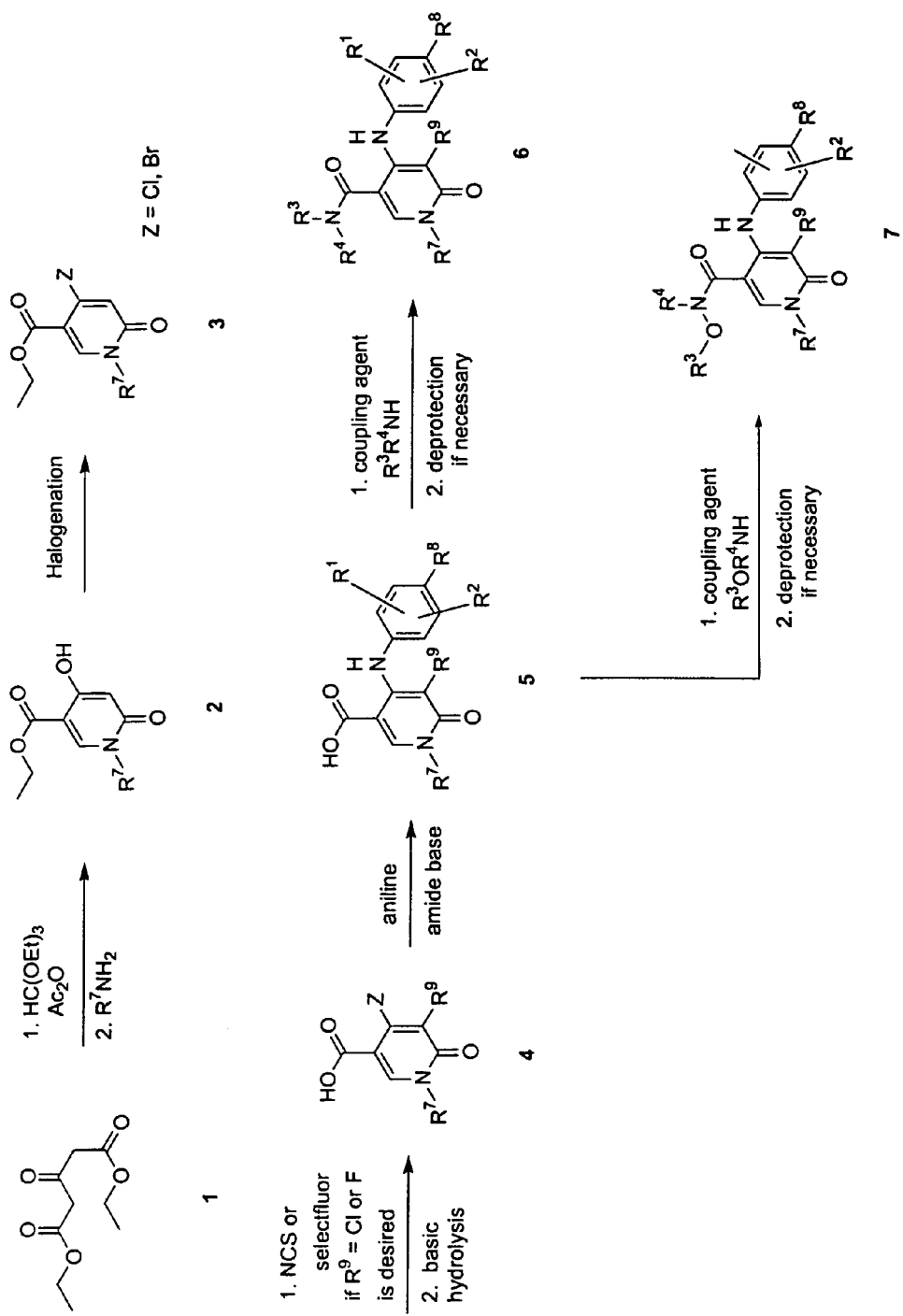
FIG. 1 shows a reaction scheme for the synthesis of compounds 5-7.

The inventive compounds of the Formulas I-V and tautomers, metabolites, resolved enantiomers, diastereomers, solvates and pharmaceutically acceptable salts and prodrugs thereof are useful in the treatment of hyperproliferative diseases. In general, one aspect the present invention relates to compounds of Formula I-V that act as MEK inhibitors.

Specifically, one aspect of the invention relates to compounds having the general Formula I

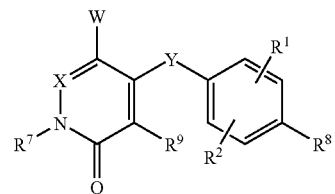

and tautomers, pharmaceutically accepted salts, pharmaceutically acceptable prodrugs, metabolites, and solvates thereof, wherein:

X is N or $CR^{10}$;

Y is $NR^3$, O, S, S(O), $S(O)_2$, C(O) or $CH_2$;

$R^1$, $R^2$, $R^8$, $R^9$ and $R^{10}$ are independently hydrogen, hydroxy, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said aryl, heteroaryl, arylalkyl, heteroarylalkyl, heterocyclyl or heterocyclylalkyl rings are optionally substituted independently with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R$^7$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, C$_1$-C$_{10}$ alkyl, C$_2$-C$_{10}$ alkenyl, C$_2$-C$_{10}$ alkynyl, C$_3$-C$_{10}$ cycloalkyl, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R$^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl, or R$^3$ and R$^4$ together with the atom to which they are attached from a 4 to 10 membered heteroaryl or heterocyclic ring, wherein said heteroaryl and heterocyclic rings are optionally substituted independently with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

R$^4$ and R$^5$ independently are hydrogen or C$_1$-C$_6$ alkyl, or

R$^4$ and R$^5$ together with the atom to which they are attached form a 4 to 10 membered carbocyclic ring, wherein said alkyl and said carbocyclic ring are optionally substituted independently with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —N$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

R$^{11}$, R$^{12}$ and R$^{13}$ independently are hydrogen, lower alkyl, lower alkenyl, aryl and arylalkyl, and R$^{14}$ is lower alkyl, lower alkenyl, aryl and arylalkyl, or any two of R$^{11}$, R$^{12}$, R$^{13}$ and R$^{14}$ together with the atom to which they are attached form a 4 to 10 membered heteroaryl or heterocyclic ring, wherein said alkyl, alkenyl, aryl, arylalkyl, heteroaryl ring and heterocyclic ring are optionally substituted independently with one or more groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) or —CR$^3$OR$^3$ wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) and CR$^3$OR$^3$ are optionally substituted independently with one or more groups independently selected from halogen, cyano, nitro, azido, —NR$^3$R$^4$, —OR$^3$, C$_1$-C$_{10}$ alkyl, C$_2$-C$_{10}$ alkenyl, C$_2$-C$_{10}$ alkynyl, cycloalkyl and heterocycloalkyl, wherein any of said C$_1$-C$_{10}$ alkyl, C$_2$-C$_{10}$ alkenyl, $C_2$-$C_{10}$ alkynyl, cycloalkyl and heterocycloalkyl are optionally substituted independently with 1 or more groups independently selected from —$NR^3R^4$ and —$OR^3$;

m is 0, 1, 2, 3, 4 or 5; and j is 0, 1 or 2.

In one embodiment, X is N and Y is NH.

In another embodiment, W is selected from heteroaryl, —$C(O)OR^3$, —$C(O)NR^3R^4$, —$C(O)NR^4OR^3$ and —$C(O)NR^4S(O)_2R^3$.

In yet another embodiment, W is selected from

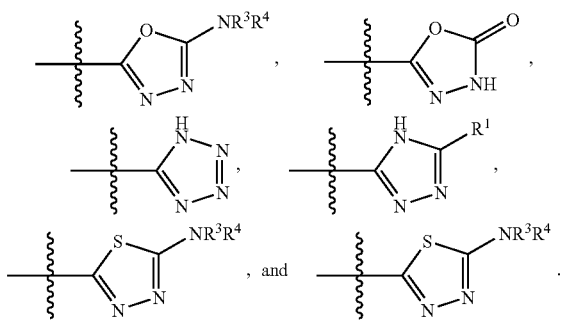

In a further embodiment, W is selected from

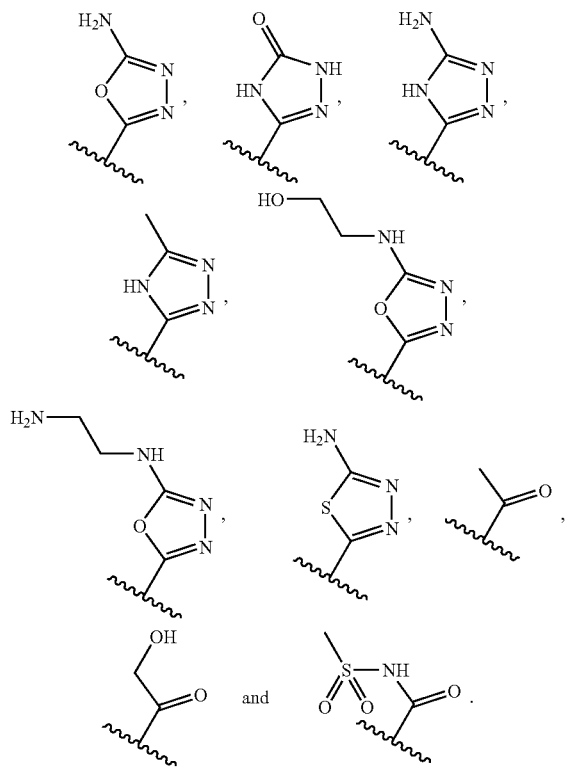

FIGS. 1-3, 6, 7, 10-14 and 35-36 show non-limiting examples of the synthesis of compounds of this invention having the general Formula I.

In addition to compounds of the general Formula I, this invention further includes compounds of the general Formula II:

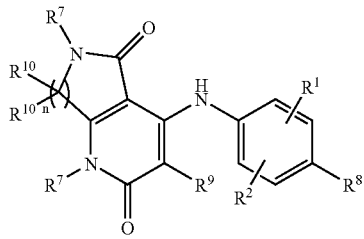

and tautomers, metabolites, resolved enantiomers, diastereomers, solvates and pharmaceutically acceptable salts and prodrugs thereof, wherein:

where $R^1$, $R^2$, $R^8$ and $R^9$ are independently hydrogen, halogen, cyano, nitro, trifluoromethyl, difluoromethyl, fluoromethyl, fluoromethoxy, difluoromethoxy, trifluoromethoxy, azido, —$SR^{11}$, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$ ($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, and wherein said aryl, heteroaryl, arylalkyl, heteroarylalkyl heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-C4 alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^7$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, difluoromethoxy, trifluoromethoxy, azido, —$NR^{11}SO_2R^{14}$, —$SO_2NR^{11}R^{12}$, —$C(O)R^{11}$, —$C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, $C_1$-$C_{10}$ alkyl, $C_2$-$C_{10}$ alkenyl, $C_2$-$C_{10}$ alkynyl, $C_3$-$C_{10}$ cycloalkyl, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

each $R^{10}$ is independently hydrogen, cyano, nitro, trifluoromethyl, difluoromethoxy, trifluoromethoxy, azido, —C(O)$R^3$, —C(O)O$R^3$, —SO$_2$N$R^3R^4$, —C(O)N$R^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$(CR$^4$R$^5$)$_m$-aryl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, NR$^3$R$^4$ and OR$^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl, or $R^3$ and $R^4$ together with the atom to which they are attached form a 4 to 10 membered heteroaryl or heterocyclic ring, wherein said heteroaryl and heterocyclic rings are optionally substituted independently with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic ring, wherein said alkyl and carbocyclic ring are optionally substituted independently with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

$R^{11}$, $R^{12}$ and $R^{13}$ independently are hydrogen, lower alkyl, lower alkenyl, aryl and arylalkyl, and $R^{14}$ is lower alkyl, lower alkenyl, aryl and arylalkyl, or any two of $R^{11}$, $R^{12}$, $R^{13}$ and $R^{14}$ together with the atom to which they are attached form a 4 to 10 membered heteroaryl or heterocyclic ring, wherein said alkyl, alkenyl, aryl, arylalkyl, heteroaryl ring and heterocyclic ring are optionally substituted independently with one or more groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

m is 0, 1, 2, 3, 4 or 5;

n is 1 or 2; and j is 0, 1 or 2.

Figure 5:
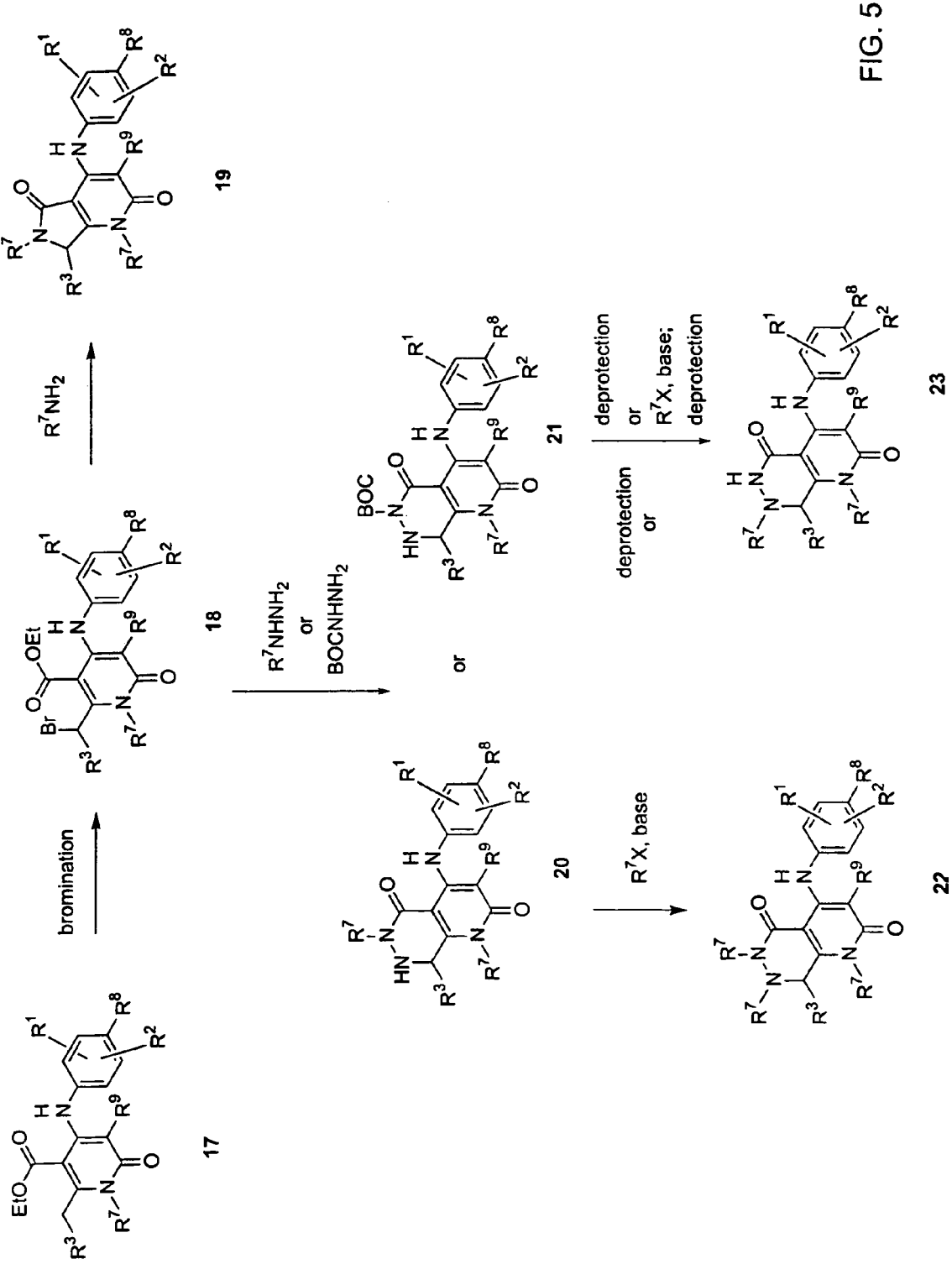
FIG. 5 shows a reaction scheme for the synthesis of compounds 18-23.

FIG. 5 shows non-limiting examples of the synthesis of compounds of this invention having the general Formula II.

In another embodiment, this invention relates to compounds of the general Formula III

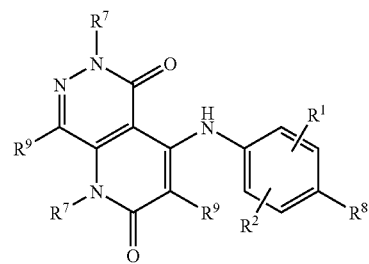

and tautomers, metabolites, resolved enantiomers, diastereomers, solvates and pharmaceutically acceptable salts and prodrugs thereof, wherein:

$R^1$, $R^2$, $R^8$ and each $R^9$ are independently hydrogen, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R$^7$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, C$_1$-C$_{10}$ alkyl, C$_2$-C$_{10}$ alkenyl, C$_2$-C$_{10}$ alkynyl, C$_3$-C$_{10}$ cycloalkyl, aryl, heteroaryl, arylalkyl, heteroarylalkyl, heterocyclyl and heterocyclylalkyl, and wherein said aryl, heteroaryl, arylalkyl, heteroarylalkyl, heterocyclyl or heterocyclylalkyl rings are optionally substituted independently with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R$^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^4$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl, or R$^3$ and R$^4$ together with the atom to which they are attached form a 4 to 10 membered heteroaryl and heterocyclic ring, wherein said heteroaryl and heterocyclic rings are optionally substituted independently with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

R$^4$ and R$^5$ independently are hydrogen or C$_1$-C$_6$ alkyl, or

R$^4$ and R$^5$ together with the atom to which they are attached form a 4 to 10 membered carbocyclic ring, wherein said alkyl and carbocyclic ring are optionally substituted independently with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl and heterocyclylalkyl;

R$^{11}$, R$^{12}$ and R$^{13}$ independently are hydrogen, lower alkyl, lower alkenyl, aryl and arylalkyl, and R$^{14}$ is lower alkyl, lower alkenyl, aryl and arylalkyl;

or any two of R$^{11}$, R$^{12}$, R$^{13}$ and R$^{14}$ together with the atom to which they are attached form a 4 to 10 membered heteroaryl or heterocyclic ring, wherein said alkyl, alkenyl, aryl, arylalkyl, heteroaryl ring and heterocyclic ring are optionally substituted independently with one or more groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

m is 0, 1, 2, 3,4 or 5; and j is 0, 1 or 2.

Figure 8:
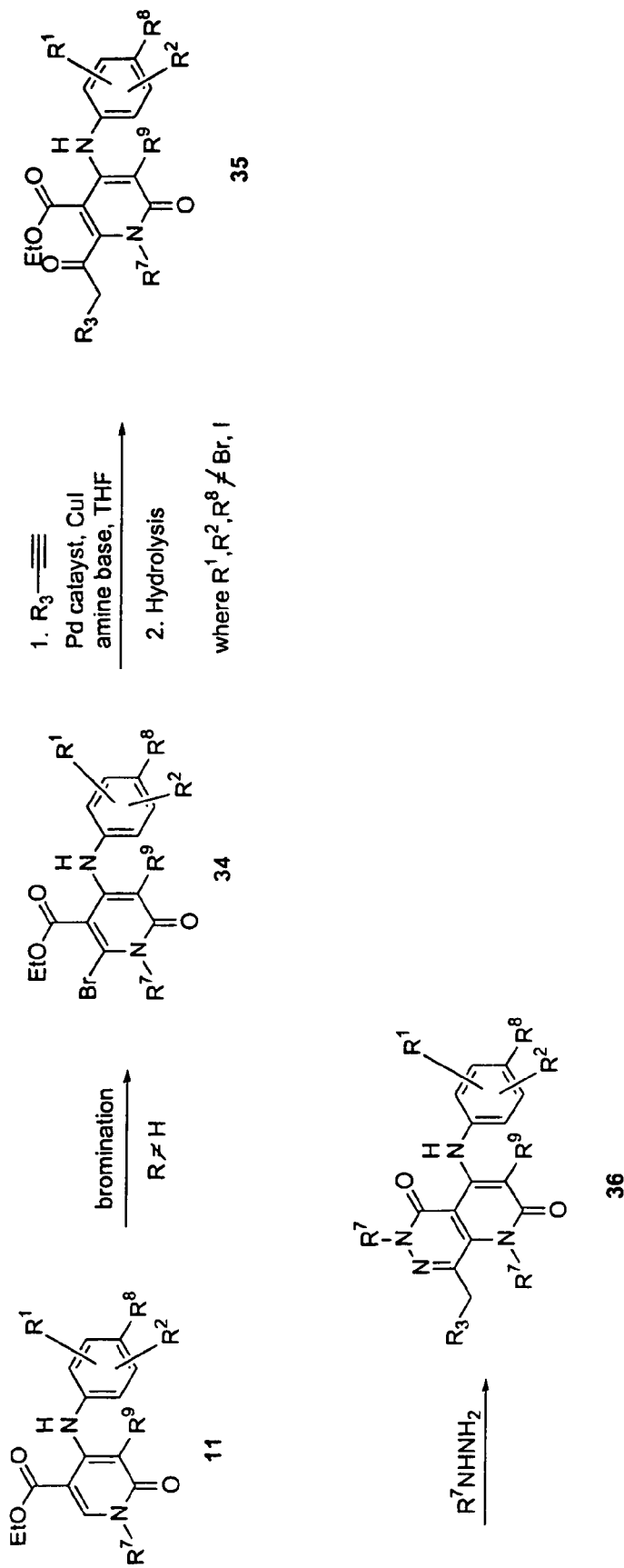
FIG. 8 shows a reaction scheme for the synthesis of compounds 34-36.
Figure 9:
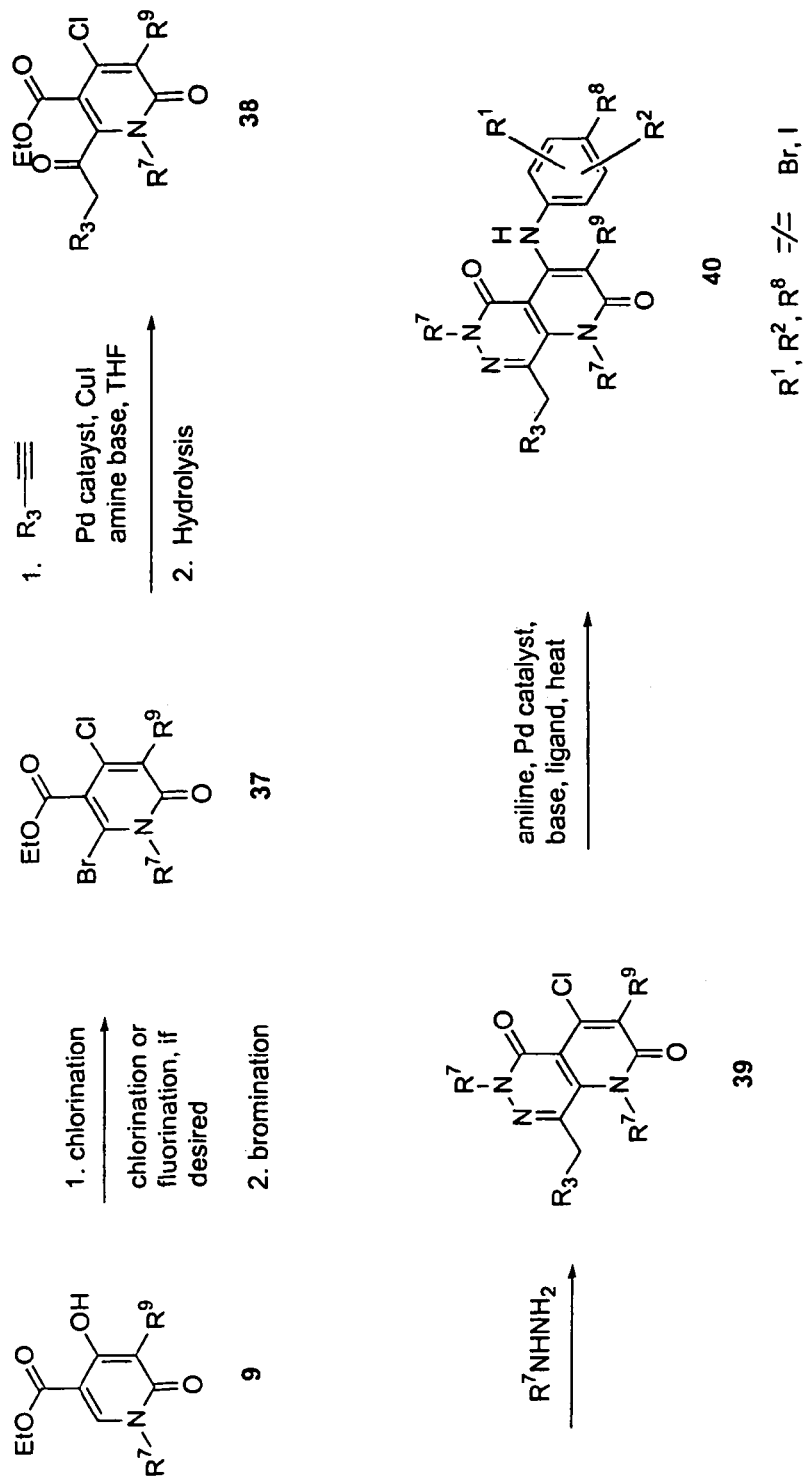
FIG. 9 shows a reaction scheme for the synthesis of compound 40.

FIGS. 8 and 9 show non-limiting examples of the synthesis of compounds of this invention having the general Formula III.

In another embodiment, this invention relates to compounds of the general Formula IV

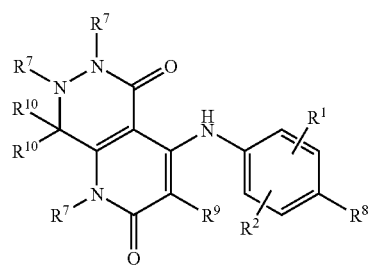

and tautomers, metabolites, resolved enantiomers, diastereomers, solvates and pharmaceutically acceptable salts and prodrugs thereof, wherein:

$R^1$, $R^2$, $R^8$ and $R^9$ are independently hydrogen, halogen, cyano, nitro, trifluoromethyl, difluoromethyl, fluoromethyl, fluoromethoxy, difluoromethoxy, trifluoromethoxy, azido, —$SR^{11}$, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, difluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

each $R^7$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, $C_1$-$C_{10}$ alkyl, $C_2$-$C_{10}$ alkenyl, $C_2$-$C_{10}$ alkynyl, $C_3$-$C_{10}$ cycloalkyl, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

each $R^{10}$ is independently hydrogen, cyano, nitro, trifluoromethyl, difluoromethoxy, trifluoromethoxy, azido, —$C(O)R^3$, —$C(O)OR^3$, —$SO_2NR^3R^4$, —$C(O)NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl, or $R^3$ and $R^4$ together with the atom to which they are attached form a 4 to 10 membered heteroaryl or heterocyclic ring, wherein said heteroaryl and heterocyclic rings are optionally substituted independently with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, —$C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic ring, wherein said alkyl and carbocyclic ring are optionally substituted independently with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, —$C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, —$C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl and heterocyclylalkyl;

$R^{11}$, $R^{12}$ and $R^{13}$ independently are hydrogen, lower alkyl, lower alkenyl, aryl and arylalkyl, and $R^{14}$ is lower alkyl, lower alkenyl, aryl and arylalkyl, or any two of $R^{11}$, $R^{12}$, $R^{13}$ and $R^{14}$ together with the atom to which they are attached form a 4 to 10 membered heteroaryl or heterocyclic ring, wherein said alkyl, alkenyl, aryl, arylalkyl, heteroaryl ring and heterocyclic ring are optionally substituted independently with one or more groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

m is 0, 1, 2, 3, 4 or 5; and j is 0, 1 or 2.

FIG. 5 shows non-limiting examples of the synthesis of compounds of this invention having the general Formula IV.

In another embodiment, this invention relates to compounds of the general Formula V

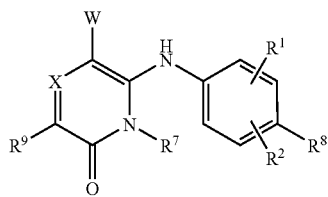

V and tautomers, metabolites, resolved enantiomers, diastereomers, solvates and pharmaceutically acceptable salts and prodrugs thereof, wherein:

X is N or $CR^{10}$;

$R^1$, $R^2$, $R^8$, $R^9$ and $R^{10}$ are independently hydrogen, halogen, cyano, nitro, trifluoromethyl, difluoromethyl, fluoromethyl, fluoromethoxy, difluoromethoxy, trifluoromethoxy, azido, —$SR^{11}$, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$ ($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^7$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethyl, fluoromethyl, difluoromethoxy, trifluoromethoxy, azido, —$NR^{11}SO_2R^{14}$, —$SO_2NR^{11}R^{12}$, —$C(O)R^{11}$, —$C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, $C_1$-$C_{10}$ alkyl, $C_2$-$C_{10}$ alkenyl, $C_2$-$C_{10}$ alkynyl, $C_3$-$C_{10}$ cycloalkyl, aryl, heteroaryl, arylalkyl, heteroarylalkyl, heterocyclyl and heterocyclylalkyl, and wherein said aryl, heteroaryl, arylalkyl, heteroarylalkyl, heterocyclyl and heterocyclylalkyl rings are optionally substituted independently with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl and heterocyclylalkyl, or $R^3$ and $R^4$ together with the atom to which they are attached form a 4 to 10 membered heteroaryl and heterocyclic ring, wherein said heteroaryl and heterocyclic rings are optionally substituted independently with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl heterocyclyl and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic ring, wherein said alkyl and carbocyclic ring are optionally substituted independently with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, —$C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein said alkyl, cycloalkyl, aryl, arylalkyl, heteroaryl, heteroarylalkyl, heterocyclyl and heterocyclylalkyl portions are optionally substituted independently with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, —C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^{11}$, R$^{12}$ and R$^{13}$ independently are hydrogen, lower alkyl, lower alkenyl, aryl and arylalkyl, and R$^{14}$ is lower alkyl, lower alkenyl, aryl and arylalkyl, or any two of R$^{11}$, R$^{12}$, R$^{13}$ and R$^{14}$ together with the atom to which they are attached form a 4 to 10 membered heteroaryl or heterocyclic ring, wherein said alkyl, alkenyl, aryl, arylalkyl, heteroaryl ring and heterocyclic ring are optionally substituted independently with one or more groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) or —CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) and CR$^3$OR$^3$ are optionally substituted independently with one or more groups independently selected from halogen, cyano, nitro, azido, —NR$^3$R$^4$, —OR$^3$, C$_1$-C$_{10}$ alkyl, C$_2$-C$_{10}$ alkenyl, C$_2$-C$_{10}$ alkynyl, cycloalkyl and heterocycloalkyl, wherein any of said C$_1$-C$_{10}$ alkyl, C$_2$-C$_{10}$ alkenyl, C$_2$-C$_{10}$ alkynyl, cycloalkyl and heterocycloalkyl are optionally substituted independently with 1 or more groups independently selected from —NR$^3$R$^4$ and —OR$^3$;

provided that when X is CH, W cannot be —C(O)aryl or —C(O)heteroaryl;

further provided that when X is CH, W is —C(O)OR$^3$ and R$^9$ is F, R$^7$ cannot be H;

m is 0, 1, 2, 3, 4 or 5; and j is 0, 1 or 2.

In certain embodiments, X is CR$^{10}$. In one embodiment, R$^{10}$ is H, provided that when R$^{10}$ is H, W cannot be —C(O)aryl or —C(O)heteroaryl, and further provided that when R$^{10}$ is H, W is C(O)OR$^3$ and R$^9$ is F, R$^7$ cannot be H.

In certain embodiments, W is selected from heteroaryl, —C(O)OR$^3$, —C(O)NR$^3$R$^4$, —C(O)NR$^4$OR$^3$ and —C(O)NR$^4$S(O)$_2$R$^3$.

In another embodiment, W is selected from

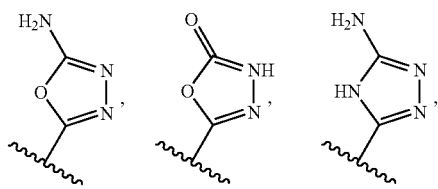

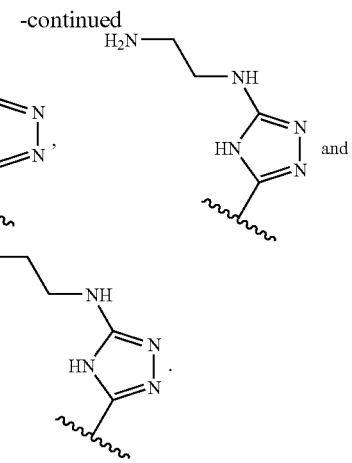

FIGS. 15-34 and 37-39 show non-limiting examples of the synthesis of compounds of this invention having the general Formula V.

Certain compounds of this invention can exist as two or more tautomeric forms. A "tautomer" is one of two or more structural isomers that exist in equilibrium and are readily converted from one isomeric form to another, such as structures formed by the movement of a hydrogen from one site to another within the same molecule. Other tautomeric forms of the compounds may interchange, for example, via enolization/deenolization and the like. Accordingly, the present invention includes the preparation of all tautomeric forms of compounds of this invention.

The terms "C$_1$-C$_{10}$ alkyl", "alkyl" and "lower alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "C$_2$-C$_{10}$ alkenyl", "lower alkenyl" and "alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "C$_2$-C$_{10}$ alkynyl," "lower alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "allyl" refers to a radical having the formula RC=CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The terms "carbocycle," "carbocyclyl," "cycloalkyl" or "C$_3$-C$_{10}$ cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "hetercyclyl" refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes fused ring systems which include a heterocycle fused to one or more aromatic groups. "Heterocycloalkyl" also includes radicals where heterocycle radicals are fused with one or more carbocyclic and/or heterocyclic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono ($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

The term "halogen" represents fluorine, bromine, chlorine, and iodine.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include, oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

The term "amino acid residue" includes, but is not limited to, the 20 naturally occurring amino acids commonly designated by three letter symbols, and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone.

In general, the various moieties or functional groups of the compounds of Formulas I-V may be optionally substituted by one or more substituents. Examples of substituents suitable for purposes of this invention include, but are not limited to, oxo (with the proviso that it is not on an aryl or heteroaryl), halogen, cyano, nitro, trifluoromethyl, difluoromethoxy, trifluoromethoxy, azido, —$NR^4SO_2R^6$, —$SO_2NR^3R^4$, —C(O) $R^3$, —C(O)O$R^3$, —OC(O)$R^3$, —$NR^4$C(O)O$R^6$, —$NR^4$C(O) $R^3$, —C(O)$NR^3R^4$, —$NR^3R^4$, —$NR^5$C(O)$NR^3R^4$, —$NR^5$C (NCN)$NR^3R^4$, —O$R^3$, aryl, heteroaryl, arylalkyl, heteroarylalkyl, heterocyclyl, and heterocyclylalkyl, where $R^3$, $R^4$, $R^5$ and $R^6$ are as defined herein.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the compounds of the present invention, where a term such as $(CR^4R^5)_m$ is used, $R^4$ and $R^5$ may vary with each iteration of m above 1. For instance, where m is 2, the term $(CR^4R^5)_m$ may equal —$CH_2CH_2$— or —$CH(CH_3)C$ $(CH_2CH_3)(CH_2CH_2CH_3)$— or any number of similar moieties falling within the scope of the definitions of $R^4$ and $R^5$.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and resolved enantiomers of the Formulas I-V. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

This invention also encompasses pharmaceutical compositions containing a compound of Formula I-V and methods of treating proliferative disorders, or abnormal cell growth, by administering compounds of the present invention. Compounds of the present invention having free amino, amido, hydroxy or carboxylic groups can be converted into pharmaceutically acceptable prodrugs.

A "prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of Formula I-V covalently joined to a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group to a phosphate ester, hemisuccinates dimethylaminoacetate, or phosphoryloxymethyloxycarbonyl, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, P(O) $(OH)_2$, —$P(O)(O(C_1-C_6)$alkyl$)_2$ or glycosyl (the radical resulting from the removal of a hydroxyl group of the hemiacetal form of a carbohydrate).

Free amines can also be derivatized as amides, sulfonamides or phosphonamides. For example, a prodrug can be formed by the replacement of a hydrogen atom in the amine group with a group such as R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural .alpha.-aminoacyl-natural α-aminoacyl, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is $(C_1-C_6)$alkyl, carboxy$(C_1-C_6)$alkyl, amino$(C_1-C_4)$alkyl or mono-N- or di-N,N-$(C_1-C_6)$alkylaminoalkyl, —C(Y$_2$)Y$_3$ wherein Y$_2$ is H or methyl and Y$_3$ is mono-N- or di-N,N-$(C_1-C_6)$ alkylamino, morpholino, piperidin-1-yl or pyrrolidin-1-yl.

All of these prodrug moieties may incorporate groups including but not limited to ether, amine and carboxylic acid functionalities.

Prodrugs of a compound of Formula I-V may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs," by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

In addition, the invention also includes solvates, metabolites, and pharmaceutically acceptable salts of compounds of Formulas I-V.

The term "solvate" refers to an aggregate of a molecule with one or more solvent molecules.

A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of Formulas I-V, including compounds produced by a process comprising contacting a compound of this invention with a mammal for a period of time sufficient to yield a metabolic product thereof.

Metabolites are typically identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

A "pharmaceutically acceptable salt" as used herein, unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

Processes for the manufacture of the compounds of Formula I, Formula II, Formula III, Formula IV and Formula V are provided as further features of the invention. The inventive compounds may be prepared using the reaction routes and synthesis schemes as described below, employing the techniques available in the art using starting materials that are readily available or can be synthesized using methods known in the art.

Illustrations of the preparation of compounds of the present invention are shown in FIGS. 1-34.

FIG. 1 illustrates synthesis of compounds of Formula I. Pyridone ester 2 can be prepared in a two-step, one-pot procedure. Treatment of 3-oxo-pentanedioic acid diethyl ester 1 with triethyl orthoformate and acetic acid at elevated temperatures (120 to 150° C.) gives the intermediate enol ether. Cyclization of the enol ether intermediate is accomplished by cooling the concentrated reaction residue and treating with the appropriate amine at low temperature (about 0° C.). Halogenation of the pyridone ester 2 can be accomplished with $POCl_3$, thionyl chloride, oxalyl chloride, $PCl_5$, $PBr_3$, or $Ph_3P$ and $Br_2$. In one embodiment this transformation is achieved with $POCl_3$ neat or in the presence of an amine like triethylamine at room temperature. If $R^9$ is Cl or F, it can be incorporated at this stage. Chlorination of pyridone ester 3 can be accomplished with NCS in a suitable organic solvent such as DMF, MeCN or mixed solvent systems at room temperature. In one embodiment the reaction is carried out in DMF. Fluorination is achieved by treating pyridone ester 3 with [1-(chloromethyl)-4-fluoro-1,4-diazoniabicyclo[2.2.2]octane-bis(tetrafluoroborate) in the presence of base in a suitable organic solvent at the appropriate temperature. Most preferable is the use of LiOH as base and MeCN as solvent at approximately 85° C.

With continued reference to FIG. 1, regardless of the identity of $R^9$, pyridone acid 4 can be prepared by basic hydrolysis under standard conditions using either LiOH or NaOH in standard mixed aqueous/organic solvent systems. Incorporation of the aniline moiety is accomplished by $S_NAr$ reaction. This can be done in a suitable organic solvent such as THF using an amide base such as LDA, LiHMDS, NaHMDS or KHMDS at appropriate temperatures (−78° C. to room temperature). In one embodiment, the aniline is added to LDA or LiHMDS in THF at low temperature (−20 to −80° C.). The pyridone 4 is then added and the reaction mixture is warmed to room temperature to generate carboxylic acid 5. Amides 6 and hydroxamates 7 can be prepared using standard coupling procedures, including but not limited to EDCI, HOBt, or PyBOP and the appropriate amine or hydroxylamine in suitable organic solvents such as DMF, THF or methylene chloride. In some instances, the amine or hydroxylamine used in the coupling reaction contains a standard protecting group. In those cases, the protecting group can be removed by standard conditions known in the art.

Figure 2:
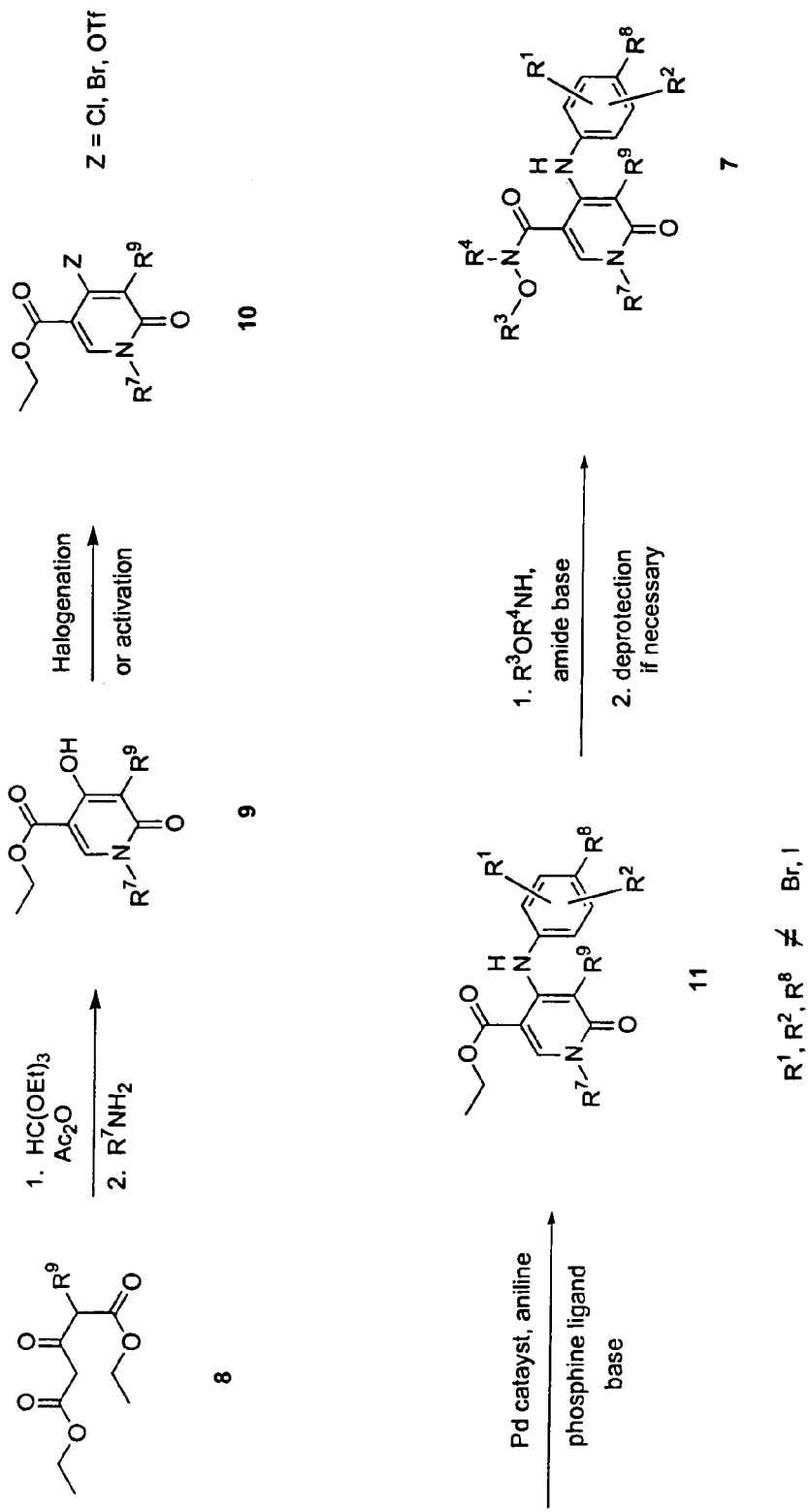
FIG. 2 shows a reaction scheme for the synthesis of compounds 7 and 11.

FIG. 2 outlines the synthesis of compounds of Formula I wherein the $R^9$ group is incorporated into the starting 3-oxo-pentanedioic acid diethyl ester 8. This route is particularly useful for analogs where $R^9$ is alkyl. The preparation of analog 10 is outlined in FIG. 2 and can be carried out as described above for FIG. 1 with the addition that activation of pyridone 9 can be accomplished by conversion to a triflate ester. For example, treating pyridone 9 with triflic anhydride or N-phenyltrifluoromethanesulfonimide and amine base in THF or methylene chloride. When Z is Cl or Br, pyridone 10 can be converted to amide 6 or hydroxmate 7 as described in FIG. 1. Alternatively, pyridone 10 can be converted to hydroxamate 7 in the route outlined in FIG. 2 in which the aniline moiety is incorporated utilizing palladium mediated cross coupling chemistry. The palladium mediated cross coupling chemistry can be accomplished by treatment of a mixture of the appropriate aniline and pyridone 10 with a Pd catalyst such as $Pd(OAc)_2$, $PdCl_2(dppf)$, $Pd(Ph_3P)_4$, $Pd_2dba_3$, a phosphine ligand and base in a suitable organic solvent such as THF, DMF, PhMe, DME or MeCN at elevated temperature. In one embodiment, $Pd(OAc)_2$, rac-2,2-bis(diphenylphosphino)-1,1'-binaphthyl and $Cs_2CO_3$ are used in PhMe at 70 to 100° C. Hydroxamate 7 can be prepared by treating pyridone ester 11 with the appropriate hydroxylamine and amide base such as LDA, LiHMDS or NaHMDS in a suitable organic solvent such as THF at low temperature. In one embodiment, a LiHMDS solution is added to a solution of pyridone ester 11 and hydroxylamine in THF at 0° C. The reaction mixture is then warmed to room temperature to yield the desired hydroxamate 7. In some instances, the hydroxylamine used in the coupling reaction contains a standard protecting group. In those cases, the protecting group can be removed by standard conditions known in the art.

Figure 3:
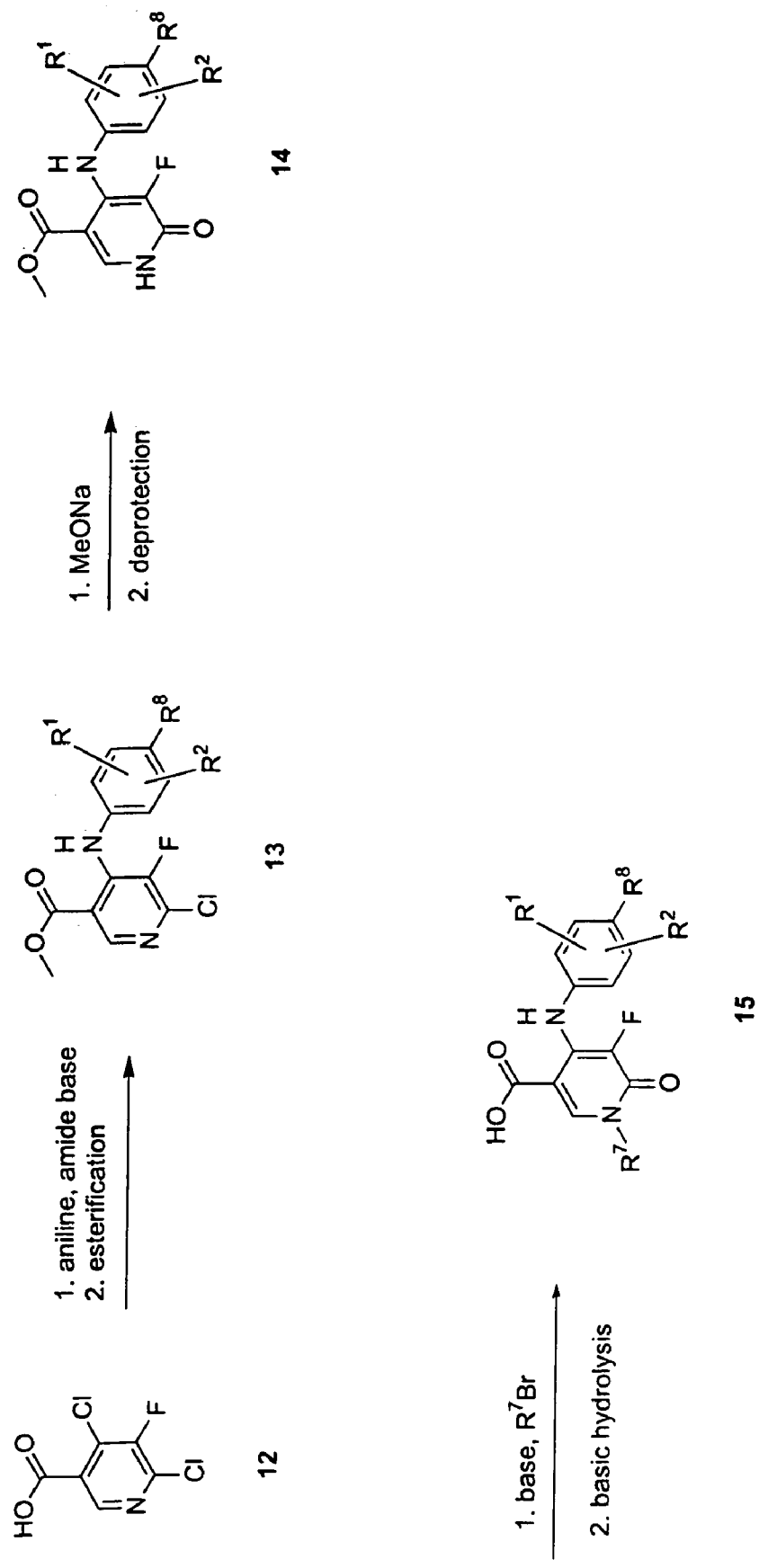
FIG. 3 shows a reaction scheme for the synthesis of compounds 14 and 15.

In FIG. 3 preparation of compounds of the Formula I is shown in which 4,6-dichloro-5-fluoronicotinic acid 12 (Sanchez et al., *J. Heterocylc. Chem.* 1993, 30 (4), 855-9) is used as the starting material. Ester 13 can be prepared in a two-step procedure. The first step is $S_NAr$ addition of the properly substituted aniline in a suitable organic solvent such as THF using an amide base such as LDA, LiHMDS, NaHMDS or KHMDS at appropriate temperatures (−78° C. to room temperature). In one embodiment, the aniline is added to LDA or LiHMDS in THF at low temperature (−20 to −80° C.). The nicotinic acid 12 is then added and the reaction mixture warmed to room temperature to generate the corresponding carboxylic acid. The methyl ester 13 can then be prepared by standard conditions including but not limited to TMSCl in MeOH or $TMSCHN_2$ in suitable organic solvents such as PhMe/MeOH. Pyridone 14 can be made in a two-step sequence. In the first step, methyl ester 13 is treated with sodium methoxide in a suitable organic solvent such as MeOH or THF or MeOH/THF mixtures at temperatures ranging from 0° C. to 40° C. In one embodiment, sodium methoxide is added to a solution of methyl ester 13 in MeOH/THF at 0° C. This mixture is then warmed to room temperature and then to 40° C. to generate the desired methoxy pyridine. Demethylation can then be accomplished by standard conditions including but not limited to aqueous HCl at elevated temperature, pTsOH in acetic acid at elevated temperature and aqueous HBr in MeOH at elevated temperature. In one embodiment demethylation to give pyridone 14 is achieved by treatment of the methoxy pyridine with HBr in acetic acid at elevated temperature (80 to 120° C.). If desired, alkylation of pyridone 14 to give substituted pyridone 15 can be achieved by standard basic alkylation conditions incorporating alkyl halides. These conditions include but are not limited to $K_2CO_3$ in acetone or DMF, NaH in THF or, NaOMe in MeOH/PhMe or, phase transfer conditions using for example NaOH and $Bu_4NI$. In one embodiment, the alkylation is accomplished by treatment of pyridone 14 with LiH at 0° C. in DMF followed by addition of alkyl bromide and warming to room temperature. Carboxylic acid 15 can then be prepared using standard saponification conditions such as LiOH or NaOH in standard mixed aqueous/organic solvent systems. Pyridone 15 can be converted to amide 6 or hydroxmate 7 as described in FIG. 1.

Figure 4:
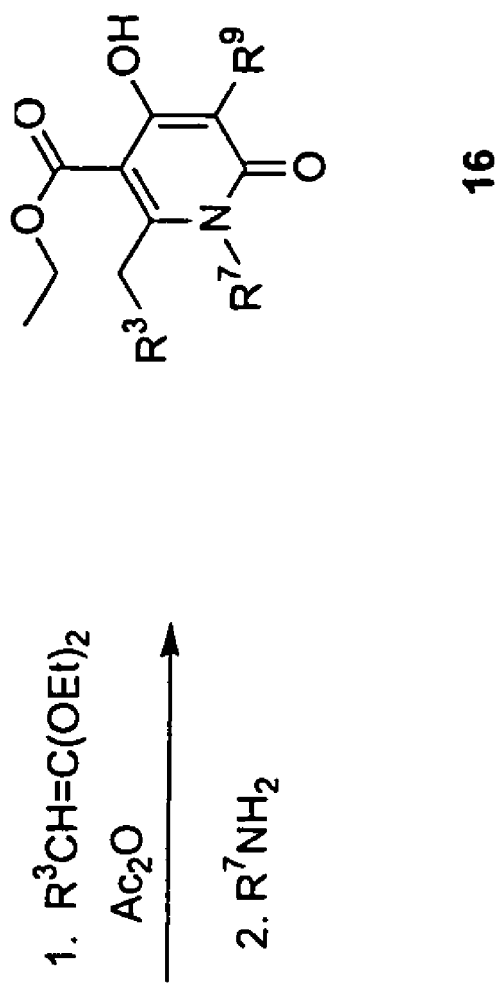
FIG. 4 shows a reaction scheme for the synthesis of compound 16.
Figure 4:
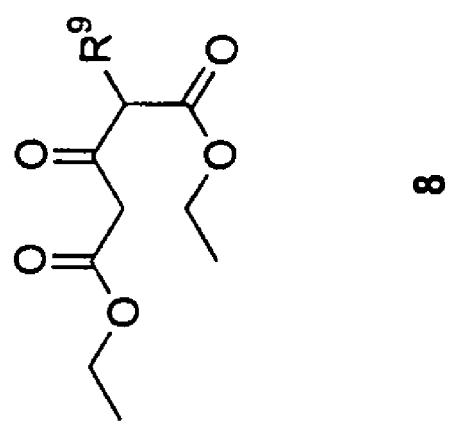

FIG. 4 describes the initial steps in the preparation of analogs of compounds of the Formula I. Treatment of 3-oxopentanedioic acid diethyl ester 8 with a ketene acetal and acetic acid at elevated temperatures (120 to 150° C.) gives the intermediate enol ether. Cyclization of the enol ether intermediate can be accomplished by cooling the concentrated reaction residue and treating with the appropriate amine at low temperature (about 0° C.) to give pyridone 16. If $R^9$ is Cl or F is desired, then a chlorination or fluorination step as described in FIG. 1 can be incorporated at this time. Furthermore, pyridone 16 can be converted to amide 6 or hydroxamate 7 through the $S_NAr$ chemistry as described in FIG. 1 or through palladium mediated cross-coupling chemistry as described in FIG. 2.

In FIG. 5 syntheses of compounds of Formula II and IV are depicted. Bromination of pyridone 17 (prepared as described in FIGS. 2 and 4) to give pyridone 18 can be accomplished using standard conditions such as NBS in a suitable organic solvent. Cyclization to form lactam 19 can be achieved by treatment with ammonia or a primary amine in a suitable organic solvent at temperatures ranging from ambient to slightly elevated temperatures. In one embodiment, this cyclization is accomplished in an alcoholic solvent such as MeOH or EtOH. Pyridone 18 can also be converted to pyridazinones 20 and 21 by treatment with substituted or unsubstituted hydrazines or t-butyl carbazate in a suitable organic solvent such as DMF, THF, MeOH or EtOH. Pyridazinones 20 and 21 can then be substituted further by standard basic alkylation conditions with alkyl halides. These conditions include but are not limited to $K_2CO_3$ in acetone or DMF at room or elevated temperature, NaH in THF or DMF at ambient or elevated temperature, and NaOMe in MeOH/PhMe at elevated temperature. Pyridazinone 21 can then be deprotected under standard conditions including, but not limited to, TFA in methylene chloride or HCl in a suitable organic solvent such as dioxane.

Figure 6:
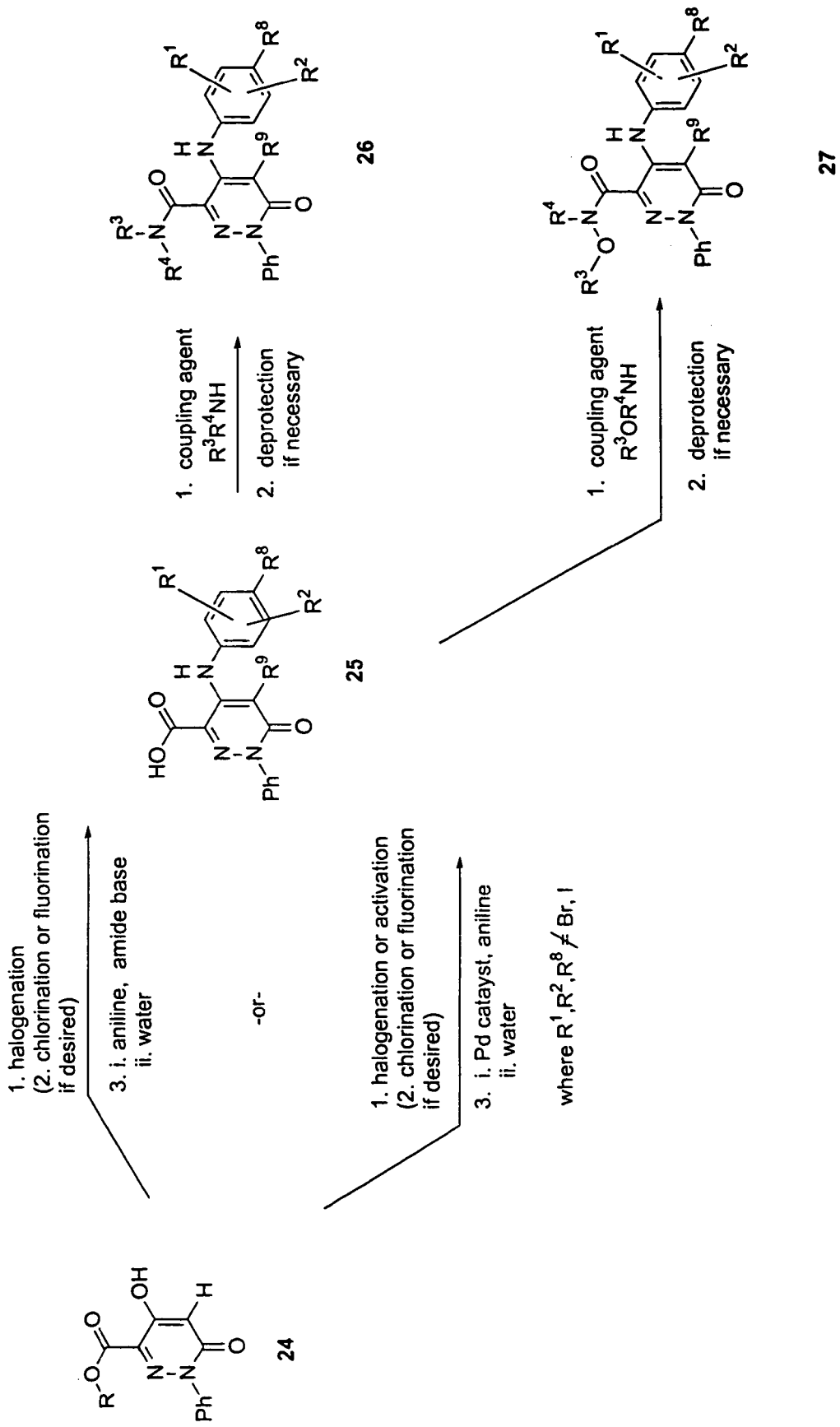
FIG. 6 shows a reaction scheme for the synthesis of compounds 25-27.

FIG. 6 depicts the preparation of compounds of the Formula I where X is N. In FIG. 6, 4-hydroxy-6-oxo-1-phenyl-1,6-dihydropyridazine-3-carboxylic acid methyl ester 24 (Schober, et al., *J. Heterocyclc. Chem.* 1989, 26, 169-176) can be converted to dihydropyridazine 25 in one of two procedures. The first method involves halogenation followed by $S_NAr$ reaction and in situ saponification. Halogenation of the pyridazine ester 24 can be accomplished with $POCl_3$, thionyl chloride, oxalyl chloride, $PCl_5$, $PBr_3$, or $Ph_3P$ and $Br_2$. In one embodiment this transformation is achieved with $POCl_3$ neat at elevated temperature (about 85° C.). If $R^9$ is Cl or F is desired, then chlorination or fluorination as described in FIG. 1 can be incorporated at this time. In the second step, aniline addition and saponification can be carried out in the same pot. The $S_NAr$ reaction can be done in a suitable organic solvent such as 1,2-dichlorobenzene, xylenes, or toluene in the presence of a base such as $Cs_2CO_3$ or $K_2CO_3$ at elevated temperature (80 to 200° C.). In one embodiment the $S_NAr$ reaction is accomplished by treating the halogenated pyridazine with aniline and $Cs_2CO_3$ in 1,2-dichlorobenzene and heating to 180° C. for 24 hours. Saponification to generate dihydropyridazine 25 is accomplished by the addition of water to the crude reaction mixture stirring at room temperature. The second method involves halogenation or activation of pyridazine ester 24 followed by palladium-mediated cross-coupling. Halogenation is accomplished as described above. Activation is accomplished by treating pyridazine ester 24 with triflic anhydride or N-phenyltrifluoromethanesulfonimide and amine base in THF or methylene chloride. In the case where halogenation is used, if $R^9$ is Cl or F is desired, then a chlorination or fluorination step as described in FIG. 1 can be incorporated at this time. The palladium-mediated cross-coupling reaction can be achieved by standard methods including but not limited to treating the halogenated or activated pyridazine with aniline, Pd catalyst such as $Pd(OAc)_2$, $PdCl_2$(dppf), $Pd(Ph_3P)_4$, $Pd_2dba_3$, a phosphine ligand and base in a suitable organic solvent such as THF, DMF, PhMe, DME or MeCN at elevated temperature. Saponification to generated dihydropyridazine 25 can be achieved as described above by the addition of water to the crude reaction mixture stirring at room temperature or by basic hydrolysis under standard conditions using either LiOH or NaOH in standard mixed aqueous/organic solvent systems. Dihydropyridazine 25 can be converted to amide 26 or hydroxmate 27 by the standard methods described in FIG. 1 or FIG. 2.

Figure 7:
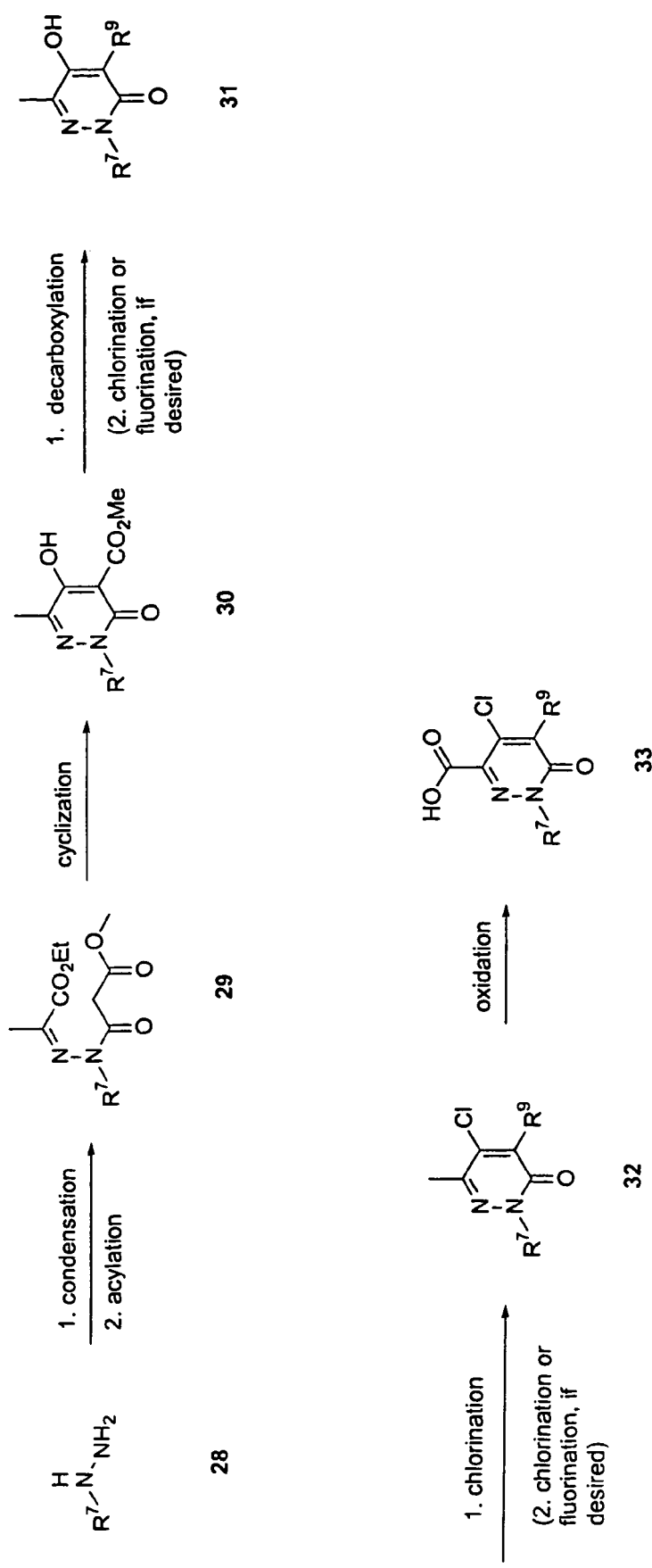
FIG. 7 shows a reaction scheme for the synthesis of compound 33.

The preparation of compounds of the Formula I where X=N is depicted in FIG. 7. Substituted hydrazine 28 can be converted to hydrazono-propionic acid ethyl ester 29 by a two-step procedure. In the first step, hydrazine 28 is condensed with ethyl pyruvate under standard dehydrating conditions such as in the presence of $MgSO_4$ in a suitable organic solvent such as chloroform or methylene chloride at temperatures ranging from 0° C. to ambient temperature. In the second step, acylation is achieved by treatment with base at low temperature in a suitable organic solvent such as THF, DMF, dioxane or MeCN followed by the addition of methyl malonyl chloride. In one embodiment, the hydrazone is treated with LiH in THF at 0° C. followed by the addition of methyl malonyl chloride and warming to room temperature. 5-Hydroxy-2H-pyridazin-3-one 31 is prepared from hydrazono-propionic acid ethyl ester 29 by cyclization under strongly basic conditions followed by saponification and decarboxylation. The cyclization can be accomplished by treatment of hydrazono-propionic acid ethyl ester 29 with a strong base such as DBU, LDA or NaH in a suitable organic solvent such as THF or MeCN at room temperature. In one embodiment, cyclization is achieved with DBU in MeCN at room temperature. Decarboxylation to form 5-hydroxy-2H-pyridazin-3-one 31 can be achieved by heating 5-hydroxy-3-oxo-2,3-dihydropyridazine-4-carboxylic acid methyl ester 30 in a suitable organic solvent such as dioxane or decalin or dioxane/decalin mixture to high temperatures in the presence of concentrated HCl. 5-Chloro-2H-pyridazin-3-one 32 can be prepared from 5-hydroxy-2H-pyridazin-3-one 31 by treatment with $POCl_3$, thionyl chloride, oxalyl chloride or $PCl_5$. In one embodiment this transformation is achieved with $POCl_3$ neat at elevated temperature (~85° C.). If $R^9$ is Cl or F is desired, then a chlorination or fluorination step as described in FIG. 1 can be incorporated either after decarboxylation or after chlorination. Carboxylic acid 33 can be prepared by oxidation under standard conditions including but not limited to $KMnO_4$ in water, $SeO_2$ in organic solvent like dioxane, xylene, or pyridine, $NaOCl/RuCl_3$, $CrO_3$ in aqueous $H_2SO_4$, $K_2Cr_2O_7$, and $Na_2Cr_2O_7$ in water. In one embodiment this transformation is achieved with $K_2Cr_2O_7$—$H_2SO_4$. Carboxylic acid 33 can be converted to amide 26 or hydroxmate 27 by the standard methods such as those described in FIGS. 1, 2 and 6.

FIG. 8 illustrates the preparation of compounds of Formula III. Pyridone 11 can be converted to bromide 34 with standard reagents including but not limited to NBS or bromine with or without a variety of additives such as AcOH, $H_2O_2$, silica, $AlCl_3$ and t-$BuNH_2$, in a suitable solvent such as $CCl_4$ or water. Synthesis of ketone 35 can be accomplished in a two-step procedure. In the first step, palladium mediated alkyne cross coupling reaction is used to generate the corresponding alkyne intermediate. This palladium-mediated cross-coupling reaction can be achieved by standard methods including but not limited to treating bromide 34 with the desired alkyne, a Pd catalyst such as $Pd(OAc)_2$ and $Ph_3P$, $PdCl_2(dppf)$, $Pd(Ph_3P)_2Cl_2$, $Pd(Ph_3P)_4$ or $Pd_2dba_3$ and $Ph_3P$, CuI, and amine base such as $Et_3N$, $Et_2NH$, or $iPr_2NH$, in a suitable organic solvent such as THF, DMF, PhMe, DME or MeCN at elevated temperature. In one embodiment, the bromide 34 and alkyne are treated with $Pd(Ph_3P)_2Cl_2$, CuI and amine base in THF or DMF at 50 to 100° C. In the second step, the intermediate alkyne is hydrolysized to the ketone 35 by standard methods including, but not limited to, $H_2SO_4$, TFA, trifluorosulfonamide, $FeCl_3$ or $HgSO_4/H_2SO_4$. Cyclization to form pyrido-pyridazine-dione 36 can be accomplished by treating ketone 35 with substituted or unsubstituted hydrazine in a suitable organic solvent such as EtOH, iPrOH, DMF, DME or mixtures thereof at temperatures ranging from ambient to about 100° C.

Compounds of Formula III can be prepared as outlined in FIG. 9. Bromide 37 can be synthesized from pyridone 9 by chlorination followed by aromatic bromination. The chlorination can be accomplished with $POCl_3$, thionyl chloride, oxalyl chloride, $PCl_5$, $PBr_3$, or $Ph_3P$ and $Br_2$. In one embodiment this transformation is achieved with $POCl_3$ neat at elevated temperature (about 85° C.). If $R^9$=Cl or F is desired, then a chlorination or fluorination step as described in FIG. 1 can be incorporated at this time. Aromatic bromination can be achieved with standard reagents including but not limited to NBS or bromine with or without a variety of additives such as AcOH, $H_2O_2$, silica, $AlCl_3$ and t-$BuNH_2$, in a suitable solvent such as $CCl_4$ or water. Ketone 38 and pyrido-pyridazine-dione 39 can be prepared as described in FIG. 8. Pyridopyridazine-dione 40 can be made from pyridopyridazine-dione 39 by palladium-mediated cross-coupling chemistry. The palladium-mediated cross-coupling reaction can be achieved by standard methods including, but not limited to, treating pyridopyridazine-dione 39 with the appropriate aniline, a Pd catalyst such as $Pd(OAc)_2$, $PdCl_2(dppf)$, $Pd(Ph_3P)_4$, $Pd_2dba_3$, a phosphine ligand and base in a suitable organic solvent such as THF, DMF, PhMe, DME or MeCN at elevated temperature.

Figure 10:
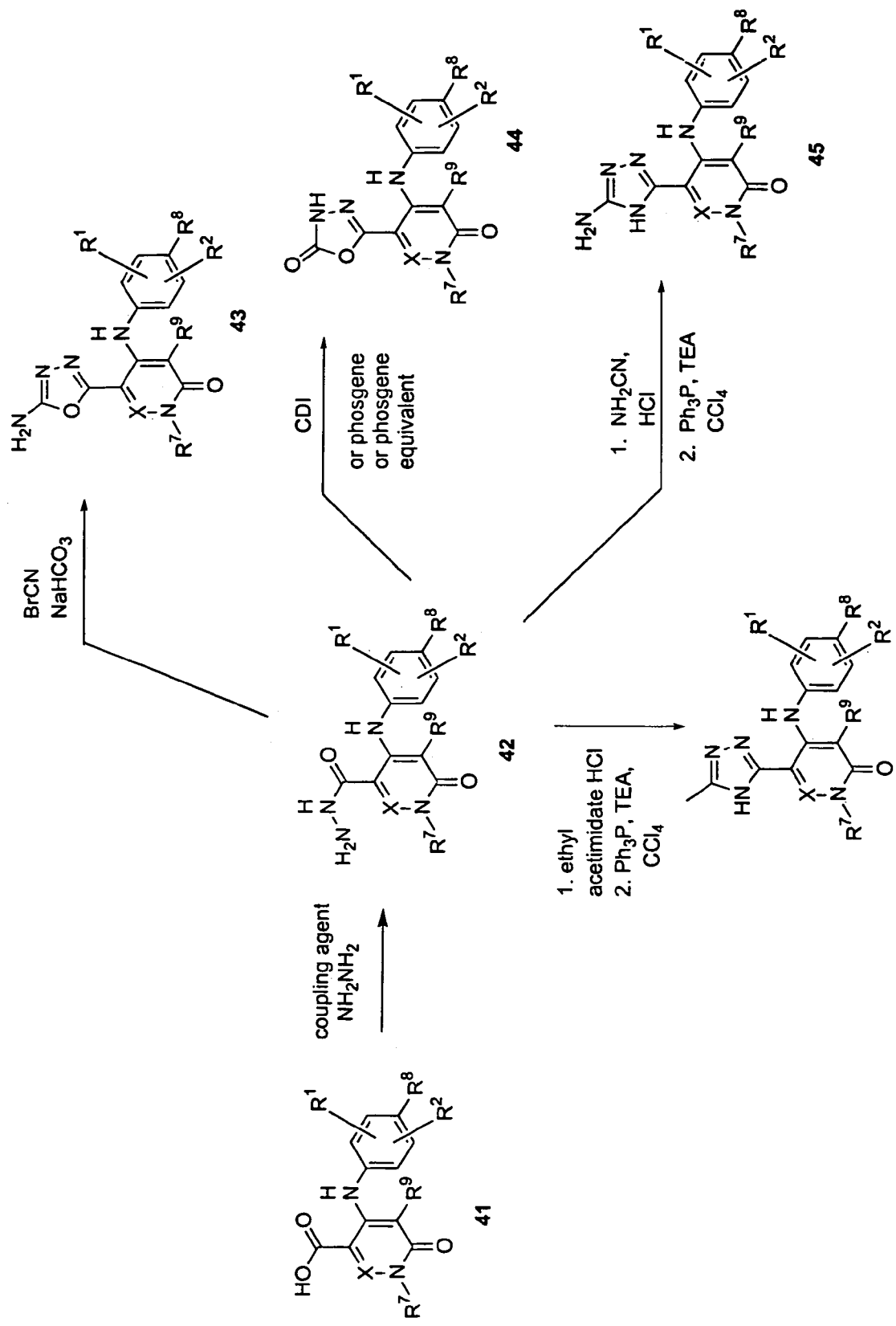
FIG. 10 shows a reaction scheme for the synthesis of compounds 42-46.
Figure 11:
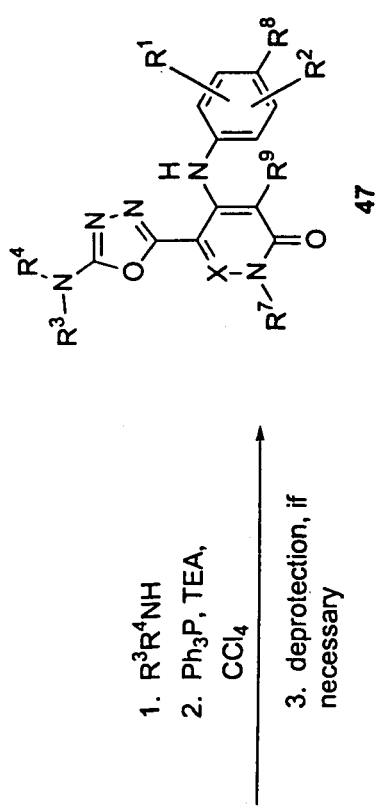
FIG. 11 shows a reaction scheme for the synthesis of compound 47.
Figure 12:
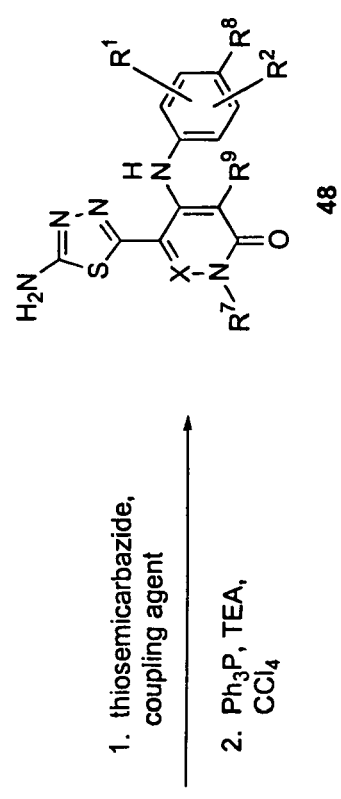
FIG. 12 shows a reaction scheme for the synthesis of compound 48.

FIGS. 10-12 illustrate the preparation of compounds of Formula I of the present invention where W is heterocyclic or heteroaromatic. Hydrazide 42 can be prepared from carboxylic acid 41 using standard coupling reagents including but not limited to EDCI, HOBt, or PyBOP and hydrazine in suitable organic solvents such as DMF, THF or dichloromethane. Amino oxadiazole 43 is prepared from hydrazide 42 by treatment with BrCN and a base such as $NaHCO_3$, in a suitable biphasic solvent system such as dioxane and water at room temperature. Oxadiazolone 44 can be prepared from hydrazide 42 using CDI, phosgene or a phosgene equivalent in a suitable organic solvent such as DMF, PhMe, methylene chloride or mixtures thereof. In one embodiment, cyclization to form oxadiazolone 44 is accomplished by treating hydrazide 42 with CDI in DMF at room temperature. Amino triazole 45 can be prepared by treatment of the hydrazide 42 with cyanamide, followed by cyclization using $PPh_3$, TEA, and $CCl_4$ in dichloromethane. Similarly, triazole 46 can be prepared by treatment of the hydrazide 42 with ethyl acetimidate, followed by cyclization using $PPh_3$, TEA, and $CCl_4$ in dichloromethane. Substituted amino oxadiazole 47 can be prepared in a two-step procedure from oxadiazolone 44 as outlined in FIG. 11. Oxadiazolone 44 is treated with a primary or secondary amine at elevated temperature in alcoholic solvents such as MeOH, EtOH or iPrOH. In one embodiment, a primary or secondary amine is stirred with oxadiazolone 44 in EtOH at approximately 90° C. The ring-opened intermediate is then cyclized by treatment with $PPh_3$, TEA, and $CCl_4$ in dichloromethane to give substituted amino oxadiazole 47. In some cases the primary or secondary amine used in the addition step contains a functionality that requires protection with a standard protecting group. In these cases, the protecting group can be removed under standard conditions to yield the desired substituted amino oxadiazole 47. The thiazole 48 can be prepared from the carboxylic acid 41 with thiosemicarbazide using standard EDCI coupling conditions followed by cyclization of the intermediate obtained employing $PPh_3$, TEA, and $CCl_4$ in dichloromethane as outlined in FIG. 12.

Figure 13:
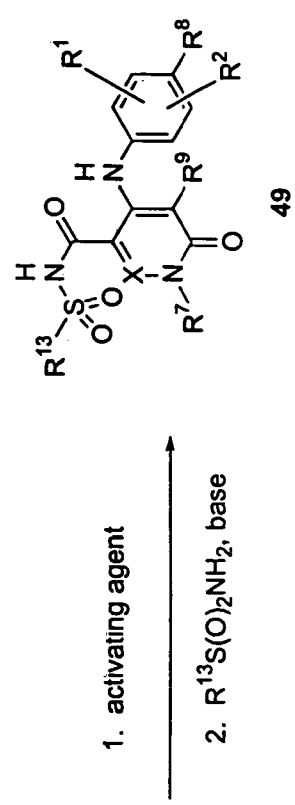
FIG. 13 shows a reaction scheme for the synthesis of compound 49.

FIG. 13 illustrates the preparation of compounds of Formula I. Acyl sulfonamide 49 can be prepared from carboxylic acid 41 using standard coupling reagents including but not limited to CDI or EDCI, HOBt, or PyBOP and the appropriate sulfonamide in suitable organic solvents such as DMF, THF or dichloromethane in the presence of base. In one embodiment, carboxylic acid 41 is treated with CDI in DMF at room temperature followed, a few hours later, by the addition of the appropriate sulfonamide and DBU.

Figure 14:
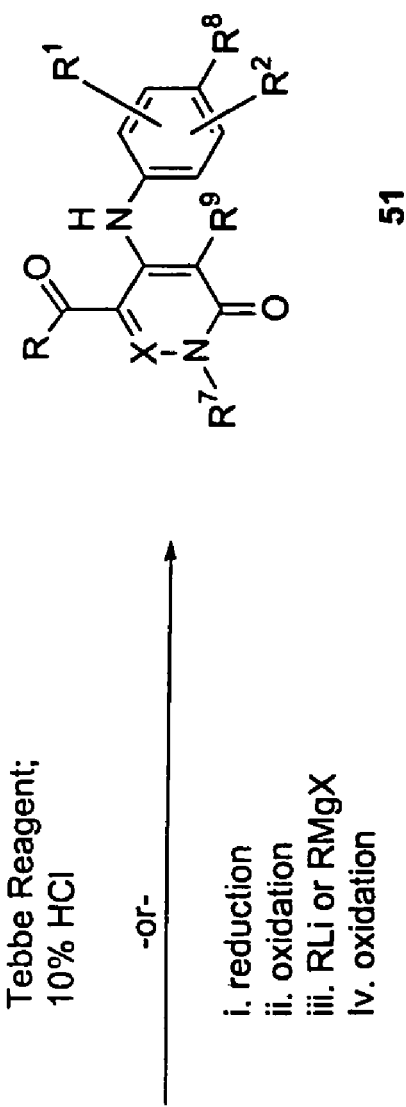
FIG. 14 shows a reaction scheme for the synthesis of compound 51.
Figure 14:
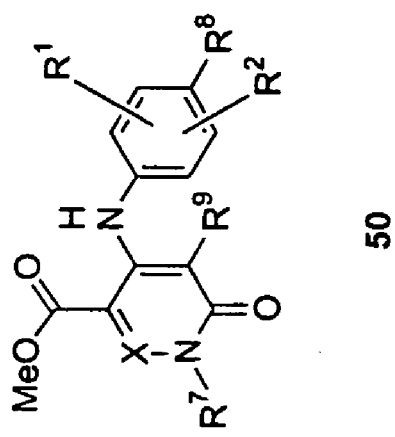

FIG. 14 illustrates the synthesis of compounds of Formula I where W is a ketone. Ketone 51 can be prepared either by treating methyl ester 50 with Tebbe's reagent followed by aqueous acid or in a four-step oxidative reduction protocol which includes addition of an alkyllithium or Grignard reagent to the corresponding aldehyde. The four-step protocol can be accomplished as follows. The methyl ester 50 is reduced with $NaBH_4$ in EtOH at room temperature followed by oxidation with $MnO_2$ in THF:acetone at 50° C. to give the corresponding aldehyde. The secondary alcohol is then prepared by adding either a Grignard reagent or an alkyllithium to the aldehyde at −78° C. The ketone 51 is then prepared by $MnO_2$ oxidation of the corresponding secondary alcohol in THF:acetone at 50° C.

Figure 15:
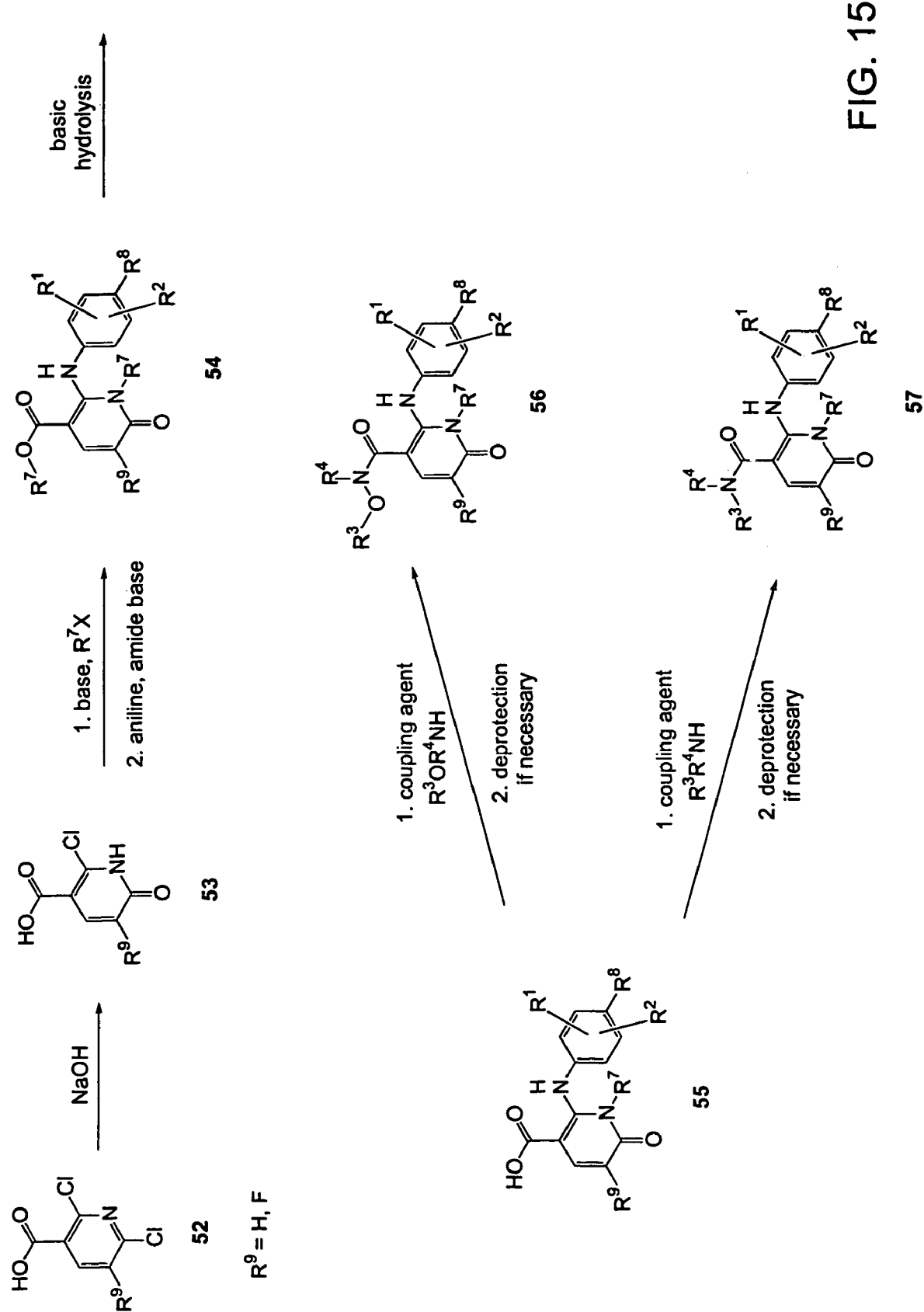
FIG. 15 shows a reaction scheme for the synthesis of compounds 54-57.

In FIG. 15, the syntheses of compounds of Formula V where X is CH and $R^9$ is H or F is depicted, in which 2,6-dichloronicotinic acid or 2,6-dichloro-5-fluoronicotinic acid is used as the starting material. The nicotinic acid 52 is converted to the monochloro acid 53 by refluxing in 2N aqueous NaOH following the procedure described in U.S. Pat. No. 3,682,932. Alkylation of 53 can be achieved by standard basic alkylation conditions incorporating alkyl halides, with two equivalents of the appropriate alkyl halide and base to give a mixture of the N-alkyl pyridone ester and the regioisomeric O-alkyl pyridine ester, which are easily separated by column chromatography. These conditions include but are not limited to $K_2CO_3$ in acetone or DMF at room or elevated temperature or NaH in THF at ambient or elevated temperature, followed by the addition of an alkyl halide. In one embodiment this alkylation is achieved with LiH in DMF at 0° C., followed by addition of alkyl bromide or alkyl iodide and warming to room temperature. Incorporation of the properly substituted aniline moiety is accomplished by $S_NAR$ reaction. This can be done in a suitable organic solvent such as THF using an amide base such as LDA, LiHMDS, NaHMDS or KHMDS at appropriate temperatures (−78° C. to room temperature). In one embodiment the aniline is added to LDA or LiHMDS in THF at low temperature (−20 to −80° C.). The pyridone is then added and the mixture is stirred at low temperature to generate ester 54. Carboxylic acid 55 can then be prepared using standard saponification conditions such as LiOH or NaOH in standard mixed aqueous/organic solvent systems. Hydroxamate 56 and amide 57 can be prepared using standard coupling procedures, including but not limited to EDCI, HOBt, or PyBOP and the appropriate amine or hydroxylamine in suitable organic solvents such as DMF, THF, or methylene chloride. In one embodiment, the coupling is accomplished with HOBt and EDCI in DMF. In some instances, the amine or hydroxylamine used in the coupling reaction contains a standard protecting group. In those cases, the protecting group can be removed by standard conditions known in the art.

Figure 16:
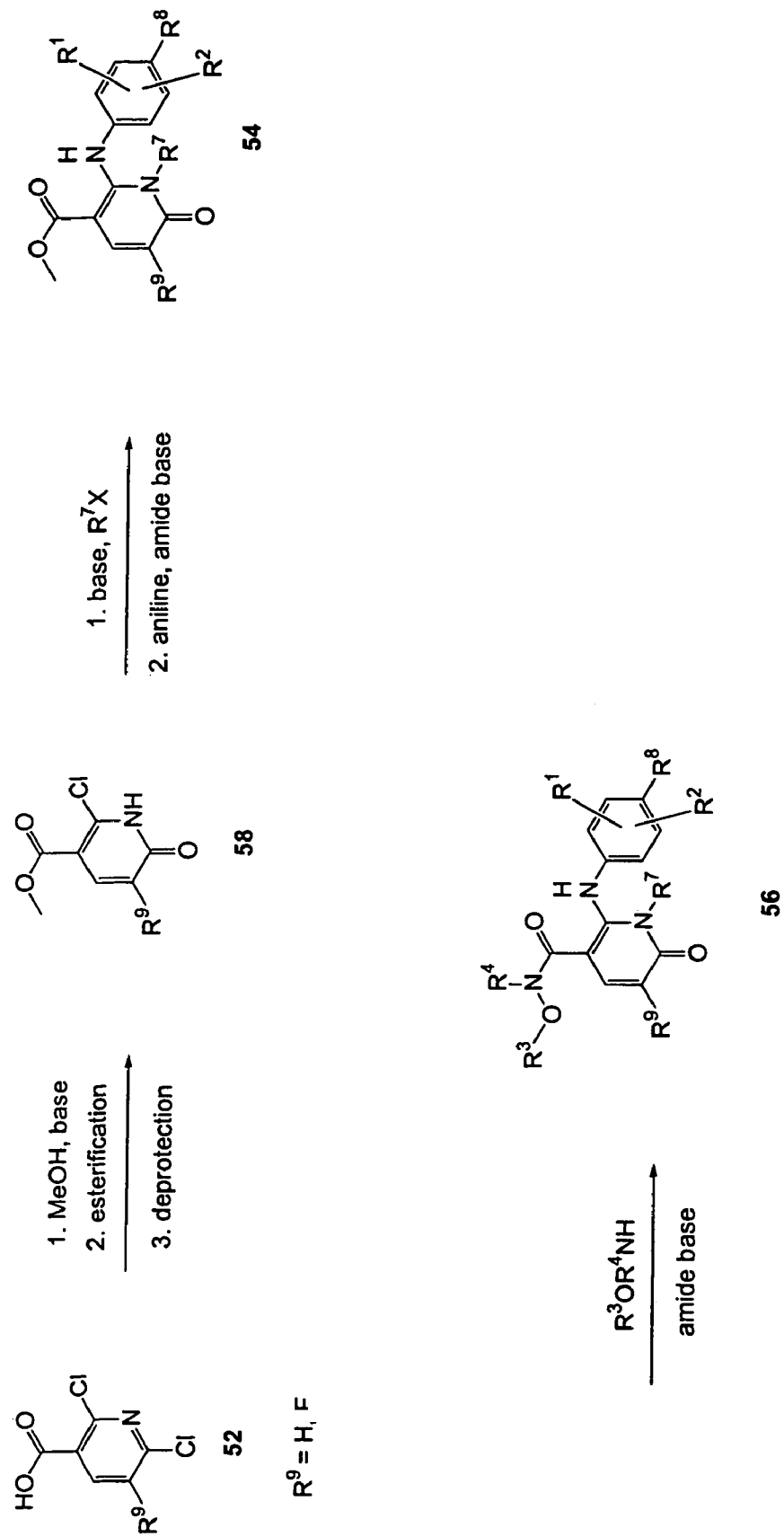
FIG. 16 shows a reaction scheme for the synthesis of compounds 54 and 56.

In FIG. 16, an alternative synthesis of compounds of Formula V where X is CH and $R^9$ is H or F is depicted, in which 2,6-dichloronicotinic acid or 2,6-dichloro-5-fluoronicotinic acid is used as the starting material. This route is particularly useful for analogs where $R^7$ is not Me or Et. Nicotinic acid 52 can be converted to the N-alkyl pyridone methyl ester 54 following a five step procedure, where 2,6-dichloronicotinic acid 52 is first converted to the methoxy pyridine acid, which is esterified to give the methyl ester and then deprotected to yield the monochloro ester 58. In one embodiment, the conversion to the methoxypyridine acid is carried out by adding potassium t-butoxide to a solution of the acid 52 in MeOH, and the reaction mixture is heated to reflux for several days. Esterification to give the methyl ester can be carried out under standard conditions including, but not limited to, Fisher esterification (MeOH, $H_2SO_4$), TMSCl in MeOH or $TMSCHN_2$ in suitable organic solvents such as PhMe/MeOH. Demethylation of the methoxy pyridine can then be accomplished by standard conditions including but not limited to HCl at elevated temperature, pTsOH in acetic acid at elevated temperature and aqueous HBr in MeOH at elevated temperature. Demethylation to give pyridone 58 is achieved by treatment of the methoxypyridine with aqueous HBr in acetic acid at elevated temperature (80 to 120° C.). Alkylation of 58 can be achieved by standard basic alkylation conditions incorporating alkyl halides, with one equivalent of the appropriate alkyl halide and base to give a mixture of the N-alkyl pyridone ester and the regioisomeric O-alkyl pyridine ester, which are easily separated by column chromatography. These conditions include but are not limited to $K_2CO_3$ in acetone or DMF at room or elevated temperature or NaH in THF at ambient or elevated temperature and then addition of the alkyl halide. For example, in one embodiment alkylation is achieved with LiH in DMF at 0° C., followed by addition of alkyl bromide or alkyl iodide and warming to room temperature. Incorporation of the properly substituted aniline moiety is accomplished by $S_NAR$ reaction. This can be done in a suitable organic solvent such as THF using an amide base such as LDA, LiHMDS, NaHMDS, or KHMDS at appropriate temperatures (−78° C. to room temperature). In one embodiment, the aniline is added to LDA or LiHMDS in THF at low temperature (−20 to −80° C.). The pyridone is then added and the mixture is stirred at low temperature to generate ester 54. Hydroxamate 56 can be prepared directly from methyl ester 54 in a suitable organic solvent such as THF using the appropriate hydroxylamine and amide base such as LDA, LiHMDS, NaHMDS, or KHMDS at appropriate temperatures (−78° C. to room temperature). In one embodiment, a solution of LiHMDS is added to a solution of the methyl ester 54 and the hydroxylamine in THF at 0° C. The reaction mixture is then warmed to room temperature to yield the desired hydroxamate 56. In some instances, the hydroxylamine used in the coupling reaction contains a standard protecting group. In those cases, the protecting group can be removed by standard conditions known in the art.

Figure 17:
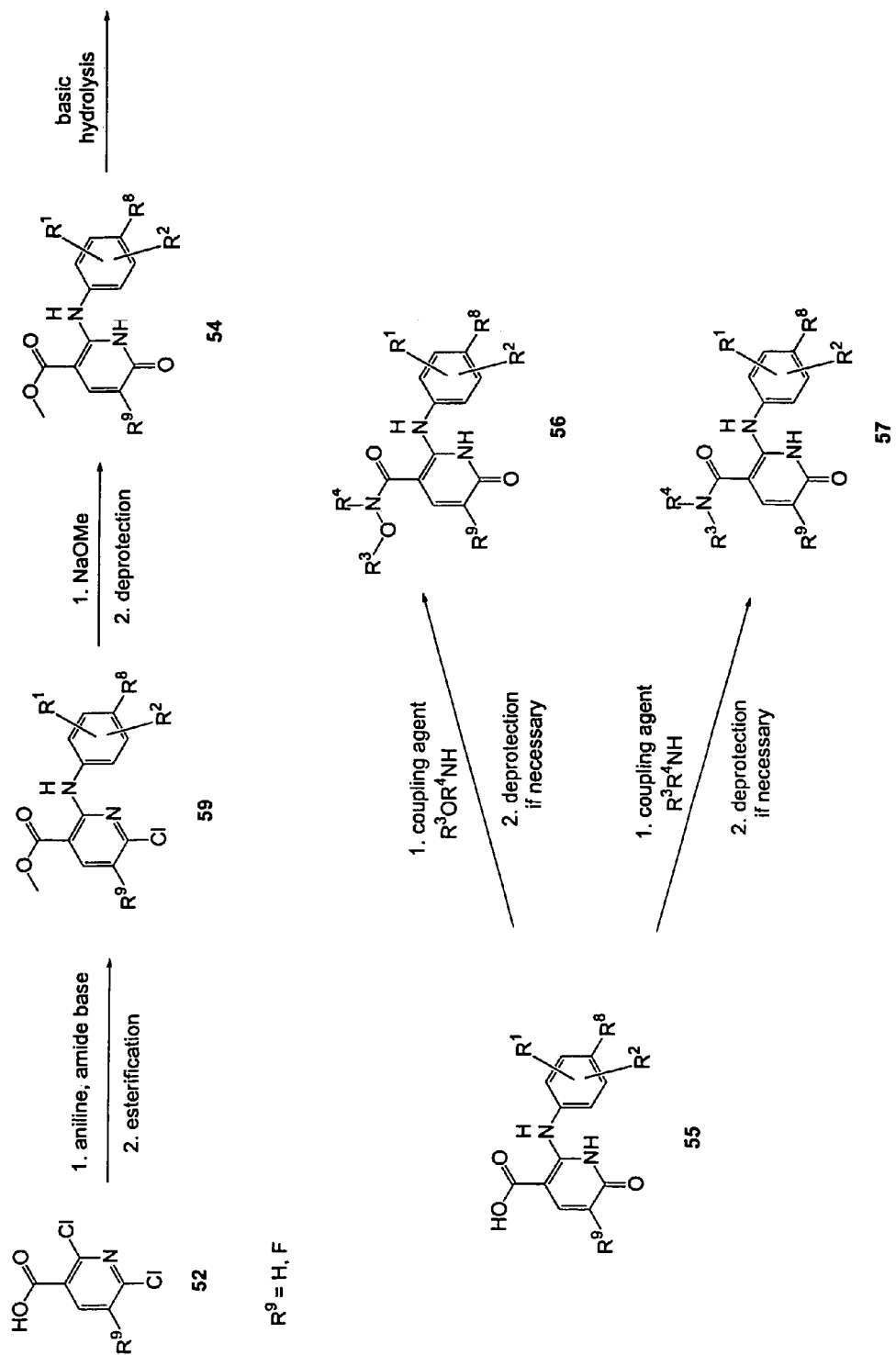
FIG. 17 shows a reaction scheme for an alternate synthesis of compounds 54-57.

In FIG. 17, another alternative synthesis of compounds of Formula V where X is CH and $R^9$ is H or F and $R^7$ is H is depicted, in which either 2,6-dichloronicotinic acid or 2,6- dichloro-5-fluoronicotinic acid is used as the starting material. Formation of 59 is accomplished by incorporation of the properly substituted aniline moiety into nicotinic acid 52 by $S_NAR$ reaction. This can be done in a suitable organic solvent such as THF using an amide base such as LDA, LiHMDS, NaHMDS, or KHMDS at appropriate temperatures (−78° C. to room temperature. In one embodiment the aniline is added to LDA or LiHMDS in THF at low temperature (−20 to −80° C.). Nicotinic acid 52 is then added and the mixture is stirred at low temperature to generate the coupled product. Esterification to give the methyl ester can be carried out under standard conditions, including but not limited to Fisher esterification (MeOH, $H_2SO_4$), TMSCl in MeOH or $TMSCHN_2$ in suitable organic solvents such as PhMe/MeOH. Pyridone 54 can be made in a two-step sequence. In the first step, methyl ester 59 is treated with sodium methoxide in a suitable organic solvent such as MeOH or THF or MeOH/THF mixtures at temperatures ranging from 0° C. to reflux. In one embodiment, sodium methoxide is added to a solution of methyl ester 59 in MeOH at room temperature. This mixture is then refluxed for 4 days to generate the desired methoxypyridine. Demethylation of the methoxypyridine can then be accomplished by standard conditions including but not limited to HCl at elevated temperature, pTsOH in acetic acid at elevated temperature and aqueous HBr in MeOH at elevated temperature. Preferable demethylation to give pyridone 54 is achieved by treatment of the methoxypyridine with aqueous HBr in acetic acid at elevated temperature (80 to 120° C.). Carboxylic acid 55, as well as hydroxamate 56 and amide 57 can then be prepared as described for FIG. 15.

Figure 18:
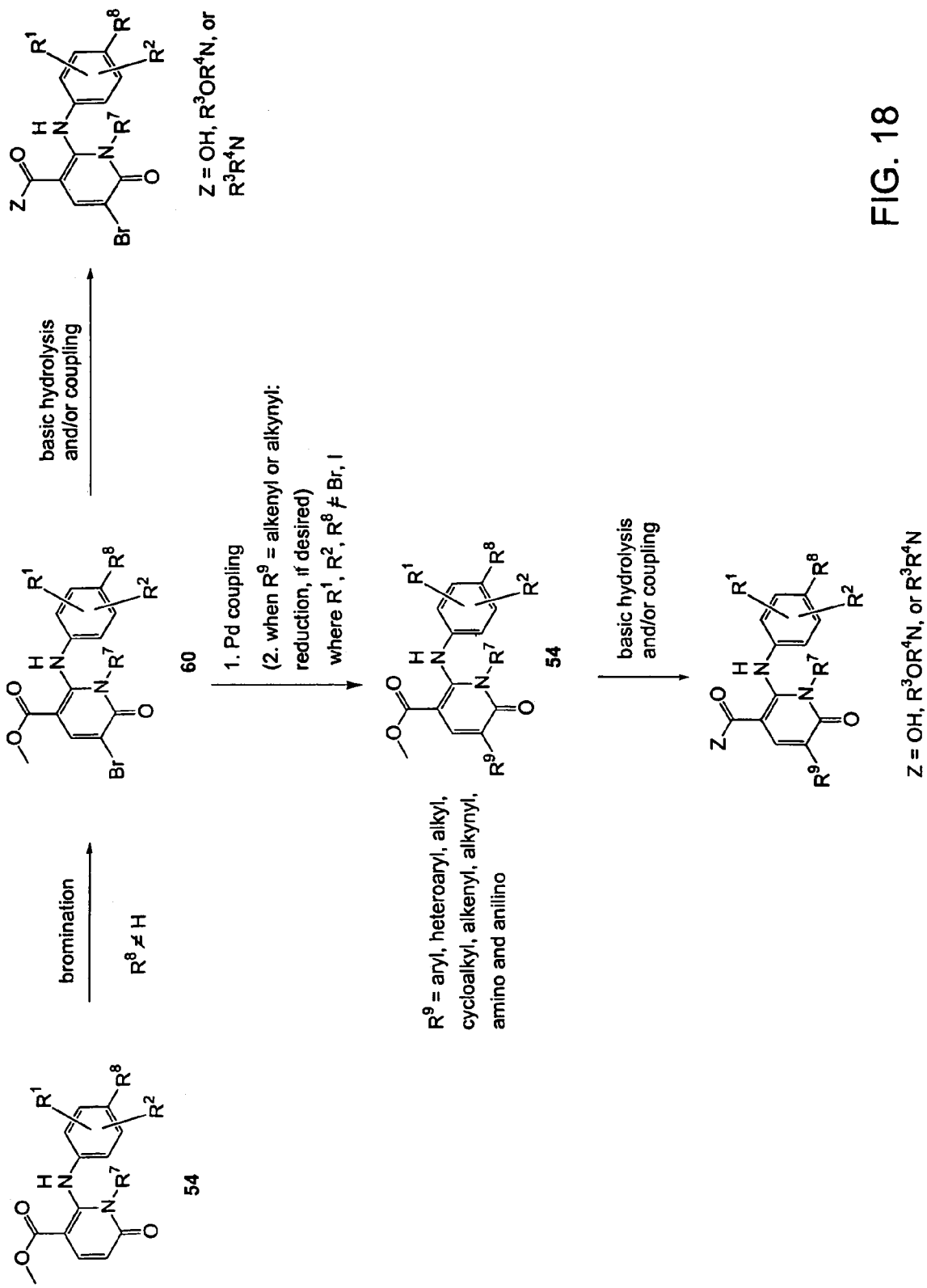
FIG. 18 shows a reaction scheme for the synthesis of compounds 54 and 60.

In FIG. 18, the synthesis of compounds of Formula V where X is CH and $R^8$ is not H is depicted, in which 2,6-dichloronicotinic acid is used as the starting material. Bromination of pyridone ester 54 can be accomplished with either $Br_2$ and acetic acid or NBS in a suitable organic solvent such as DMF. In one embodiment NBS is added to a solution of pyridone ester 54 in DMF to yield 60. Conversion of 60 to carboxylic acid 55, as well as hydroxamate 56 and amide 57 (where $R^9$ is Br) can be accomplished as described for FIGS. 15 and/or 16. Conversion of bromide 60 to compounds of Formula V where $R^9$ is aryl, heteroaryl, alkyl, cycloalkyl, alkenyl, alkynyl, amino or anilino can be achieved using palladium-mediated cross-coupling conditions. When $R^9$ of Formula V is alkenyl or alkynyl, these compounds can be further reduced using the appropriate reducing agent to provide alkyl substituents at $R^9$. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^9$. These palladium-mediated cross-coupling reactions are well documented in the literature and are known by anyone skilled in the art. Conversion of 54 to carboxylic acid 55, as well as hydroxamate 56 and amide 57 can be accomplished as described for FIGS. 15 and/or 16.

Figure 19:
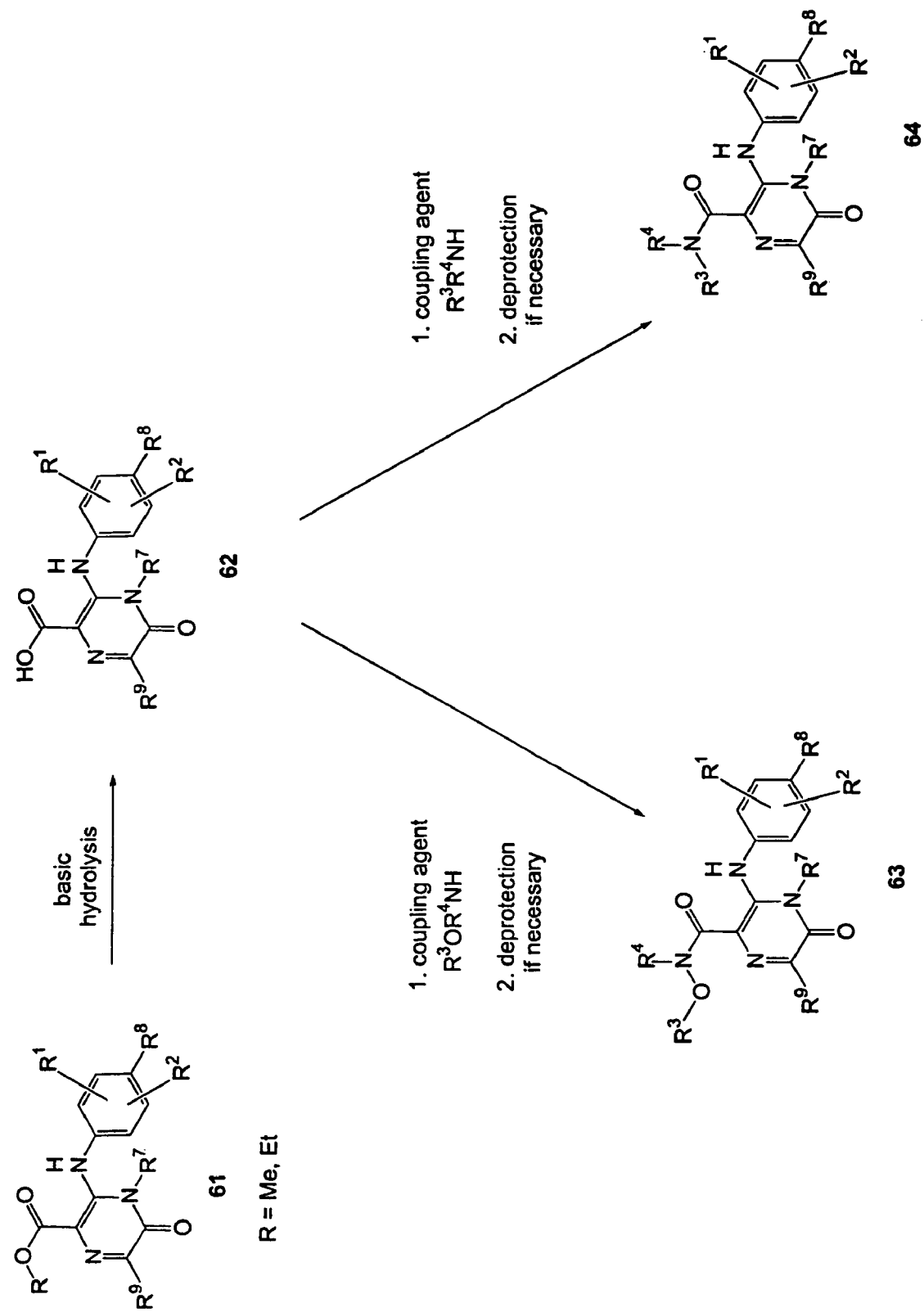
FIG. 19 shows a reaction scheme for the synthesis of compounds 62-64.
Figure 21:
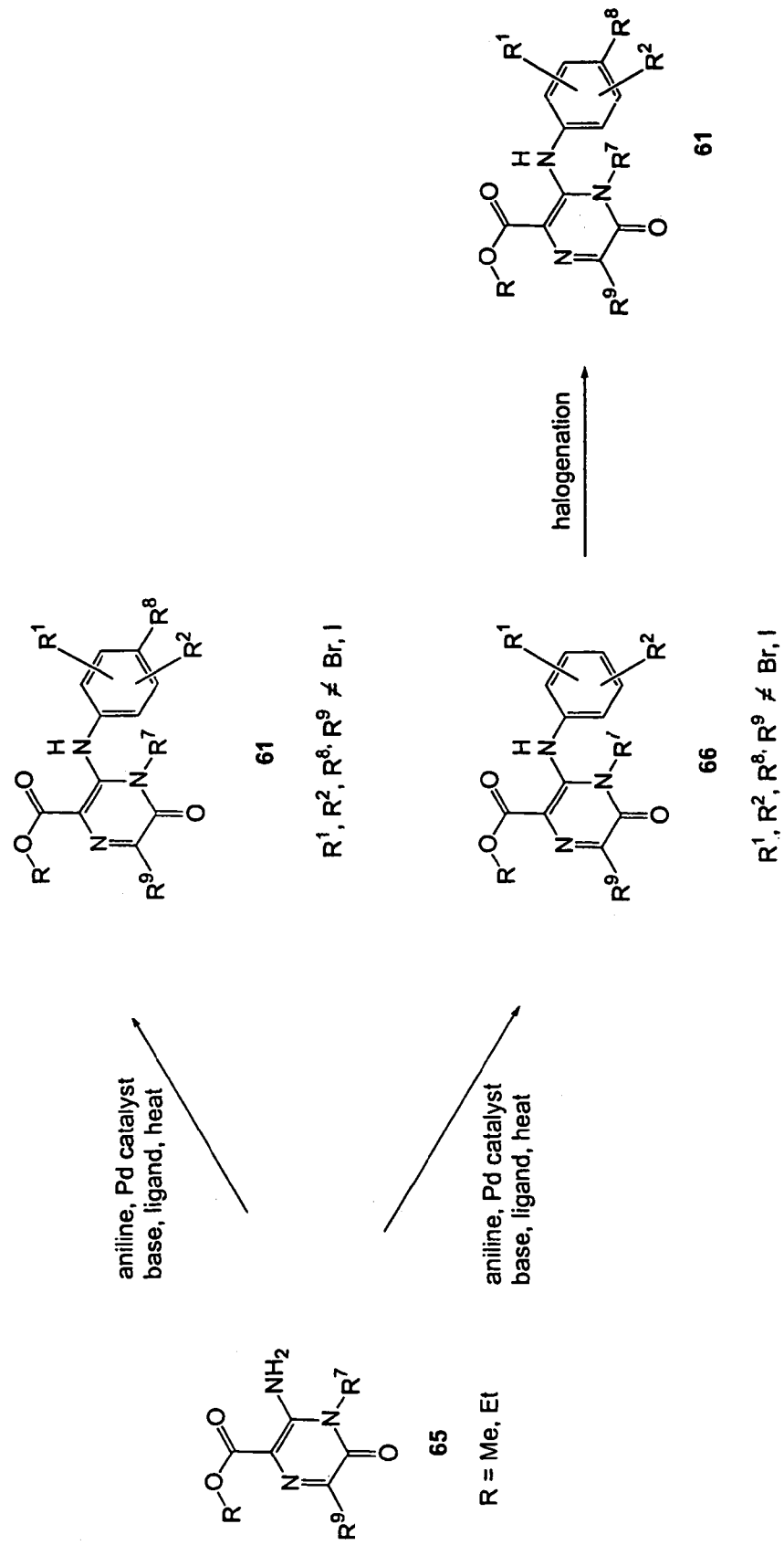
FIG. 21 shows a reaction scheme for the synthesis of compounds 61 and 66.
Figure 22:
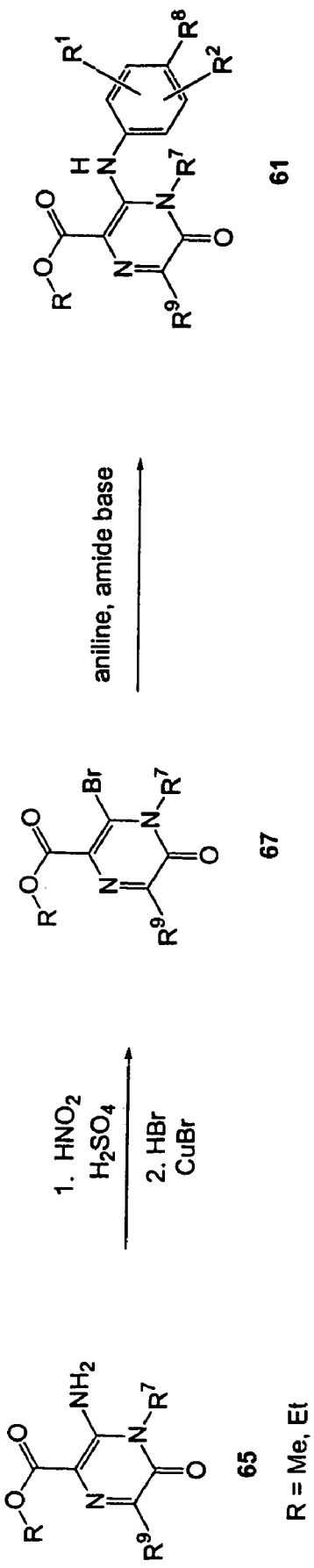
FIG. 22 shows a reaction scheme for an alternate synthesis of compound 61.

In FIG. 19, the synthesis of compounds of Formula V is depicted, where X is N. Pyrazinone ester 61, which can be synthesized as shown in FIG. 21 or 22, can be converted to carboxylic acid 62 using standard saponification conditions such as LiOH or NaOH in standard mixed aqueous/organic solvent systems. Hydroxamate 63 and amide 64 can be prepared using standard coupling procedures, including but not limited to EDCI, HOBt, or PyBOP and the appropriate amine or hydroxylamine in suitable organic solvents such as DMF, THF, or methylene chloride. In some instances, the amine or hydroxylamine used in the coupling reaction contains a standard protecting group. In those cases, the protecting group can be removed by standard conditions known in the art.

Figure 20:
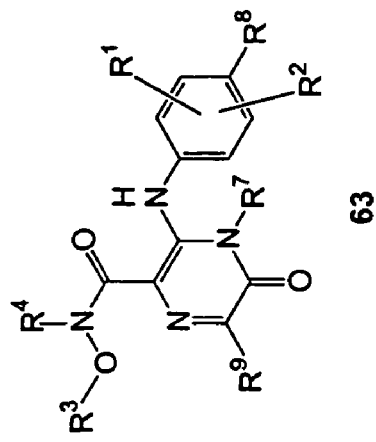
FIG. 20 shows a reaction scheme for the synthesis of compound 63.
Figure 20:
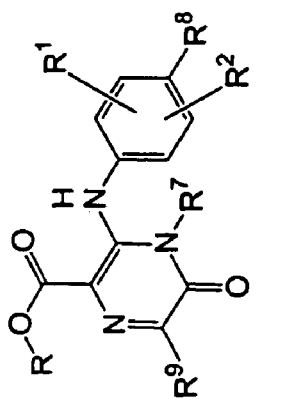

In FIG. 20, the synthesis of compounds of Formula V is depicted, where X is N. Pyrazinone ester 61, which can be synthesized as shown in FIG. 21 or 22, can be directly converted to hydroxamate 63 in a suitable organic solvent such as THF using the appropriate hydroxylamine and an amide base such as LDA, LiHMDS, NaHMDS or KHMDS at appropriate temperatures (−78° C. to room temperature). In some instances, the hydroxylamine used in the coupling reaction contains a standard protecting group. In those cases, the protecting group can be removed by standard conditions known in the art.

In FIG. 21, the synthesis of pyrazinone ester 61, which is utilized as starting material in FIGS. 19 and 20, is depicted. The aniline moiety is incorporated into aminopyrazinone 65 utilizing palladium-mediated cross-coupling chemistry. The palladium-mediated cross coupling chemistry can be accomplished by treating a mixture of aniline and aminopyrazinone 65 with a Pd catalyst such as $Pd(OAc)_2$, $PdCl_2(dppf)$, $Pd(Ph_3P)_4$, or $Pd_2dba_3$, a phosphine ligand and base in a suitable organic solvent such as THF, DMF, PhMe, DME or MeCN at elevated temperature. If $R^8$ is Br or I, then a bromination or iodination step can be incorporated after the cross-coupling reaction. Thus, halogenation of 66 can be accomplished with either NIS or NBS in a suitable organic solvent such as DMF, MeCN or mixed solvent systems at room temperature to provide 61.

In FIG. 22, an alternative synthesis of pyrazinone ester 61, which is utilized as starting material in FIGS. 19 and 20, is depicted. Diazotization of 61 with nitrous acid in the presence of sulfuric acid yields the dizaonium salt, which can be further reacted with HBr and CuBr to yield bromide 67. Formation of 61 can then be accomplished by incorporation of the properly substituted aniline moiety into bromide 67 by an $S_NAR$ reaction. This can be done in a suitable organic solvent such as THF using an amide base such as LDA, LiHMDS, NaHMDS, or KHMDS at appropriate temperatures (−78° C. to room temperature). In one embodiment the aniline is added to LDA or LiHMDS in THF at low temperature (−20 to −80° C.). Bromide 67 is then added and the mixture is stirred at low temperature to generate the coupled product 61.

Figure 23:
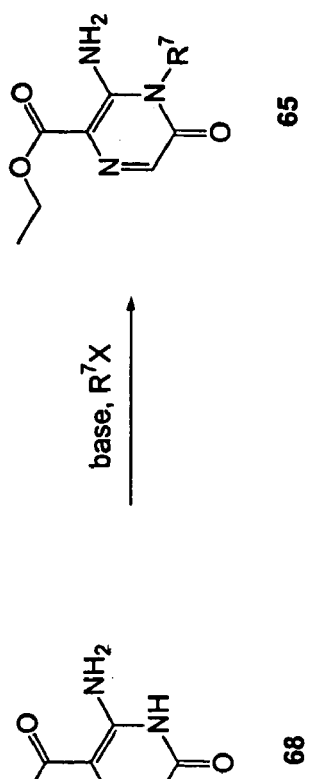
FIG. 23 shows a reaction scheme for the synthesis of compound 65.

In FIGS. 23-27, several syntheses of aminopyrazinone 65, which is used as the starting material in FIGS. 21 and 22, are depicted, depending on the identity of $R^9$. FIG. 23 depicts the synthesis of the aminopyrazinone core where $R^9$ is H. 3-Amino-5-oxo-4,5-dihydropyrazine-2-carboxylic acid ethyl ester 68 can be synthesized as described in the literature (*Journal of Organic Chemistry* 1975, 40, 2341-2346). Alkylation of 68 can be achieved by standard basic alkylation conditions incorporating alkyl halides, using one equivalent of the appropriate alkyl halide and base to give a mixture of the N-alkyl pyrazinone 65 ($R^9$ is H) and the regioisomeric O-alkyl pyrazine, which can be separated by column chromatography. These reaction conditions include but are not limited to $K_2CO_3$ in acetone or DMF at room or elevated temperature or NaH in THF at ambient or elevated temperature and then addition of the alkyl halide.

Figure 24:
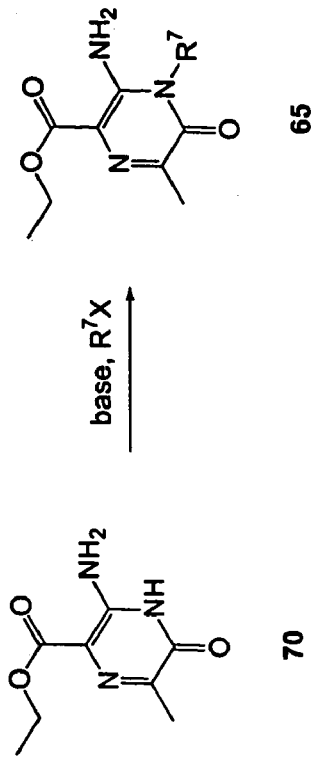
FIG. 24 shows a reaction scheme for the synthesis of compounds 65 and 70.
Figure 24:
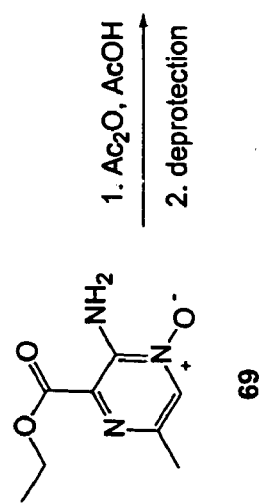

FIG. 24 depicts the synthesis of an aminopyrazinone core structure where $R^9$=Me. 3-Amino-6-methylpyrazine-2-carboxylic acid ethyl ester N-oxide 69 can be synthesized as described in the literature (*J. Heterocyclic Chemistry* 1987, 24, 1621-1628). Rearrangement of N-oxide 69 can be achieved with either acetic anhydride and acetic acid or trifluoroacetic anhydride and trifluoroacetic acid, which is then followed by deprotection with MeOH or EtOH to provide 70. Alkylation of 70 can be achieved by standard basic alkylation conditions incorporating alkyl halides, with one equivalent of the appropriate alkyl halide and base to give a mixture of the N-alkyl pyrazinone 65 ($R^9$=Me) and the regioisomeric O-alkyl pyrazine, which can be separated by column chromatography. These conditions include but are not limited to $K_2CO_3$ in acetone or DMF at room or elevated temperature or NaH in THF at ambient or elevated temperature and then addition of the alkyl halide.

Figure 25:
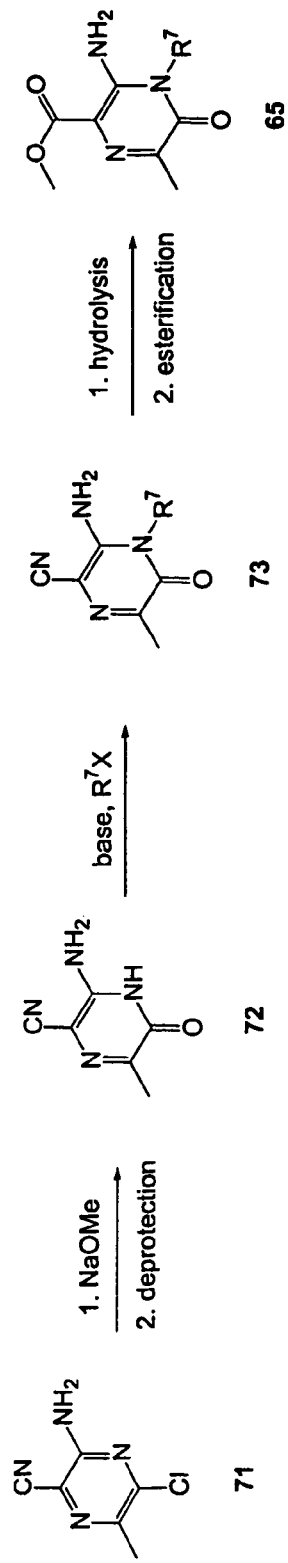
FIG. 25 shows a reaction scheme for an alternate synthesis of compound 65.

FIG. 25 also depicts the synthesis of an aminopyrazinone core structure where $R^9$=Me. 3-Amino-5-chloro-6-methylpyrazine-2-carbonitrile 71 can be synthesized as described in the literature (*J. Heterocyclic Chemistry* 1987, 24, 1621-1628). Pyrazinone 72 can be made in a two-step sequence. In the first step, pyrazine 71 is treated with sodium methoxide in a suitable organic solvent such as MeOH or THF or MeOH/THF mixture at temperatures ranging from 0° C. to reflux. Demethylation of the methoxy pyrazine to provide 72 can then be accomplished by standard conditions including but not limited to pTsOH in acetic acid at elevated temperature or aqueous HBr in MeOH at elevated temperature. Alkylation of 72 can be achieved by standard basic alkylation conditions incorporating alkyl halides, using one equivalent of the appropriate alkyl halide and base to give a mixture of the N-alkyl pyrazinone 73 and the regioisomeric O-alkyl pyrazine, which can be separated by column chromatography. These conditions include but are not limited to $K_2CO_3$ in acetone or DMF at room or elevated temperature or NaH in THF at ambient or elevated temperature, followed by the addition of an alkyl halide. Hydrolysis of nitrile 73 is followed by esterification to give ester 65 ($R^9$=Me). Hydrolysis of the nitrile can be achieved with either an acidic or basic aqueous solution including but not limited to aqueous HCl, KOH, or NaOH. Esterification to give the methyl ester 65 ($R^9$=Me) can be carried out under standard conditions, including but not limited to Fisher esterification (MeOH, $H_2SO_4$), TMSCl in MeOH or $TMSCHN_2$ in suitable organic solvents such as PhMe/MeOH.

Figure 26:
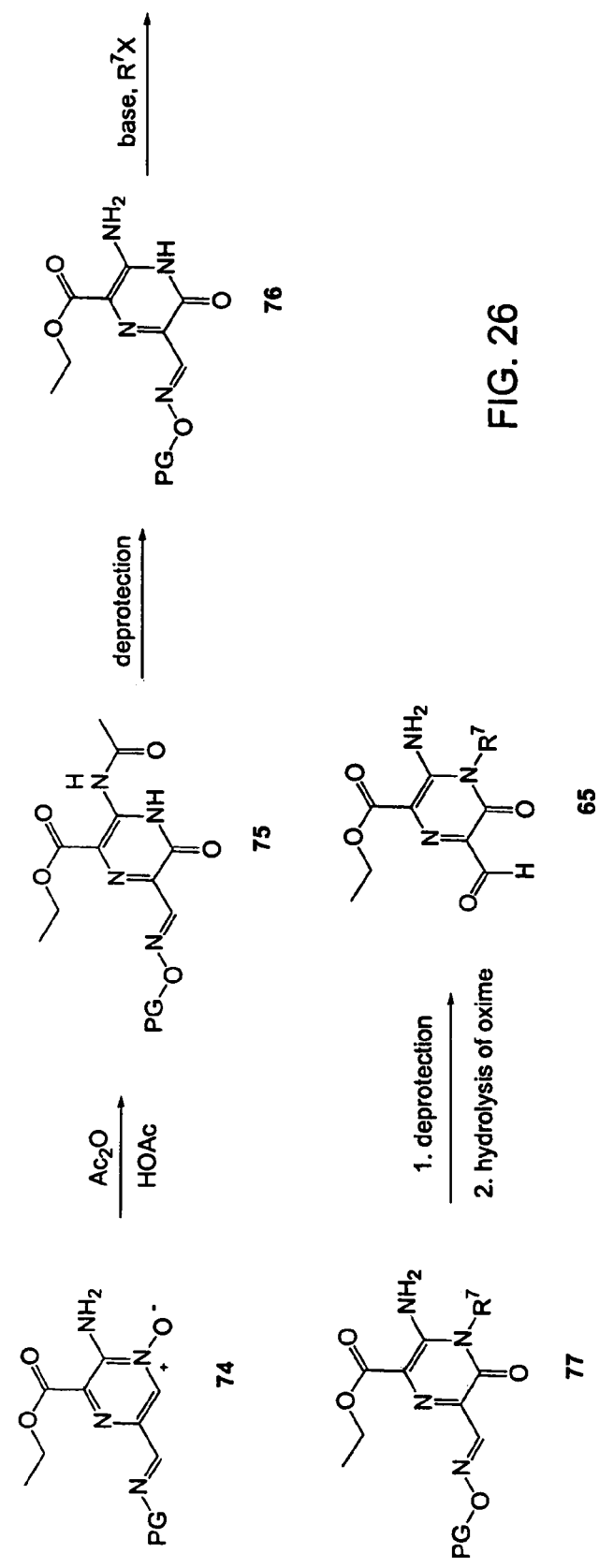
FIG. 26 shows a reaction scheme for an alternate synthesis of compound 65.

FIG. 26 depicts the synthesis of an aminopyrazinone core structure where $R^9$ is —C(=O)H. A protected oxime analog, 3-amino-6-(benzyliminomethyl)-pyrazine-2-carboxylic acid ethyl ester N-oxide 74, can be synthesized as described in the literature (*Justus Liebigs Annalen der Chemie* 1969, 726, 100-102), with the use of O-benzyl-hydroxylamine in place of hydroxylamine. Protection of the oxime functionality with a standard protecting group includes, but is not limited to O-benzyl. This is followed by rearrangement of N-oxide 74 with either acetic anhydride and acetic acid or trifluoroacetic anhydride and trifluoroacetic acid. Removal of the N-acyl functionality of 75 can be achieved with MeOH or EtOH to provide 76. Alkylation of 76 can be achieved by standard basic alkylation conditions incorporating alkyl halides, with one equivalent of the appropriate alkyl halide and base to give a mixture of the N-alkyl pyrazinone 77 and the regioisomeric O-alkyl pyrazine, which can be separated by column chromatography. These conditions include but are not limited to $K_2CO_3$ in acetone or DMF at room or elevated temperature or NaH in THF at ambient or elevated temperature, followed by the addition of the alkyl halide. Deprotection of oxime 77 is followed by cleavage to the aldehyde 65 ($R^9$=—C(O)H). Deprotection of the oxime depends on the nature of the protecting group chosen. If the protecting group chosen is benzyl, it can be removed under catalytic hydrogenation conditions with a suitable Pd or Pt catalyst, including but not limited to Pd—C or $PtO_2$ under an atmosphere of hydrogen in a suitable organic solvent. Conversion of oxime to aldehyde 65 ($R^9$=—C(O)H) can be achieved under hydrolysis conditions, including but not limited to aqueous HCl in an appropriate organic solvent such as dioxane.

Figure 27:
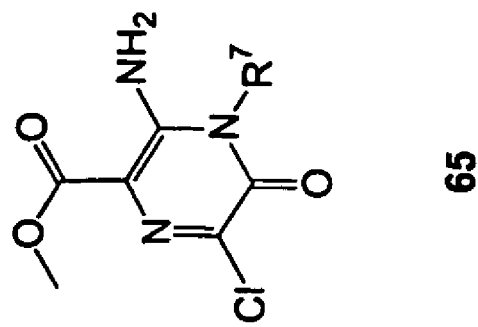
FIG. 27 shows a reaction scheme for an alternate synthesis of compound 65.
Figure 27:
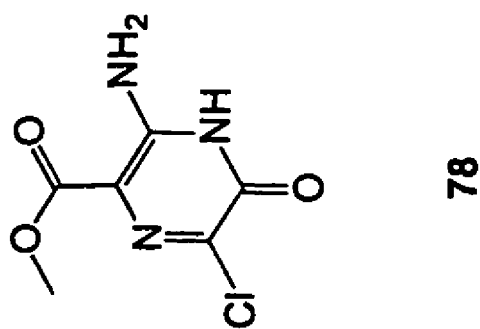

FIG. 27 depicts the synthesis of an aminopyrazinone core structure where $R^9$ is Cl. 3-Amino-6-chloro-5-oxo-4,5-dihydropyrazine-2-carboxylic acid methyl ester 78 can be synthesized as described in the literature (*J. Medicinal Chemistry* 1967, 10, 66-75). Alkylation of 78 can be achieved by standard basic alkylation conditions incorporating alkyl halides, with one equivalent of the appropriate alkyl halide and base to give a mixture of the N-alkyl pyrazinone 65 ($R^9$=Cl) and the regioisomeric O-alkyl pyrazine, which can be separated by column chromatography. These conditions include but are not limited to $K_2CO_3$ in acetone or DMF at room or elevated temperature or NaH in THF at ambient or elevated temperature, followed by the addition of the alkyl halide.

Figure 28:
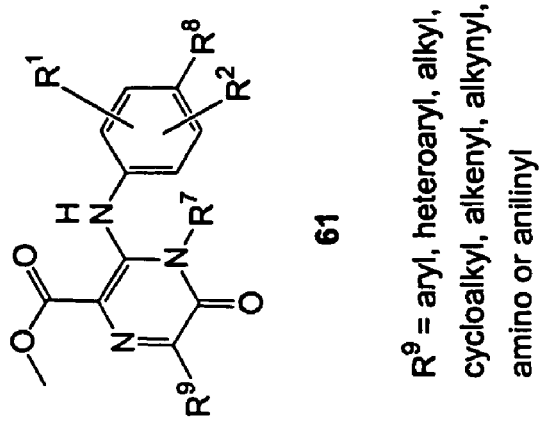
FIG. 28 shows a reaction scheme for an alternate synthesis of compound 61.
Figure 28:
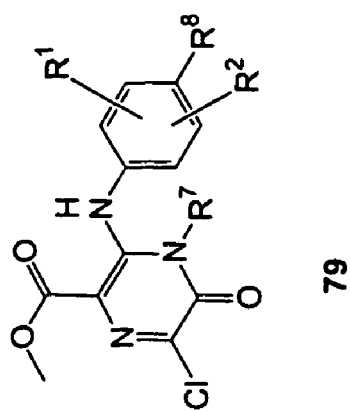

In FIG. 28, the synthesis of compounds of Formula V is depicted, where X is N. The conversion of chloride 79 to compounds 61, where $R^9$=aryl, heteroaryl, alkyl, cycloalkyl, alkenyl, alkynyl, amino or aniline, can be achieved using palladium-mediated cross-coupling conditions. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^9$. These palladium-mediated cross couplings are well documented in the literature and are known by anyone skilled in the art. When $R^9$ is alkenyl or alkynyl, these can be further reduced using the appropriate reducing agent to provide alkyl substituents at $R^9$.

Figure 29:
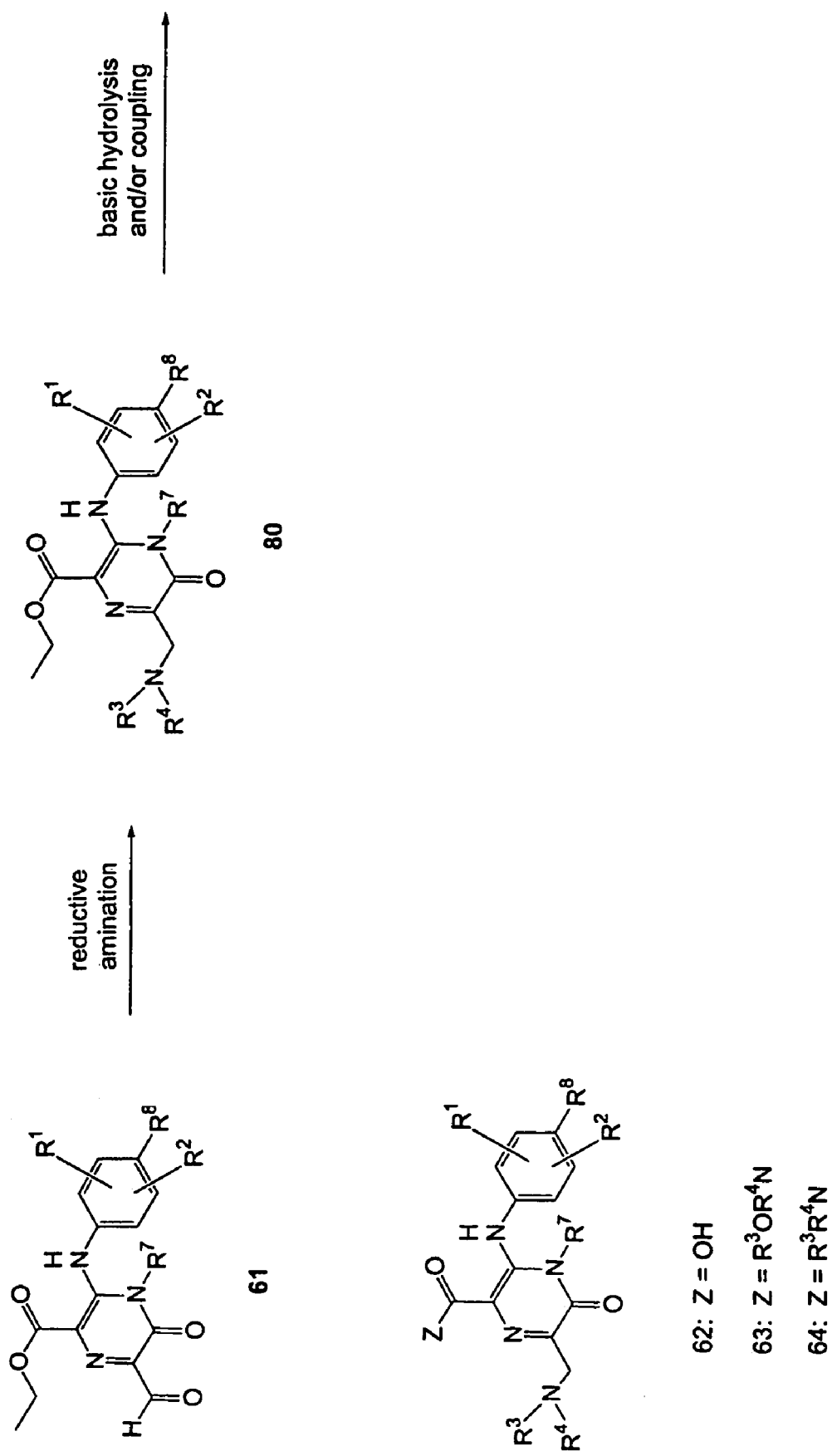
FIG. 29 shows a reaction scheme for the synthesis of compound 80.

FIGS. 29-32 depict the synthesis of compounds of Formula V, where X is N. In these syntheses, aldehyde 61 ($R^9$=—C(O)H) is converted to various other functionalities. FIG. 29 depicts the conversion of aldehyde 61 to amine 80. This can be accomplished by reductive amination, which involves the reaction of the aldehyde with the desired amine and AcOH, followed by reduction with a suitable reducing agent, including but not limited to $Me_4NBH(OAc)_3$, in a suitable organic solvent such as $CH_3CN$ at ambient temperature. Carboxylic acid 62, as well as hydroxamate 63 and amide 64, where $R^9$ is equal to $CH_2NR^3R^4$, can then be prepared from 80 as described in FIGS. 19 and 20.

Figure 30:
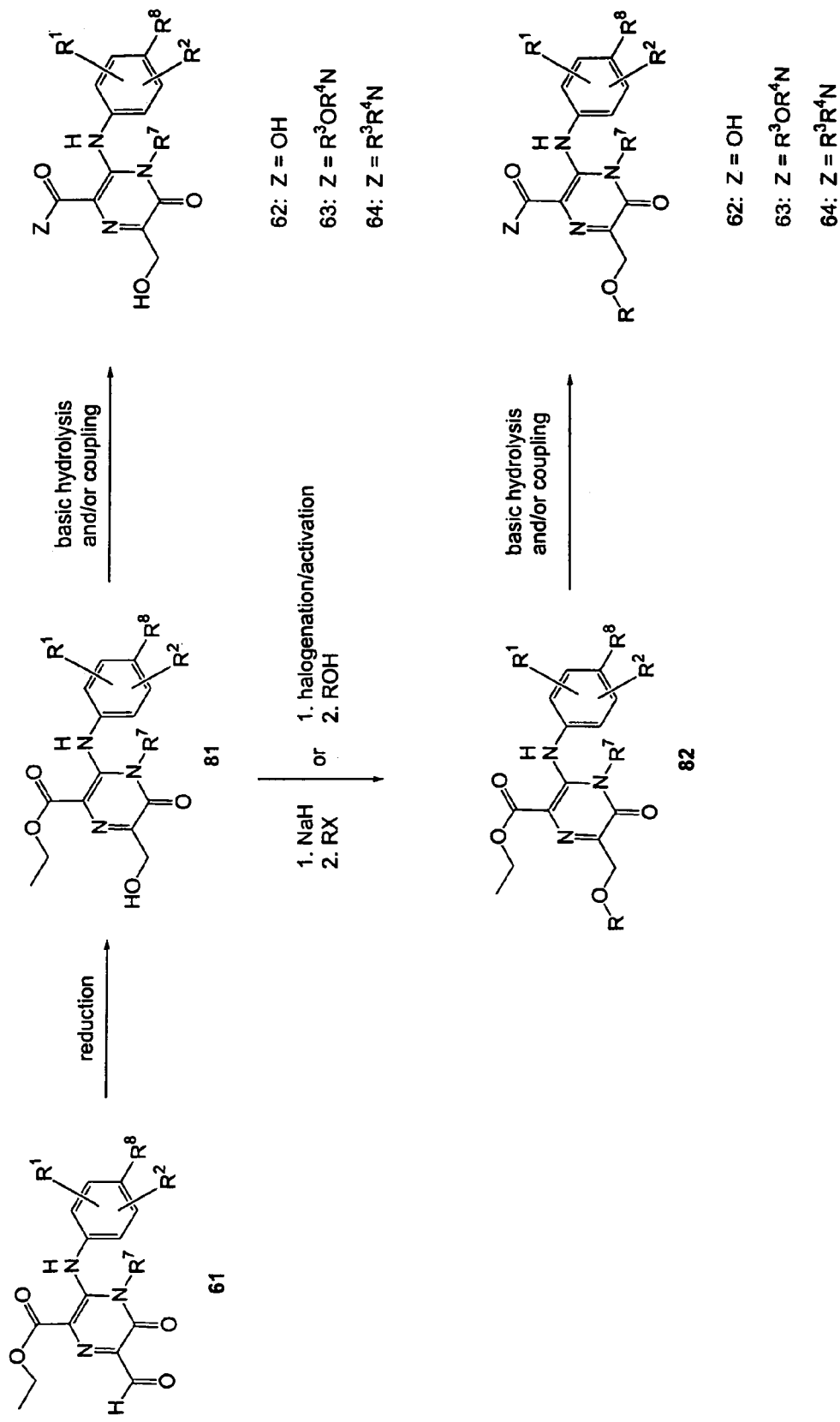
FIG. 30 shows a reaction scheme for the synthesis of compounds 81 and 82.

FIG. 30 depicts the conversion of aldehyde 61 ($R^9$=—C(O)H) to alcohol 81 and ether 82. Reduction of aldehyde 61 ($R^9$=—C(O)H) with a suitable reducing agent, including but not limited to $NaBH_4$, provides alcohol 81. Alcohol 81 can be converted to ether 82 by reaction with a suitable base and the desired alkyl halide, including but not limited to addition of NaH to alcohol 81, followed by the addition of an alkyl bromide or alkyl iodide. Alcohol 81 can also be converted to ether 82 by halogenation or activation followed by addition of a desired alcohol. Halogenation can be accomplished with $POCl_3$, thionyl chloride, oxalyl chloride, $PCl_5$, $PBr_3$, or $Ph_3P$ and $Br_2$, and activation can be achieved by reaction of aldehyde 61 ($R^9$=—C(O)H) with, for example, MsCl or TsCl. Both the halogenation and activation steps are followed by addition of a desired alcohol to yield 82. Carboxylic acid 62, as well as hydroxamate 63 and amide 64, where $R^9$ is —$CH_2OH$ or —$CH_2OR$, can then be prepared from 81 or 82 as described in FIGS. 19 and 20.

Figure 31:
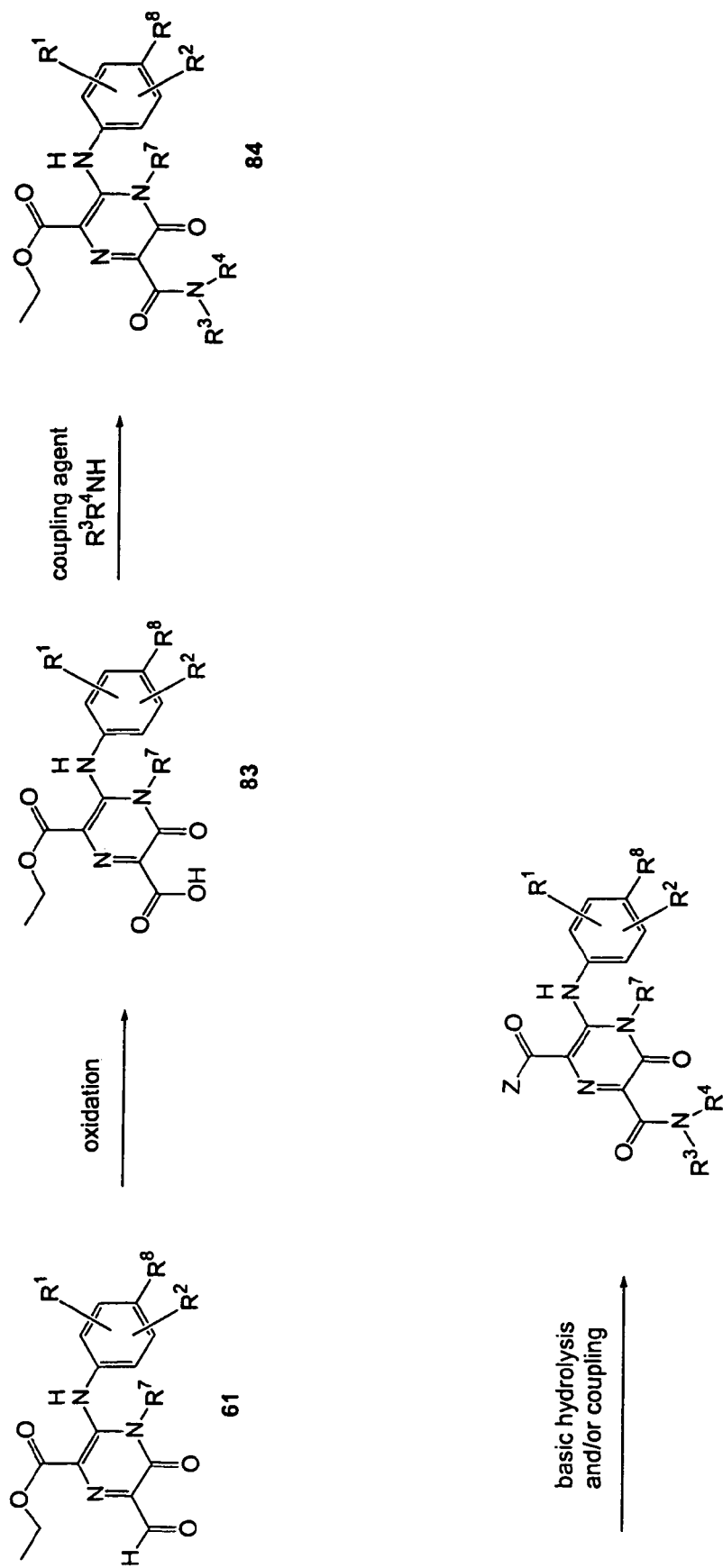
FIG. 31 shows a reaction scheme for the synthesis of compounds 83 and 84.

FIG. 31 depicts the conversion of aldehyde 61 ($R^9$=—C(O)H) to amide 84. Oxidation of aldehyde 61 ($R^9$=—C(O)H) with a suitable oxidizing agent, such as but not limited to $KMnO_4$, $CrO_3$ or $Na_2Cr_2O_7$, provides carboxylic acid 83. Conversion of acid 83 to amide 84 can be accomplished using standard coupling procedures, including but not limited to EDCI, HOBt, or PyBOP and the appropriate amine in suitable organic solvents such as DMF, THF, or methylene chloride. In some instances, the amine used in the coupling reaction contains a standard protecting group. In those cases, the protecting group can be removed by standard conditions known in the art. Carboxylic acid 62, as well as hydroxamate 63 and amide 64, where $R^9$=—C(O)NR$^3$R$^4$, can then be prepared from 84 as described in FIGS. 19 and 20.

Figure 32:
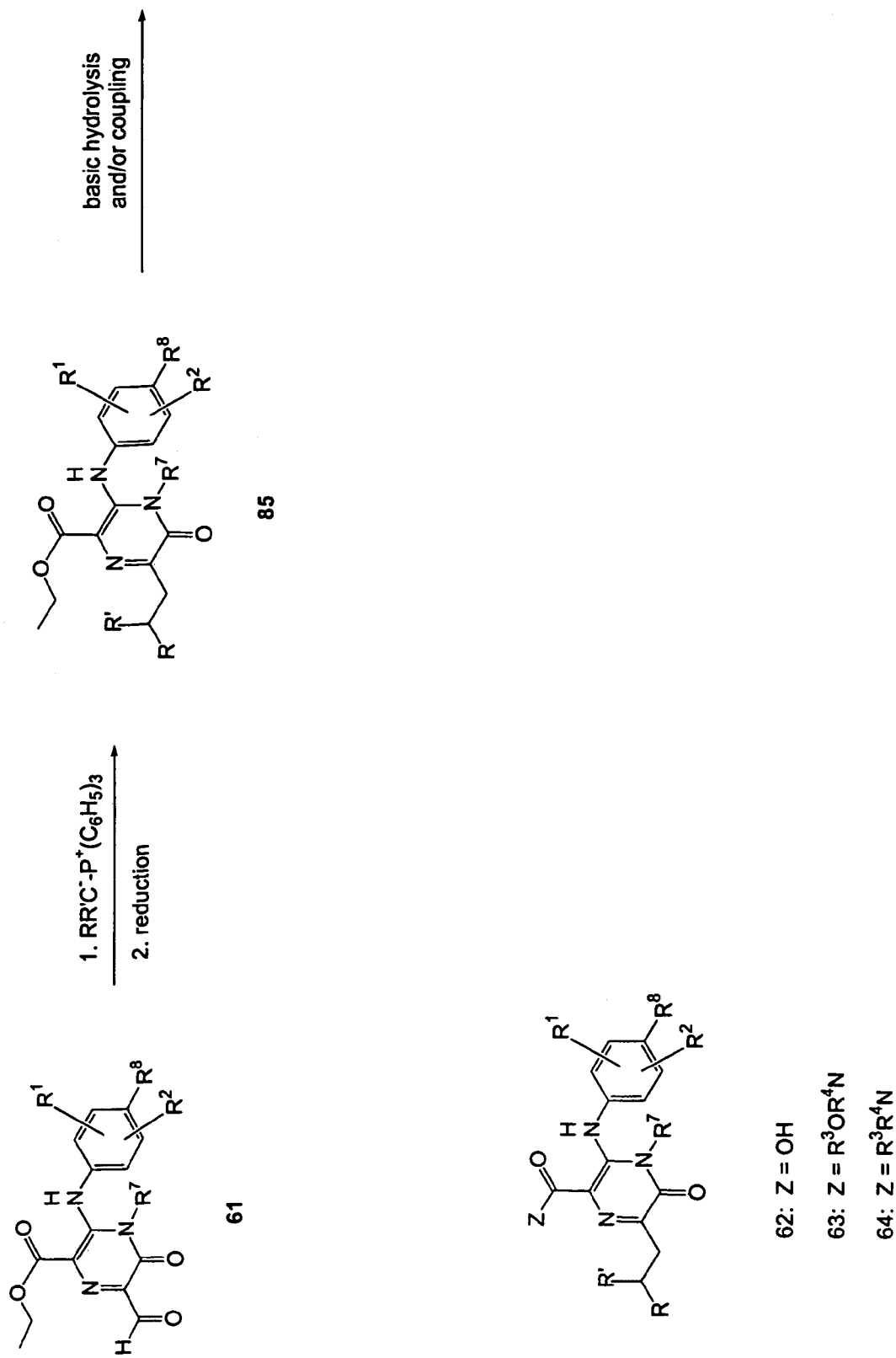
FIG. 32 shows a reaction scheme for the synthesis of compound 85.

FIG. 32 depicts the conversion of aldehyde 61 ($R^9$=—C(O)H) to alkyl 85. Reaction of aldehyde 61 ($R^9$=C(O)H) under standard Wittig reaction conditions, followed by reduction of the resulting alkene provides alkyl 85. The Wittig reaction involves the addition of a desired phosphorous ylide, $R_2C$—P($C_6H_5$)$_3$, to the aldehyde in a suitable organic solvent such as THF. The conditions for formation of the desired phosphorous ylide are well documented in the literature and are known by anyone skilled in the art. Reduction of the alkene to provide 85 can be accomplished under a hydrogen atmosphere with a suitable catalyst, such as $PtO_2$ or Pd/C. Carboxylic acid 62, as well as hydroxamate 63 and amide 64, where R9 is equal to $CH_2CR_2$, can then be prepared from 85 as described in FIGS. 19 and 20.

Figure 33:
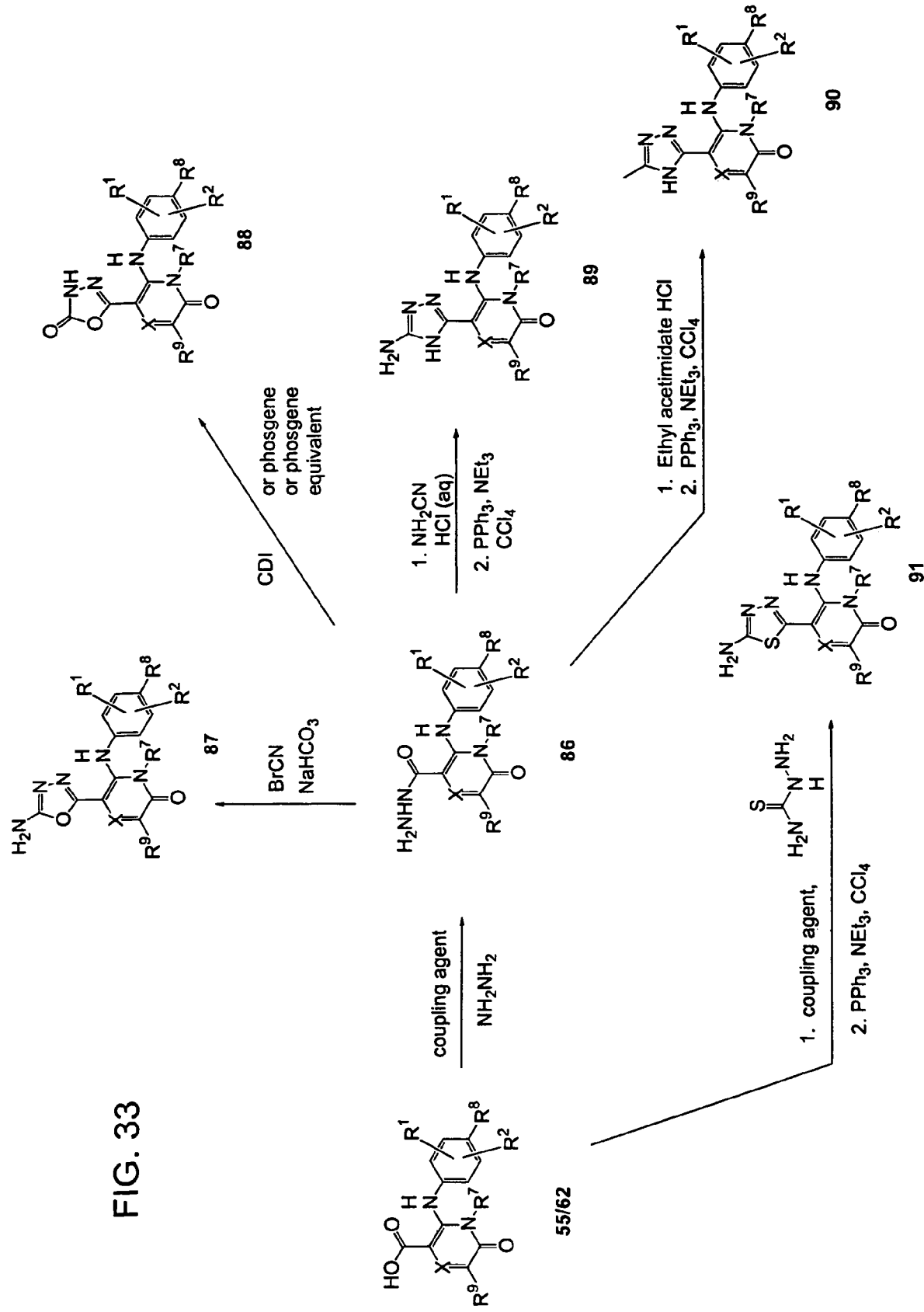
FIG. 33 shows a reaction scheme for the synthesis of compounds 86-91.

In FIG. 33, the synthesis of compounds of Formula V is depicted where W is heterocyclic. Carboxylic acid 55 or 62 can be converted to hydrazide 86 using standard coupling procedures, including but not limited to EDCI, HOBt, or PyBOP and hydrazine in suitable organic solvents such as DMF, THF, or methylene chloride. Hydrazide 86 can then be converted to several desired heterocyclic analogs by cyclization with an appropriate reagent. Conversion of 86 to amino oxadiazole 87 can be accomplished using cyanogen bromide and a base such as $NaHCO_3$, in a suitable biphasic solvent system such as dioxane and water at room temperature. Conversion of 86 to the oxadiazolone 88 can be accomplished by reaction with phosgene, CDI, or a phosgene equivalent. Conversion of 86 to the amino triazole 89 can be accomplished in a two-step procedure, first by reaction with $NH_3CN$ and aqueous HCl, followed by cyclization with triphenylphosphine, triethylamine and carbon tetrachloride. Conversion of 86 to the methyl trizole 90 can be accomplished in a two step procedure, first by reaction with an appropriate coupling agent such as cyanamide or ethyl acetimidate, followed by cyclization with triphenylphosphine, triethylamine and carbon tetrachloride in dichloromethane. Finally, conversion of carboxylic acid 55 or 62 to the aminothiazole 91 can be accomplished with thiosemicarbazide using standard coupling reagents, such as EDCI, followed by cyclization with triphenylphosphine, triethylamine and carbon tetrachloride in dichloromethane.

Figure 34:
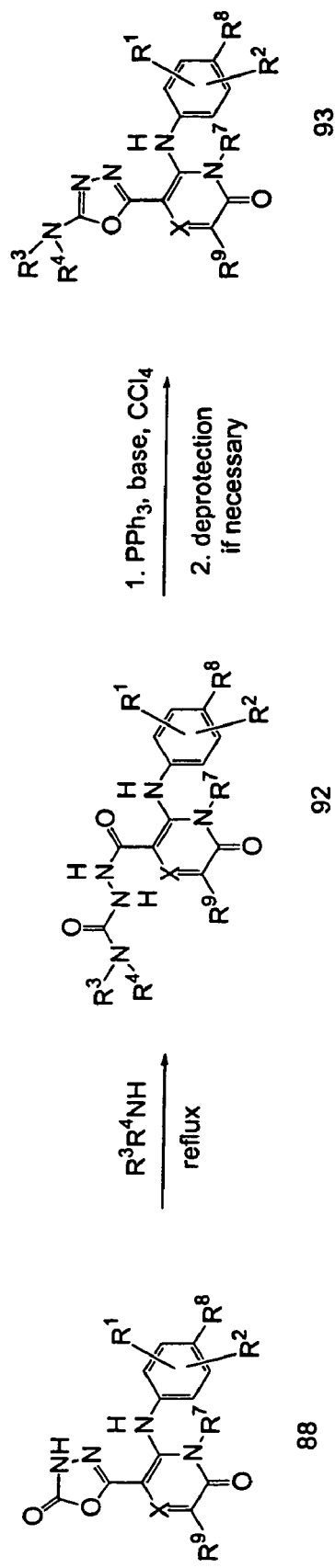
FIG. 34 shows a reaction scheme for the synthesis of compounds 92 and 93.

In FIG. 34, the synthesis of compounds of Formula V is depicted where W is heterocyclic. Ring opening of oxadiazolone 88 with a desired amine is accomplished in EtOH under refluxing conditions to yield 92, which can be recyclized to 93 with triphenylphosphine, triethylamine and carbon tetrachloride in dichloromethane. In some instances, the amine used in the ring-opening reaction contains a standard protecting group. In those cases, the protecting group can be removed by standard conditions known in the art.

Figure 35:
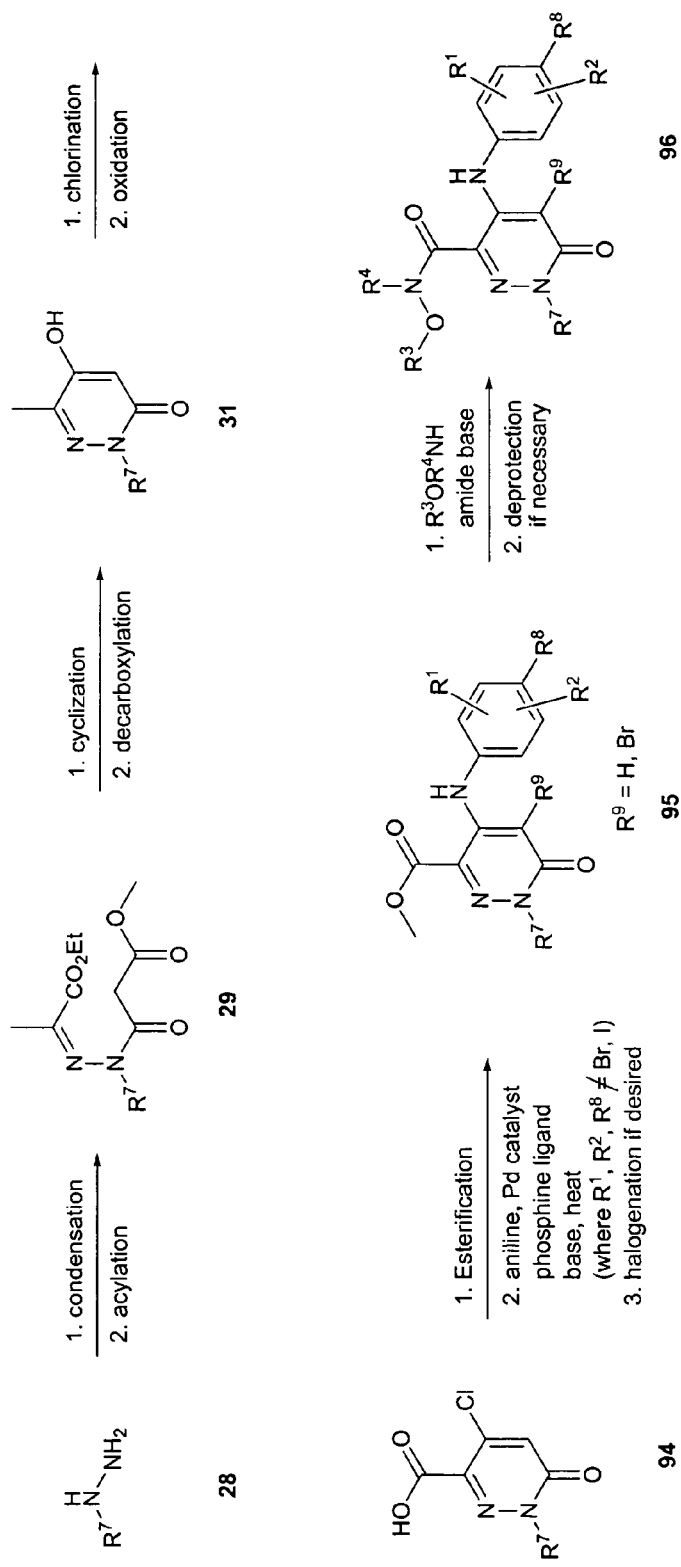
FIG. 35 shows a reaction scheme for the synthesis of compound 96.

The preparation of compounds of the Formula I wherein X=N and $R^9$ is H or Br is depicted in FIG. 35. Substituted hydrazine 28 can be converted to hydrazono propanoate 29 by a two-step procedure. In the first step, hydrazine 28 is condensed with ethyl pyruvate under standard dehydrating conditions such as in the presence of $MgSO_4$ in a suitable organic solvent such as chloroform or methylene chloride at temperatures ranging from 0° to ambient. In the second step, acylation is achieved by treatment with base at low temperature in a suitable organic solvent such as THF, DMF, dioxane or MeCN, followed by the addition of methyl malonyl chloride. In one embodiment, the hydrazone is treated with LiH in THF at 0° C. followed by the addition of methyl malonyl chloride and warming to room temperature. Hydroxy pyridazinone 31 is prepared from hydrazono propanoate 29 by cyclization under strongly basic conditions followed by decarboxylation. The cyclization can be accomplished by treatment of hydrazono propanoate 29 with a strong base such as DBU, LDA or NaH in a suitable organic solvent such as THF or MeCN at room temperature. In one embodiment, cyclization is achieved with DBU in MeCN at room temperature. Decarboxylation to form hydroxypyridazinone 31 can be achieved by heating the methyl ester pyrazinone moiety in a suitable organic solvent such as dioxane or decalin or dioxane/decalin mixture to high temperatures in the presence of concentrated HCl. Carboxylic acid 94 can be prepared from hydroxy pyridazinone 31 in a two-step process, i.e., chlorination followed by oxidation. The chlorination step can be achieved by treatment with $POCl_3$, thionyl chloride, oxalyl chloride or $PCl_5$. In one embodiment, this transformation is achieved with $POCl_3$ neat at elevated temperature (~85° C.). Following the chlorination step, carboxylic acid 94 can be prepared by oxidation under standard conditions including but not limited to $KMnO_4$ in water, $SeO_2$ in organic solvent such as dioxane, xylene, or pyridine, NaOCl/$RuCl_3$, $CrO_3$ in aqueous $H_2SO_4$, $K_2Cr_2O_7$, and $Na_2Cr_2O_7$ in water. In one embodiment this transformation is achieved with $K_2Cr_2O_7$—$H_2SO_4$. Carboxylic acid 94 can be converted to pyridazinone ester 95 in a two-step procedure which includes esterification of pyridazinone acid 94 followed by a palladium-mediated cross-coupling reaction. The esterification can be performed under standard conditions including, but not limited to, concentrated HCl in MeOH, TMSCl in MeOH or $TMSCHN_2$ in suitable organic solvents such as ether/MeOH, THF/MeOH or PhMe/MeOH. The palladium-mediated cross-coupling reaction can be achieved by standard methods including, but not limited to, treating the chloropyridazinone ester with an aniline, a palladium catalyst such as Pd(OAc)$_2$, PdCl$_2$(dppf), Pd(Ph$_3$P)$_4$, or Pd$_2$dba$_3$, a phosphine ligand and a base in a suitable organic solvent such as THF, DMF, PhMe, DME or MeCN at elevated temperature. In one embodiment, the cross-coupling reaction comprises treating the ester 94 with Pd(OAc)$_2$, rac-2,2-bis(diphenylphosphino)-1,1'-binaphthyl and Cs$_2$CO$_3$ in toluene at 70 to 100° C. In embodiments of compound 95 where $R^9$=Br is desired, the bromine substituent can be incorporated after the cross-coupling reaction. Bromination of pyridazinone can be accomplished with NBS in a suitable organic solvent such as DMF, MeCN or mixed solvent systems at room temperature. In one embodiment the bromination is carried out in DMF. Hydroxamate 96 can be prepared by treating pyridazinone ester 95 with the appropriate hydroxylamine and amide base such as LDA, LiHMDS or NaHMDS in a suitable organic solvent such as THF at low temperature. In one embodiment, a LiHMDS solution is added to a solution of pyridazinone ester 95 and hydroxylamine in THF at 0° C. The reaction mixture is then warmed to room temperature to yield the desired hydroxamate 96. In some instances, the hydroxylamine used in the coupling reaction contains a standard protecting group. In those cases, the protecting group can be removed by standard conditions known in the art.

Figure 36:
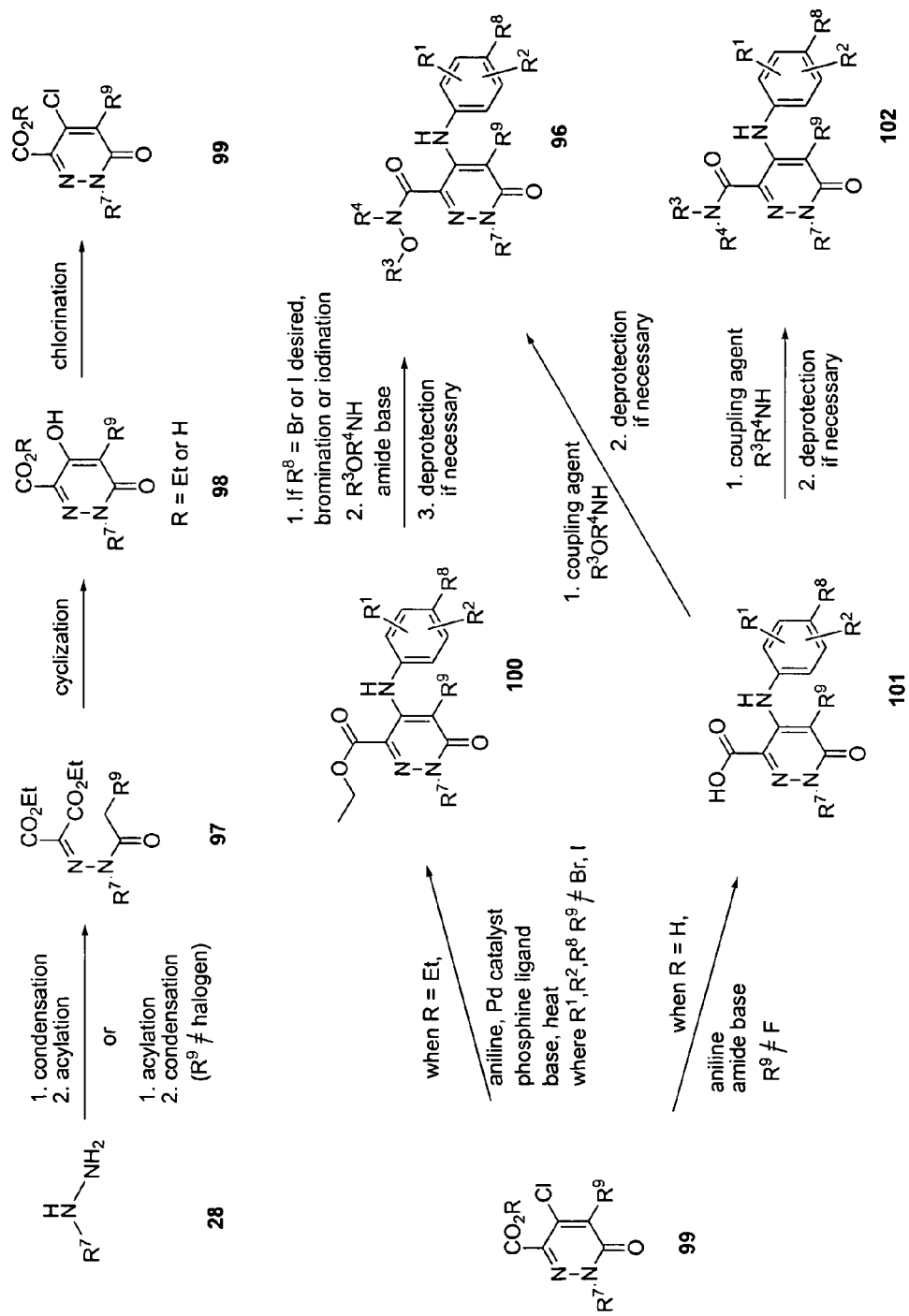
FIG. 36 shows a reaction scheme for the synthesis of compounds 96, 100, 101 and 102.

FIG. 36 outlines the synthesis of compounds of Formula I wherein X=N and $R^9$ is halogen or alkyl. Substituted hydrazine 28 can be converted to hydrazono malonate 97 according to one of two procedures. In one embodiment, condensation of substituted hydrazine 28 followed by acylation is particularly useful for analogs where $R^9$ is alkyl or halogen. In this embodiment, hydrazine 28 can be condensed with diethyl 2-oxomalonate under standard dehydrating conditions using a Dean-Stark trap in a suitable organic solvent such as benzene or toluene at temperatures ranging from 80 to 120° C. Acylation with a reagent that delivers an acyl group to provide the hydrazono malonate 97 is achieved by treatment with base at the appropriate temperature in a suitable organic solvent such as THF, DMF, dioxane or MeCN followed by the addition of the acylating reagent. Examples of acylating reagents are well known to persons skilled in the art and include, but are not limited to, acid chlorides, acid anhydrides, and activated esters. In one embodiment, the hydrazone is treated with LiH in THF at 0° C. followed by the addition of an acid chloride and stirred at 25 to 60° C. to provide compound 97. An alternative method for synthesizing compound 97 wherein $R^9$ is not halogen involves acylating the hydrazine 28 with a reagent that delivers an acyl group, followed by condensation with diethyl 2-oxomalonate to provide the hydrazono malonate 97. According to this method, the substituted hydrazine 28 can be converted to the hydrazide by standard acylation methods. In one embodiment this transformation is achieved with the appropriate acid chloride in methylene chloride at 0° C. to ambient temperature. The hydrazide obtained is condensed with diethyl ketomalonate under standard dehydrating conditions using a Dean-Stark trap in a suitable organic solvent such as benzene or toluene at temperature from 80 to 130° C. Pyridazinone 99 is prepared from hydrazono malonate 97 by cyclization under basic conditions to provide the intermediated acid or ester 98, followed by chlorination to provide the pyridazinone 99. The cyclization can be accomplished by treatment of hydrazono malonate 7 with an amide base such as LiHMDS, NaHMDS, KHMDS or LDA in a suitable organic solvent such as THF or ether at low temperature. In one embodiment, cyclization is achieved with LiHMDS in THF at low temperature (−78 to −40° C.), followed by treatment with concentrated HCl to yield the ester derivative of 98 (R=Et). In another embodiment, the acid derivative of 98 (R=H) is obtained by in-situ saponification of the pyridazinone ester 98. Upon completion of cyclization, the reaction mixture is quenched with water at low temperatures (−78 to −40° C.), then warmed to ambient temperature with stirring followed by acidification. Pyridazinone 99 is then prepared from pyridazinone acid or ester 98 by treatment with $POCl_3$, thionyl chloride, oxalyl chloride or $PCl_5$. In one embodiment this transformation is achieved with $POCl_3$ neat at elevated temperature (~85° C.). When $R^9$ is not F, pyridazinone acid 99 (when R=H) can then be converted to pyridazinone 101. Incorporation of the aniline moiety is accomplished by an $S_NAr$ reaction in a suitable organic solvent such as THF using an amide base such as LDA, LiHMDS, NaHMDS or KHMDS at appropriate temperatures (−78° C. to room temperature). In one embodiment, the aniline is added to LDA or LiHMDS in THF at low temperature (−20 to −80° C.). The pyridazinone acid 99 (R=H) is then added and the reaction mixture is warmed to room temperature to generate carboxylic acid 101. Hydroxamates 96 and amides 102 can then be prepared from acid 101 using standard coupling reagents including, but not limited to, EDCI, HOBt, or PyBOP and the appropriate amine or hydroxylamine in a suitable organic solvent such as DMF, THF or methylene chloride. In some instances, the amine or hydroxylamine contains a standard protecting group. In those cases, the protecting group can be removed by standard conditions known in the art. Alternatively, ester pyridazinone 99 (R=Et) can be converted to hydroxamate 96 through pyridazinone ester 100 by the standard methods described in FIG. 35. When $R^8$=Br or I is desired, the desired halogen can be incorporated using NBS or NIS in a suitable organic solvent or mixed solvent system such as DMF, THF-MeOH, or AcOH-THF in the presence of an appropriate acid catalyst.

Figure 37:
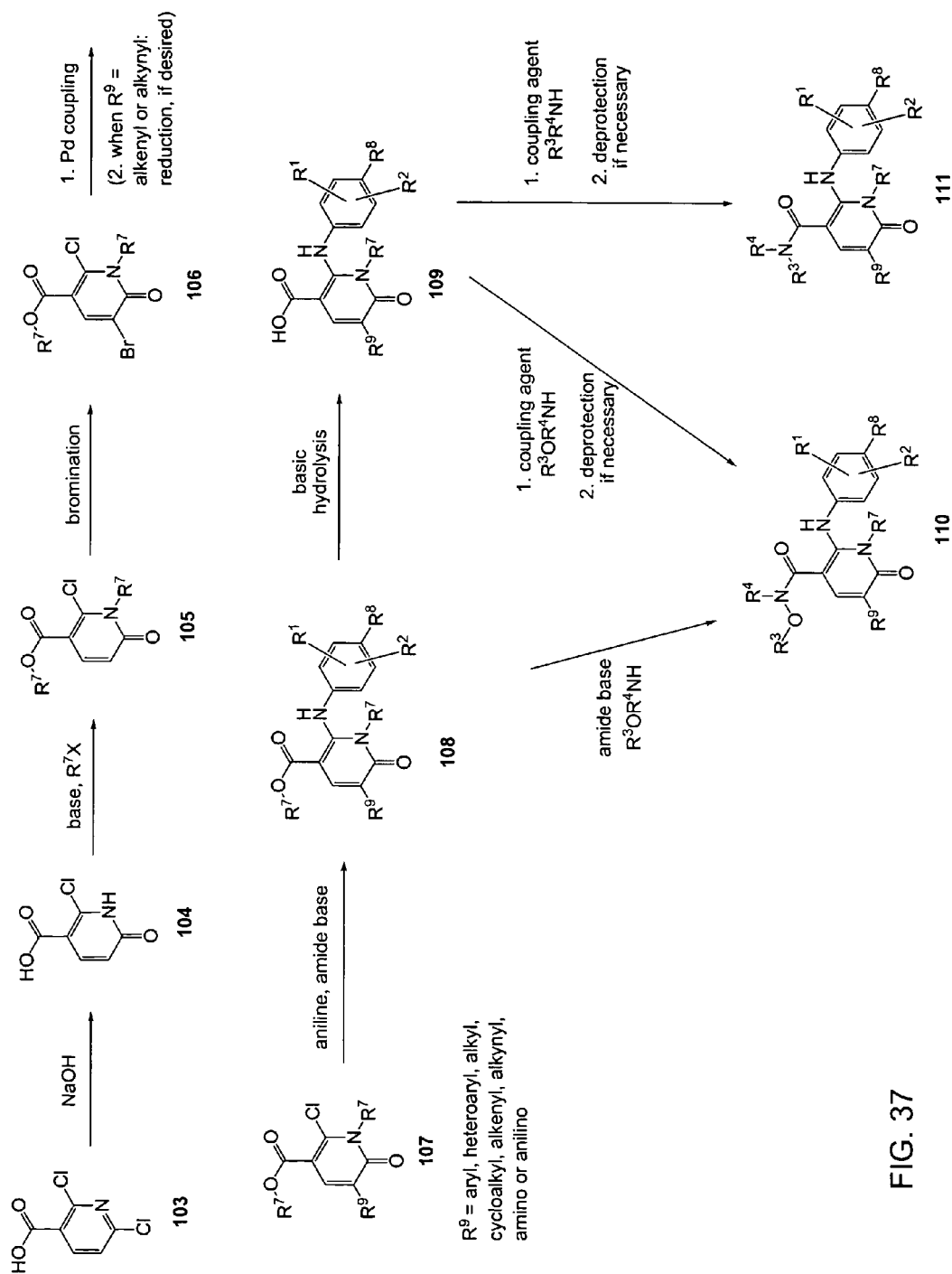
FIG. 37 shows a reaction scheme for the synthesis of compounds 109, 110 and 111.

In FIG. 37, the synthesis of compounds of Formula V where X=N and $R^9$=aryl, heteroaryl, alkyl, cycloalkyl, alkenyl, alkynyl, cyano, amino or anilino is shown, in which 2,6-dichloro-nicotinic acid is used as the starting material. The nicotinic acid 103 is converted to the mono chloro acid 104 by refluxing in 2 N aqueous NaOH following the procedure described in U.S. Pat. No. 3,682,932. Alkylation of 104 to provide 105 can be achieved by standard basic alkylation conditions incorporating alkyl halides, with two equivalents of the appropriate alkyl halide and base to give a mixture of the N-alkyl pyridone ester 105 and the regioisomeric O-alkyl pyridine ester, which are easily separated by column chromatography. These conditions include, but are not limited to, $K_2CO_3$ in acetone or DMF at room or elevated temperature or NaH in THF at ambient or elevated temperature and then addition of the alkyl halide. In certain embodiments this alkylation is achieved with LiH in DMF at 0° C., followed by addition of alkyl bromide or alkyl iodide and warming to room temperature. Bromination of pyridone ester 105 can be accomplished with either $Br_2$ and acetic acid or NBS in a suitable organic solvent such as DMF. In certain embodiments NBS is added to a solution of pyridone ester 105 in DMF to yield 106. Conversion of bromide 106 to compound 107 can be achieved using Pd mediated cross coupling conditions. When $R^9$=alkenyl or alkynyl, these can be further reduced using the appropriate reducing agent to provide alkyl substituents at $R^9$. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^9$. For example, if $R^9$=CN is desired, the coupling partner is $Zn(CN)_2$. This reaction can be carried out with $Pd_2dba_3$ and dppf in NMP at 120° C. These palladium-mediated cross couplings are well documented in the literature and are well known to one skilled in the art. Incorporation of the properly substituted aniline moiety to provide 108 is accomplished by $S_NAR$ reaction. This can be done in a suitable organic solvent such as THF using an amide base such as LDA, LiHMDS, NaHMDS, or KHMDS at appropriate temperatures (−78° C. to room temperature). In certain embodiments the aniline is added to LDA or LiHMDS in THF at low temperature (−20 to −80° C.). The pyridone 105 is then added and the mixture is stirred at low temperature to generate ester 108. Carboxylic acid 109 can then be prepared using standard saponification conditions such as LiOH or NaOH in standard mixed aqueous/organic solvent systems. Hydroxamate 110 and amide 111 can be prepared using standard coupling procedures, including but not limited to EDCI, HOBt, or PyBOP and the appropriate amine or hydroxylamine in suitable organic solvents such as DMF, THF, or methylene chloride. In certain embodiments, the coupling is accomplished with HOBt and EDCI in DMF. In some instances, the amine or hydroxylamine used in the coupling reaction contains a standard protecting group. In those cases, the protecting group can be removed by standard conditions known in the art.

Figure 38:
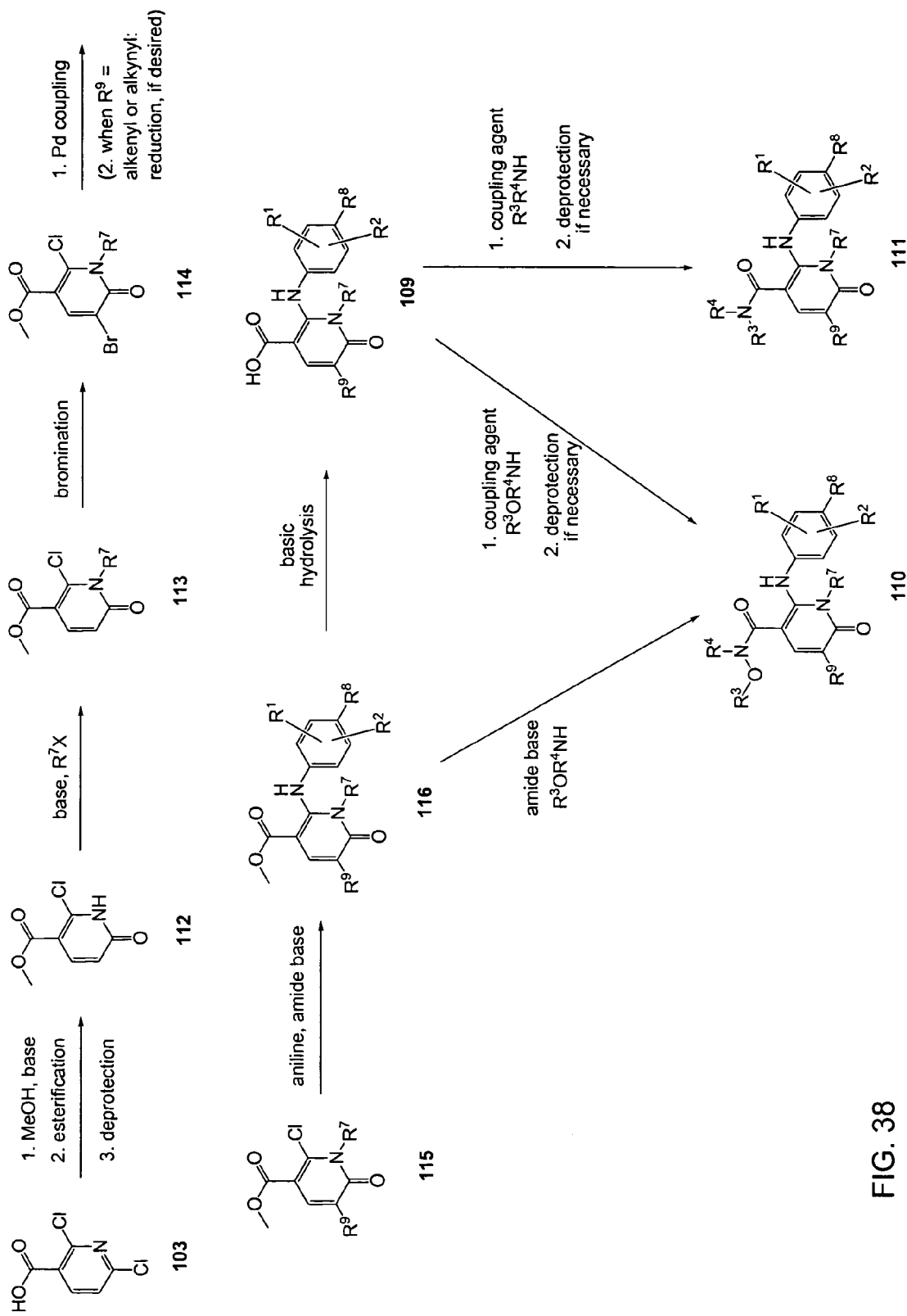
FIG. 38 shows an alternate reaction scheme for the synthesis of compounds 109, 110 and 111.

In FIG. 38, an alternative synthesis of compounds of Formula V where X=N and $R^9$=aryl, heteroaryl, alkyl, cycloalkyl, alkenyl, alkynyl, cyano, amino or anilino is depicted, in which 2,6-dichloro-nicotinic acid is used as the starting material. This route is particularly useful for analogs where $R^7$ is not equal to Me or Et. Nicotinic acid 103 can be converted to the N-alkyl pyridone methyl ester 114 following a seven step procedure, where 2,6-dichloro-nicotinic acid 103 is first converted to the methoxy pyridine acid, which is esterified to give the methyl ester and then deprotected to yield the mono chloro ester 112. In certain embodiments the conversion to the methoxy pyridine acid is carried out by adding potassium t-butoxide to a solution of the acid 103 in MeOH and this mixture is then heated to reflux for several days. Esterification to give the methyl ester can be carried out under standard conditions, including but not limited to Fisher esterification (MeOH, $H_2SO_4$), TMSCl in MeOH or $TMSCHN_2$ in suitable organic solvents such as PhMe/ MeOH. Demethylation of the methoxy pyridine can then be accomplished by standard conditions including but not limited to HCl at elevated temperature, pTsOH in acetic acid at elevated temperature and aqueous HBr in MeOH at elevated temperature. Preferable demethylation to give pyridone 112 is achieved by treatment of the methoxy pyridine with aqueous HBr in acetic acid at elevated temperature (80 to 120° C.). Alkylation of 112 can be achieved by standard basic alkylation conditions incorporating alkyl halides, with one equivalent of the appropriate alkyl halide and base to give a mixture of the N-alkyl pyridone ester 113 and the regioisomeric O-alkyl pyridine ester, which are easily separated by column chromatography. These conditions include but are not limited to $K_2CO_3$ in acetone or DMF at room or elevated temperature or NaH in THF at ambient or elevated temperature and then addition of the alkyl halide. In certain embodiments this alkylation is achieved with LiH in DMF at 0° C., followed by addition of alkyl bromide or alkyl iodide and warming to room temperature. Bromination of pyridone ester 113 can be accomplished with either $Br_2$ and acetic acid or NBS in a suitable organic solvent such as DMF. In certain embodiments NBS is added to a solution of pyridone ester 113 in DMF to yield 114. Conversion of bromide 114 to compound 115 can be achieved using palladium-mediated cross-coupling conditions. When $R^9$=alkenyl or alkynyl, these can be further reduced using the appropriate reducing agent to provide alkyl substituents at $R^9$. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^9$. These Pd mediated cross-couplings are well documented in the literature and are well known to one skilled in the art. Incorporation of the properly substituted aniline moiety to provide 116 is accomplished by $S_NAR$ reaction. This can be done in a suitable organic solvent such as THF using an amide base such as LDA, LiHMDS, NaHMDS, or KHMDS at appropriate temperatures (−78° C. to room temperature). In certain embodiments the aniline is added to LDA or LiHMDS in THF at low temperature (−20 to −80° C.). The pyridone 115 is then added and the mixture is stirred at low temperature to generate ester 116. Conversion of 116 to carboxylic acid 109, as well as hydroxamate 110 and amide 111 can be accomplished as described for FIG. 37. Alternatively, hydroxamate 110 can be prepared directly from methyl ester 116 in a suitable organic solvent such as THF using the appropriate hydroxylamine and amide base such as LDA, LiHMDS, NaHMDS, or KHMDS at appropriate temperatures (−78° C. to room temperature). In certain embodiments, a solution of LiHMDS is added to a solution of the ester 116 and the hydroxylamine in THF at 0° C. The reaction mixture is then warmed to room temperature to yield the desired hydroxamate 110. In some instances, the hydroxylamine used in the coupling reaction contains a standard protecting group. In those cases, the protecting group can be removed by standard conditions known in the art.

Figure 39:
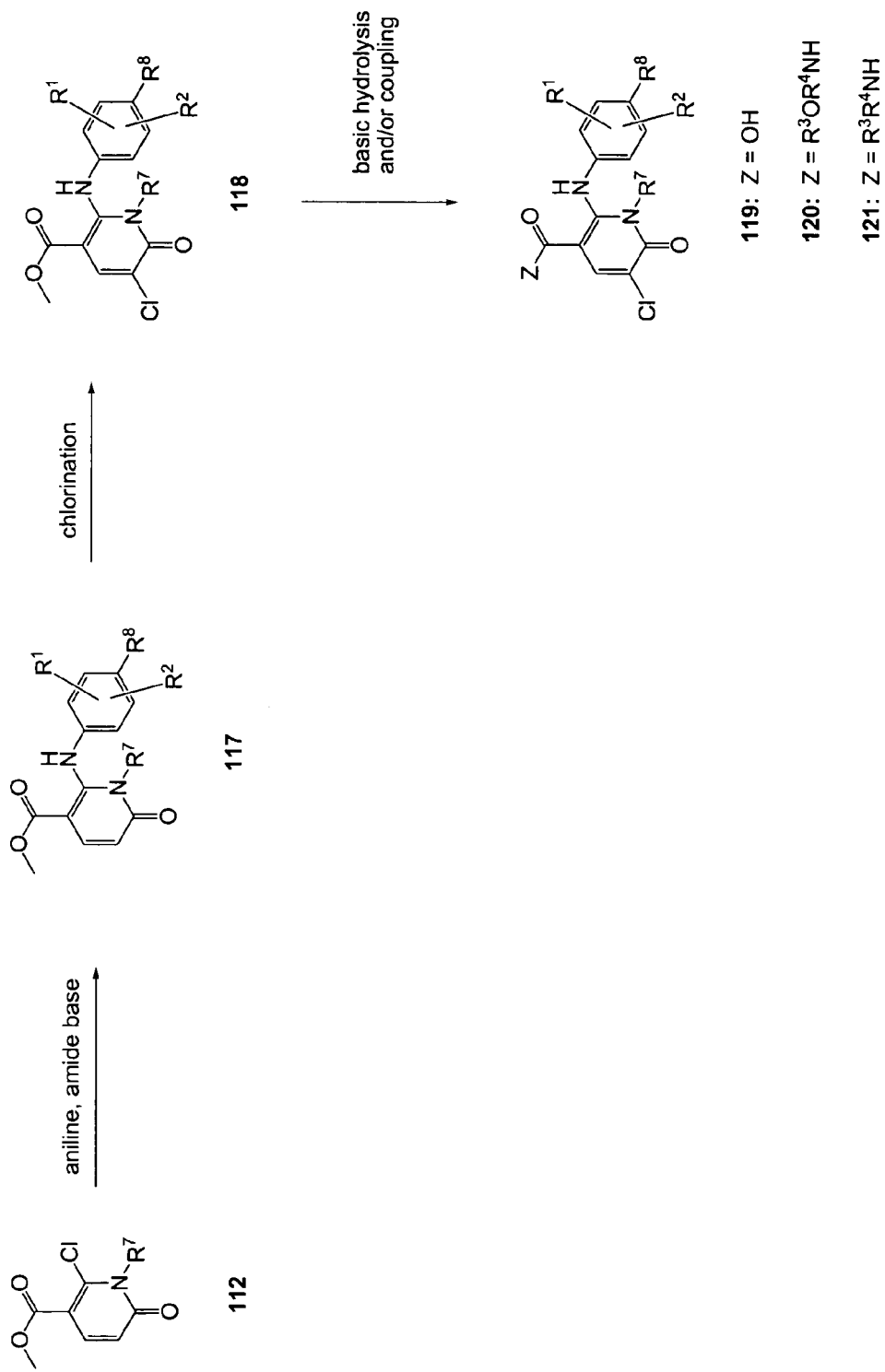
FIG. 39 shows a reaction scheme for the synthesis of compounds 119, 120 and 121.

In FIG. 39, the synthesis of compounds of Formula V where X=N and $R^9$=Cl is depicted, in which N-alkyl pyridone methyl ester 112 is used as the starting material. Formation of 117 can be accomplished by incorporation of the properly substituted aniline moiety by $S_NAR$ reaction. This can be done in a suitable organic solvent such as THF using an amide base such as LDA, LiHMDS, NaHMDS, or KHMDS at appropriate temperatures (−78° C. to room temperature). In certain embodiments the aniline is added to LDA or LiHMDS in THF at low temperature (−20 to −80° C.). The pyridone 112 is then added and the mixture is stirred at low temperature to generate ester 117. This can be done in a suitable organic solvent such as THF using an amide base such as LDA, LiHMDS, NaHMDS, or KHMDS at appropriate temperatures (−78° C. to room temperature). Chlorination of pyridone 117 to give pyridone 118 can be accomplished using standard conditions such as NCS in a suitable organic solvent, such as DMF. Conversion of 118 to carboxylic acid 119, as well as hydroxamate 120 and amide 121 can be accomplished as described for FIGS. 37 and 38.

Figure 40:
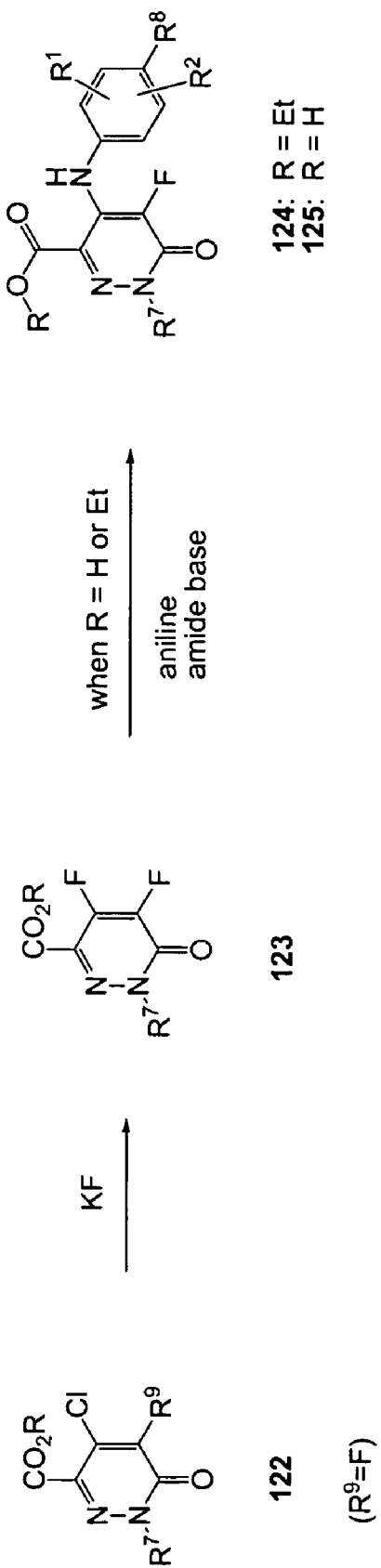
FIG. 40 shows a reaction scheme for the synthesis of compounds 124 and 125.

FIG. 40 illustrates the synthesis of compounds of Formula I wherein $R^9$=F. 4-Fluoropyridazinone 123 can be prepared from 4-chloropyridazinone 122 by treatment with KF or HF with or without base such as $Et_3N$ or $Me_3N$ in suitable organic solvents such as $CH_3CN$, THF, DMF, NMP or DMSO. In one embodiment, this transformation is achieved with KF in DMSO at elevated temperature (e.g., 160° C.). Pyridazinone ester 123 (when R=Et) can be converted to pyridazinone 124, wherein incorporation of the aniline moiety is accomplished by SnAr reaction. This can be done in a suitable organic solvent such as DMF, EtOH, iPrOH, $CH_3CN$ or THF using a base such as $Cs_2CO_3$, $NaHCO_3$, $K_2CO_3$ or $Na_2CO_3$ at temperature from 80 to 160° C. In one embodiment, the aniline and $Cs_2CO_3$ are added to a solution of pyridazinone 123 in DMF and the reaction mixture is heated to 80° C. Alternatively, pyridazinone acid 123 (R=H) can be converted to pyridazinone 125 by standard methods such as those described in FIG. 36. Pyridazinone 124 or 125 can be converted to hydroxamates or amides as described in FIG. 35 or 36.

Figure 41:
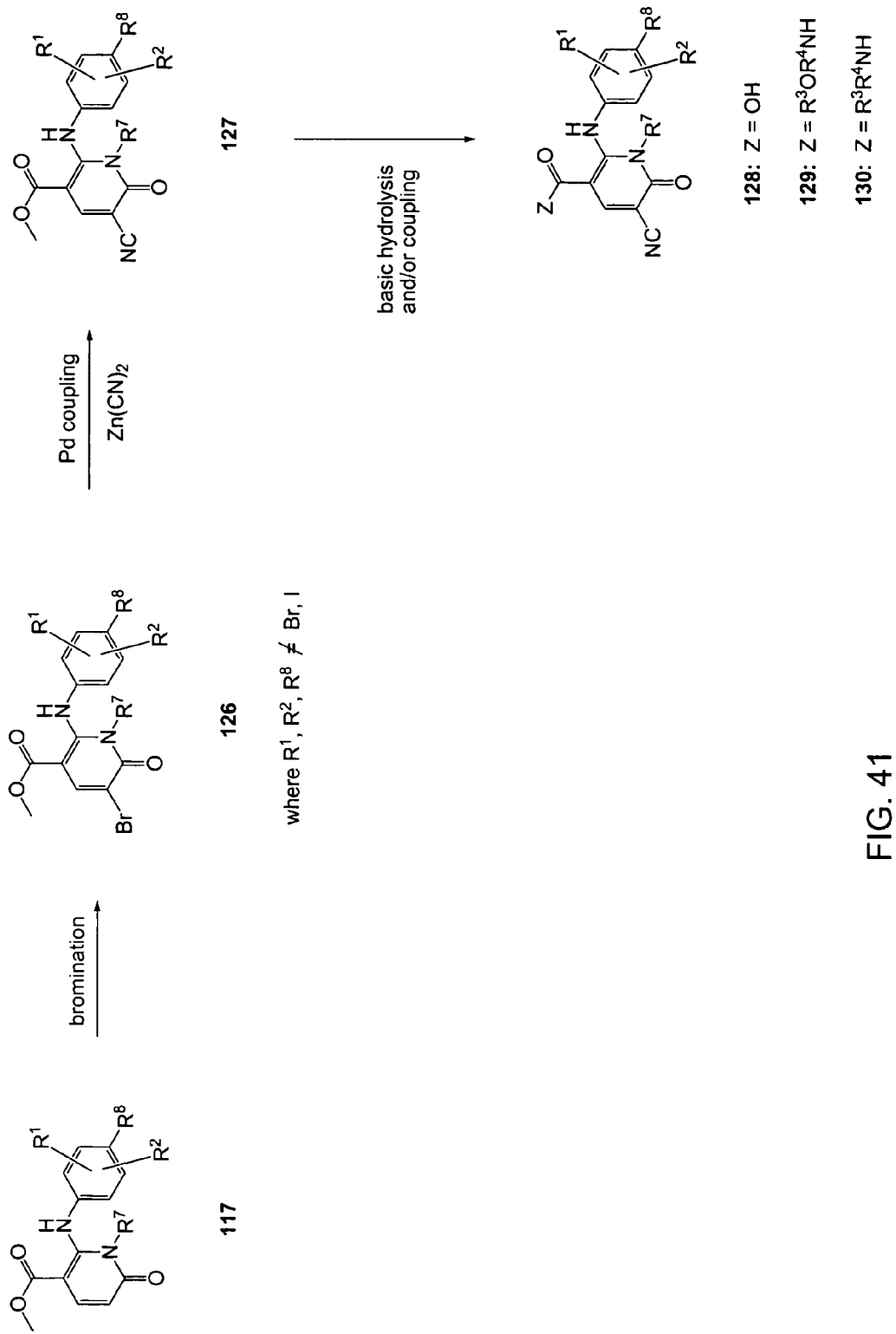
FIG. 41 shows a reaction scheme for the synthesis of compounds 128, 129 and 130.

In FIG. 41, the synthesis of compounds of Formula I where $R^9$=CN and $R^1$, $R^2$ or $R^8$ do not equal Br or I is depicted, in which pyridone methyl ester 117 is used as the starting material. Bromination of pyridone ester 117 can be accomplished with either $Br_2$ and acetic acid or NBS in a suitable organic solvent such as DMF. Preferably NBS is added to a solution of pyridone ester 117 in DMF to yield 126. Conversion of bromide 126 to compound 127 where $R^9$ is cyano can be achieved using Pd mediated cross coupling conditions. In general, this chemistry can be accomplished using a wide variety of Pd catalysts and ligands, with or without added base, in a suitable organic solvent such as DMF, PhMe, DME, THF, $CH_3CN$ or NMP at elevated temperature. Preferably, this reaction is carried out with $Zn(CN)_2$ and $Pd_2dba_3$ and dppf in DMF at 120° C. Conversion of 127 to carboxylic acid 128, as well as hydroxamate 129 and amide 130 can be accomplished as described for FIGS. 37 and 38.

The invention also relates to a pharmaceutical composition for the treatment of a hyperproliferative disorder in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastic, pancreatic, breast, head, neck, renal, kidney, ovarian, prostate, colorectal, esophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or the treatment of pain in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease or other inflammatory condition such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, prodrug or hydrate thereof. In one embodiment, said method relates to the treatment of cancer such as brain, lung, squamous cell, bladder, gastic, pancreatic, breast, head, neck, renal, kidney, ovarian, prostate, colorectal, esophageal, testicular, gynecological or thyroid cancer. In another embodiment, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a pharmaceutical composition for treating a disease or condition related to inflammatory disease, autoimmune disease, destructive bone disorders, proliferative disorders, infectious disease, viral disease, fibrotic disease or neurodegenerative disease in a mammal which comprises a therapeutically effective amount of a compound of the present invention, or a pharmaceutically acceptable salt, prodrug or hydrate thereof, and a pharmaceutically acceptable carrier. Examples of the above diseases and/or conditions include but is not limited to rheumatoid arthritis, atherosclerosis, inflammatory bowel disease, skin diseases such as psoriasis, eczema, and scleroderma, diabetes and diabetic complications, diabetic retinopathy, retinopathy of prematurity, age-related macular degeneration, hemangioma, chronic obstructive pulmonary disease, idiopathic pulmonary fibrosis, allergic responses including asthma allergic rhinitis and atopic dermatitis, renal disease and renal failure, polycystic kidney disease, acute coronary syndrome, congestive heart failure, osteoarthritis, neurofibromatosis, organ transplant rejection, cachexia and pain.

Further provided is a compound of Formula I, Formula II, Formula III, Formula IV or Formula V for use as a medicament in the treatment of the diseases and conditions described above in a warm-blooded animal, preferably a mammal, more preferably a human, suffering from such disorder. Also provided is the use of a compound of Formula I, Formula II, Formula III, Formula IV or Formula V in the preparation of a medicament for the treatment of the diseases and conditions described above in a warm-blooded animal, preferably a mammal, more preferably a human, suffering from such disorder.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloprotienase inhibitors are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

The amount of a given agent that will correspond to such an amount will vary depending upon factors such as the particular compound, disease condition and its severity, the identity (e. g., weight) of the mammal in need of treatment, but can nevertheless be routinely determined by one skilled in the art. "Treating" is intended to mean at least the mitigation of a disease condition in a mammal, such as a human, that is affected, at least in part, by the activity of MEK, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I-V or a pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-V, or a pharmaceutically acceptable salt or prodrug thereof, as defined hereinbefore in association with a pharmaceutically acceptable diluent or carrier.

To prepare the pharmaceutical compositions according to one embodiment of this invention, a therapeutically or prophylactically effective amount of a compound of Formula I-V or a pharmaceutically acceptable salt, solvate, metabolite or prodrug thereof (alone or together with an additional therapeutic agent) is intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I-V, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose. methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insulation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 1 mg/kg/day to about 35 mg/kg/day, in single or divided doses. For a 70 kg human, this would amount to about 0.07 to 2.45 g/day, preferably about 0.05 to about 1.0 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I-V will naturally vary according to the nature and severity of the conditions, the age and sex of the animal or patient and the route of administration, according to well known principles of medicine.

The compounds of this invention may be used alone in combination with other drugs and therapies used in the treatment of disease states which would benefit from the inhibition of MEK. Such treatment may involve, in addition to the compounds of the invention, conventional surgery or radiotherapy or chemotherapy. Such chemotherapy may include one or more of the following categories of anti-tumor agents:

(i) antiproliferative/anti-neoplastic drugs and combinations thereof, as used in medical oncology, such as alkylating agents (for example, cis-platin, carboplatin, cyclophosphamide, nitorgen mustard, melphalan, chlorambucil, busulphan and nitorsoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example epipodophyllotoxins like eptoposide and teniposide, amsacrine, topotecan and campothecin):

(ii) cytostatic agents such as antiestrogens (for example, tamoxifen, toremifene, raloxifene, droloxifene and iodoxyfene), estrogen receptor down regulators (for example, fulvestratrant) antiandrogens (for example, bicalutamide, flutamide, nilutamide, cyproxerone acetate and Casodex™ (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, asanastrozole, letrozole, vorazole and exemestane) and inhibitors of 5α-reductase such as finasteride;

(iii) agents which inhibit cancer cell invasion (for example, metalloproteinase inhibitors like marimastat and inhibitors of urokinase plasminogne activator receptor function);

(iv) inhibitors of growth factor function like growth factor antibodies, growth factor receptor antibodies (for example, the anti-erbB2 antibody trastumuzab [Herceptin™] and the anti-erbB1 antibody cetuximab [C225]), famesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), inhibitors of the platelet-derived growth factor family and inhibitors of the hepatocyte growth factor family;

(v) antiangiogenic agents such as those which inhibit the effects of vascular endothelial growth factor (for example, the anti-vascular endothelial cell growth factor antibody bevacizumab [Avastin™], compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon; and (x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies.

Such conjoint treatment may be achieved by way of the simultaneous, sequential or separate dosing of the individual components of treatment. Such combination products employ the compounds of this invention within the dose range described hereinbefore and the other pharmaceutically active agent within its approved dose range.

According to this aspect of the invention there is provided a pharmaceutical product comprising a compound of Formula I-V as defined herein and an additional anti-tumor agent as defined hereinbefore for the conjoint treatment of cancer.

Although the compounds of Formula I-V are primarily of value as therapeutic agents for use in warm-blooded animals (including man), they are also useful whenever it is required to inhibit the effects of MEK. Thus, they are useful as pharmacological standards for use in the development of new biological tests and in the search for new pharmacological agents.

The activity of the compounds of the present invention may be determined by the following procedure. N-terminal 6 His-tagged, constitutively active MEK-1 (2-393) is expressed in *E. coli* and protein is purified by conventional methods (Ahn et al., Science 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in *E. coli* and is purified by conventional methods, in the presence of MEK-1. The assay is carried out in 96-well polypropylene plate. The incubation mixture (100 μL) comprises of 25 mM Hepes, pH 7.4, 10 mM $MgCl_2$, 5 mM $\beta$-glycerolphosphate, 100 μM Na-orthovanadate, 5 mM DTT, 5 nM MEK1, and 1 μM ERK2. Inhibitors are suspended in DMSO, and all reactions, including controls are performed at a final concentration of 1% DMSO. Reactions are initiated by the addition of 10 μM ATP (with 0.5 μCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvester. Plates are allowed to air-dry prior to adding 30 μL/well of Packard Microscint 20, and plates are counted using a Packard TopCount. In this assay, compounds of the invention exhibited an $IC_{50}$ of less than 50 micromolar.

Representative compounds of the present invention, which are encompassed by the present invention include, but are not limited to the compounds of the examples and their pharmaceutically acceptable acid or base addition salts or prodrugs thereof. The examples presented below are intended to illustrate particular embodiments of the invention, and are not intended to limit the scope of the specification or the claims in any way.

The disclosures in this application of all articles and references, including patents, are incorporated herein by reference.

In another embodiment of the invention, an article of manufacture, or "kit", containing materials useful for the treatment of the disorders described above is provided. In one embodiment, the kit comprises a container comprising a compound of Formula I-V or a formulation thereof. The kit may also comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container holds a compound of Formula I-V or a formulation thereof which is effective for treating the condition and may have a sterile access port (for example, the container may be an intravenous solution bag or a vial having a stopper pierceable by a hypodermic injection needle). The label or package insert may indicate that the composition is used for treating the condition of choice, such as cancer. In one embodiment, the label or package inserts indicates that the compound of Formula I-V or a formulation thereof can be used to treat a disease or medical condition mediated by MEK. In addition, the label or package insert may indicate that the patient to be treated is one having a disease or medical condition mediated by MEK such as a hyperproliferative disorder or an inflammatory condition. The label or package insert may also indicate that the composition can be used to treat other disorders. Alternatively, or additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

According to another embodiment, a kit may comprise (a) a first container with a compound of Formula I-V or a formulation thereof contained therein; and optionally (b) a second container with a second pharmaceutical formulation contained therein, wherein the second pharmaceutical formulation comprises a second compound with anti-hyperproliferative or anti-inflammatory activity. Alternatively, or additionally, the article of manufacture may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of a compound of Formula I or a formulation thereof and, if present, the second pharmaceutical formulation. For example, if the kit comprises a compound of Formula I-V or a formulation thereof ("first formulation") and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I-V, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

In certain other embodiments wherein the kit comprises a compound of Formula I-V or a formulation thereof and a second therapeutic agent, the kit may comprise a container for containing the separate components such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

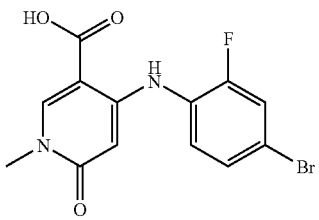

4-(4-Bromo-2-fluorophenylamino)-1-methyl-6-oxo-1,6-dihydropyridine-3-carboxylic acid Step A: Preparation of 4-hydroxy-1-methyl-6-oxo-1,6-dihydropyridine-3-carboxylic acid ethyl ester: Triethyl orthoformate (45.82 mL, 275.5 mmol) and acetic anhydride (52.08 mL, 550.9 mmol) were added to diethyl acetone dicarboxylate (50 mL, 275.5 mmol) and heated to 135° C. After 1 hour, the reaction mixture was cooled to room temperature and concentrated. The resulting residue was cooled to 0° C. and methylamine (40% in water) was added with stirring. After the addition of water (200 mL) the reaction mixture was stirred at room temperature for 16 hours. The reaction mixture was diluted with EtOAc (300 mL), and the resulting layers separated. The aqueous phase was neutralized with 10% HCl solution to produce the desired product as a white precipitate, which was filtered and washed with water. The filtrate was extracted with EtOAc, and the combined organic extracts dried (MgSO$_4$), and concentrated to give a white solid. This second crop of product was rinsed with Et$_2$O and combined with the first crop to yield 29 g (54%) desired product after drying.

Step B: Preparation of 4-chloro-1-methyl-6-oxo-1,6-dihydropyridine-3-carboxylic acid ethyl ester: Triethyl amine (7.07 mL, 50.7 mmol) was added to a suspension of 4-hydroxy-1-methyl-6-oxo-1,6-dihydropyridine-3-carboxylic acid ethyl ester (10.0 g, 50.7 mmol) and POCl$_3$ (27.85 mL, 304.3 mmol). After stirring 16 hours, the reaction mixture was concentrated under reduced pressure. The resulting residue was poured onto ice, carefully neutralized with saturated K$_2$CO$_3$ solution, and diluted with EtOAc. The layers were separated and the aqueous phase further extracted with EtOAc. The combined organic extracts were dried (MgSO$_4$) and concentrated under reduced pressure to yield 7.3 g (67%) clean desired product.

Step C: Preparation of 4-chloro-1-methyl-6-oxo-1,6-dihydropyridine-3-carboxylic acid: To a solution of 4-chloro-1-methyl-6-oxo-1,6-dihydropyridine-3-carboxylic acid ethyl ester (0.925 g, 4.29 mmol) in a 4:1 mixture of THF:MeOH (20 mL) was added a 1 M solution of LiOH (8.6 mL). After stirring for 30 minutes, the reaction mixture was acidified to pH 1 with 10% HCl and extracted with EtOAc. The combined organic extracts were washed with brine, dried (MgSO$_4$) and concentrated under reduced pressure to give 0.732 g (91%) clean desired product.

Step D: Preparation of 4-(4-bromo-2-fluorophenylamino)-1-methyl-6-oxo-1,6-dihydropyridine-3-carboxylic acid: To a solution of i-Pr$_2$NH (0.39 mL, 2.80 mmol) in THF (4 mL) at 0° C. was added n-BuLi (1.1 mL, 2.80 mmol, 2.5 M solution in hexanes). After stirring 15 minutes, the mixture was cooled to −78° C. 4-Bromo-2-fluorophenylamine (0.38 g, 2.0 mmol) was added. After vigorous stirring for 10 minutes, a mixture of the 4-chloro-1-methyl-6-oxo-1,6-dihydropyridine-3-carboxylic acid (0.15 g, 0.80 mmol) in THF (5 mL) was added. The dry-ice bath was removed after 30 minutes, and the reaction mixture was stirred for 17 hours at room temperature. The reaction mixture was treated with a 10% aqueous HCl solution (15 mL), extracted with EtOAc, dried (MgSO$_4$), and concentrated. Trituration with methylene chloride gave 0.21 g (77%) desired product. MS APCI (−) m/z 339, 341 (M−, Br pattern) detected; $^1$H NMR (400 mHz, DMSO-d$_6$) δ 9.61 (s, 1H), 8.53 (s, 1H), 7.69 (dd, 1H), 7.46 (m, 2H), 3.41 (s, 3H).

In the foregoing examples a variety of anilines can be used in replace of 4-bromo-2-fluorophenylamine in Step D of Example 1.

Example 2

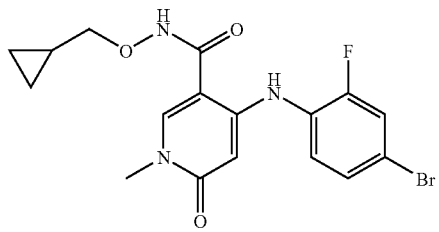

4-(4-Bromo-2-fluorophenylamino)-1-methyl-6-oxo-1,6-dihydropyridine-3-carboxylic acid cyclopropylmethoxy-amide Preparation of 4-(4-bromo-2-fluorophenylamino)-1-methyl-6-oxo-1,6-dihydropyridine-3-carboxylic acid cyclopropylmethyl-hydroxyamine: A mixture of 4-(4-bromo-2-fluorophenylamino)-1-methyl-6-oxo-1,6-dihydropyridine-3-carboxylic acid (0.078 g, 0.229 mmol), EDCI (0.13 g, 0.69 mmol), and HOBt (0.093 g, 0.69 mmol) in DMF (5 mL) was stirred for 30 minutes. O-Cyclopropylmethyl-hydroxylamine (0.060 g, 0.69 mmol) was added followed by $Et_3N$ (0.096 mL, 0.69 mmol). After 1 hour, the reaction mixture was diluted with EtOAc and washed with saturated $NH_4Cl$ solution, saturated $NaHCO_3$ solution and brine. The organic layer was dried ($MgSO_4$) and concentrated to yield 83 mg (89%) clean desired product. MS APCI (+) m/z 410, 412 (M+, Br pattern) detected; $^1H$ NMR (400 mHz, DMSO-$d_6$) δ 11.57 (s, 1H), 9.42 (s, 1H), 8.10 (s, 1H), 7.67 (d, 1H), 7.43 (m, 2H), 3.70 (d, 2H), 3.35 (s, 3H), 1.11 (m, 1H), 0.54 (m, 2H), 0.27 (m, 2H).

Any of the hydroxylamines used in the foregoing examples can be coupled as described in Example 2. In some instances, a final deprotection step may be required. These deprotections can be accomplished by standard literature methods. Example 3 is one such example in which a final deprotection step is required.

Example 3

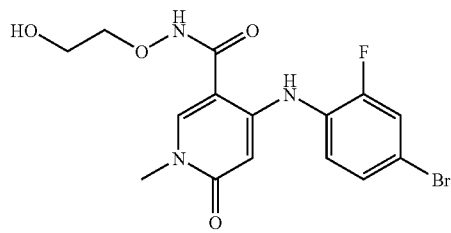

4-(4-Bromo-2-fluorophenylamino)-1-methyl-6-oxo-1,6-dihydropyridine-3-carboxylic acid (2-hydroxyethoxy)-amide Step A: Preparation of 4-(4-bromo-2-fluorophenylamino)-1-methyl-6-oxo-1,6-dihydropyridine-3-carboxylic acid (2-vinyloxyethoxy)-amide: A mixture of 4-(4-bromo-2-fluorophenylamino)-1-methyl-6-oxo-1,6-dihydropyridine-3-carboxylic acid (0.120 g, 0.352 mmol), EDCI (0.10 g, 0.53 mmol), and HOBt (0.071 g, 0.53 mmol) in DMF (5 mL) was stirred for 3 hours. O-(2-Vinyloxy-ethyl)-hydroxylamine (0.071 mL, 0.70 mmol) was added followed by $Et_3N$ (0.098 mL, 0.70 mmol). After 2 hours, the reaction mixture was diluted with EtOAc and washed with saturated $NH_4Cl$ solution, saturated $NaHCO_3$ solution and brine. The organic layer was dried (MgSO4) and concentrated under reduced pressure. Purification by flash column chromatography (3% MeOH in methylene chloride) gave 0.078 g (52%) clean desired product.

Step B: Preparation of 4-(4-bromo-2-fluorophenylamino)-1-methyl-6-oxo-1,6-dihydropyridine-3-carboxylic acid (2-hydroxyethoxy)-amide: 1 N HCl solution (0.36 mL) was added to a stirred solution of 4-(4-bromo-2-fluorophenylamino)-1-methyl-6-oxo-1,6-dihydropyridine-3-carboxylic acid (2-vinyloxyethoxy)-amide (0.077 g, 0.181 mmol) in a 1:1 mixture of EtOH:THF (6 mL). After 1 hour, the pH of the reaction mixture was adjusted to 5 to 7 with 2 N NaOH solution. The reaction mixture was diluted with EtOAc, washed with water, dried ($MgSO_4$) and concentrated. Trituration with diethyl ether yielded 55 mg (76%) clean desired product as a white solid. MS APCI (−) m/z 398, 400 (M−, Br pattern) detected; $^1H$ NMR (400 mHz, DMSO-$d_6$) δ 11.65 (s, 1H), 9.41 (s, 1H), 8.13 (s, 1H), 7.68 (d, 1H), 7.43 (m, 3H), 4.74 (t, 1H), 3.91 (t, 2H), 3.62 (m, 2H), 3.36 (s, 3H).

Example 4

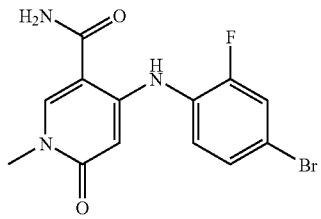

4-(4-Bromo-2-fluorophenylamino)-1-methyl-6-oxo-1,6-dihydropyridine-3-carboxylic acid amide Preparation of 4-(4-bromo-2-fluorophenylamino)-1-methyl-6-oxo-1,6-dihydropyridine-3-carboxylic acid amide: A mixture of 4-(4-bromo-2-fluorophenylamino)-1-methyl-6-oxo-1,6-dihydropyridine-3-carboxylic acid (0.069 g, 0.202 mmol), EDCI (0.12 g, 0.61 mmol), and HOBt (0.082 g, 0.61 mmol) in DMF (5 mL) was stirred for 30 minutes. $NH_4Cl$ (0.033 g, 0.61 mmol) was added followed by $Et_3N$ (0.085 mL, 0.61 mmol). After 1 hour, the reaction mixture was diluted with EtOAc and washed with saturated $NH_4Cl$ solution, saturated $NaHCO_3$ solution and brine. The organic layer was dried ($MgSO_4$) and concentrated to yield 52 mg (76%) clean desired product as an off-white solid. MS APCI (+) m/z 340, 342 (M+, Br pattern) detected; $^1H$ NMR (400 mHz, DMSO-$d_6$) δ 10.39 (s, 1H), 8.34 (s, 1H), 7.67 (dd, 1H), 7.43 (m, 2H), 3.36 (s, 3H).

The following compounds were prepared as described in Examples 1, 2 and 3 using benzyl amine in place of methylamine in Step A of Example 1 and no $Et_3N$ in Step B of Example 1.

Example 5

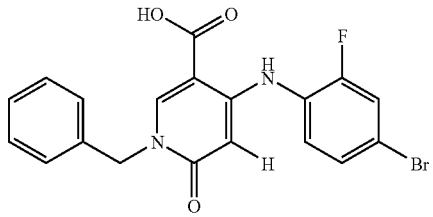

1-Benzyl-4-(4-bromo-2-fluorophenylamino)-6-oxo-1,6-dihydropyridine-3-carboxylic acid MS APCI (−) m/z 415, 417 (M−, Br pattern) detected; $^1H$ NMR (400 mHz, DMSO-$d_6$) δ 9.62 (s, 1H), 8.60 (s, 1H), 7.65 (dd, 1H), 7.48 (m, 2H), 7.32 (m, 5H), 5.49 (s, 1H), 5.12 (s, 2H).

Example 6

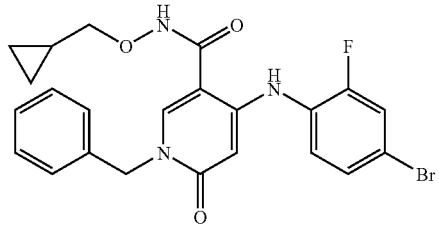

1-Benzyl-4-(4-bromo-2-fluorophenylamino)-6-oxo-1,6-dihydropyridine-3-carboxylic acid cyclopropylmethoxy amide MS APCI (−) m/z 484, 486 (M−, Br pattern) detected; $^1$H NMR (400 mHz, CD$_3$OD) δ 8.04 (s, 1H), 7.49 (d, 1H), 7.40 (m, 2H), 7.32 (m, 6H), 5.12 (s, 2H), 3.75 (d, 2H), 1.14 (m, 1H), 0.57 (m, 2H), 0.28 (m, 2H).

Example 7

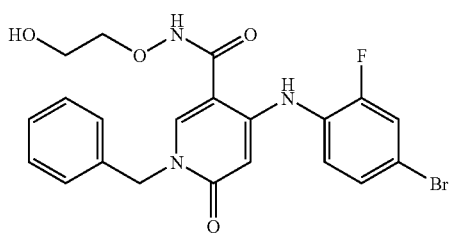

1-Benzyl-4-(4-bromo-2-fluorophenylamino)-6-oxo-1,6-dihydropyridine-3-carboxylic acid (2-hydroxyethoxy) amide MS APCI (−) m/z 474, 476 (M−, Br pattern) detected; $^1$H NMR (400 mHz, CD$_3$OD) δ 8.10 (s, 1H), 7.49 (d, 1H), 7.40 (m, 2H), 7.33 (m, 6H), 5.12 (s, 2H), 4.03 (t, 2H), 3.77 (t, 2H).

The following compounds were prepared as previously described with the addition of a chlorination step. An example of such a chlorination is described below.

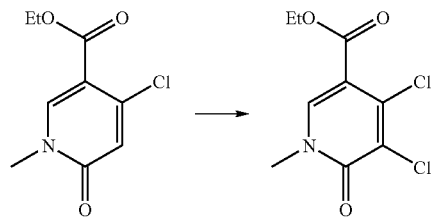

A mixture of 4-chloro-1-methyl-6-oxo-1,6-dihydropyridine-3-carboxylic acid ethyl ester (1.00 g, 4.64 mmol) and NCS (0.68 g, 5.10 mmol) in DMF (30 mL) was stirred for 1 hour. The reaction mixture was diluted with EtOAc and washed with 0.1 N HCl solution. The organic layer was dried (MgSO$_4$) and concentrated under reduced pressure to give 1.10 g (95%) of 4,5-dichloro-1-methyl-6-oxo-1,6-dihydropyridine-3-carboxylic acid ethyl ester.

Example 8

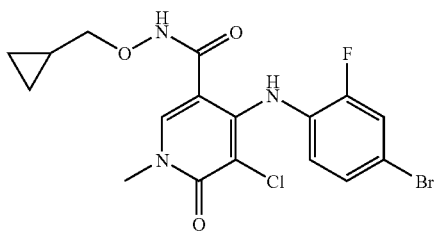

4-(4-Bromo-2-fluorophenylamino)-5-chloro-1-methyl-6-oxo-1,6-dihydropyridine-3-carboxylic acid cyclopropylmethoxy amide MS APCI (+) m/z 444, 446 (M+, Cl, Br pattern) detected; $^1$H NMR (400 mHz, DMSO-d$_6$) δ 11.52 (s, 1H), 8.78 (s, 1H), 7.98 (s, 1H), 7.52 (dd, 1H), 7.29 (dd, 1H), 6.93 (t, 1H), 3.47 (s, 3H), 3.40 (d, 2H), 1.01 (m, 1H), 0.50 (m, 2H), 0.20 (m, 2H).

Example 9

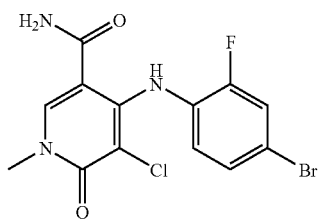

4-(4-Bromo-2-fluorophenylamino)-5-chloro-1-methyl-6-oxo-1,6-dihydropyridine-3-carboxylic acid amide MS APCI (+) m/z 374, 376 (M+, Cl, Br pattern) detected; $^1$H NMR (400 mHz, DMSO-d$_6$) δ 10.16 (s, 1H), 8.33 (s, 1H), 7.99 (br. s, 1H), 7.64 (br. s, 1H), 7.55 (dd, 1H), 7.30 (dd, 1H), 6.90 (m, 1H), 3.48 (s, 3H).

Example 10

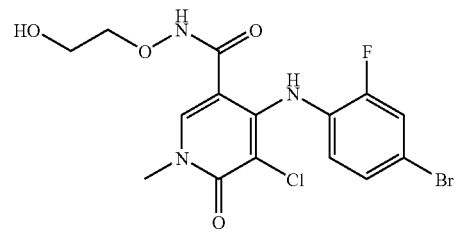

4-(4-Bromo-2-fluorophenylamino)-5-chloro-1-methyl-6-oxo-1,6-dihydropyridine-3-carboxylic acid (2-hydroxyethoxy)-amide MS APCI (+) m/z 434, 436 (M+, Cl, Br pattern) detected; $^1$H NMR (400 mHz, DMSO-d$_6$) δ 11.60 (s, 1H), 8.82 (s, 1H), 8.03 (s, 1H), 7.52 (dd, 1H), 7.28 (d, 1H), 6.92 (t, 1H), 4.69 (t, 1H), 3.68 (m, 2H), 3.52 (m, 2H), 3.47 (s, 3H).

Example 11

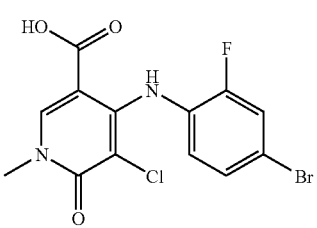

4-(4-Bromo-2-fluorophenylamino)-5-chloro-1-methyl-6-oxo-1,6-dihydropyridine-3-carboxylic acid MS APCI (+) m/z 375, 377 (M+, Cl, Br pattern) detected; $^1$H NMR (400 mHz, DMSO) δ 9.58 (s, 1H), 8.58 (s, 1H), 7.57 (dd, 1H), 7.33 (d, 1H), 7.0 (t, 1H), 3.53 (s, 3H).

Example 12

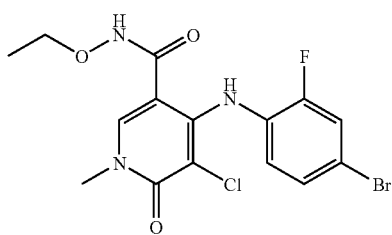

4-(4-Bromo-2-fluorophenylamino)-5-chloro-1-methyl-6-oxo-1,6-dihydropyridine-3-carboxylic acid ethoxy-amide MS APCI (+) m/z 418, 420 (M+, Cl, Br pattern) detected; $^1$H NMR (400 mHz, CD$_3$OD) δ 7.85 (s, 1H), 7.34 (dd, 1H), 7.26 (dd, 1H), 6.97 (t, 1H), 3.69 (q, 2H), 3.58 (s, 3H), 1.20 (t, 3H).

Example 13

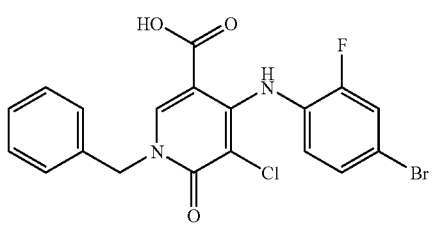

1-Benzyl-4-(4-bromo-2-fluorophenylamino)-5-chloro-6-oxo-1,6-dihydropyridine-3-carboxylic acid MS APCI (−) m/z 449, 451 (M−, Cl, Br pattern) detected; $^1$H NMR (400 mHz, DMSO-d$_6$) δ 9.66 (s, 1H), 8.67 (s, 1H), 7.56 (d, 1H), 7.34 (m, 6H), 7.03 (t, 1H), 5.23 (s, 2H).

Example 14

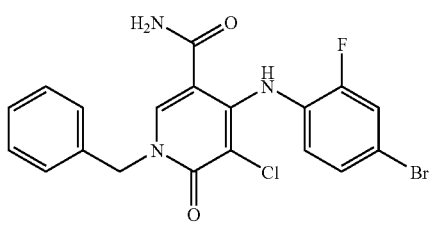

1-Benzyl-4-(4-bromo-2-fluorophenylamino)-5-chloro-6-oxo-1,6-dihydropyridine-3-carboxylic acid amide MS APCI (−) m/z 448, 450 (M−, Cl, Br pattern) detected; $^1$H NMR (400 mHz, DMSO-D$_6$) δ 10.21 (s, 1H), 8.45 (s, 1H), 8.07 (br. s, 1H), 7.65 (br. s, 1H), 7.53 (dd, 1H), 7.33 (m, 6H), 6.94 (t, 1H), 5.12 (s, 2H).

Example 15

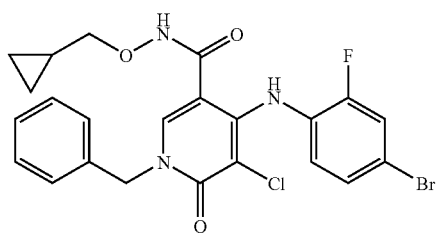

1-Benzyl-4-(4-bromo-2-fluorophenylamino)-5-chloro-6-oxo-1,6-dihydropyridine-3-carboxylic acid cyclopropylmethoxy-amide MS APCI (−) m/z 518, 520 (M−, Cl, Br pattern) detected; $^1$H NMR (400 mHz, DMSO-d$_6$) δ 8076 (s, 1H), 8.08 (s, 1H), 7.51 (d, 1H), 7.35 (m, 6H), 6.96 (t, 1H), 5.11 (s, 2H), 3.36 (d, 2H), 0.99 (m, 1H), 0.49 (m, 2H), 0.19 (m, 2H).

Example 16

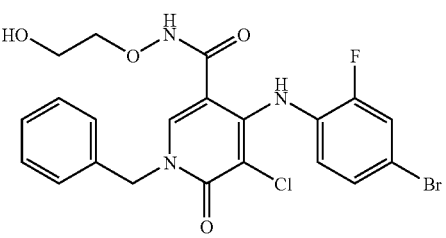

1-Benzyl-4-(4-bromo-2-fluorophenylamino)-5-chloro-6-oxo-1,6-dihydropyridine-3-carboxylic acid (2-hydroxyethoxy)-amide MS APCI (−) m/z 508, 510 (M−, Cl, Br pattern) detected; $^1$H NMR (400 mHz, DMSO-d$_6$) δ 8.80 (s, 1H), 8.13 (s, 1H), 7.51 (dd, 1H), 7.35 (m, 6H), 7.27 (d, 1H), 6.95 (t, 1H), 5.12 (s, 2H), 4.67 (t, 1H), 3.65 (m, 2H), 3.51 (m, 2H).

The following compounds were prepared as previously described with the addition of a fluorination step. An example of such a fluorination is described below.

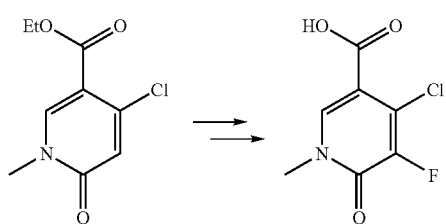

A mixture of 4-chloro-1-methyl-6-oxo-1,6-dihydropyridine-3-carboxylic acid ethyl ester (1.00 g, 4.64 mmol), LiOH (0.22 g, 9.30 mmol) and [1-(chloromethyl)-4-fluoro-1,4-diazoniabicyclo[2.2.2]octane-bis(tetrafluoroborate) (3.30 g, 9.30 mmol) in MeCN (50 mL) was stirred at 85° C. for 1 hour. The reaction was cooled to room temperature and concentrated under reduced pressure. The residue was dissolved in water and extracted with EtOAc. The combined organic extracts were dried (MgSO$_4$) and concentrated under reduced pressure. Flash column chromatography (60:40 hexanes:EtOAc) removed starting material. The partially purified ethyl ester was then hydrolyzed by dissolving in 4:1 THF:MeOH (10 mL) followed by treatment with 1 M LiOH solution (2.8 mL). After 1 hour, the reaction mixture was acidified to pH 1 with 10% HCl solution and extracted with EtOAc. The combined organic extracts were washed with brine, dried (MgSO$_4$) and concentrated to yield 0.25 g (26% for two steps) 4-chloro-5-fluoro-1-methyl-6-oxo-1,6-dihydropyridine-3-carboxylic acid, which could be further purified by trituration with diethyl ether.

Example 17

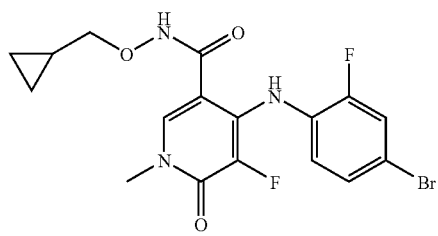

4-(4-Bromo-2-fluorophenylamino)-5-fluoro-1-methyl-6-oxo-1,6-dihydropyridine-3-carboxylic acid cyclopropylmethoxy-amide MS APCI (+) m/z 428, 430 (M+, Br pattern) detected; $^1$H NMR (400 mHz, CD$_3$OD) δ 7.85 (s, 1H), 7.36 (dd, 1H), 7.28 (d, 1H), 7.01 (m, 1H), 3.69 (d, 2H), 3.57 (s, 3H), 0.89 (m, 1H), 0.58 (m, 2H), 0.30 (m, 2H).

Example 18

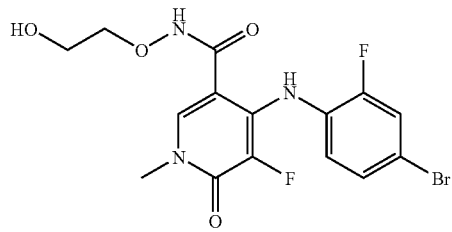

4-(4-Bromo-2-fluorophenylamino)-5-fluoro-1-methyl-6-oxo-1,6-dihydropyridine-3-carboxylic acid (2-hydroxyethoxy)-amide MS APCI (+) m/z 418, 420 (M+, Br pattern) detected; $^1$H NMR (400 mHz, CD$_3$OD) δ 7.90 (s, 1H), 7.36 (dd, 1H), 7.28 (dd, 1H), 7.01 (m, 1H), 3.98 (m, 2H), 3.75 (m, 2H), 3.58 (s, 3H).

Example 19

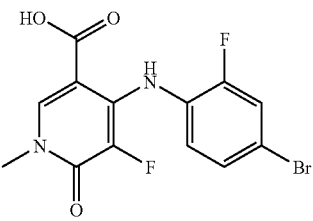

4-(4-Bromo-2-fluorophenylamino)-5-fluoro-1-methyl-6-oxo-1,6-dihydropyridine-3-carboxylic acid MS APCI (−) m/z 357, 359 (M−1, Br pattern) detected; $^1$H NMR (400 mHz, CD$_3$OD) δ 8.33 (s, 1H), 7.30 (d, 1H), 7.26 (d, 1H), 7.03 (td, 1H), 3.62 (s, 3H).

Example 20

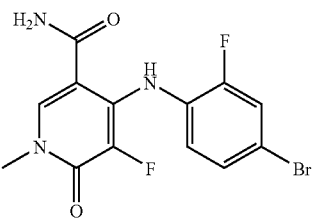

4-(4-Bromo-2-fluorophenylamino)-5-fluoro-1-methyl-6-oxo-1,6-dihydropyridine-3-carboxylic acid amide MS (+) m/z 358, 360 (M+, Br pattern) detected; $^1$H NMR (400 mHz, CD$_3$OD) δ 8.11 (s, 1H), 7.36 (dd, 1H), 7.28 (dd, 1H), 7.02 (m, 1H), 3.58 (s, 3H).

Example 21

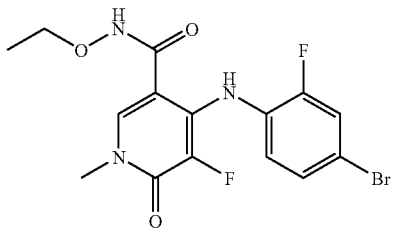

4-(4-Bromo-2-fluorophenylamino)-5-fluoro-1-methyl-6-oxo-1,6-dihydropyridine-3-carboxylic acid ethoxy-amide MS APCI (+) m/z 402, 404 (M+, Br pattern) detected; $^1$H NMR (400 mHz, CD$_3$OD) δ 7.87 (s, 1H), 7.35 (dd, 1H), 7.27 (d, 1H), 7.01 (td, 1H), 3.94 (q, 2H), 3.58 (s, 3H), 1.27 (t, 3H).

Example 22

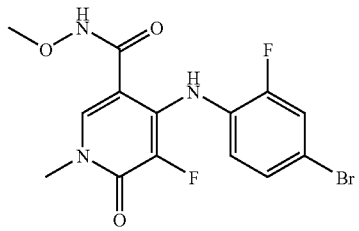

4-(4-Bromo-2-fluorophenylamino)-5-fluoro-1-methyl-6-oxo-1,6-dihydropyridine-3-carboxylic acid methoxy-amide MS APCI (+) m/z 388, 390 (M+, Br pattern) detected; $^1$H NMR (400 mHz, CD$_3$OD) δ 7.87 (s, 1H), 7.35 (dd, 1H), 7.27 (d, 1H), 7.01 (td, 1H), 3.75 (s, 3H), 3.58 (s, 3H).

Example 23

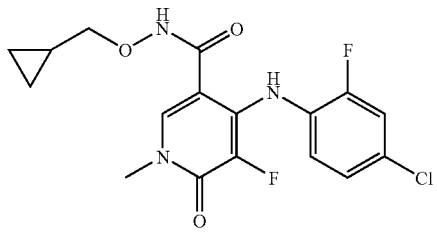

4-(4-Chloro-2-fluorophenylamino)-5-fluoro-1-methyl-6-oxo-1,6-dihydropyridine-3-carboxylic acid cyclopropylmethoxy-amide MS APCI (+) m/z 384, 386 (M+, Cl pattern) detected; $^1$H NMR (400 mHz, CD$_3$OD) δ 7.56 (s, 1H), 6.93 (dd, 1H), 6.85 (d, 1H), 6.79 (td, 1H), 3.41 (d, 2H), 3.28 (s, 3H), 0.87 (m, 1H), 0.29 (q, 2H), 0.01 (q, 2H).

Example 24

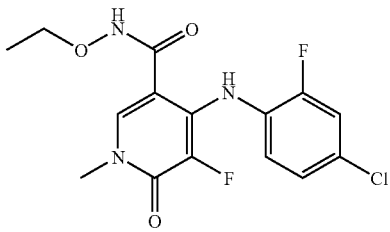

4-(4-Chloro-2-fluorophenylamino)-5-fluoro-1-methyl-6-oxo-1,6-dihydropyridine-3-carboxylic acid ethoxy-amide MS APCI (+) m/z 358, 360 (M+, Cl pattern) detected; $^1$H NMR (400 mHz, CD$_3$OD) δ 7.88 (s, 1H), 7.22 (d, 1H), 7.14 (d, 1H), 7.08 (td, 1H), 3.95 (q, 2H), 3.58 (s, 3H), 1.28 (t, 3H).

Example 25

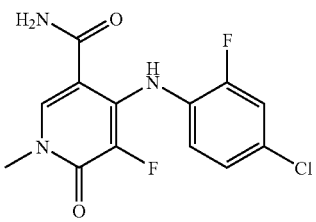

4-(4-Chloro-2-fluorophenylamino)-5-fluoro-1-methyl-6-oxo-1,6-dihydropyridine-3-carboxylic acid amide MS APCI (+) m/z 314, 316 (M+, Cl pattern) detected; $^1$H NMR (400 mHz, DMSO) δ 9.96 (s, 1H), 8.23 (s, 1H), 7.99 (bs, 1H), 7.64 (bs, 1H), 7.45 (dd, 1H), 7.21 (d, 1H), 7.09 (td, 1H), 3.46 (s, 3H).

Example 26

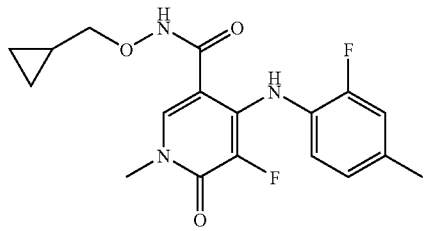

5-Fluoro-4-(2-fluoro-4-methylphenylamino)-1l-methyl-6-oxo-1,6-dihydropyridine-3-carboxylic acid cyclopropylmethoxy-amide MS APCI (+) m/z 364 (M+1) detected; $^1$H NMR (400 mHz, CD$_3$OD) δ 7.82 (s, 1H), 7.0 (td, 1H), 6.94 (d, 1H), 6.93 (s, 1H), 3.69 (d, 2H), 3.56 (s, 3H), 2.32 (s, 3H), 1.16 (m, 1H), 0.58 (q, 2H), 0.30 (q, 2H).

Example 27

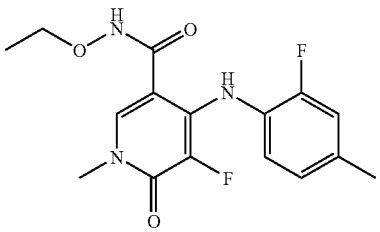

5-Fluoro-4-(2-fluoro-4-methylphenylamino)-1-methyl-6-oxo-1,6-dihydropyridine-3-carboxylic acid ethoxy-amide MS APCI (+) m/z 338 (M+1) detected; ¹H NMR (400 mHz, CD₃OD) δ 7.85 (s, 1H), 7.0 (td, 1H), 6.94 (d, 1H), 6.93 (s, 1H), 3.93 (q, 2H), 3.56 (s, 3H), 2.32 (s, 3H), 1.27 (t, 3H).

Example 28

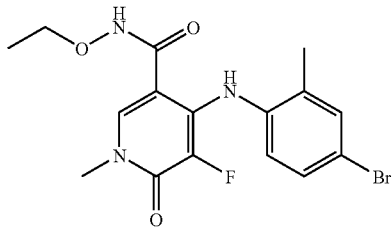

4-(4-Bromo-2-methylphenylamino)-5-fluoro-1-methyl-6-oxo-1,6-dihydropyridine-3-carboxylic acid ethoxy-amide MS APCI (+) m/z 398, 400 (M+, Br pattern) detected; ¹H NMR (400 mHz, CD₃OD) δ 7.84 (s, 1H), 7.35 (s, 1H), 7.25 (dd, 1H), 6.85 (dd, 1H), 3.92 (q, 2H), 3.57 (s, 3H), 2.30 (s, 3H), 1.28 (t, 3H).

Example 29

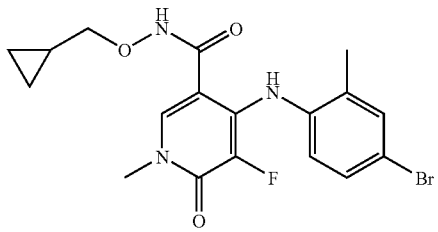

4-(4-Bromo-2-methylphenylamino)-5-fluoro-1-methyl-6-oxo-1,6-dihydropyridine-3-carboxylic acid cyclopropylmethoxy-amide MS APCI (+) m/z 424, 426 (M+, Br pattern) detected; ¹H NMR (400 mHz, CD₃OD) δ 7.82 (s, 1H), 7.35 (s, 1H), 7.25 (dd, 1H), 6.85 (dd, 1H), 3.67 (d, 2H), 3.57 (s, 3H), 2.29 (s, 3H), 1.16 (m, 1H), 0.59 (q, 2H), 0.31 (q, 2H).

Example 30

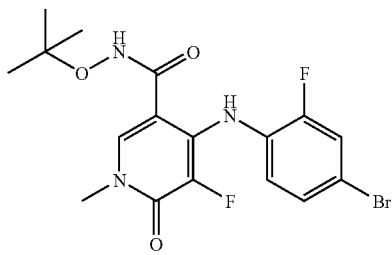

4-(4-Bromo-2-fluorophenylamino)-5-fluoro-1-methyl-6-oxo-1,6-dihydropyridine-3-carboxylic acid tert-butoxy-amide MS APCI (+) m/z 430, 432 (M+, Br pattern) detected; ¹H NMR (400 mHz, CD₃OD) δ 7.94 (s, 1H), 7.36 (dd, 1H), 7.28 (d, 1H), 7.01 (td, 1H), 3.60 (s, 3H), 1.30 (s, 9H).

Example 31

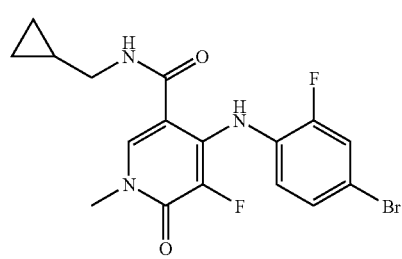

4-(4-Bromo-2-fluorophenylamino)-5-fluoro-1-methyl-6-oxo-1,6-dihydropyridine-3-carboxylic acid cyclopropylmethyl-amide MS APCI (+) m/z 412, 414 (M+, Br pattern) detected; ¹H NMR (400 mHz, CD₃OD) δ 7.97 (s, 1H), 7.32 (dd, 1H), 7.25 (d, 1H), 6.98 (td, 1H), 3.60 (s, 3H), 3.15 (d, 2H), 1.04 (m, 1H), 0.54 (q, 2H), 0.26 (q, 2H).

Example 32

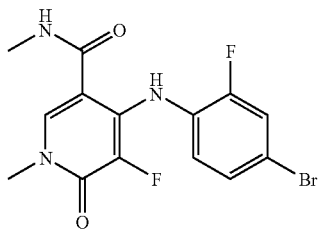

4-(4-Bromo-2-fluorophenylamino)-5-fluoro-1-methyl-6-oxo-1,6-dihydropyridine-3-carboxylic acid methylamide MS APCI (+) m/z 372, 374 (M+, Br pattern) detected; ¹H NMR (400 mHz, CD₃OD) δ 7.93 (s, 1H), 7.35 (dd, 1H), 7.27 (d, 1H), 7.0 (td, 1H), 3.57 (s, 3H), 2.83 (s, 3H).

Example 33

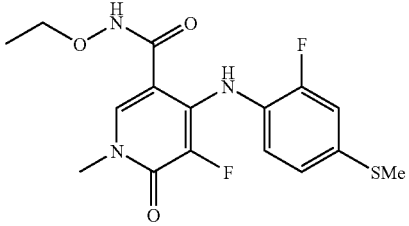

5-Fluoro-4-(2-fluoro-4-methylsulfanyl-phenylamino)-1-methyl-6-oxo-1,6-dihydropyridine-3-carboxylic acid ethoxy-amide Prepared as described previously using 2-fluoro-4-methylsulfanyl-phenylamine, which was prepared according to WO 03/062191.

MS APCI (+) m/z 370 (M+1) detected; ¹H NMR (400 mHz, CD₃OD) δ 7.83 (s, 1H), 7.03 (m, 3H), 3.96 (q, 2H), 3.58 (s, 3H), 2.48 (s, 3H), 1.29 (t, 3H).

Example 34

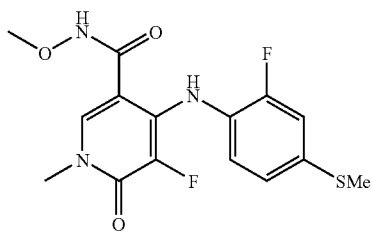

5-Fluoro-4-(2-fluoro-4-methylsulfanyl-phenylamino)-1-methyl-6-oxo-1,6-dihydropyridine-3-carboxylic acid methoxy-amide MS APCI (+) m/z 370 (M+1) detected; ¹H NMR (400 mHz, CD₃OD) δ 7.83 (s, 1H), 7.03 (m, 3H), 3.96 (q, 2H), 3.58 (s, 3H), 2.48 (s, 3H), 1.29 (t, 3H).

Example 35

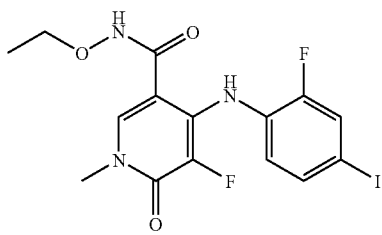

5-Fluoro-4-(2-fluoro-4-iodophenylamino)-1l-methyl-6-oxo-1,6-dihydropyridine-3-carboxylic acid ethoxy-amide MS APCI (+) m/z 450 (M+1) detected; ¹H NMR (400 mHz, CD₃OD) δ 7.86 (s, 1H), 7.48 (dd, 1H), 7.44 (d, 1H), 6.84 (td, 1H), 3.95 (q, 2H), 3.58 (s, 3H), 1.28 (t, 3H).

Example 36

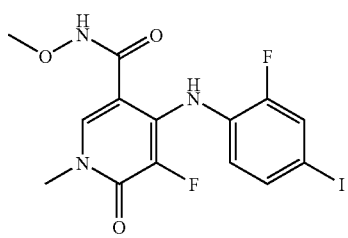

5-Fluoro-4-(2-fluoro-4-iodophenylamino)-1-methyl-6-oxo-1,6-dihydropyridine-3-carboxylic acid methoxy-amide MS APCI (+) m/z 436 (M+1) detected; ¹H NMR (400 mHz, CD₃OD) δ 7.84 (s, 1H), 7.47 (dd, 1H), 7.44 (d, 1H), 6.83 (td, 1H), 3.77 (s, 3H), 3.59 (s, 3H).

Example 37

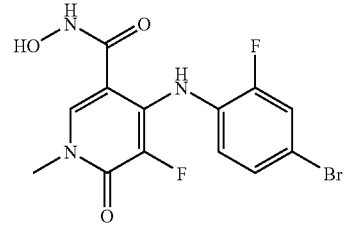

4-(4-Bromo-2-fluorophenylamino)-5-fluoro-1-methyl-6-oxo-1,6-dihydropyridine-3-carboxylic acid hydroxyamide 4-(4-Bromo-2-fluorophenylamino)-5-fluoro-1-methyl-6-oxo-1,6-dihydropyridine-3-carboxylic acid hydroxyamide was prepared from 4-(4-bromo-2-fluorophenylamino)-5-fluoro-1-methyl-6-oxo-1,6-dihydropyridine-3-carboxylic acid tert-butoxy-amide by TFA mediated deprotection. 4-(4-Bromo-2-fluorophenylamino)-5-fluoro-1-methyl-6-oxo-1,6-dihydropyridine-3-carboxylic acid tert-butoxy-amide (35 mg, 0.081 mmol) was treated with TFA (0.63 mL). After 4 days stirring, the reaction mixture was concentrated under reduced pressure. Purification by flash column chromatography (10% MeOH in methylene chloride) followed by saturated NaHCO₃ solution wash of an ethyl acetate solution of the product gave clean desired product (10 mg, 33%); MS APCI (+) m/z 356, 358 (M–OH, Br pattern) detected; ¹H NMR (400 mHz, CD₃OD) δ 7.84 (s, 1H), 7.35 (dd, 1H), 7.28 (d, 1H), 7.01 (td, 1H), 3.57 (s, 3H).

Example 38

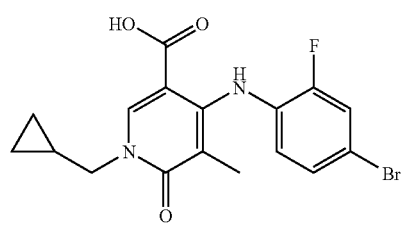

4-(4-Bromo-2-fluorophenylamino)-1-cyclopropylmethyl-5-methyl-6-oxo-1,6-dihydropyridine-3-carboxylic acid MS APCI (−) m/z 393, 395 (M−, Br pattern) detected; ¹H NMR (400 MHz, DMSO-d₆) δ 9.12 (s, 1H), 8.51 (s, 1H), 7.56

(d, 1H), 7.28 (d, 1H), 6.69 (t, 1H), 3.84 (d, 2H), 1.61 (s, 3H), 1.25 (m, 1H), 0.50 (q, 2H), 0.39 (q, 2H).

Example 39

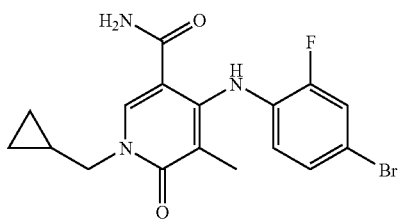

4-(4-Bromo-2-fluorophenylamino)-1-cyclopropylm-ethyl-5-methyl-6-oxo-1,6-dihydropyridine-3-carboxylic acid amide MS APCI (−) m/z 392, 394 (M−, Br pattern) detected; $^1$H NMR (400 MHz, CD$_3$OD) δ 8.14 (s, 1H), 7.33 (d, 1H), 7.21 (d, 1H), 6.63 (t, 1H), 3.87 (d, 2H), 1.76 (s, 3H), 1.35 (m, 1H), 0.60 (q, 2H), 0.46 (q, 2H).

Example 40

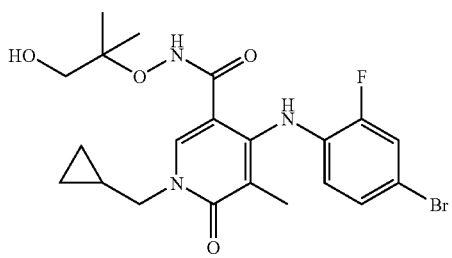

4-(4-Bromo-2-fluorophenylamino)-1-cyclopropylm-ethyl-5-methyl-6-oxo-1,6-dihydropyridine-3-carboxylic acid (2-hydroxy-1,1-dimethylethoxy)-amide MS APCI (−) m/z 480, 482 (M−, Br pattern) detected; $^1$H NMR (400 MHz, DMSO-d$_6$) δ 11.06 (s, 1H), 8.36 (s, 1H), 8.02 (s, 1H), 7.50 (d, 1H), 7.22 (d, 1H), 6.57 (t, 1H), 4.60 (t, 1H), 3.78 (d, 2H), 3.16 (m, 2H), 1.71 (s, 3H), 1.29 (m, 1H), 1.11 (s, 6H), 0.51 (q, 2H), 0.43 (q, 2H).

Example 41

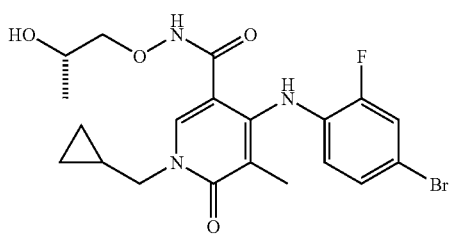

(S)-4-(4-Bromo-2-fluorophenylamino)-1-cyclopro-pylmethyl-5-methyl-6-oxo-1,6-dihydropyridine-3-carboxylic acid (2-hydroxy-propoxy)-amide MS APCI (−) m/z 466, 468 (M−, Br pattern) detected; $^1$H NMR (400 MHz, CD$_3$OD) δ 7.93 (s, 1H), 7.34 (dd, 1H), 7.20 (d, 1H), 6.66 (t, 1H), 3.88 (m, 1H), 3.86 (d, 2H), 3.71 (dd, 1H), 3.59 (dd, 1H), 1.86 (s, 3H), 1.33 (m, 1H), 1.12 (d, 3H), 0.91 (q, 2H), 0.46 (q, 2H).

Example 42

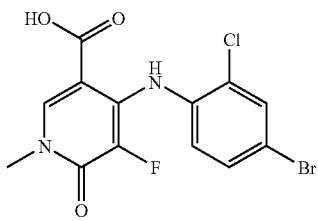

4-(4-Bromo-2-chlorophenylamino)-5-fluoro-1-me-thyl-6-oxo-1,6-dihydropyridine-3-carboxylic acid MS APCI (−) m/z 373, 375 (M−, Cl, Br pattern) detected; $^1$H NMR (400 mHz, CD$_3$OD) δ 8.43 (s, 1H), 7.62 (s, 1H), 7.42 (dd, 1H), 7.01 (m, 1H), 3.61 (s, 3H).

Example 43

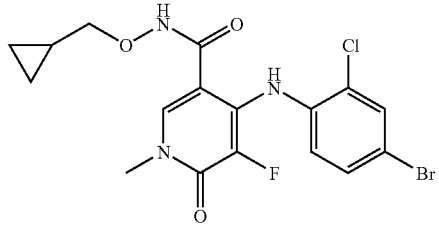

4-(4-Bromo-2-chlorophenylamino)-5-fluoro-1-me-thyl-6-oxo-1,6-dihydropyridine-3-carboxylic acid cyclopropylmethoxy-amide MS APCI (+) m/z 444, 446 (M+, Cl, Br pattern) detected; $^1$H NMR (400 mHz, CD$_3$OD) δ 7.89 (s, 1H), 7.60 (d, 1H), 7.39 (dd, 1H), 6.92 (dd, 1H), 3.73 (d, 2H), 3.59 (s, 3H), 1.17 (m, 1H), 0.58 (m, 2H), 0.30 (m, 2H).

Example 44

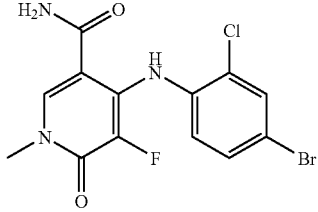

4-(4-Bromo-2-chlorophenylamino)-5-fluoro-1-methyl-6-oxo-1,6-dihydropyridine-3-carboxylic acid amide MS APCI (+) m/z 374, 376 (M+, Cl, Br pattern) detected; $^1$H NMR (400 mHz, CD$_3$OD) δ 8.13 (s, 1H), 7.59 (d, 1H), 7.39 (dd, 1H), 6.92 (dd, 1H), 3.60 (s, 3H).

Example 45

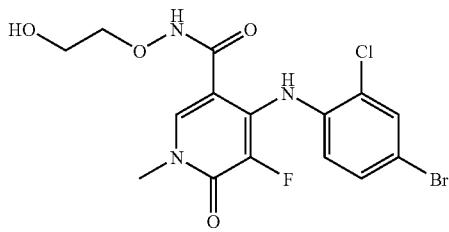

4-(4-Bromo-2-chlorophenylamino)-5-fluoro-1-methyl-6-oxo-1,6-dihydropyridine-3-carboxylic acid (2-hydroxyethoxy)-amide MS APCI (+) m/z 434, 436 (M+, Cl, Br pattern) detected; $^1$H NMR (400 mHz, CD$_3$OD) δ 7.94 (s, 1H), 7.60 (d, 1H), 7.40 (dd, 1H), 6.92 (dd, 1H), 4.01 (m, 2H), 3.76 (m, 2H), 3.59 (s, 3H).

Example 46

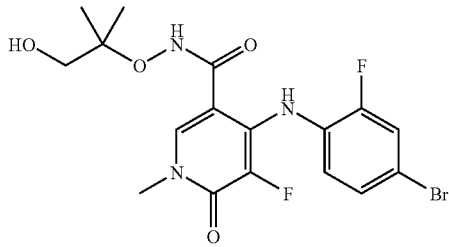

4-(4-Bromo-2-fluorophenylamino)-5-fluoro-1-methyl-6-oxo-1,6-dihydropyridine-3-carboxylic acid (2-hydroxy-1,1-dimethylethoxy)-amide MS APCI (+) m/z 446, 448 (M+, Br pattern) detected; $^1$H NMR (400 mHz, CD$_3$OD) δ 7.94 (s, 1H), 7.36 (d, 1H), 7.28 (d, 1H), 7.02 (td, 1H), 3.59 (s, 3H), 3.41 (s, 2H), 1.27 (s, 6H).

Example 47

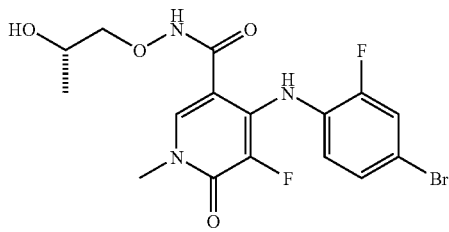

(S)-4-(4-Bromo-2-fluorophenylamino)-5-fluoro-1-methyl-6-oxo-1,6-dihydropyridine-3-carboxylic acid (2-hydroxy-propoxy)-amide MS APCI (+) m/z 432, 434 (M+, Br pattern) detected; $^1$H NMR (400 mHz, CD$_3$OD) δ 7.89 (s, 1H), 7.36 (d, 1H), 7.28 (d, 1H), 7.02 (td, 1H), 3.99 (m, 1H), 3.83 (dd, 1H), 3.72 (dd, 1H), 3.58 (s, 3H), 1.16 (d, 3H).

The following compounds were prepared as previously described by using the appropriate amine in place of methylamine in Step A of Example 1.

Example 48

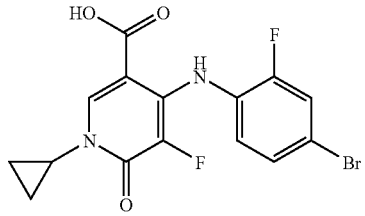

4-(4-Bromo-2-fluorophenylamino)-1-cyclopropyl-5-fluoro-6-oxo-1,6-dihydropyridine-3-carboxylic acid MS APCI (+) m/z 385, 387 (M+, Br pattern) detected; $^1$H NMR (400 mHz, DMSO-D$_6$) δ 9.29 (s, 1H), 8.08 (s, 1H), 7.58 (dd, 1H), 7.36 (d, 1H), 7.12 (m, 1H), 3.35 (m, 1H), 1.02 (m, 2H), 0.90 (m, 2H).

Example 49

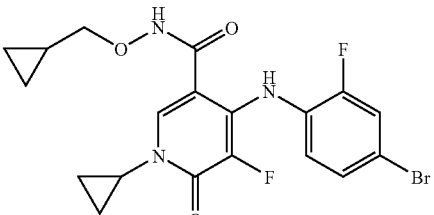

4-(4-Bromo-2-fluorophenylamino)-1-cyclopropyl-5-fluoro-6-oxo-1,6-dihydropyridine-3-carboxylic acid cyclopropylmethoxy-amide MS APCI (+) m/z 454, 456 (M+, Br pattern) detected; $^1$H NMR (400 mHz, DMSO-D$_6$) δ 11.78 (s, 1H), 9.07 (s, 1H), 7.70 (s, 1H), 7.55 (dd, 1H), 7.32 (dd, 1H), 7.03 (m, 1H), 3.66 (d, 2H), 3.35 (m, 1H), 1.07 (m, 1H), 0.98 (m, 4H), 0.53 (m, 2H), 0.25 (m, 2H).

Example 50

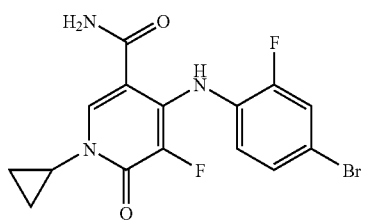

4-(4-Bromo-2-fluorophenylamino)-1-cyclopropyl-5-fluoro-6-oxo-1,6-dihydropyridine-3-carboxylic acid amide MS APCI (+) m/z 384, 386 (M+, Br pattern) detected; ¹H NMR (400 mHz, DMSO-D₆) δ 10.03 (s, 1H), 8.24 (br. s, 1H), 7.95 (s, 1H), 7.63 (br. s, 1H), 7.56 (dd, 1H), 7.33 (d, 1H), 7.00 (m, 1H), 3.35 (m, 1H), 0.99 (m, 4H).

Example 51

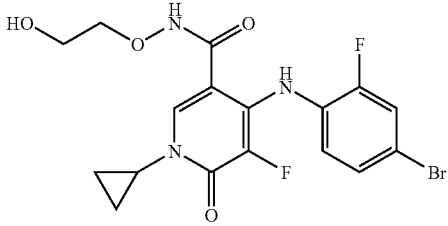

4-(4-Bromo-2-fluorophenylamino)-1-cyclopropyl-5-fluoro-6-oxo-1,6-dihydropyridine-3-carboxylic acid (2-hydroxyethoxy)-amide MS APCI (+) m/z 444, 446 (M+, Br pattern) detected; ¹H NMR (400 mHz, DMSO-D₆) δ 11.87 (s, 1H), 9.09 (s, 1H), 7.74 (s, 1H), 7.56 (dd, 1H), 7.32 (d, 1H), 7.02 (m, 1H), 3.89 (m, 2H), 3.59 (m, 2H), 3.38 (m, 1H), 0.99 (m, 4H).

Example 52

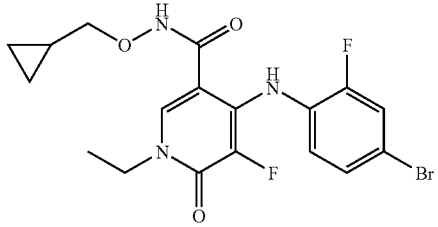

4-(4-Bromo-2-fluorophenylamino)-1-ethyl-5-fluoro-6-oxo-1,6-dihydropyridine-3-carboxylic acid cyclopropylmethoxy-amide MS APCI (+) m/z 442, 444 (M+, Br pattern) detected; ¹H NMR (400 mHz, CD₃OD) δ 7.85 (s, 1H), 7.36 (dd, 1H), 7.28 (d, 1H), 7.02 (td, 1H), 4.05 (q, 2H), 3.70 (d, 2H), 1.36 (t, 3H), 1.17 (m, 1H), 0.58 (q, 2H), 0.31 (q, 2H).

Example 53

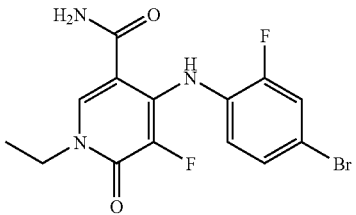

4-(4-Bromo-2-fluorophenylamino)-1-ethyl-5-fluoro-6-oxo-1,6-dihydropyridine-3-carboxylic acid amide MS APCI (+) m/z 372, 374 (M+, Br pattern) detected; ¹H NMR (400 mHz, CD₃OD) δ 8.10 (s, 1H), 7.35 (dd, 1H), 7.28 (d, 1H), 7.02 (td, 1H), 4.05 (q, 2H), 1.37 (t, 3H).

Example 54

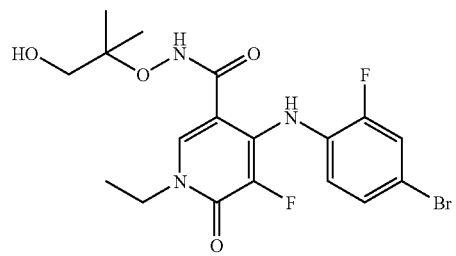

4-(4-Bromo-2-fluorophenylamino)-1-ethyl-5-fluoro-6-oxo-1,6-dihydropyridine-3-carboxylic acid (2-hydroxy-1,1-dimethylethoxy)-amide MS APCI (+) m/z 460, 462 (M+, Br pattern) detected; ¹H NMR (400 mHz, DMSO) δ 11.20 (bs, 1H), 8.80 (bs, 1H), 8.01 (s, 1H), 7.55 (d, 1H), 7.32 (d, 1H), 7.03 (td, 1H), 4.40 (q, 2H), 3.28 (s, 2H), 1.27 (t, 3H), 1.17 (s, 6H).

Example 55

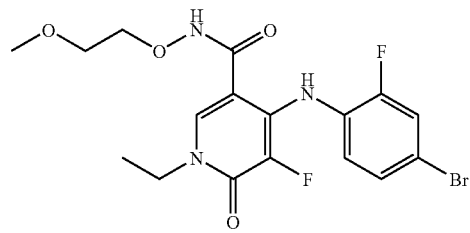

4-(4-Bromo-2-fluorophenylamino)-1-ethyl-5-fluoro-6-oxo-1,6-dihydropyridine-3-carboxylic acid (2-methoxy-ethoxy)-amide MS APCI (+) m/z 446, 448 (M+, Br pattern) detected; ¹H NMR (400 mHz, CD₃OD) δ 7.88 (s, 1H), 7.36 (dd, 1H), 7.28 (d, 1H), 7.02 (td, 1H), 4.05 (m, 4H), 3.64 (m, 2H), 3.37 (s, 3H), 1.37 (t, 3H).

Example 56

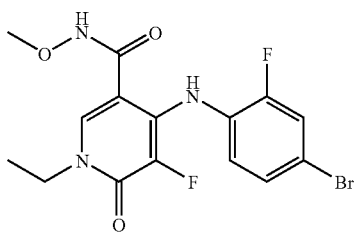

4-(4-Bromo-2-fluorophenylamino)-1-ethyl-5-fluoro-6-oxo-1,6-dihydropyridine-3-carboxylic acid methoxy-amide MS APCI (+) m/z 402, 404 (M+, Br pattern) detected; $^1$H NMR (400 mHz, CD$_3$OD) δ 7.87 (s, 1H), 7.36 (d, 1H), 7.29 (d, 1H), 7.02 (td, 1H), 4.02 (q, 2H), 3.75 (s, 3H), 1.36 (t, 3H).

Example 57

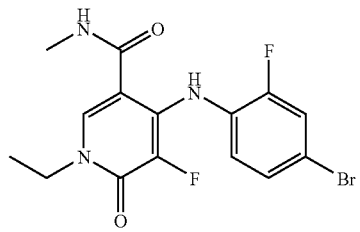

4-(4-Bromo-2-fluorophenylamino)-1-ethyl-5-fluoro-6-oxo-1,6-dihydropyridine-3-carboxylic acid methylamide MS APCI (+) m/z 386, 388 (M+, Br pattern) detected; $^1$H NMR (400 mHz, CD$_3$OD) δ 7.93 (s, 1H), 7.35 (dd, 1H), 7.27 (d, 1H), 7.0 (td, 1H), 4.04 (q, 2H), 2.83 (s, 3H), 1.37 (t, 3H).

Example 58

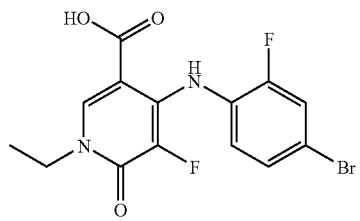

4-(4-Bromo-2-fluorophenylamino)-1-ethyl-5-fluoro-6-oxo-1,6-dihydropyridine-3-carboxylic acid MS APCI (−) m/z 371, 373 (M−, Br pattern) detected; $^1$H NMR (400 mHz, CD$_3$OD) δ 8.41 (s, 1H), 7.38 (d, 1H), 7.30 (d, 1H), 7.10 (td, 1H), 4.08 (q, 2H), 1.36 (t, 3H).

Example 59

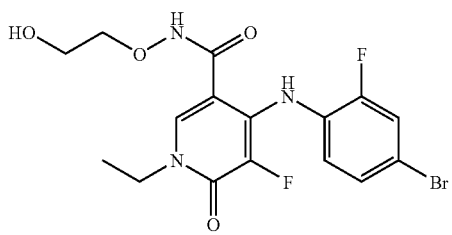

4-(4-Bromo-2-fluorophenylamino)-1-ethyl-5-fluoro-6-oxo-1,6-dihydropyridine-3-carboxylic acid (2-hydroxyethoxy)-amide MS APCI (+) m/z 432, 434 (M+, Br pattern) detected; $^1$H NMR (400 mHz, CD$_3$OD) δ 7.90 (s, 1H), 7.36 (dd, 1H), 7.28 (d, 1H), 7.02 (td, 1H), 4.05 (q, 2H), 3.99 (t, 2H), 3.75 (t, 2H), 1.37 (t, 3H).

Example 60

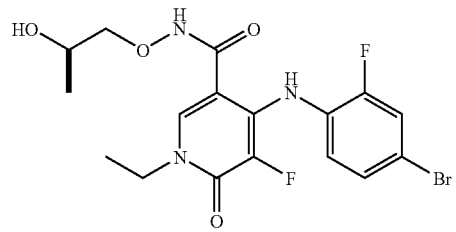

(R)-4-(4-Bromo-2-fluorophenylamino)-1-ethyl-5-fluoro-6-oxo-1,6-dihydropyridine-3-carboxylic acid (2-hydroxy-propoxy)-amide MS APCI (+) m/z 446, 448 (M+, Br pattern) detected; $^1$H NMR (400 mHz, CD$_3$OD) δ 7.90 (s, 1H), 7.36 (dd, 1H), 7.28 (d, 1H), 7.02 (td, 1H), 4.05 (q, 2H), 3.99 (m, 1H), 3.83 (dd, 1H), 3.73 (dd, 1H), 1.36 (t, 3H), 1.16 (d, 3H).

Example 61

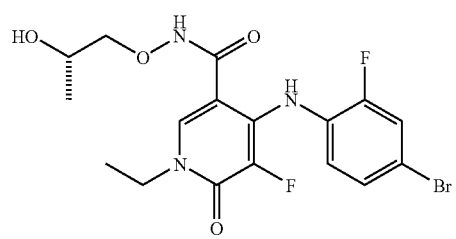

(S)-4-(4-Bromo-2-fluorophenylamino)-1-ethyl-5-fluoro-6-oxo-1,6-dihydropyridine-3-carboxylic acid (2-hydroxy-propoxy)-amide MS APCI (+) m/z 446, 448 (M+, Br pattern) detected; $^1$H NMR (400 mHz, CD$_3$OD) δ 7.90 (s, 1H), 7.36 (d, 1H), 7.28 (d, 1H), 7.02 (td, 1H), 4.04 (q, 2H), 3.99 (m, 1H), 3.83 (dd, 1H), 3.72 (dd, 1H), 1.36 (t, 3H), 1.16 (d, 3H).

Example 62

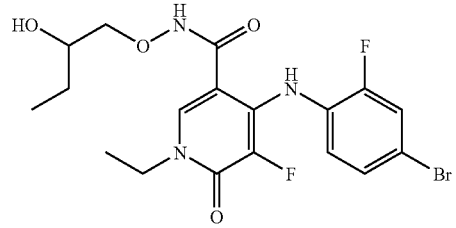

4-(4-Bromo-2-fluorophenylamino)-1-ethyl-5-fluoro-6-oxo-1,6-dihydropyridine-3-carboxylic acid (2-hydroxybutoxy)-amide MS APCI (+) m/z 460, 462 (M+, Br pattern) detected; $^1$H NMR (400 MHz, CD$_3$OD) δ 7.90 (s, 1H), 7.36 (dd, 1H), 7.28 (d, 1H), 7.02 (td, 1H), 4.05 (q, 2H), 3.89 (d, 1H), 3.75 (m, 2H), 1.54 (m, 1H), 1.45 (m, 1H), 1.36 (t, 3H), 0.98 (t, 3H).

Example 63

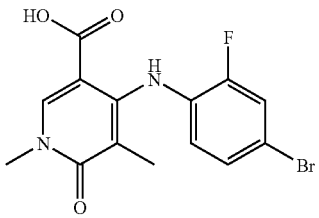

4-(4-Bromo-2-fluorophenylamino)-1,5-dimethyl-6-oxo-1,6-dihydropyridine-3-carboxylic acid Preparation of 4-hydroxy-1,5-dimethyl-6-oxo-1,6-dihydropyridine-3-carboxylic acid ethyl ester: Triethyl orthoformate (3.85 mL, 23.12 mmol) and acetic anhydride (4.37 mL, 46.25 mmol) were added to 2-methyl-3-oxo-pentanedioic acid diethyl ester (Caliskan et al *Aust. J. Chem.* 1999, 52 (11), 1013-1020) (5.0 g, 23.1 mmol) and the reaction mixture heated to 135° C. After 1 hour, the reaction mixture was cooled to room temperature and concentrated under reduced pressure. The residue was cooled to 0° C. and methylamine (40% in water, 5.0 mL, 57.81 mmol) was added with stirring. Water (20 mL) was added and the reaction mixture stirred for 16 hours. The reaction mixture was extracted with ethyl acetate and the aqueous layer acidified to pH 2 with 10% aqueous HCl. The acidified aqueous layer was extracted with ethyl acetate. The combined organic extracts were dried (MgSO$_4$) and concentrated to give a solid. Trituration with diethyl ether yielded 4.88 g (55%) clean desired product. 4-Hydroxy-1,5-dimethyl-6-oxo-1,6-dihydropyridine-3-carboxylic acid ethyl ester was carried forward as described in Example 1, Steps B-D. MS APCI (−) m/z 353, 355 (M−, Br pattern) detected; $^1$H NMR (400 mHz, CD$_3$OD) δ 8.49 (s, 1H), 7.36 (dd, 1H), 7.24 (dd, 1H), 6.71 (m, 1H), 3.60 (s, 3H), 1.68 (s, 3H).

The following compounds were prepared as described in Examples 1 (Steps B-D), 2, 3 and 63.

Example 64

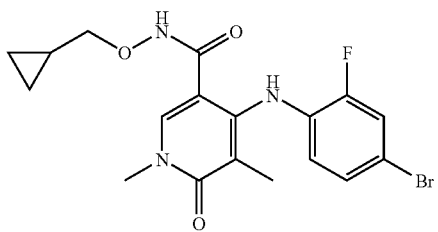

4-(4-Bromo-2-fluorophenylamino)-1,5-dimethyl-6-oxo-1,6-dihydropyridine-3-carboxylic acid cyclopropylmethoxy-amide MS APCI (+) m/z 424, 426 (M+, Br pattern) detected; $^1$H NMR (400 mHz, CD$_3$OD) δ 7.88 (s, 1H), 7.33 (dd, 1H), 7.20 (dd, 1H), 6.65 (m, 1H), 3.59 (d, 2H), 3.57 (s, 3H), 1.83 (s, 3H), 1.10 (m, 1H), 0.54 (m, 2H), 0.25 (m, 2H).

Example 65

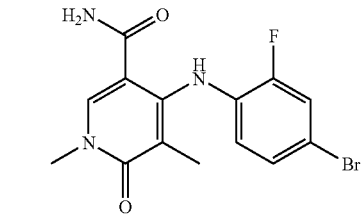

4-(4-Bromo-2-fluorophenylamino)-1,5-dimethyl-6-oxo-1,6-dihydropyridine-3-carboxylic acid amide MS APCI (+) m/z 354, 356 (M+, Br pattern) detected; $^1$H NMR (400 mHz, CD$_3$OD) δ 8.14 (s, 1H), 7.33 (dd, 1H), 7.20 (d, 1H), 6.63 (m, 1H), 3.58 (s, 3H), 1.75 (s, 3H).

Example 66

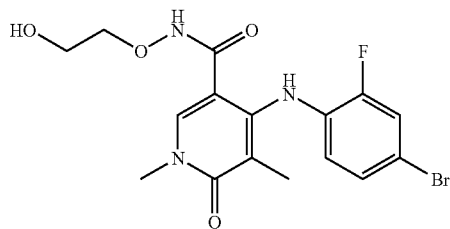

4-(4-Bromo-2-fluorophenylamino)-1,5-dimethyl-6-oxo-1,6-dihydropyridine-3-carboxylic acid (2-hydroxyethoxy)-amide MS APCI (+) m/z 414, 416 (M+, Br pattern) detected; $^1$H NMR (400 mHz, CD$_3$OD) δ 7.93 (s, 1H), 7.33 (dd, 1H), 7.20 (d, 1H), 6.65 (m, 1H), 3.88 (m, 2H), 3.68 (m, 2H), 3.57 (s, 3H), 1.83 (s, 3H).

Example 67

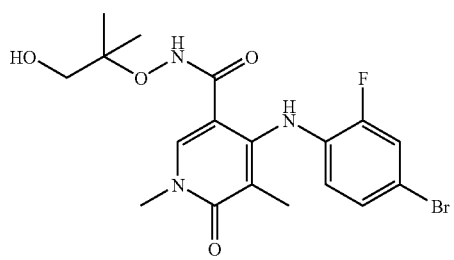

4-(4-Bromo-2-fluorophenylamino)-1,5-dimethyl-6-oxo-1,6-dihydropyridine-3-carboxylic acid (2-hydroxy-1,1-dimethylethoxy)-amide MS APCI (+) m/z 442, 444 (M+, Br pattern) detected; ¹H NMR (400 mHz, CD₃OD) δ 7.98 (s, 1H), 7.33 (dd, 1H), 7.20 (d, 1H), 6.62 (t, 1H), 3.59 (s, 3H), 1.82 (s, 3H), 1.21 (s, 6H).

Example 68

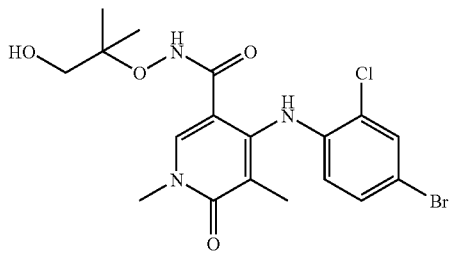

4-(4-Bromo-2-chlorophenylamino)-1,5-dimethyl-6-oxo-1,6-dihydropyridine-3-carboxylic acid (2-hydroxy-1,1-dimethylethoxy)-amide MS APCI (−) m/z 456, 458 (M−, Cl, Br pattern) detected; ¹H NMR (400 MHz, CD₃OD) δ 8.01 (s, 1H), 7.57 (d, 1H), 7.32 (dd, 1H), 6.52 (d, 1H), 3.60 (s, 3H), 3.34 (s, 2H), 1.76 (s, 3H), 1.22 (s, 6H).

Example 69

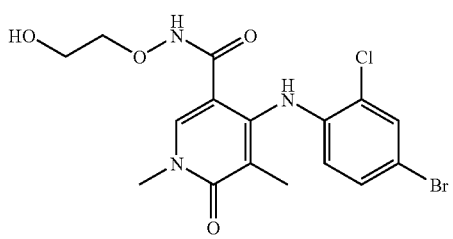

4-(4-Bromo-2-chlorophenylamino)-1,5-dimethyl-6-oxo-1,6-dihydropyridine-3-carboxylic acid (2-hydroxyethoxy)-amide MS APCI (−) m/z 428, 430 (M−, Cl, Br pattern) detected; ¹H NMR (400 MHz, CD₃OD) δ 7.98 (s, 1H), 7.57 (d, 1H), 7.32 (dd, 1H), 6.53 (d, 1H), 3.94 (t, 2H), 3.71 (t, 2H), 3.58 (s, 3H), 1.76 (s, 3H).

Example 70

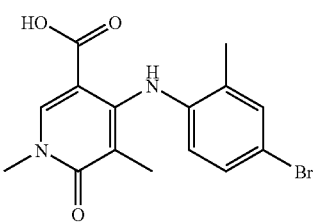

4-(4-Bromo-2-methylphenylamino)-1,5-dimethyl-6-oxo-1,6-dihydropyridine-3-carboxylic acid MS APCI (−) m/z 349, 351 (M−, Br pattern) detected; ¹H NMR (400 MHz, DMSO-d₆) δ 9.04 (s, 1H), 8.50 (s, 1H), 7.41 (s, 1H), 7.26 (d, 1H), 6.51 (d, 1H), 3.49 (s, 3H), 2.26 (s, 3H), 1.50 (s, 3H).

Example 71

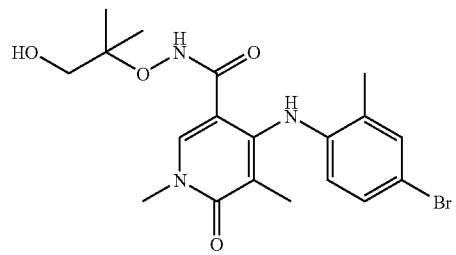

4-(4-Bromo-2-methylphenylamino)-1,5-dimethyl-6-oxo-1,6-dihydropyridine-3-carboxylic acid (2-hydroxy-1,1-dimethylethoxy)-amide MS APCI (−) m/z 436, 438 (M−, Br pattern) detected; ¹H NMR (400 MHz, CD₃OD) δ 7.96 (s, 1H), 7.34 (s, 1H), 7.20 (d, 1H), 6.50 (d, 1H), 3.58 (s, 3H), 3.28 (s, 2H), 2.29 (s, 3H), 1.72 (s, 3H), 1.21 (s, 6H).

Example 72

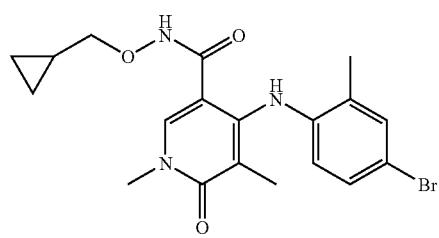

4-(4-Bromo-2-methylphenylamino)-1,5-dimethyl-6-oxo-1,6-dihydropyridine-3-carboxylic acid cyclopropylmethoxy-amide MS APCI (−) m/z 418, 420 (M−, Br pattern) detected; ¹H NMR (400 MHz, CD₃OD) δ 7.86 (s, 1H), 7.34 (d, 1H), 7.20 (dd, 1H), 6.52 (d, 1H), 3.57 (d, 2H), 3.56 (s, 3H), 2.29 (s, 3H), 1.74 (s, 3H), 1.10 (m, 1H), 0.54 (q, 2H), 0.26 (q, 2H).

Example 73

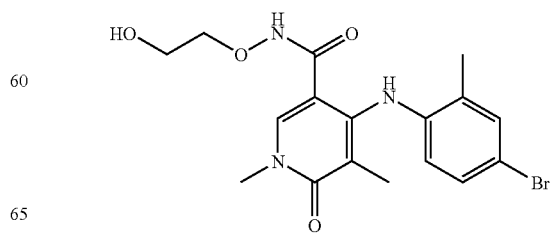

4-(4-Bromo-2-methylphenylamino)-1,5-dimethyl-6-oxo-1,6-dihydropyridine-3-carboxylic acid (2-hydroxyethoxy)-amide MS APCI (−) m/z 408, 410 (M−, Br pattern) detected; $^1$H NMR (400 MHz, CD$_3$OD) δ 7.91 (s, 1H), 7.34 (d, 1H), 7.20 (dd, 1H), 6.52 (d, 1H), 3.87 (t, 2H), 3.68 (t, 2H), 3.56 (s, 3H), 2.30 (s, 3H), 1.74 (s, 3H).

Example 74

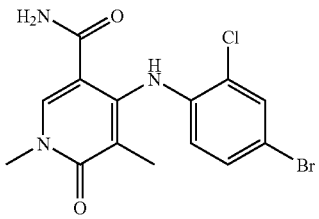

4-(4-Bromo-2-chlorophenylamino)-1,5-dimethyl-6-oxo-1,6-dihydropyridine-3-carboxylic acid amide MS APCI (−) m/z 368, 370 (M−, Cl, Br pattern) detected; $^1$H NMR (400 MHz, CD$_3$OD) δ 8.16 (s, 1H), 7.57 (d, 1H), 7.32 (dd, 1H), 6.53 (d, 1H), 3.59 (s, 3H), 1.70 (s, 3H).

Example 75

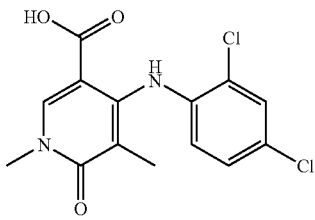

4-(2,4-Dichlorophenylamino)-1,5-dimethyl-6-oxo-1,6-dihydropyridine-3-carboxylic acid MS APCI (−) m/z 325, 327 (M−, Cl pattern) detected; $^1$H NMR (400 MHz, DMSO-d$_6$) δ 9.27 (s, 1H), 8.52 (s, 1H), 7.62 (d, 1H), 7.29 (dd, 1H), 6.66 (d, 1H), 3.51 (s, 3H), 1.56 (s, 3H).

Example 76

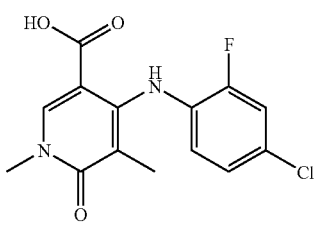

4-(4-Chloro-2-fluorophenylamino)-1,5-dimethyl-6-oxo-1,6-dihydropyridine-3-carboxylic acid MS APCI (−) m/z 309, 311 (M−, Cl pattern) detected; $^1$H NMR (400 MHz, DMSO-d$_6$) δ 9.14 (s, 1H), 8.50 (s, 1H), 7.45 (dd, 1H), 7.16 (d, 1H), 6.74 (t, 1H), 3.50 (s, 3H), 1.60 (s, 3H).

Example 77

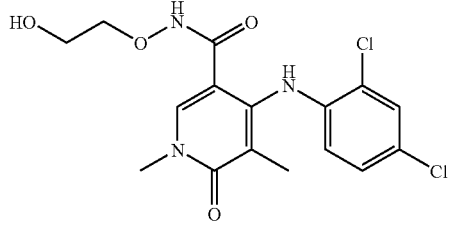

4-(2,4-Dichlorophenylamino)-1,5-dimethyl-6-oxo-1,6-dihydropyridine-3-carboxylic acid (2-hydroxyethoxy)-amide MS APCI (−) m/z 384, 386 (M−, Cl pattern) detected; $^1$H NMR (400 MHz, CD$_3$OD) δ 7.98 (s, 1H), 7.45 (d, 1H), 7.19 (dd, 1H), 6.60 (d, 1H), 3.94 (t, 2H), 3.71 (t, 2H), 3.58 (s, 3H), 1.76 (s, 3H).

Example 78

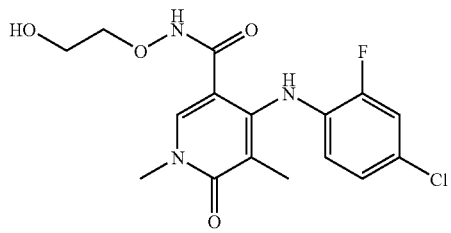

4-(4-Chloro-2-fluorophenylamino)-1,5-dimethyl-6-oxo-1,6-dihydropyridine-3-carboxylic acid (2-hydroxyethoxy)-amide MS APCI (−) m/z 368, 370 (M−, Cl pattern) detected; $^1$H NMR (400 MHz, CD$_3$OD) δ 7.93 (s, 1H), 7.20 (dd, 1H), 7.07 (d, 1H), 6.71 (t, 1H), 3.88 (t, 2H), 3.68 (t, 2H), 3.57 (s, 3H), 1.82 (s, 3H).

Example 79

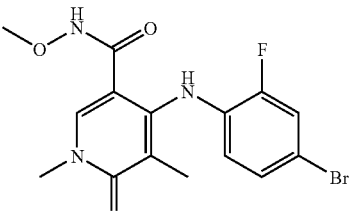

4-(4-Bromo-2-fluorophenylamino)-1,5-dimethyl-6-oxo-1,6-dihydropyridine-3-carboxylic acid methoxy-amide MS APCI (−) m/z 382, 384 (M−, Br pattern) detected; $^1$H NMR (400 MHz, CD$_3$OD) δ 7.90 (s, 1H), 7.33 (m, 1H), 7.20 (m, 1H), 6.66 (t, 1H), 3.65 (s, 3H), 3.57 (s, 3H), 1.83 (s, 3H).

Example 80

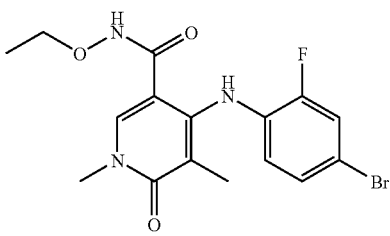

4-(4-Bromo-2-fluorophenylamino)-1,5-dimethyl-6-oxo-1,6-dihydropyridine-3-carboxylic acid ethoxy-amide MS APCI (−) m/z 396, 398 (M−, Br pattern) detected; $^1$H NMR (400 MHz, CD$_3$OD) δ 7.90 (s, 1H), 7.33 (dd, 1H), 7.20 (m, 1H), 6.65 (t, 1H), 3.83 (q, 2H), 3.57 (s, 3H), 1.83 (s, 3H), 1.22 (t, 3H).

Example 81

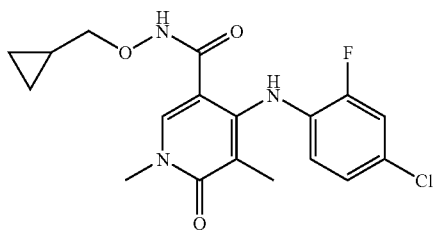

4-(4-Chloro-2-fluorophenylamino)-1,5-dimethyl-6-oxo-1,6-dihydropyridine-3-carboxylic acid cyclopropylmethoxy-amide MS APCI (−) m/z 378, 380 (M−, Cl pattern) detected; $^1$H NMR (400 MHz, CD$_3$OD) δ 7.88 (s, 1H), 7.20 (d, 1H), 7.07 (d, 1H), 6.72 (t, 1H), 3.58 (d, 2H), 3.57 (s, 3H), 1.83 (s, 3H), 1.10 (m, 1H), 0.54 (q, 2H), 0.26 (q, 2H).

Example 82

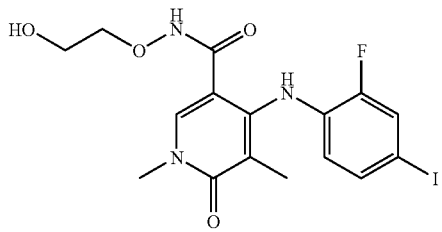

4-(2-Fluoro-4-iodophenylamino)-1,5-dimethyl-6-oxo-1,6-dihydropyridine-3-carboxylic acid (2-hydroxyethoxy)-amide MS APCI (−) m/z 460 (M−1) detected; $^1$H NMR (400 MHz, CD$_3$OD) δ 7.92 (s, 1H), 7.46 (d, 1H), 7.37 (d, 1H), 6.50 (t, 1H), 3.86 (t, 2H), 3.68 (t, 2H), 3.57 (s, 3H), 1.83 (s, 3H).

Example 83

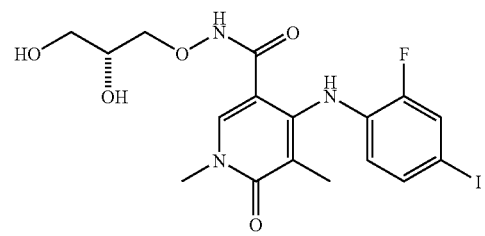

(R)-4-(2-Fluoro-4-iodophenylamino)-1,5-dimethyl-6-oxo-1,6-dihydropyridine-3-carboxylic acid (2,3-dihydroxypropoxy)-amide MS APCI (−) m/z 490 (M−1) detected; $^1$H NMR (400 MHz, CD$_3$OD) δ 7.93 (s, 1H), 7.47 (d, 1H), 7.37 (d, 1H), 6.50 (t, 1H), 3.90 (m, 1H), 3.80 (m, 2H), 3.57 (s, 3H), 3.56 (m, 2H), 1.82 (s, 3H).

Example 84

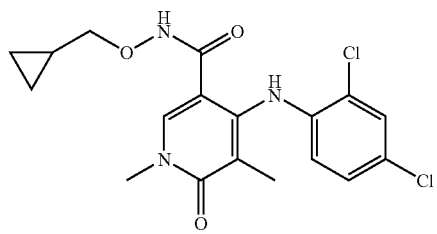

4-(2,4-Dichlorophenylamino)-1,5-dimethyl-6-oxo-1,6-dihydropyridine-3-carboxylic acid cyclopropylmethoxy-amide MS APCI (−) m/z 394, 396 (M−, Cl pattern) detected; $^1$H NMR (400 MHz, CD$_3$OD) δ 7.93 (s, 1H), 7.45 (s, 1H), 7.18 (d, 1H), 6.60 (d, 1H), 3.65 (d, 2H), 3.58 (s, 3H), 1.75 (s, 3H), 1.12 (m, 1H), 0.53 (q, 2H), 0.25 (q, 2H).

Example 85

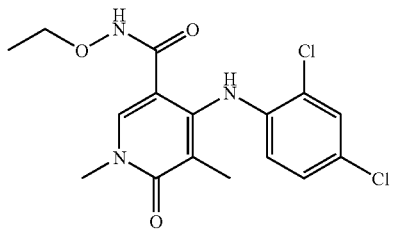

4-(2,4-Dichlorophenylamino)-1,5-dimethyl-6-oxo-1,6-dihydropyridine-3-carboxylic acid ethoxy-amide MS APCI (−) m/z 368, 370 (M−, Cl pattern) detected; ¹H NMR (400 MHz, CD₃OD) δ 7.93 (s, 1H), 7.42 (d, 1H), 7.17 (dd, 1H), 6.58 (d, 1H), 3.92 (q, 2H), 3.59 (s, 3H), 1.75 (s, 3H), 1.26 (t, 3H).

Example 86

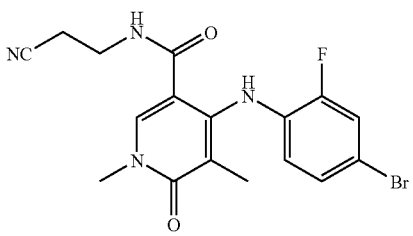

4-(4-Bromo-2-fluorophenylamino)-1,5-dimethyl-6-oxo-1,6-dihydropyridine-3-carboxylic acid (2-cyano-ethyl)-amide MS APCI (−) m/z 405, 407 (M−, Br pattern) detected; ¹H NMR (400 MHz, CD₃OD) δ 8.00 (s, 1H), 7.33 (dd, 1H), 7.20 (dd, 1H), 6.65 (t, 1H), 3.59 (s, 3H), 3.47 (t, 2H), 2.65 (t, 2H), 1.80 (s, 3H).

Example 87

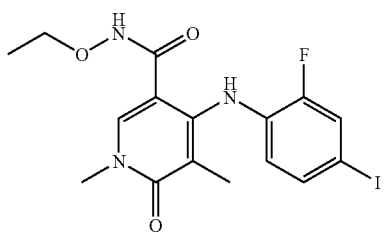

4-(2-Fluoro-4-iodophenylamino)-1,5-dimethyl-6-oxo-1,6-dihydropyridine-3-carboxylic acid ethoxy-amide MS APCI (−) m/z 444 (M−1) detected; ¹H NMR (400 MHz, CD₃OD) δ 7.89 (s, 1H), 7.46 (dd, 1H), 7.37 (dd, 1H), 6.50 (t, 1H), 3.82 (q, 2H), 3.57 (s, 3H), 1.84 (s, 3H), 1.22 (t, 3H).

Example 88

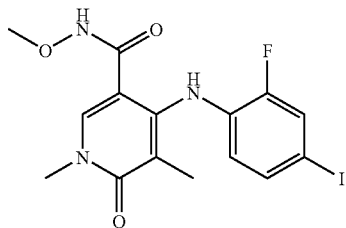

4-(2-Fluoro-4-iodophenylamino)-1,5-dimethyl-6-oxo-1,6-dihydropyridine-3-carboxylic acid methoxy-amide MS APCI (−) m/z 430 (M−1) detected; ¹H NMR (400 MHz, CD₃OD) δ 7.89 (s, 1H), 7.47 (dd, 1H), 7.37 (dd, 1H), 6.50 (t, 1H), 3.64 (s, 3H), 3.57 (s, 3H), 1.83 (s, 3H).

Example 89

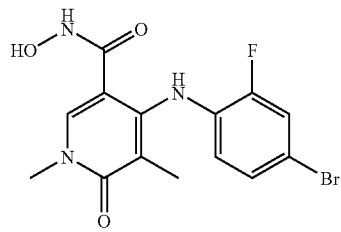

4-(4-Bromo-2-fluorophenylamino)-1,5-dimethyl-6-oxo-1,6-dihydropyridine-3-carboxylic acid hydroxyamide 4-(4-Bromo-2-fluorophenylamino)-1,5-dimethyl-6-oxo-1,6-dihydropyridine-3-carboxylic acid hydroxyamide was prepared from 4-(4-bromo-2-fluorophenylamino)-1,5-dimethyl-6-oxo-1,6-dihydropyridine-3-carboxylic acid tert-butoxy-amide by TFA deprotection as described in Example 37. MS APCI (+) m/z 370, 372 (M+, Br pattern) detected; ¹H NMR (400 MHz, CD₃OD) δ 7.88 (s, 1H), 7.32 (dd, 1H), 7.20 (dd, 1H), 6.61 (t, 1H), 3.56 (s, 3H), 1.77 (s, 3H).

Example 90

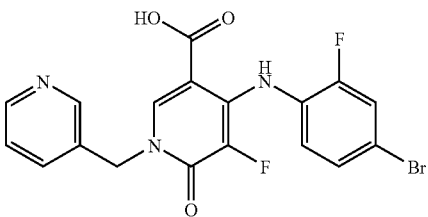

4-(4-Bromo-2-fluorophenylamino)-5-fluoro-6-oxo-1-pyridin-3-ylmethyl-1,6-dihydropyridine-3-carboxylic acid Step A: Preparation of 4-(4-bromo-2-fluorophenylamino)-6-chloro-5-fluoro-nicotinic acid: nBuLi (14.7 mL, 36.7 mmol, 2.5 M solution in hexanes) was added to a stirred solution of diisopropylamine (5.15 mL, 36.7 mmol) in THF (20 mL) at 0° C. After 20 minutes, the reaction mixture was cooled to −78° C. and a solution of 4-bromo-2-fluorophenylamine (4.65 g, 24.5 mmol) in THF (10 mL) was added. After 20 minutes, a solution of 4,6-dichloro-5-fluoro-nicotinic acid (Sanchez et al *J Heterocylc. Chem*. 1993, 30 (4), 855-9) (2.57 g, 12.25 mmol) in THF (10 mL) was added. After 10 minutes, the reaction mixture was allowed to warm to room temperature and stirred for 1 hour. After quenching the reaction mixture with 10% HCl (20 mL), it was extracted with ethyl acetate. The combined organic extracts were dried (MgSO₄)

and concentrated under reduced pressure. Trituration with methylene chloride yielded 3.21 g (72%) of clean desired product.

Step B: Preparation of 4-(4-bromo-2-fluorophenylamino)-6-chloro-5-fluoro-nicotinic acid methyl ester: A hexanes solution of TMSCH$_2$N$_2$ (9.46 mL, 18,9 mmol) was added to 4-(4-bromo-2-fluorophenylamino)-6-chloro-5-fluoro-nicotinic acid (4.59 g, 12.62 mmol) in a solution of 3:1 THF:MeOH (48 mL) at 0° C. The reaction mixture was warmed to room temperature and stirred for 1 hour. After quenching with AcOH, the reaction mixture was diluted with ethyl acetate and water. The layers were separated and the organic layer was washed with water, saturated NaHCO$_3$ solution and brine. The organic layer was dried (MgSO$_4$) and concentrated to give 4.40 g (92%) clean desired product.

Step C: Preparation of 4-(4-bromo-2-fluorophenylamino)-5-fluoro-6-methoxy-nicotinic acid methyl ester: Sodium methoxide (2.20 g, 40.8 mmol) was slowly added to a stirred solution of 4-(4-bromo-2-fluorophenylamino)-6-chloro-5-fluoro-nicotinic acid methyl ester in 4:1 MeOH:THF (20 mL) at 0° C. The reaction mixture was warmed to room temperature, stirred for 17 hours and then warmed to 40° C. and stirred for 5 hours. After cooling to room temperature, the reaction mixture was quenched with water and extracted with ethyl acetate. The combined organic extracts were dried (MgSO4) and concentrated under reduced pressure. The desired product, contaminated with some starting material, was carried forward without purification.

Step D: Preparation of 4-(4-bromo-2-fluorophenylamino)-5-fluoro-6-oxo-1,6-dihydropyridine-3-carboxylic acid methyl ester: Hydrobromic acid (5.82 mL, 51.5 mmol) was added to a mixture of 4-(4-bromo-2-fluorophenylamino)-5-fluoro-6-methoxy-nicotinic acid methyl ester (0.64 g, 1.72 mmol) and acetic acid (5.9 mL, 103 mmol). The reaction mixture was stirred at 90° C. for 20 minutes and then cooled to room temperature. After water was added to the mixture, a white precipitate formed. The white solid was collected by filtered and washed with water and diethyl ether to yield 0.60 g (97%) clean desired product.

Step E: Preparation of 4-(4-bromo-2-fluorophenylamino)-5-fluoro-6-oxo-1-pyridin-3-ylmethyl-1,6-dihydropyridine-3-carboxylic acid: Lithium hydride (14 mg, 1.64 mmol) was added to a stirred solution of 4-(4-bromo-2-fluorophenylamino)-5-fluoro-6-oxo-1,6-dihydropyridine-3-carboxylic acid methyl ester (0.190 g, 0.529 mmol) in DMF (5 mL) at 0° C. After stirring for 30 minutes, 3-bromomethyl-pyridine hydrobromide (0.14 g, 0.53 mmol) was added. The reaction mixture was warmed to room temperature and stirred for 16 hours. After quenching with ice water, the reaction mixture was extracted with ethyl acetate. The combined organic extracts were dried (MgSO$_4$) and concentrated under reduced pressure. Purification by flash column chromatography (1% MeOH in methylene chloride) yielded 4-(4-bromo-2-fluorophenylamino)-5-fluoro-6-oxo-1-pyridin-3-ylmethyl-1,6-dihydropyridine-3-carboxylic acid methyl ester. The methyl ester was dissolved in 4:1 THF:MeOH (5 mL) and 1 M LiOH solution (1.1 mL) was added. After 1 hour, the reaction mixture was acidified to pH 1 with 10% aqueous HCl solution and extracted with ethyl acetate. The combined organic extracts were washed with brine, dried (MgSO4) and concentrated under reduced pressure. Trituration with diethyl ether gave 0.160 g (69% two step yield) clean desired product. MS APCI (−) m/z 434, 436 (M−, Br pattern) detected; $^1$H NMR (400 mHz, DMSO-d$_6$) δ 9.40 (bs, 1H), 8.65 (s, 1H), 8.61 (s, 1H), 8.51 (d, 1H), 7.74 (d, 1H), 7.58 (d, 1H), 7.39 (m, 1H), 7.34 (s, 1H), 7.16 (m, 1H), .525 (s, 1H).

Example 91

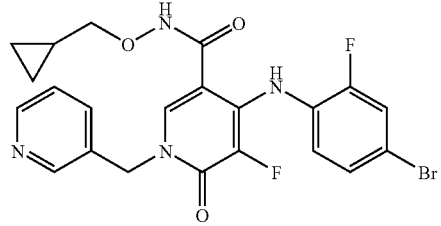

4-(4-Bromo-2-fluorophenylamino)-5-fluoro-6-oxo-1-pyridin-3-ylmethyl-1,6-dihydropyridine-3-carboxylic acid cyclopropylmethoxy-amide Prepared as described in Example 2 from 4-(4-bromo-2-fluorophenylamino)-5-fluoro-6-oxo-1-pyridin-3-ylmethyl-1,6-dihydropyridine-3-carboxylic acid. MS APCI (+) m/z 505, 507 (M+, Br pattern) detected; $^1$H NMR (400 mHz, DMSO) δ 11.75 (bs, 1H), 8.97 (bs, 1H), 8.63 (s, 1H), 8.53 (d, 1H), 8.13 (s, 1H), 7.78 (d, 1H), 7.55 (dd, 1H), 7.40 (dd, 1H), 7.31 (d, 1H), 7.07 (td, 1H), 5.14 (s, 2H), 3.64 (d, 2H), 1.08 (m, 1H), 0.52 (d, 2H), 0.25 (d, 2H).

The following compounds were prepared as described in Examples 1, 2, 3, 90 and 91 using the appropriate alkyl halide.

Example 92

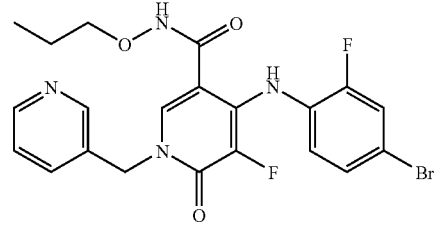

4-(4-Bromo-2-fluorophenylamino)-5-fluoro-6-oxo-1-pyridin-3-ylmethyl-1,6-dihydropyridine-3-carboxylic acid propoxy-amide MS APCI (+) m/z 493, 495 (M+, Br pattern) detected; $^1$H NMR (400 mHz, CD$_3$OD) δ 8.62 (s, 1H), 8.51 (d, 1H), 8.03 (s, 1H), 7.88 (d, 1H), 7.44 (dd, 1H), 7.36 (dd, 1H), 7.27 (d, 1H), 7.02 (td, 1H), 5.24 (s, 2H), 3.82 (t, 2H), 1.68 (m, 2H), 0.97 (t, 3H).

Example 93

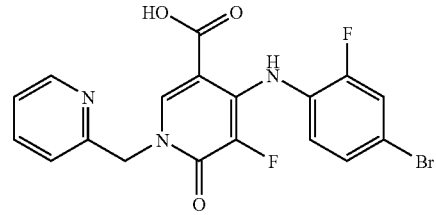

4-(4-Bromo-2-fluorophenylamino)-5-fluoro-6-oxo-1-pyridin-2-ylmethyl-1,6-dihydropyridine-3-carboxylic acid MS APCI (−) m/z 434, 436 (M−, Br pattern) detected; ¹H NMR (400 mHz, DMSO) δ 9.40 (s, 1H), 8.56 (s, 1H), 8.51 (d, 1H), 7.79 (t, 1H), 7.59 (d, 1H), 7.34 (m, 3H), 7.15 (m, 1H), 5.29 (s, 2H).

Example 94

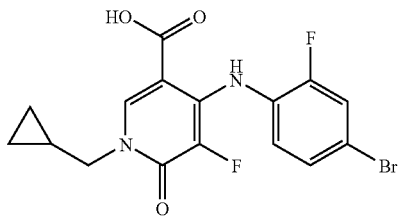

4-(4-Bromo-2-fluorophenylamino)-1-cyclopropylmethyl-5-fluoro-6-oxo-1,6-dihydropyridine-3-carboxylic acid MS APCI (−) m/z 397, 399 (M−, Br pattern) detected; ¹H NMR (400 mHz, DMSO) δ 9.35 (bs, 1H), 8.46 (s, 1H), 7.59 (d, 1H), 7.36 (d, 1H), 7.13 (td, 1H), 3.85 (d, 2H), 1.23 (m, 1H), 0.50 (d, 2H), 0.39 (d, 2H).

Example 95

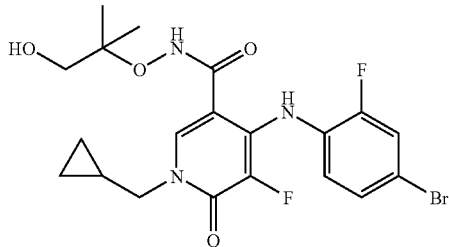

4-(4-Bromo-2-fluorophenylamino)-1-cyclopropylmethyl-5-fluoro-6-oxo-1,6-dihydropyridine-3-carboxylic acid (2-hydroxy-1,1-dimethylethoxy)-amide MS APCI (+) m/z 486, 488 (M+, Br pattern) detected; ¹H NMR (400 mHz, DMSO) δ 8.02 (s, 1H), 7.56 (d, 1H), 7.32 (d, 1H), 7.04 (td, 1H), 3.79 (d, 2H), 3.28 (s, 2H), 1.28 (m, 1H), 1.17 (s. 6H), 0.52 (d, 2H), 0.43 (d, 2H).

Example 96

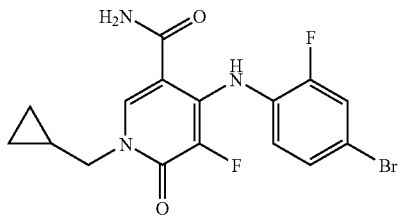

4-(4-Bromo-2-fluorophenylamino)-1-cyclopropylmethyl-5-fluoro-6-oxo-1,6-dihydropyridine-3-carboxylic acid amide MS APCI (+) m/z 398, 400 (M+, Br pattern) detected; ¹H NMR (400 mHz, DMSO) δ 10.04 (s, 1H), 8.22 (s, 1H), 8.05 (bs, 1H), 7.66 (bs, 1H), 7.56 (d, 1H), 7.33 (d, 1H), 7.04 (td, 1H), 3.75 (d, 2H), 1.27 (m, 1H), 0.51 (d, 2H), 0.43 (d, 2H).

Example 97

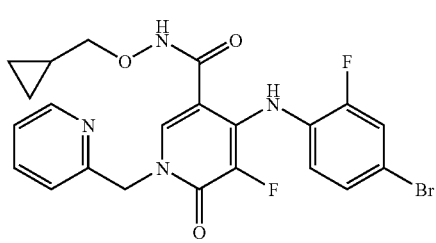

4-(4-Bromo-2-fluorophenylamino)-5-fluoro-6-oxo-1-pyridin-2-ylmethyl-1,6-dihydropyridine-3-carboxylic acid cyclopropylmethoxy-amide MS APCI (+) m/z 505, 507 (M+, Br pattern) detected; ¹H NMR (400 mHz, DMSO) δ 11.71 (bs, 1H), 9.04 (bs, 1H), 8.52 (d, 1H), 8.07 (s, 1H), 7.80 (t, 1H), 7.56 (d, 1H), 7.31 (m, 3H), 7.07 (td, 1H), 5.21 (s, 2H), 3.63 (d, 2H), 1.07 (m, 1H), 0.51 (q, 2H), 0.24 (q, 2H).

Example 98

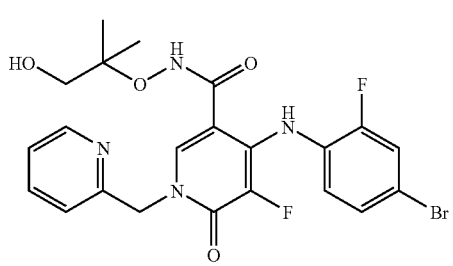

4-(4-Bromo-2-fluorophenylamino)-5-fluoro-6-oxo-1-pyridin-2-ylmethyl-1,6-dihydropyridine-3-carboxylic acid (2-hydroxy-1,1-dimethylethoxy)-amide MS APCI (+) m/z 523, 525 (M+, Br pattern) detected; ¹H NMR (400 mHz, DMSO) δ 11.23 (bs, 1H), 8.86 (bs, 1H), 8.53 (d, 1H), 8.18 (s, 1H), 7.80 (t, 1H), 7.56 (d, 1H), 7.31 (m, 3H), 7.08 (td, 1H), 5.25 (s, 2H), 3.28 (s, 2H), 1.56 (s, 6H).

Example 99

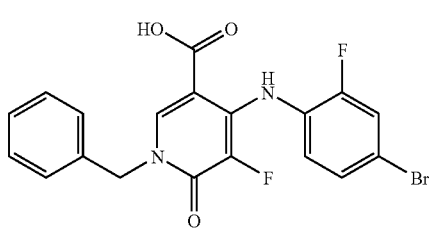

1-Benzyl-4-(4-bromo-2-fluorophenylamino)-5-
fluoro-6-oxo-1,6-dihydropyridine-3-carboxylic acid MS APCI (+) m/z 433, 435 (M+, Br pattern) detected; $^1$H NMR (400 mHz, DMSO-D$_6$) δ 9.35 (s, 1H), 8.54 (s, 1H), 7.59 (dd, 1H), 7.35 (m, 6H), 7.15 (m, 1H), 5.22 (s, 2H).

Example 100

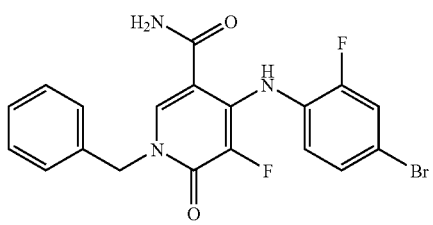

1-Benzyl-4-(4-bromo-2-fluorophenylamino)-5-
fluoro-6-oxo-1,6-dihydropyridine-3-carboxylic acid
amide MS APCI (−) m/z 432, 434 (M−, Br pattern) detected; $^1$H NMR (400 mHz, CD$_3$OD) δ 7.18 (s, 1H), 7.36 (m, 6H), 7.27 (d, 1H), 7.02 (m, 1H), 5.20 (s, 2H).

Example 101

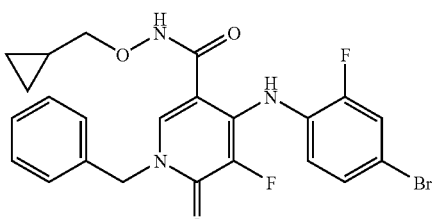

1-Benzyl-4-(4-bromo-2-fluorophenylamino)-5-
fluoro-6-oxo-1,6-dihydropyridine-3-carboxylic acid
cyclopropylmethoxy-amide MS APCI (−) m/z 502, 504 (M−, Br pattern) detected; $^1$H NMR (400 mHz, CD$_3$OD) δ 7.89 (s, 1H), 7.34 (m, 7H), 7.27 (d, 1H), 7.02 (m, 1H), 5.19 (s, 2H), 3.65 (d, 2H), 1.11 (m, 1H), 0.55 (m, 2H), 0.26 (m, 2H).

Example 102

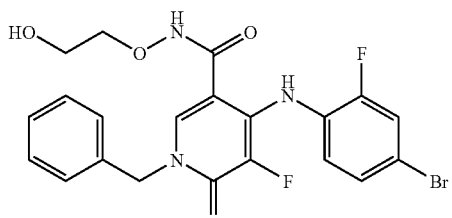

1-Benzyl-4-(4-bromo-2-fluorophenylamino)-5-
fluoro-6-oxo-1,6-dihydropyridine-3-carboxylic acid
(2-hydroxyethoxy)-amide MS APCI (−) m/z 492, 494 (M−, Br pattern) detected; $^1$H NMR (400 mHz, CD$_3$OD) δ 7.96 (s, 1H), 7.36 (m, 7H), 7.27 (d, 1H), 7.04 (m, 1H), 5.19 (s, 2H), 3.96 (t, 2H), 3.73 (t, 2H).

Example 103

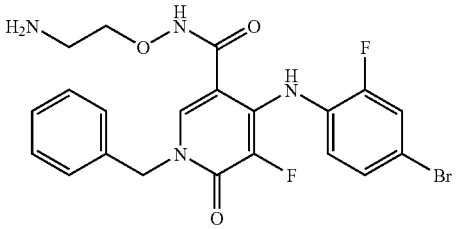

1-Benzyl-4-(4-bromo-2-fluorophenylamino)-5-
fluoro-6-oxo-1,6-dihydropyridine-3-carboxylic acid
(2-amino-ethoxy)-amide hydrogen chloride 1-Benzyl-4-(4-bromo-2-fluorophenylamino)-5-fluoro-6-oxo-1,6-dihydropyridine-3-carboxylic acid (2-amino-ethoxy)-amide was prepared by deprotecting 4(2-{[1-benzyl-4-(4-bromo-2-fluorophenylamino)-5-fluoro-6-oxo-1,6-dihydropyridine-3-carbonyl]-aminooxy}-ethyl)-carbamic acid tert-butyl ester under standard conditions; MS APCI (+) m/z 493, 495 (M+, Br pattern) detected; $^1$H NMR (400 mHz, CD$_3$OD) δ 8.03 (s, 1H), 7.36 (m, 6H), 7.29 (d, 1H), 7.04 (td, 1H), 5.20 (s, 2H), 4.12 (t, 2H), 3.17 (t, 2H).

Example 104

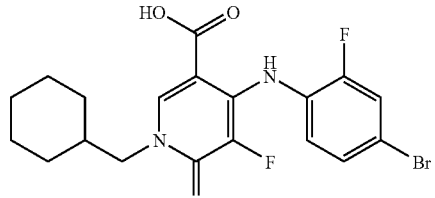

4-(4-Bromo-2-fluorophenylamino)-1-cyclohexylm-
ethyl-5-fluoro-6-oxo-1,6-dihydropyridine-3-carboxy-
lic acid MS APCI (−) m/z 439, 441 (M−, Br pattern) detected; $^1$H NMR (400 mHz, CD$_3$OD) δ 8.21 (s, 1H), 7.32 (dd, 1H), 7.27 (d, 1H), 7.05 (td, 1H), 3.88 (d, 2H), 1.85 (m, 1H), 1.79 (m, 2H), 1.69 (m, 3H), 1.25 (m, 3H), 1.05 (q, 2H).

Example 105

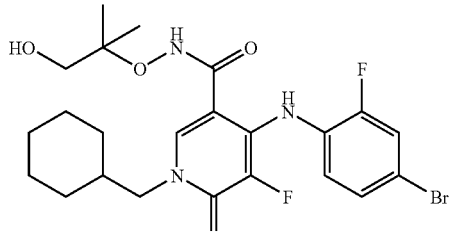

4-(4-Bromo-2-fluorophenylamino)-1-cyclohexylmethyl-5-fluoro-6-oxo-1,6-dihydropyridine-3-carboxylic acid (2-hydroxy-1,1-dimethylethoxy)-amide MS APCI (+) m/z 528, 530 (M+, Br pattern) detected; ¹H NMR (400 mHz, CD₃OD) δ 7.85 (s, 1H), 7.36 (d, 1H), 7.28 (d, 1H), 7.02 (td, 1H), 3.86 (d, 2H), 3.42 (s, 2H), 1.88 (m, 1H), 1.76 (m, 2H), 1.67 (m, 3H), 1.29 (m, 3H), 1.26 (s, 6H), 1.06 (m, 2H), 0.90 (m, 2H).

Example 106

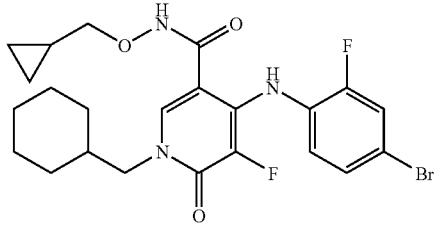

4-(4-Bromo-2-fluorophenylamino)-1-cyclohexylmethyl-5-fluoro-6-oxo-1,6-dihydropyridine-3-carboxylic acid cyclopropylmethoxy-amide MS APCI (+) m/z 510, 512 (M+, Br pattern) detected; ¹H NMR (400 mHz, CD₃OD) δ 7.76 (s, 1H), 7.36 (d, 1H), 7.28 (d, 1H), 7.02 (td, 1H), 3.84 (d, 2H), 3.69 (d, 2H), 1.86 (m, 1H), 1.75 (m, 2H), 1.66 (m, 2H), 1.26 (m, 3H), 1.07 (m, 2H), 0.90 (m, 2H), 0.58 (d, 2H), 0.29 (d, 2H).

Example 107

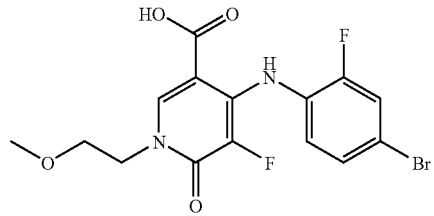

4-(4-Bromo-2-fluorophenylamino)-5-fluoro-1-(2-methoxyethyl)-6-oxo-1,6-dihydropyridine-3-carboxylic acid MS APCI (−) m/z 401, 403 (M−, Br pattern) detected; ¹H NMR (400 mHz, CD₃OD) δ 8.32 (s, 1H), 7.38 (dd, 1H), 7.31 (d, 1H), 7.10 (td, 1H), 4.21 (t, 2H), 3.66 (t, 2H), 3.35 (s, 3H).

Example 108

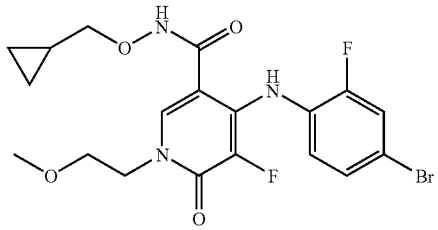

4-(4-Bromo-2-fluorophenylamino)-5-fluoro-1-(2-methoxyethyl)-6-oxo-1,6-dihydropyridine-3-carboxylic acid cyclopropylmethoxy-amide MS APCI (+) m/z 472, 474 (M+, Br pattern) detected; ¹H NMR (400 mHz, CD₃OD) δ 7.79 (s, 1H), 7.36 (dd, 1H), 7.28 (dd, 1H), 7.03 (td, 1H), 4.18 (t, 2H), 3.68 (m, 4H), 3.35 (s, 3H), 1.15 (m, 1H), 0.59 (q, 2H), 0.30 (q, 2H).

Example 109

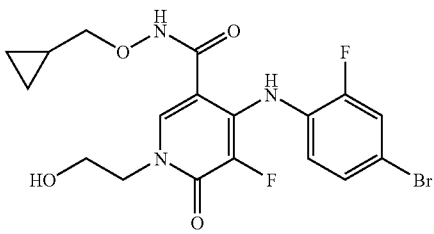

4-(4-Bromo-2-fluorophenylamino)-5-fluoro-1-(2-hydroxyethyl)-6-oxo-1,6-dihydropyridine-3-carboxylic acid cyclopropylmethoxy-amide 4-(4-Bromo-2-fluorophenylamino)-5-fluoro-1-(2-hydroxyethyl)-6-oxo-1,6-dihydropyridine-3-carboxylic acid cyclopropylmethoxy-amide was prepared by deprotecting 4-(4-bromo-2-fluorophenylamino)-1-[2-(tert-butyl-dimethylsilanyloxy)-ethyl]-5-fluoro-6-oxo-1,6-dihydropyridine-3-carboxylic acid cyclopropylmethoxy-amide under standard conditions. MS APCI (+) m/z 458, 460 (M+, Br pattern) detected; ¹H NMR (400 mHz, CD₃OD) δ 7.82 (s, 1H), 7.35 (dd, 1H), 7.27 (d, 1H), 7.02 (m, 1H), 4.11 (t, 2H), 3.84 (t, 2H), 3.72 (m, 2H), 1.16 (m, 1H), 0.59 (m, 2H), 0.31 (m, 2H).

Example 110

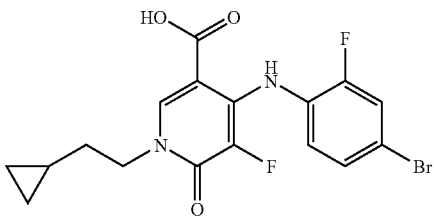

4-(4-Bromo-2-fluorophenylamino)-1-(2-cyclopropylethyl)-5-fluoro-6-oxo-1,6-dihydropyridine-3-carboxylic acid MS APCI (−) m/z 411, 413 (M−, Br pattern) detected; ¹H NMR (400 mHz, CD₃OD) δ 8.37 (s, 1H), 7.34 (dd, 1H), 7.27 (d, 1H), 7.04 (td, 1H), 4.10 (t, 2H), 1.62 (q, 2H), 0.67 (m, 1H), 0.43 (q, 2H), 0.01 (q, 2H).

Example 111

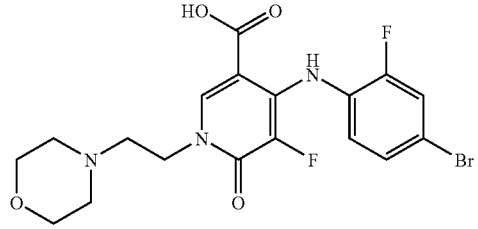

4-(4-Bromo-2-fluorophenylamino)-5-fluoro-1-(2-morpholin-4-yl-ethyl)-6-oxo-1,6-dihydropyridine-3-carboxylic acid MS ESI (+) m/z 458, 460 (M+, Br pattern) detected; ¹H NMR (400 mHz, DMSO) δ 8.34 (s, 1H), 7.58 (d, 1H), 7.35 (d, 1H), 7.10 (td, 1H), 4.10 (t, 2H), 3.56 (m, 4H), 3.17 (m, 2H), 2.62 (m, 2H).

Example 112

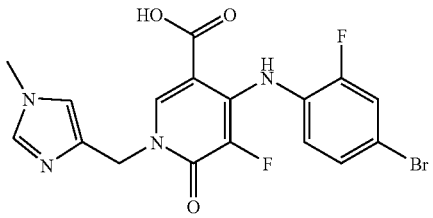

4-(4-Bromo-2-fluorophenylamino)-5-fluoro-1-(1-methyl-1H-imidazol-4-ylmethyl)-6-oxo-1,6-dihydro-pyridine-3-carboxylic acid ¹H NMR (400 mHz, DMSO) δ 9.37 (s, 1H), 8.68 (bs, 1H), 8.60 (s, 1H), 7.60 (d, 1H), 7.56 (s, 1H), 7.37 (d, 1H), 7.14 (td, 1H), 5.20 (s, 2H), 3.77 (s, 3H).

Example 113

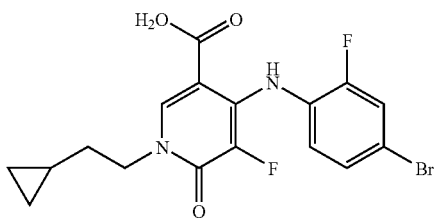

4-(4-Bromo-2-fluorophenylamino)-1-(2-cyclopropy-lethyl)-5-fluoro-6-oxo-1,6-dihydropyridine-3-carboxylic acid amide MS APCI (+) m/z 412, 414 (M+, Br pattern) detected; ¹H NMR (400 mHz, CD₃OD) δ 8.12 (s, 1H), 7.35 (dd, 1H), 7.28 (d, 1H), 7.02 (td, 1H), 4.10 (t, 2H), 1.76 (q, 2H), 0.72 (m, 1H), 0.47 (q, 2H), 0.05 (q, 2H).

Example 114

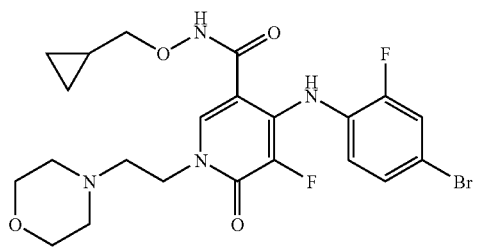

4-(4-Bromo-2-fluorophenylamino)-5-fluoro-1-(2-morpholin-4-yl-ethyl)-6-oxo-1,6-dihydropyridine-3-carboxylic acid cyclopropylmethoxy-amide MS APCI (+) m/z 527, 529 (M+, Br pattern) detected; ¹H NMR (400 mHz, CD₃OD) δ 7.85 (s, 1H), 7.36 (d, 1H), 7.28 (d, 1H), 7.03 (td, 1H), 4.13 (t, 2H), 3.68 (m, 6H), 2.71 (t, 2H), 2.55 (m, 4H), 1.17 (m, 1H), 0.59 (q, 2H), 0.31 (q, 2H).

Example 115

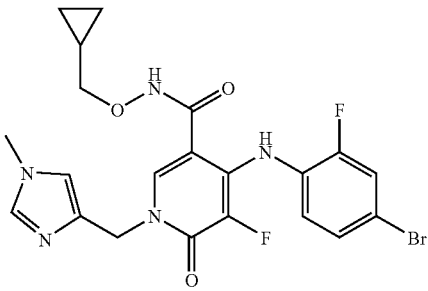

4-(4-Bromo-2-fluorophenylamino)-5-fluoro-1-(1-methyl-1H-imidazol-4-ylmethyl)-6-oxo-1,6-dihydro-pyridine-3-carboxylic acid cyclopropylmethoxy-amide MS APCI (+) m/z 508, 510 (M+, Br pattern) detected; ¹H NMR (400 mHz, CD₃OD) δ 7.98 (s, 1H), 7.62 (s, 1H), 7.34 (dd, 1H), 7.26 (dd, 1H), 7.16 (s, 1H), 7.0 (td, 1H), 5.04 (s, 2H), 3.72 (d, 2H), 3.70 (s, 3H), 1.18 (m, 1H), 0.59 (q, 2H), 0.31 (q, 2H).

Example 116

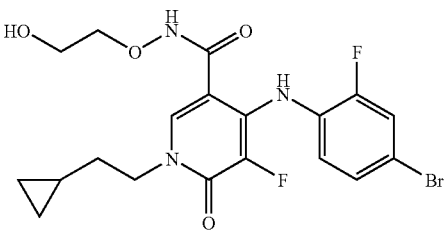

4-(4-Bromo-2-fluorophenylamino)-1-(2-cyclopropy-lethyl)-5-fluoro-6-oxo-1,6-dihydropyridine-3-carboxylic acid (2-hydroxyethoxy)-amide MS APCI (+) m/z 472, 474 (M+, Br pattern) detected; ¹H NMR (400 mHz, CD₃OD) δ 7.90 (s, 1H), 7.36 (d, 1H), 7.28 (d, 1H), 7.02 (td, 1H), 4.09 (t, 2H), 3.98 (t, 2H), 3.75 (t, 2H), 1.66 (q, 2H), 0.72 (m, 1H), 0.47 (q, 2H), 0.06 (q, 2H).

Example 117

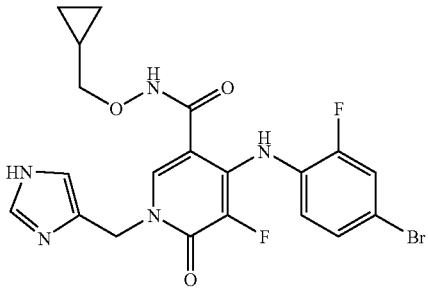

4-(4-Bromo-2-fluorophenylamino)-5-fluoro-1-(1H-imidazol-4-ylmethyl)-6-oxo-1,6-dihydropyridine-3-carboxylic acid cyclopropylmethoxy-amide MS APCI (+) m/z 494, 496 (M+, Br pattern) detected; ¹H NMR (400 mHz, CD₃OD) δ 7.99 (s, 1H), 7.70 (s, 1H), 7.35 (dd, 1H), 7.26 (d, 1H), 7.20 (s, 1H), 7.0 (td, 1H), 5.10 (s, 2H), 3.72 (d, 2H), 1.16 (m, 1H), 0.59 (q, 2H), 0.31 (q, 2H).

Example 118

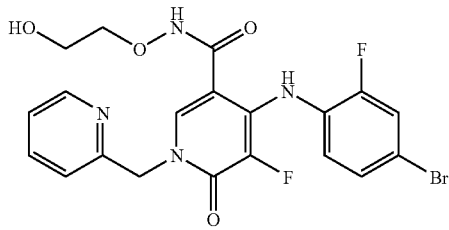

4-(4-Bromo-2-fluorophenylamino)-5-fluoro-6-oxo-1-pyridin-2-ylmethyl-1,6-dihydropyridine-3-carboxylic acid (2-hydroxyethoxy)-amide MS APCI (+) m/z 495, 497 (M+, Br pattern) detected; ¹H NMR (400 mHz, CD₃OD) δ 8.52 (d, 1H), 8.08 (s, 1H), 7.84 (t, 1H), 7.44 (d, 1H), 7.36 (m, 2H), 7.27 (d, 1H), 7.04 (td, 1H), 5.27 (s, 2H), 4.0 (t, 2H), 3.75 (t, 2H).

Example 119

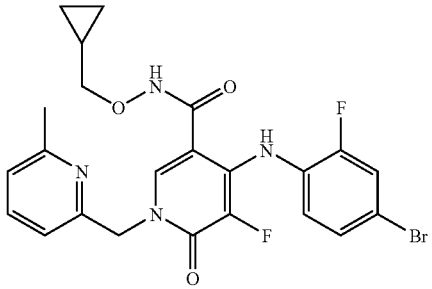

4-(4-Bromo-2-fluorophenylamino)-5-fluoro-1-(6-methylpyridin-2-ylmethyl)-6-oxo-1,6-dihydropyridine-3-carboxylic acid cyclopropylmethoxy-amide MS APCI (+) m/z 519, 521 (M+, Br pattern) detected; ¹H NMR (400 mHz, CD₃OD) δ 8.03 (s, 1H), 7.70 (t, 1H), 7.36 (d, 1H), 7.28 (d, 1H), 7.21 (d, 1H), 7.16 (d, 1H), 7.04 (td, 1H), 5.22 (s, 2H), 3.70 (d, 2H), 2.52 (s, 3H), 1.17 (m, 1H), 0.58 (q, 2H), 0.30 (q, 2H).

Example 120

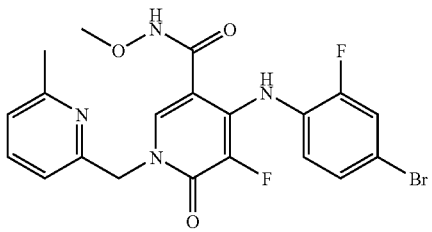

4-(4-Bromo-2-fluorophenylamino)-5-fluoro-1-(6-methyl-pyridin-2-ylmethyl)-6-oxo-1,6-dihydropyridine-3-carboxylic acid methoxy-amide MS APCI (+) m/z 479, 481 (M+, Br pattern) detected; ¹H NMR (400 mHz, CD₃OD) δ 8.05 (s, 1H), 7.69 (t, 1H), 7.36 (dd, 1H), 7.28 (d, 1H), 7.21 (d, 1H), 7.14 (d, 1H), 7.04 (td, 1H), 5.22 (s, 2H), 3.75 (s, 3H), 2.52 (s, 3H).

Example 121

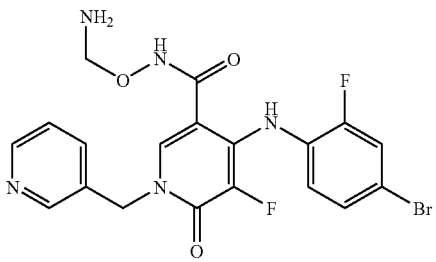

4-(4-Bromo-2-fluorophenylamino)-5-fluoro-6-oxo-1-pyridin-3-ylmethyl-1,6-dihydropyridine-3-carboxylic acid (3-aminopropoxy)-amide hydrogen chloride 4-(4-Bromo-2-fluorophenylamino)-5-fluoro-6-oxo-1-pyridin-3-ylmethyl-1,6-dihydropyridine-3-carboxylic acid (3-aminopropoxy)-amide was prepared by deprotecting (3-{[4-(4-bromo-2-fluorophenylamino)-5-fluoro-6-oxo-1-pyridin-3-ylmethyl-1,6-dihydropyridine-3-carbonyl]-aminooxy}-propyl)-carbamic acid tert-butyl ester under standard conditions. MS APCI (+) m/z 508, 510 (M+, Br pattern) detected; ¹H NMR (400 mHz, DMSO) δ 9.01 (s, 1H), 8.92 (m, 2H), 8.61 (d, 1H), 8.29 (s, 1H), 8.12 (m, 1H), 7.81 (m, 2H), 7.57 (d, 1H), 7.35 (d, 1H), 7.22 (td, 1H), 5.34 (s, 2H), 3.97 (t, 2H), 3.01 (q, 2H), 1.91 (m, 2H).

Example 122

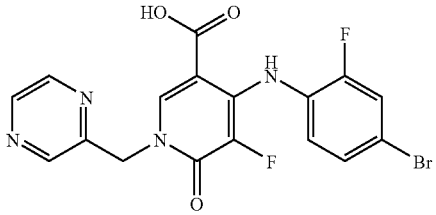

4-(4-Bromo-2-fluorophenylamino)-5-fluoro-6-oxo-1-pyrazin-2-ylmethyl-1,6-dihydropyridine-3-carboxylic acid MS APCI (−) m/z 435, 437 (M−, Br pattern) detected; ¹H NMR (400 mHz, DMSO) δ 9.42 (bs, 1H), 8.71 (s, 1H), 8.63 (s, 1H), 8.58 (s, 2H), 7.59 (dd, 1H), 7.36 (d, 1H), 7.15 (td, 1H), 5.39 (s, 2H).

Example 123

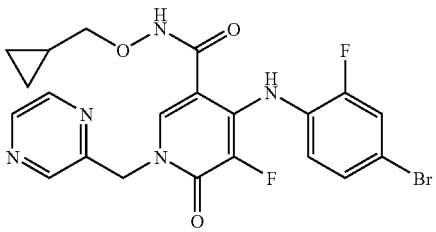

4-(4-Bromo-2-fluorophenylamino)-5-fluoro-6-oxo-1-pyrazin-2-ylmethyl-1,6-dihydropyridine-3-carboxylic acid cyclopropylmethoxy-amide MS APCI (+) m/z 506, 508 (M+, Br pattern) detected; ¹H NMR (400 mHz, CD₃OD) δ 8.72 (s, 1H), 8.57 (s, 1H), 8.55 (s, 1H), 8.05 (s, 1H), 7.36 (dd, 1H), 7.28 (d, 1H), 7.04 (td, 1H), 5.33 (s, 2H), 3.70 (d, 2H), 1.56 (m, 1H), 0.59 (q, 2H), 0.30 (q, 2H).

Example 124

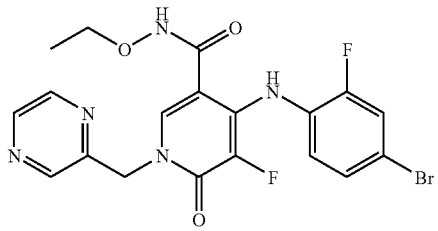

4-(4-Bromo-2-fluorophenylamino)-5-fluoro-6-oxo-1-pyrazin-2-ylmethyl-1,6-dihydropyridine-3-carboxylic acid ethoxy-amide MS APCI (+) m/z 480, 482 (M+, Br pattern) detected; ¹H NMR (400 mHz, CD₃OD) δ 8.71 (s, 1H), 8.57 (s, 1H), 8.55 (s, 1H), 8.07 (s, 1H), 7.36 (dd, 1H), 7.28 (d, 1H), 7.04 (td, 1H), 5.33 (s, 2H), 3.95 (q, 2H), 1.28 (t, 3H).

Example 125

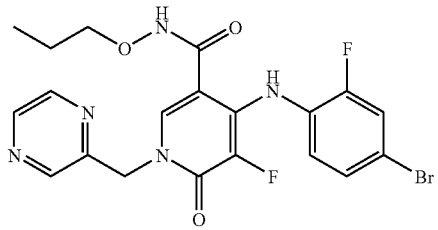

4-(4-Bromo-2-fluorophenylamino)-5-fluoro-6-oxo-1-pyrazin-2-ylmethyl-1,6-dihydropyridine-3-carboxylic acid propoxy-amide MS APCI (+) m/z 494, 496 (M+, Br pattern) detected; ¹H NMR (400 mHz, CD₃OD) δ 8.72 (s, 1H), 8.58 (s, 1H), 8.55 (s, 1H), 8.07 (s, 1H), 7.36 (dd, 1H), 7.28 (d, 1H), 7.04 (td, 1H), 5.34 (s, 2H), 3.84 (t, 2H), 1.69 (m, 2H), 0.98 (t, 3H).

Example 126

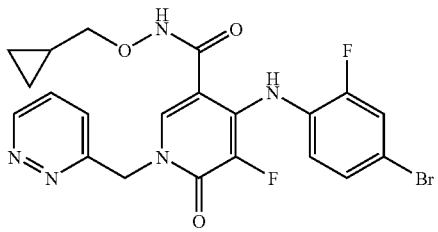

4-(4-Bromo-2-fluorophenylamino)-5-fluoro-6-oxo-1-pyridazin-3-ylmethyl-1,6-dihydropyridine-3-carboxylic acid cyclopropylmethoxy-amide MS APCI (+) m/z 506, 508 (M+, Br pattern) detected; ¹H NMR (400 mHz, CD₃OD) δ 9.14 (d, 1H), 8.10 (s, 1H), 7.80 (m, 1H), 7.74 (m, 1H), 7.36 (dd, 1H), 7.27 (d, 1H), 7.05 (td, 1H), 5.46 (s, 2H), 3.70 (d, 2H), 1.17 (m, 1H), 0.58 (q, 2H), 0.30 (q, 2H).

Example 127

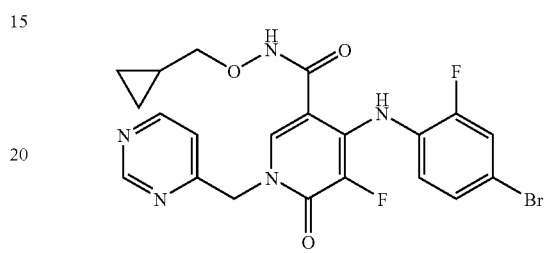

4-(4-Bromo-2-fluorophenylamino)-5-fluoro-6-oxo-1-pyrimidin-4-ylmethyl-1,6-dihydropyridine-3-carboxylic acid cyclopropylmethoxy-amide MS APCI (+) m/z 506, 508 (M+, Br pattern) detected; ¹H NMR (400 mHz, CD₃OD) δ 9.09 (s, 1H), 8.75 (d, 1H), 8.0 (s, 1H), 7.48 (d, 1H), 7.38 (d, 1H), 7.29 (d, 1H), 7.07 (td, 1H), 5.30 (s, 2H), 3.69 (d, 2H), 1.16 (m, 1H), 0.58 (q, 2H), 0.30 (q, 2H).

Example 128

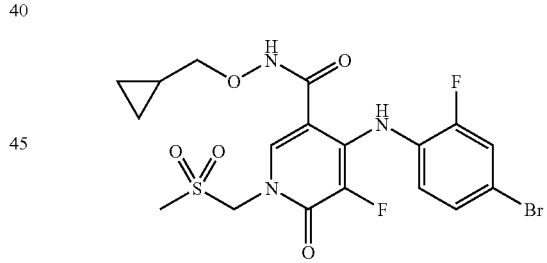

4-(4-Bromo-2-fluorophenylamino)-5-fluoro-1-methanesulfonylmethyl-6-oxo-1,6-dihydropyridine-3-carboxylic acid cyclopropylmethoxy-amide Step A: 4-(4-Bromo-2-fluorophenylamino)-5-fluoro-1-methylsulfanylmethyl-6-oxo-1,6-dihydropyridine-3-carboxylic acid methyl ester was prepared as previously described using chloromethylsulfanylmethane as the electrophile.

Step B: 4-(4-Bromo-2-fluorophenylamino)-5-fluoro-1-methanesulfonylmethyl-6-oxo-1,6-dihydropyridine-3-carboxylic acid methyl ester was prepared from 4-(4-bromo-2-fluorophenylamino)-5-fluoro-1-methylsulfanylmethyl-6-oxo-1,6-dihydropyridine-3-carboxylic acid methyl ester as follows. A solution of Oxone® (84 mg, 0.14 mmol) in water (2 mL) was added dropwise to a stirred solution of 4-(4-bromo-2-fluorophenylamino)-5-fluoro-1-methylsulfanylmethyl-6-oxo-1,6-dihydropyridine-3-carboxylic acid methyl ester (38 mg, 0.091 mmol) in MeOH (2 mL) at room temperature. After 4 days stirring, the reaction mixture was diluted with water (20 mL), extracted with ethyl acetate, dried (MgSO$_4$) and concentrated under reduced pressure. Purification by flash column chromatography (0.5% MeOH in methylene chloride) gave clean desired product (25 mg, 61%).

Step C: 4-(4-Bromo-2-fluorophenylamino)-5-fluoro-1-methanesulfonylmethyl-6-oxo-1,6-dihydropyridine-3-carboxylic acid cyclopropylmethoxy-amide was prepared from 4-(4-bromo-2-fluorophenylamino)-5-fluoro-1-methanesulfonylmethyl-6-oxo-1,6-dihydropyridine-3-carboxylic acid methyl ester as previously described. MS APCI (+) m/z 506, 508 (M+, Br pattern) detected; $^1$H NMR (400 mHz, CD$_3$OD) δ 7.84 (s, 1H), 7.31 (dd, 1H), 7.27 (d, 1H), 7.04 (td, 1H), 5.37 (s, 2H), 3.78 (d, 2H), 3.06 (s, 3H), 1.21 (m, 1H), 0.63 (q, 2H), 0.33 (q, 2H).

Example 129

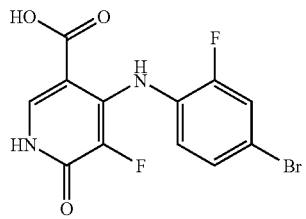

4-(4-Bromo-2-fluorophenylamino)-5-fluoro-6-oxo-1,6-dihydropyridine-3-carboxylic acid A stirred solution of 4-(4-bromo-2-fluorophenylamino)-5-fluoro-6-oxo-1,6-dihydropyridine-3-carboxylic acid methyl ester (0.10 g, 0.278 mmol) in 4:1 THF:MeOH (5 mL) was treated with 1 M LiOH solution (0.75 mL). After 8 hours, the reaction mixture was acidified to pH 1 with 1 N HCl and extracted with ethyl acetate. The combined organic extracts were washed with brine, dried (MgSO4) and concentrated under reduced pressure to give 0.095 g (99%) of desired product as a white solid. MS APCI (−) m/z 343, 345 (M−, Br pattern) detected; $^1$H NMR (400 mHz, DMSO) δ 12.34 (bs, 1H), 9.39 (bs, 1H), 7.95 (s, 1H), 7.59 (d, 1H), 7.36 (d, 1H), 7.12 (td, 1H).

Example 130

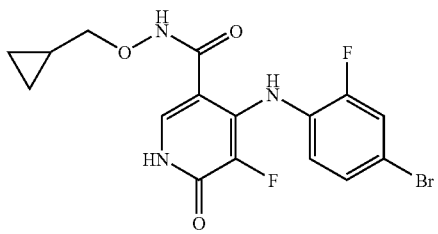

4-(4-Bromo-2-fluorophenylamino)-5-fluoro-6-oxo-1,6-dihydropyridine-3-carboxylic acid cyclopropyl-methoxy-amide Prepared as described in Example 2 from 4-(4-bromo-2-fluorophenylamino)-5-fluoro-6-oxo-1,6-dihydropyridine-3-carboxylic acid. MS APCI (+) m/z 414, 416 (M+, Br pattern) detected; $^1$H NMR (400 mHz, DMSO) δ 9.15 (bs, 1H), 7.59 (s, 1H), 7.55 (dd, 1H), 7.32 (d, 2H), 7.02 (td, 1H), 3.64 (d, 2H), 1.07 (m, 1H), 0.50 (q, 2H), 0.24 (q, 2H).

Example 131

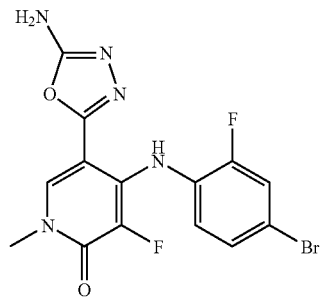

5-(5-Amino-[1,3,4]oxadiazol-2-yl)-4-(4-bromo-2-fluorophenylamino)-3-fluoro-1-methyl-1H-pyridin-2-one Step A: Preparation of 4-(4-bromo-2-fluorophenylamino)-5-fluoro-1-methyl-6-oxo-1,6-dihydropyridine-3-carboxylic acid hydrazide: A mixture of 4-(4-bromo-2-fluorophenylamino)-5-fluoro-1-methyl-6-oxo-1,6-dihydropyridine-3-carboxylic acid (70 mg, 0.195 mmol), EDCI (112 mg, 0.585 mmol), and HOBt (79 mg, 0.585 mmol) in DMF (3 mL) was stirred for 30 minutes. Hydrazine (19 mg, 0.585 mmol) was added followed by Et$_3$N (0.082 mL, 0.585 mmol). After 3 hours, the reaction mixture was diluted with EtOAc and washed with saturated NH$_4$Cl solution, saturated NaHCO$_3$ solution and brine. The organic layer was dried (MgSO$_4$) and concentrated to yield 64 mg (89%) desired product.

Step B: Preparation of 5-(5-amino-[1,3,4]oxadiazol-2-yl)-4-(4-bromo-2-fluorophenylamino)-3-fluoro-1-methyl-1H-pyridin-2-one: Cyanogen bromide (36 mg, 0.31 mmol) was added to a suspension of 4-(4-bromo-2-fluorophenylamino)-5-fluoro-1-methyl-6-oxo-1,6-dihydropyridine-3-carboxylic acid hydrazide (63 mg, 0.169 mmol) in dioxane (2 mL) followed by an aqueous NaHCO$_3$ (2 mL of a 0.09 M solution) solution. After 17 hours, additional cyanogen bromide (14 mg) was added. After 19 hours, the reaction mixture was diluted with water and extracted with ethyl acetate. The combined organic extracts were washed with brine, dried (MgSO$_4$) and concentrated under reduced pressure. Crystallization (MeOH:THF) followed by trituration (Et$_2$O:MeOH 5:1) gave clean desired product as a white solid (60 mg, 89%). MS APCI (+) m/z 398, 400 (M+, Br pattern) detected; $^1$H NMR (400 mHz, CD$_3$OD) δ 8.06 (s, 1H), 7.37 (d, 1H), 7.31 (d, 1H), 7.10 (td, 1H), 3.64 (s, 3H).

The following compounds were prepared similarly using the appropriate carboxylic acid.

Example 132

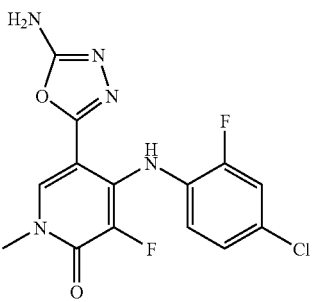

5-(5-Amino-[1,3,4]oxadiazol-2-yl)-4-(4-chloro-2-fluorophenylamino)-3-fluoro-1-methyl-1H-pyridin-2-one MS APCI (+) m/z 354, 356 (M+, Cl pattern) detected; ¹H NMR (400 mHz, CD$_3$OD) δ 8.06 (s, 1H), 7.23 (d, 1H), 7.16 (s, 2H), 3.64 (s, 3H).

Example 133

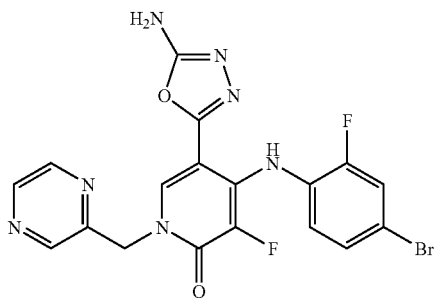

5-(5-Amino-[1,3,4]oxadiazol-2-yl)-4-(4-bromo-2-fluorophenylamino)-3-fluoro-1-pyrazin-2-ylmethyl-1H-pyridin-2-one MS APCI (+) m/z 476, 478 (M+, Br pattern) detected; ¹H NMR (400 mHz, CD$_3$OD) δ 8.75 (s, 1H), 8.58 (s, 1H), 8.55 (s, 1H), 8.26 (s, 1H), 7.35 (dd, 1H), 7.29 (d, 1H), 7.09 (td, 1H), 5.40 (s, 2H).

Example 134

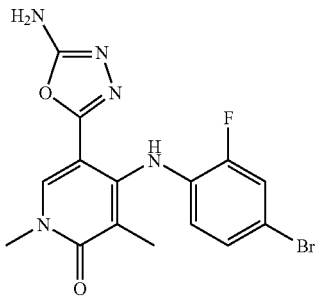

5-(5-Amino-[1,3,4]oxadiazol-2-yl)-4-(4-bromo-2-fluorophenylamino)-1,3-dimethyl-1H-pyridin-2-one MS APCI (−) m/z 392, 394 (M−, Br pattern) detected; ¹H NMR (400 MHz, CD$_3$OD) δ 8.14 (s, 1H), 7.36 (d, 1H), 7.23 (d, 1H), 6.72 (t, 1H), 3.63 (s, 3H), 1.78 (s, 3H).

Example 135

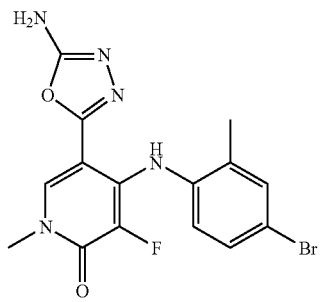

5-(5-Amino-[1,3,4]oxadiazol-2-yl)-4-(4-bromo-2-methylphenylamino)-3-fluoro-1-methyl-1H-pyridin-2-one MS APCI (+) m/z 394, 396 (M+, Br pattern) detected; ¹H NMR (400 mHz, CD$_3$OD) δ 8.05 (s, 1H), 7.39 (s, 1H), 7.30 (d, 1H), 6.95 (dd, 1H), 3.62 (s, 3H), 2.31 (s, 3H).

Example 136

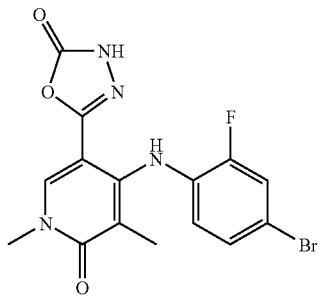

4-(4-Bromo-2-fluorophenylamino)-1,3-dimethyl-5-(5-oxo-4,5-dihydro-[1,3,4]oxadiazol-2-yl)-1H-pyridin-2-one 1,1'-Carbonyldiimidazole (275 mg, 1.70 mmol) was added to a stirred solution of 4-(4-bromo-2-fluorophenylamino)-1,5-dimethyl-6-oxo-1,6-dihydropyridine-3-carboxylic acid hydrazide (728 mg, 1.62 mmol (82% pure material)) in DMF (2 mL). After 1 hour, the reaction mixture was diluted with ethyl acetate and washed with brine. Some of the product precipitated and was collected by filtration. The filtrate was diluted with 1 N HCl and the layers separated. The aqueous layer was extracted with ethyl acetate. The combined organic extracts were washed with brine, dried (MgSO4) and concentrated under reduced pressure. The resulting residue was triturated with diethyl ether to give the desired product which was combined with the earlier obtained product. The combined yield of clean desired product was 482 mg (75%); MS APCI (−) m/z 393, 395 (M−, Br pattern) detected; ¹H NMR (400 MHz, DMSO-d$_6$) δ 8.22 (s, 1H), 7.88 (s, 1H), 7.50 (dd, 1H), 7.21 (d, 1H), 6.59 (t, 1H), 3.52 (s, 3H), 1.76 (s, 3H).

Example 137

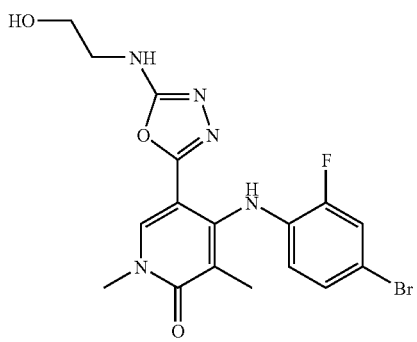

4-(4-Bromo-2-fluorophenylamino)-5-[5-(2-hydroxy-ethylamino)-[1,3,4]oxadiazol-2-yl]-1,3-dimethyl-1H-pyridin-2-one Ethanolamine (0.037 mL, 0.61 mmol) was added to a suspension of 4-(4-bromo-2-fluorophenylamino)-1,3-dimethyl-5-(5-oxo-4,5-dihydro-[1,3,4]oxadiazol-2-yl)-1H-pyridin-2-one (81 mg, 0.20 mmol) in EtOH (2 mL). The reaction mixture was heated to 90° C. with stirring for 17 hours. After cooling to room temperature, the reaction mixture was concentrated under reduced pressure and purified by flash column chromatography (5% MeOH in methylene chloride increasing to 20% MeOH in 5% steps) to give the desired intermediate adduct (58 mg, 62%). The intermediate (56 mg, 0.12 mmol) was suspended in 2:1 methylene chloride:MeCN (4.5 mL) and PPh$_3$ (98 mg, 0.37 mmol), Et$_3$N (0.14 mL, 1.0 mmol) and CCl$_4$ (0.036 mL, 0.37 mmol) were added. The resulting mixture was heated to 55° C. with stirring for 30 minutes. After cooling to room temperature, the reaction mixture was diluted with ethyl acetate and washed with brine. The aqueous layer was extracted with ethyl acetate. The organic layers were combined, washed with brine, dried (MgSO$_4$) and concentrated under reduced pressure. Purification by flash column chromatography (ethyl acetate) gave clean desired product (24 mg, 45%); MS APCI (−) m/z 436, 438 (M−, Br pattern) detected; $^1$H NMR (400 MHz, CD$_3$OD) δ 8.14 (s, 1H), 7.36 (dd, 1H), 7.22 (dd, 1H), 6.71 (t, 1H), 3.71 (t, 2H), 3.63 (s, 3H), 3.41 (t, 2H), 1.79 (s, 3H).

The following compounds were prepared similarly using the appropriate amine. In some instances a final standard deprotection step was required.

Example 138

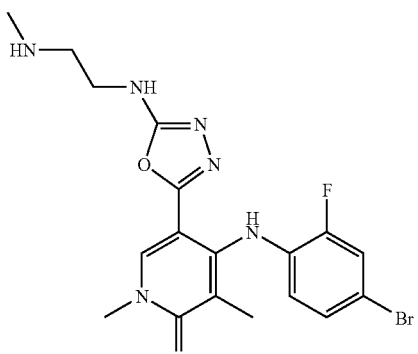

4-(4-Bromo-2-fluorophenylamino)-1,3-dimethyl-5-[5-(2-methylaminoethylamino)-[1,3,4,]oxadiazol-2-yl]-1H-pyridin-2-one MS APCI (−) m/z 449, 451 (M−, Br pattern) detected; $^1$H NMR (400 MHz, CD$_3$OD) δ 8.18 (s, 1H), 7.37 (dd, 1H), 7.23 (d, 1H), 6.71 (t, 1H), 3.66 (t, 2H), 3.64 (s, 3H), 3.29 (t, 2H), 2.75 (s, 3H), 1.80 (s, 3H).

Example 139

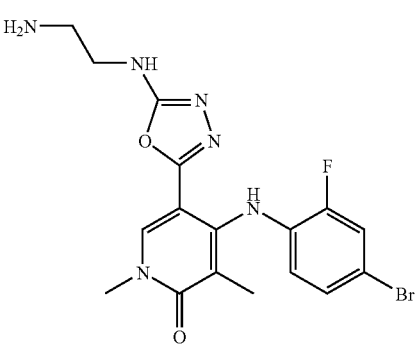

5-[5-(2-Amino-ethylamino)-[1,3,4]oxadiazol-2-yl]-4-(4-bromo-2-fluorophenylamino)-1,3-dimethyl-1H-pyridin-2-one MS APCI (+) m/z 437, 439 (M+, Br pattern) detected; $^1$H NMR (400 MHz, CD$_3$OD) δ 8.20 (s, 1H), 7.37 (dd, 1H), 7.23 (dd, 1H), 6.71 (t, 1H), 3.65 (s, 3H), 3.63 (t, 2H), 3.22 (t, 2H), 1.80 (s, 3H).

Example 140

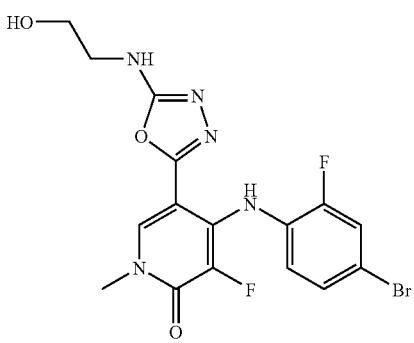

4-(4-Bromo-2-fluorophenylamino)-3-fluoro-5-[5-(2-hydroxyethylamino)-[1,3,4]oxadiazol-2-yl]-1-methyl-1H-pyridin-2-one MS APCI (+) m/z 442, 444 (M+, Br pattern) detected; $^1$H NMR (400 mHz, CD$_3$OD) δ 8.06 (s, 1H), 7.35 (dd, 1H), 7.29 (d, 1H), 7.08 (td, 1H), 3.75 (t, 2H), 3.65 (s, 3H), 3.47 (t, 2H).

Example 141

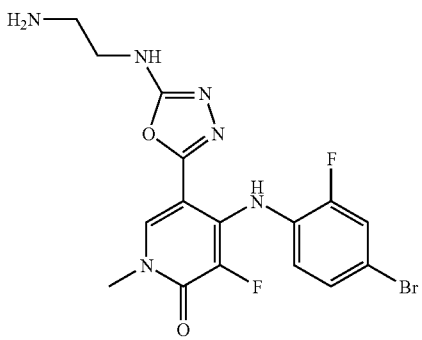

5-[5-(2-Amino-ethylamino)-[1,3,4]oxadiazol-2-yl]-4-(4-bromo-2-fluorophenylamino)-3-fluoro-1-methyl-1H-pyridin-2-one hydrogen chloride MS APCI (+) m/z 441, 443 (M+, Br pattern) detected; $^1$H NMR (400 mHz, DMSO) δ 8.94 (s, 1H), 8.17 (s, 1H), 8.06 (t, 1H), 7.95 (bs, 3H), 7.59 (dd, 1H), 7.36 (d, 1H), 7.12 (td, 1H), 3.57 (s, 3H), 3.51 (q, 2H), 3.05 (q, 2H).

Example 142

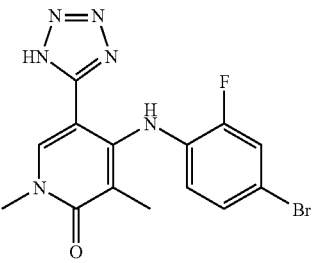

4-(4-Bromo-2-fluorophenylamino)-1,3-dimethyl-5-(1H-tetrazol-5-yl)-1H-pyridin-2-one Step A: Preparation of 3-{5-[4-(4-bromo-2-fluorophenylamino)-1,5-dimethyl-6-oxo-1,6-dihydro-pyridin-3-yl]-tetrazol-1-yl}-propionitrile: PPh$_3$ (83 mg, 0.32 mmol) was added to a stirred suspension of 4-(4-bromo-2-fluorophenylamino)-1,5-dimethyl-6-oxo-1,6-dihydropyridine-3-carboxylic acid (2-cyano-ethyl)-amide (51 mg, 0.12 mmol) in MeCN (1.5 mL). DIAD (0.065 mL, 0.31 mmol) and TMSN$_3$ (0.045 mL, 0.32) were added dropwise. After 22 hours, the reaction mixture was diluted with ethyl acetate and washed with water. The aqueous layer was extracted with ethyl acetate. The combined organic extracts were dried (MgSO$_4$) and concentrated under reduced pressure. Purification by flash column chromatography gave clean desired product (33 mg, 61%).

Step B: Preparation of 4-(4-bromo-2-fluorophenylamino)-1,3-dimethyl-5-(1H-tetrazol-5-yl)-1H-pyridin-2-one: DBU (0.030 mL, 0.21 mmol) was added to a solution of 3-{5-[4-(4-bromo-2-fluorophenylamino)-1,5-dimethyl-6-oxo-1,6-dihydro-pyridin-3-yl]-tetrazol-1-yl}-propionitrile (30 mg, 0.069 mmol) in methylene chloride (1.5 mL). After 2 hours, the reaction mixture was diluted with ethyl acetate and washed with 1 N HCl. The aqueous layer was extracted with ethyl acetate. The combined organic extracts were washed with brine, dried (MgSO$_4$) and concentrated under reduced pressure. Trituration with diethyl ether gave clean desired product (20 mg, 77%); MS APCI (−) m/z 377, 379 (M−, Br pattern) detected; $^1$H NMR (400 MHz, CD$_3$OD) δ 8.20 (s, 1H), 7.29 (dd, 1H), 7.13 (dd, 1H), 6.63 (t, 1H), 3.65 (s, 3H), 1.91 (s, 3H).

Example 143

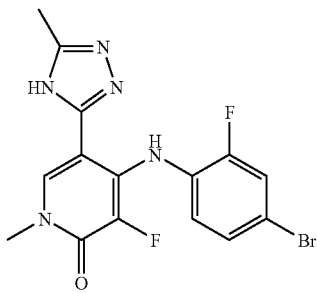

4-(4-Bromo-2-fluorophenylamino)-3-fluoro-1-methyl-5-(5-methyl-4H-[1,2,4]triazol-3-yl)-1H-pyridin-2-one Step A: Preparation of 4-(4-bromo-2-fluorophenylamino)-5-fluoro-1-methyl-6-oxo-1,6-dihydropyridine-3-carboxylic acid N'-(1-imino-ethyl)-hydrazide: Ethyl acetimidate HCl salt (40 mg, 0.32 mmol) and Et$_3$N (0.049 mL, 0.35 mmol) were added to a stirred suspension of 4-(4-bromo-2-fluorophenylamino)-5-fluoro-1-methyl-6-oxo-1,6-dihydropyridine-3-carboxylic acid hydrazide (0.10 g, 0.27 mmol) in 2:1 THF:DMF (3 mL) at 0° C. After 1.5 hours at 0° C. and 17 hours at room temperature, the reaction mixture was poured onto water, neutralized with dilute aqueous HCl and extracted with ethyl acetate. The combined organic extracts were dried (MgSO$_4$) and concentrated under reduced pressure. Trituration with methylene chloride gave the desired product.

Step B: Preparation of 4-(4-bromo-2-fluorophenylamino)-3-fluoro-1-methyl-5-(5-methyl-4H-[1,2,4]triazol-3-yl)-1H-pyridin-2-one: PPh$_3$ (0.12 g, 0.45 mmol), Et$_3$N (0.17 mL, 1.21 mmol), and CCl$_4$ (0.044 mL, 0.45 mmol) were added to a stirred suspension of 4-(4-bromo-2-fluorophenylamino)-5-fluoro-1-methyl-6-oxo-1,6-dihydropyridine-3-carboxylic acid N'-(1-imino-ethyl)-hydrazide (0.073 g, 0.18 mmol) in methylene chloride (2 mL). The reaction mixture was stirred at 50° C. for 2 hours. After cooling to room temperature, the reaction mixture was diluted with ethyl acetate, washed with water, dried (MgSO$_4$) and concentrated. Purification by flash column chromatography (4% MeOH in methylene chloride) gave clean desired product (30 mg, 50%); MS APCI (−) m/z 394, 396 (M−, Br pattern) detected; $^1$H NMR (400 mHz, CD$_3$OD) δ 8.16 (s, 1H), 7.31 (dd, 1H), 7.25 (d, 1H), 7.01 (td, 1H), 3.67 (s, 3H), 2.51 (s, 3H).

Example 144

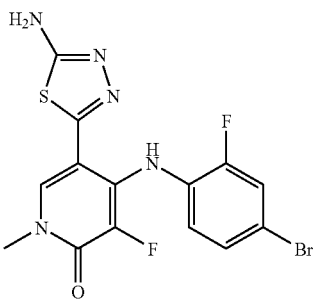

5-(5-Amino-[1,3,4]thiadiazol-2-yl)-4-(4-bromo-2-fluorophenylamino)-3-fluoro-1-methyl-1H-pyridin-2-one A mixture of 4-(4-bromo-2-fluorophenylamino)-5-fluoro-1-methyl-6-oxo-1,6-dihydropyridine-3-carboxylic acid (200 mg, 0.557 mmol), EDCI (214 mg, 1.11 mmol) and HOBt (151 mg, 1.11 mol) were stirred in DMF (10 mL) for 30 minutes. Thiosemicarbazide (51 mg, 0.562 mmol) and Et$_3$N (0.116 mL, 1.5 mmol) were added. After 1 hour, the reaction mixture was diluted with saturated aqueous NH$_4$Cl, and extracted with ethyl acetate. The combined organic extracts were dried (MgSO$_4$) and concentrated under reduced pressure. Purification by flash column chromatography (5% to 10% MeOH in methylene chloride) gave 70 mg partially pure intermediate adduct. PPh$_3$ (78 mg, 0.30 mmol), Et$_3$N (0.10 mL, 0.74 mmol), and CCl$_4$ (0.029 mL, 0.30 mmol) were added to a stirred suspension of intermediate adduct (40 mg, 0.093 mmol) in 1:1 methylene chloride:MeCN (4 mL). The reaction mixture was heated to 50° C. for 5 hours. After cooling to room temperature, the reaction mixture was diluted with ethyl acetate, washed with water, dried (MgSO$_4$) and concentrated under reduced pressure. Purification by flash column chromatography (twice) (4% MeOH in methylene chloride) gave clean desired product (10 mg, 33%); MS APCI (+) m/z 414, 416 (M+, Br pattern) detected; $^1$H NMR (400 mHz, CD$_3$OD) δ 7.80 (s, 1H), 7.31 (dd, 1H), 7.25 (d, 1H), 7.02 (td, 1H), 3.64 (s, 3H).

Example 145

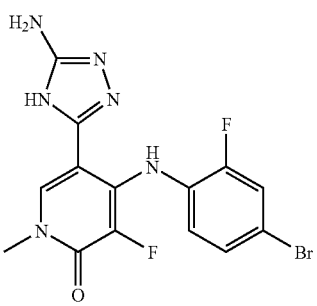

5-(5-Amino-4H-[1,2,4]triazol-3-yl)-4-(4-bromo-2-fluorophenylamino)-3-fluoro-1-methyl-1H-pyridin-2-one A mixture of 4-(4-bromo-2-fluorophenylamino)-5-fluoro-1-methyl-6-oxo-1,6-dihydropyridine-3-carboxylic acid hydrazide (100 mg, 0.268 mmol), 10% aqueous HCl (0.19 mL) and cyanamide (0.04 mL, 0.515 mmol) was heated to reflux for 3 days. The reaction mixture was concentrated under reduced pressure, diluted with water and washed with water. DMF (10 mL) was added to the aqueous layer and it was extracted with methylene chloride. The combined organic extracts were dried (MgSO$_4$) and concentrated under reduced pressure to give the desired intermediate adduct (35 mg). PPh$_3$ (76 mg, 0.29 mmol), Et$_3$N (0.10 mL, 0.74 mmol), and CCl$_4$ (0.028 mL, 0.29 mmol) were added to a stirred suspension of intermediate adduct (30 mg, 0.072 mmol) in methylene chloride (2 mL). The reaction mixture was heated to 50° C. for 5 hours. After cooling to room temperature, the reaction mixture was diluted with ethyl acetate, washed with water, dried (MgSO$_4$) and concentrated under reduced pressure. Purification by flash column chromatography (4% MeOH in methylene chloride) followed by methylene chloride trituration gave clean desired product (1 mg, 4%); MS APCI (+) m/z 397, 399 (M+, Br pattern) detected.

Example 146

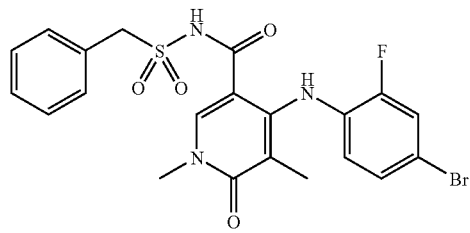

N-[4-(4-Bromo-2-fluorophenylamino)-1,5-dimethyl-6-oxo-1,6-dihydropyridine-3-carbonyl]-C-phenyl-methanesulfonamide N-[4-(4-Bromo-2-fluorophenylamino)-1,5-dimethyl-6-oxo-1,6-dihydropyridine-3-carbonyl]-C-phenyl-methanesulfonamide was prepared from 4-(4-bromo-2-fluorophenylamino)-1,5-dimethyl-6-oxo-1,6-dihydropyridine-3-carboxylic acid as follows. To a solution of 4-(4-bromo-2-fluorophenylamino)-1,5-dimethyl-6-oxo-1,6-dihydropyridine-3-carboxylic acid (0.040 mg, 0.113 mmol) in DMF (1.5 mL) was added 1,1'-carbonyldiimidazole (0.074 mg, 0.456 mmol). After stirring for two hours, α-toluenesulfonamide (0.079 mg, 0.461 mmol) was added, followed by DBU (0.070 mL, 0.459 mmol). After stirring for 16 hours at room temperature, the reaction mixture was diluted with EtOAc and 1N HCl solution. The organic layer was separated and washed with brine. The aqueous layer was extracted with EtOAc (2×) and washed with brine. The combined organic extracts were dried (MgSO$_4$) and concentrated under reduced pressure. Purification by flash column chromatography (2% MeOH in methylene chloride) gave 0.039 g (68%) clean desired product; MS APCI (−) m/z 506, 508 (M−, Br pattern) detected; $^1$H NMR (400 MHz, CD$_3$OD) δ 8.29 (s, 1H), 7.27 (m, 3H), 7.18 (d, 1H), 7.11 (m, 3H), 6.56 (t, 1H), 4.44 (s, 2H), 3.54 (s, 3H), 1.62 (s, 3H).

Example 147

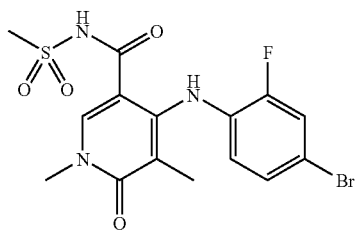

N-[4-(4-Bromo-2-fluorophenylamino)-1,5-dimethyl-6-oxo-1,6-dihydropyridine-3-carbonyl]-methanesulfonamide N-[4-(4-Bromo-2-fluorophenylamino)-1,5-dimethyl-6-oxo-1,6-dihydropyridine-3-carbonyl]-methanesulfonamide was prepared from 4-(4-bromo-2-fluorophenylamino)-1,5-dimethyl-6-oxo-1,6-dihydropyridine-3-carboxylic acid as follows. To a solution of 4-(4-bromo-2-fluorophenylamino)-1,5-dimethyl-6-oxo-1,6-dihydropyridine-3-carboxylic acid (0.041 mg, 0.115 mmol) in DMF (1 mL) was added 1,1'-carbonyldiimidazole (0.039 mg, 0.241 mmol). After stirring for two hours, methanetoluenesulfonamide (0.023 mg, 0.242 mmol) was added, followed by DBU (0.035 mL, 0.230 mmol). After stirring 16 hours at room temperature, the reaction mixture was diluted with EtOAc and 1N HCl solution. The organic layer was separated and washed with brine. The aqueous layer was extracted with EtOAc (2×) and washed with brine. The combined organic extracts were dried ($MgSO_4$) and concentrated under reduced pressure. Purification by flash column chromatography (15% MeOH in methylene chloride) gave 0.028 g (57%) clean desired product; MS APCI (−) m/z 430, 432 (M−, Br pattern) detected; $^1$H NMR (400 MHz, DMSO-$d_6$) δ 11.13 (s, 1H), 8.25 (s, 1H), 7.49 (dd, 1H), 7.23 (d, 1H), 6.55 (t, 1H), 3.46 (s, 3H), 2.83 (s, 3H), 1.56 (s, 3H).

Example 148

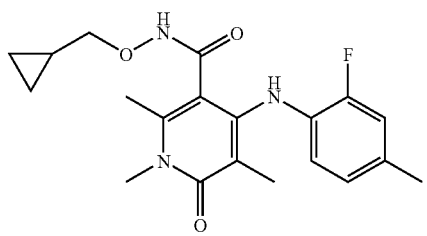

4-(2-Fluoro-4-methylphenylamino)-1,2,5-trimethyl-6-oxo-1,6-dihydropyridine-3-carboxylic acid cyclopropylmethoxy-amide Step A: Preparation of 4-hydroxy-1,2,5-trimethyl-6-oxo-1,6-dihydropyridine-3-carboxylic acid ethyl ester: A mixture of 2-methyl-3-oxo-pentanedioic acid diethyl ester (10.0 g, 46.3 mmol), 1,1-diethoxy-ethene (12.8 mL, 92.5 mmol) and sodium methoxide (0.026 mg, 0.481 mmol) was heated to 85° C. for nine hours. The reaction mixture was cooled to room temperature and concentrated. To the resulting residue was added methylamine (1.91 mL, 55.5 mmol, 40% $H_2O$). After stirring at room temperature for 16 hours, the reaction mixture was diluted with diethyl ether and washed with water. The aqueous phase was acidified to pH 1 with 10% HCl solution and extracted with EtOAc. The organic layer was dried ($MgSO_4$) and concentrated. Trituration of the resulting residue with diethyl ether and flash column chromatography (3% MeOH in methylene chloride) gave 3.55 g (34%) desired product.

Step B: Preparation of 4-Chloro-1,2,5-trimethyl-6-oxo-1,6-dihydropyridine-3-carboxylic acid ethyl ester: Phosphorous oxychloride (20.0 mL, 216 mmol) was added to 4-hydroxy-1,2,5-trimethyl-6-oxo-1,6-dihydropyridine-3-carboxylic acid ethyl ester and heated to 80° C. After two hours, the reaction mixture was concentrated under reduced pressure. The resulting residue was poured onto ice and, carefully neutralized with saturated $NaHCO_3$, and diluted with EtOAc. After stirring for 16 hours, the organic layer was separated and the aqueous layer was reextracted with EtOAc repeatedly. The pH of the aqueous layer was adjusted to pH 11 with saturated $K_2CO_3$ and extracted with EtOAc (2×). The combined organic extracts were dried ($MgSO_4$) and concentrated under reduced pressure to give 3.42 g (89%) clean desired product.

Step C: Preparation of 4-(2-fluoro-4-methylphenylamino)-1,2,5-trimethyl-6-oxo-1,6-dihydropiridine-3-carboxylic acid ethyl ester: 2-Fluoro-4-methylphenylamine (0.259 g, 2.07 mmol), palladium (II) acetate (0.046 g, 0.205 mmol), rac-2,2-bis(diphenylphosphino)-1,1'-binaphthyl (0.192 g, 0.308 mmol), and cesium carbonate (1.00 g, 3.08 mmol) were added to a solution of 4-chloro-1,2,5-trimethyl-6-oxo-1,6-dihydropyridine-3-carboxylic acid ethyl ester (0.50 g, 2.05 mmol) in toluene (7 mL) in a sealed vial. After stirring 10 minutes, the mixture was heated to 80° C. After 24 hours, the reaction mixture was cooled to room temperature and diluted with EtOAc. The resulting precipitate was filtered and washed with EtOAc. The filtrate was diluted with EtOAc and washed with water. The aqueous layer was reextracted with EtOAc. The combined organic layers were washed with brine, dried ($Na_2SO_4$) and concentrated. Purification by flash column chromatography (20:1 methylene chloride/MeOH) gave 0.048 g (71%) desired product.

Step D: Preparation of 4-(2-fluoro-4-methylphenylamino)-1,2,5-trimethyl-6-oxo-1,6-dihydropyridine-3-carboxylic acid cyclopropylmethoxy-amide: O-cyclopropylmethyl-hydroxylamine (0.046 g, 0.527 mmol) was added to a solution of 4-(2-fluoro-4-methylphenylamino)-1,2,5-trimethyl-6-oxo-1,6-dihydropyridine-3-carboxylic acid ethyl ester (0.070 g, 0.211 mmol) in THF (2 mL). The solution was cooled to 0° C. and lithium bis(trimethylsilyl)amide (1.05 mL, 1 M solution in hexanes) was added dropwise. The reaction mixture was warmed to room temperature. After stirring for 1 hour, the reaction was quenched by addition of a saturated aqueous solution of $NaHCO_3$ and partitioned between EtOAc and brine. The aqueous layer was reextracted with EtOAc. The combined organic extracts were dried ($Na_2SO_4$) and concentrated. Purification by flash column chromatography (30:1 methylene chloride/MeOH) gave 0.032 g (40%) desired product as a yellow solid; MS ESI (+) m/z 374 (M+1) detected; $^1$H NMR (400 MHz, $CD_3OD$) δ 6.91 (d,1H), 6.83 (d, 1H), 6.63 (t, 1H), 3.59 (s, 3H), 3.47 (d, 2H), 2.41 (s, 3H), 2.27 (s, 3H), 1.86 (s, 3H) 0.99 (m, 1H) 0.48 (m, 2H) 0.18 (m, 2H). $^{19}$F (376 MHz, CD$_3$OD)–132.1 (s, 1F).

Example 149

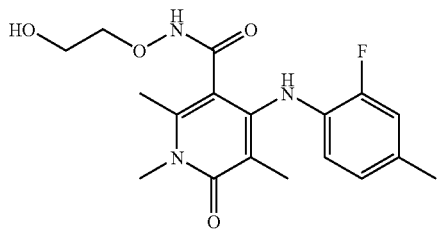

4-(2-Fluoro-4-methylphenylamino)-1,2,5-trimethyl-6-oxo-1,6-dihydropyridine-3-carboxylic acid (2-hydroxyethoxy)-amide 4-(2-Fluoro-4-methylphenylamino)-1,2,5-trimethyl-6-oxo-1,6-dihydropyridine-3-carboxylic acid (2-hydroxyethoxy)-amide was prepared as described in Example 148 using the appropriate hydroxylamine, followed by deprotection using standard literature methods. MS ESI (+) m/z 364 (M+1) detected; $^1$H NMR (400 MHz, CD$_3$OD) δ 6.91 (d, 1H), 6.83 (d, 1H), 6.63 (t, 1H), 3.80 (m, 2H), 3.63 (m, 2H), 3.60 (s, 3H), 2.42 (s, 3H), 2.27 (s, 3H) 1.85 (s, 3H). $^{19}$F (376 MHz, CD$_3$OD)–127.8 (s, 1F).

Example 150

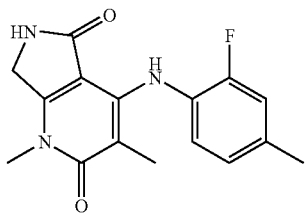

4-(2-Fluoro-4-methylphenylamino)-1,3-dimethyl-6,7-dihydro-1H-pyrrolo[3,4-b]pyridine-2,5-dione Step A: Preparation of 2-bromomethyl-4-(2-fluoro-4-methylphenylamino)-1,5-dimethyl-6-oxo-1,6-dihydropyridine-3-carboxylic acid ethyl ester: To a solution of 4-(2-fluoro-4-methylphenylamino)-1,2,5-trimethyl-6-oxo-1,6-dihydropyridine-3-carboxylic acid ethyl ester (0.150 g, 0.451 mmol) in DMF (5 mL) was added N-bromosuccinimide (0.084 g, 0.474 mmol). After stirring for 30 minutes, the reaction mixture was diluted with EtOAc, washed with water and brine, dried (Na$_2$SO$_4$) and concentrated under reduced pressure to yield a yellow residue. Purification by flash column chromatography (methylene chloride) gave 0.122 g (66%) of a yellow residue.

Step B: Preparation of 4-(2-fluoro-4-methylphenylamino)-1,3-dimethyl-6,7-dihydro-1H-pyrrolo[3,4-b]pyridine-2,5-dione: To a solution of 2-bromomethyl-4-(2-fluoro-4-methylphenylamino)-1,5-dimethyl-6-oxo-1,6-dihydropyridine-3-carboxylic acid ethyl ester (0.016 g, 0.040 mmol) in MeOH (0.50 mL) was added ammonia (0.006 mL, 0.040 mmol, 7 M solution in MeOH). After stirring for 2 hours at room temperature, the reaction mixture was heated to 40° C. for 8 hours. The resulting white precipitate was filtered to yield clean desired product (0.005 g, 46%). MS ESI (+) m/z 303 (M+1) detected; $^1$H NMR (400 MHz, DMSO) δ 8.16 (br s, 1H), 8.04 (br s, 1H), 6.81-6.94 (m, 3H), 4.33 (s, 2H), 3.45 (s, 3H), 2.33 (s, 3H), 1.63 (s, 3H). $^{19}$F (376 MHz, DMSO)–127.1 (s, 1F).

Example 151

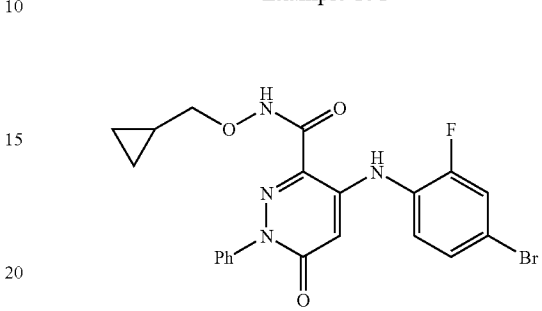

4-(4-Bromo-2-fluorophenylamino)-6-oxo-1-phenyl-1,6-dihydropyridazine-3-carboxylic acid cyclopropylmethoxy-amide Step A: Preparation of 3-oxo-2-(phenyl-hydrazono)-pentanedioic acid dimethyl ester: 3-oxo-2-(phenyl-hydrazono)-pentanedioic acid dimethyl ester was prepared from 3-oxo-pentanedioic acid dimethyl ester (7.02 mL, 45.9 mmol) according to the procedure of Schober et al. (*J. Heterocylic Chem*. 1989, 26, 169) to give 8.81 g (72%) of the desired product.

Step B: Preparation of 4-hydroxy-6-oxo-1-phenyl-1,6-dihydropyridazine-3-carboxylic acid methyl ester: A mixture of 3-oxo-2-(phenyl-hydrazono)-pentanedioic acid dimethyl ester (4.38 g, 15.7 mmol) in 1,2-dichlorobenzene (15 mL) was refluxed. After 20 hours, the reaction mixture was concentrated under reduced pressure to give 3.83 g (99%) of the desired product.

Step C: Preparation of 4-chloro-6-oxo-1-phenyl-1,6-dihydropyridazine-3-carboxylic acid methyl ester: A mixture of 4-hydroxy-6-oxo-1-phenyl-1,6-dihydropyridazine-3-carboxylic acid methyl ester (3.83 g, 15.6 mmol) and phosphorous oxychloride (50 mL) was heated to 85° C. After 20 hours, the reaction mixture was concentrated under reduced pressure. The resulting residue was quenched with water. The precipitate was filtered and dissolved in EtOAc, dried (MgSO$_4$) and concentrated under reduced pressure to yield 3.44 g (84%) of desired product.

Step D: Preparation of 4-(4-bromo-2-fluorophenylamino)-6-oxo-1-phenyl-1,6-dihydropyridazine-3-carboxylic acid: To a mixture of 4-chloro-6-oxo-1-phenyl-1,6-dihydropyridazine-3-carboxylic acid methyl ester (0.250 g, 0.944 mmol) in 1,2-dichlorobenzene (3.8 mL) was added 4-bromo-2-fluoro aniline (0.561 g, 3.78 mmol), and cesium carbonate (0.615 mg, 1.89 mmol). The reaction mixture was heated to reflux. After 1 hour, the reaction mixture was cooled to room temperature. Water was added and the mixture was diluted with EtOAc. The aqueous layer was separated, acidified with 10% HCl solution, and extracted with EtOAc. The combined organic layers were dried (MgSO4), concentrated under reduced pressure, and triturated to give 0.153 g (43%) of the desired product.

Step E. Preparation of 4-(4-Bromo-2-fluorophenylamino)-6-oxo-1-phenyl-1,6-dihydropyridazine-3-carboxylic acid cyclopropylmethoxy-amide. 4-(4-Bromo-2-fluorophenylamino)-6-oxo-1-phenyl-1,6-dihydropyridazine-3-carboxylic acid cyclopropylmethoxy-amide was prepared from 4-(4-bromo-2-fluorophenylamino)-6-oxo-1-phenyl-1,6-dihydropyridazine-3-carboxylic acid as described in Example 2. MS APCI (−) m/z 471, 473 (M−, Br pattern) detected; $^1$H NMR (400 MHz, CD$_3$OD−CDCl$_3$) δ 7.50 (m, 8H), 6.12 (s, 1H), 3.78 (d, 2H), 1.18 (m, 1H), 0.59 (q, 2H), 0.32 (q, 2H).

Example 152

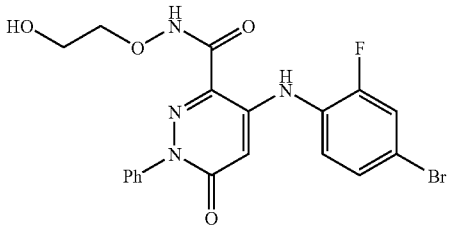

4-(4-Bromo-2-fluorophenylamino)-6-oxo-1-phenyl-1,6-dihydropyridazine-3-carboxylic acid (2-hydroxyethoxy)-amide Prepared from 4-(4-bromo-2-fluorophenylamino)-6-oxo-1-phenyl-1,6-dihydropyridazine-3-carboxylic acid as described in Example 3. MS APCI (−) m/z 461, 463 (M−, Br pattern) detected; $^1$H NMR (400 MHz, CD$_3$OD) δ 7.51 (m, 8H), 6.09 (s, 1H), 4.04 (t, 2H), 3.77 (t, 2H).

Example 153

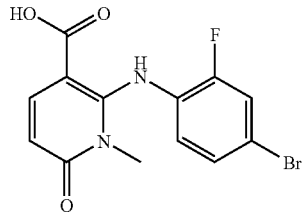

2-(4-Bromo-2-fluorophenylamino)-1-methyl-6-oxo-1,6-dihydropyridine-3-carboxylic acid Step A. Preparation of 2-chloro-6-oxo-1,6-dihydropyridine-3-carboxylic acid: 2-Chloro-6-oxo-1,6-dihydropyridine-3-carboxylic acid was prepared from dichloronicotinic acid (3.00 g, 15.6 mmol, Aldrich) according to the procedure described in U.S. Pat No. 3,682,932 (1972) to yield 1.31 g (48%) of the desired product.

Step B. Preparation of 2-chloro-1-methyl-6-oxo-1,6-dihydropyridine-3-carboxylic acid methyl ester: To a solution of 2-chloro-6-oxo-1,6-dihydropyridine-3-carboxylic acid (0.644 g, 3.71 mmol) in DMF (20 mL) was added lithium hydride (95%, 0.078 g, 9.28 mmol) and the reaction mixture was stirred for 40 minutes under N$_2$. Methyl iodide (0.508 mL, 1.16 g, 8.16 mmol) was then added and the reaction mixture was stirred for an additional 45 minutes. The reaction mixture was quenched with 2 M HCl until the pH was 6-7. The reaction mixture was diluted with EtOAc and saturated NaCl and the layers separated. The aqueous layer was back extracted with EtOAc (1×). The combined organic layers were dried (Na$_2$SO$_4$) and concentrated under reduced pressure to yield a crude yellow solid. HPLC analysis showed two products in a 4:1 ratio that were separated by flash column chromatography (methylene chloride/EtOAc, 15:1 to 10:1) to give 0.466 g (62%) pure desired product as a white crystalline solid. The minor product was also isolated as a pale yellow crystalline solid and identified as the regioisomer 2-chloro-6-methoxy-nicotinic acid methyl ester.

Step C. Preparation of 2-(4-bromo-2-fluorophenylamino)-1-methyl-6-oxo-1,6-dihydropyridine-3-carboxylic acid methyl ester: To a solution of 4-bromo-2-fluorophenylamine (0.192 g, 1.01 mmol) in THF (5 mL) at −78° C. under N$_2$ was added lithium bis(trimethylsilyl)amide (1.50 mL, 1.50 mmol, 1 M solution in hexanes) dropwise. The reaction mixture was stirred for one hour at −78° C. 2-Chloro-1-methyl-6-oxo-1,6-dihydropyridine-3-carboxylic acid methyl ester (0.202 g, 1.00 mmol) was then added dropwise as a solution in THF (5 mL) and the reaction mixture was stirred for one hour at −78° C. The reaction mixture was quenched by the addition of H$_2$O and the pH was adjusted to pH 7 with saturated NH$_4$Cl and then diluted with EtOAc. The organic layer was separated and washed with saturated NaCl, dried (Na$_2$SO$_4$), and concentrated under reduced pressure. Purification by flash column chromatography (methylene chloride/EtOAc, 15:1) gave 0.232 g (65%) pure desired product as a white crystalline solid.

Step D. Preparation of 2-(4-bromo-2-fluorophenylamino)-1-methyl-6-oxo-1,6-dihydropyridine-3-carboxylic acid: To a solution of 2-(4-bromo-2-fluorophenylamino)-1-methyl-6-oxo-1,6-dihydropyridine-3-carboxylic acid methyl ester in MeOH (1.5 mL) was added 1 M NaOH (800 uL, 0.902 mmol). The reaction mixture was stirred at 60° C. for 4 hours and then at room temperature for 16 hours. The reaction mixture was diluted with H$_2$O, acidified with 2 M HCl until the pH was 1-2, and then diluted with EtOAc. The organic layer was separated and washed with saturated NaCl, dried (Na$_2$SO$_4$), and concentrated under reduced pressure to yield 0.053 g (97%) desired product as a pale orange solid. MS ESI (+) m/z 341, 343 (M+, Br pattern) detected; $^1$H NMR (400 MHz, DMSO-d$_6$) δ 13.08 (s, 1H), 10.0 (s, 1H), 7.87 (d, 1H), 7.65 (d, 1H), 7.35 (d, 1H), 6.95 (t, 1H), 6.16 (d, 1H), 3.19 (s, 3H).

In the foregoing examples, a variety of anilines can be used in place of 4-bromo-2-fluorophenylamine in Step C of Example 153.

Example 154

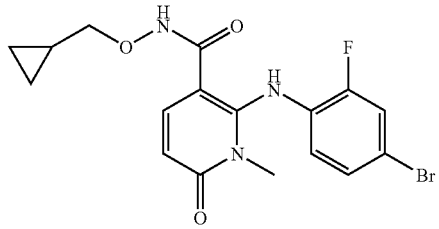

2-(4-Bromo-2-fluorophenylamino)-1-methyl-6-oxo-1,6-dihydropyridine-3-carboxylic acid cyclopropylmethoxy-amide A mixture of 2-(4-bromo-2-fluorophenylamino)-1-methyl-6-oxo-1,6-dihydropyridine-3-carboxylic acid (0.022 g, 0.064 mmol), EDCI (0.019 g, 0.097 mmol), and HOBt (0.019 g, 0.097 mmol) in DMA (1 mL) was stirred for 30 minutes at room temperature under N$_2$. O-Cyclopropylmethyl-hydroxylamine (0.017 g, 0.19 mmol) was added followed by Et$_3$N (0.022 mL, 0.016 g, 0.16 mmol). After the reaction mixture was stirred for 16 hours at room temperature, it was diluted with EtOAc and washed with saturated NH$_4$Cl solution, saturated NaHCO₃ solution and saturated NaCl. The organic layer was dried (Na₂SO₄) and concentrated under reduced pressure. Purification by flash column chromatography (methylene chloride/methanol, 20:1) gave 0.015 g (57%) pure desired product as a yellow solid. MS APCI (−) m/z 410, 411 (M−, Br pattern) detected; ¹H NMR (400 MHz, DMSO-d₆) δ 11.4 (s, 1H), 9.81 (s, 1H), 7.58 (m, 2H), 7.28 (d, 1H), 6.82 (t, 1H), 6.17 (d, 1H), 3.46 (d, 2H), 3.22 (s, 3H), 0.99 (m, 1H), 0.48 (m, 2H), 0.18 (m, 2H).

Example 155

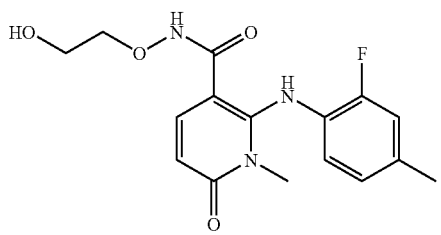

2-(2-Fluoro-4-methylphenylamino)-1-methyl-6-oxo-1,6-dihydropyridine-3-carboxylic acid (2-hydroxyethoxy)-amide Step A. Preparation of 2-(2-fluoro-4-methylphenylamino)-1-methyl-6-oxo-1,6-dihydropyridine-3-carboxylic acid (2-vinyloxyethoxy)-amide: To a solution of 2-(2-fluoro-4-methylphenylamino)-1-methyl-6-oxo-1,6-dihydropyridine-3-carboxylic acid methyl ester (0.050 g, 0.17 mmol) in THF (1.5 mL) under N₂ was added O-(2-vinyloxy-ethyl)-hydroxylamine (0.044 g, 0.43 mmol). The solution was cooled to 0° C. and lithium bis(trimethylsilyl)amide (0.86 mL, 0.86 mmol, 1 M solution in hexanes) was added dropwise. The reaction mixture was warmed to room temperature. After stirring for 40 minutes, the reaction mixture was quenched by the addition of NaHCO₃ and partitioned between EtOAc and saturated NaCl. The layers were separated and the aqueous layer was reextracted with EtOAc. The combined organic extracts were dried (Na₂SO₄) and concentrated under reduced pressure. Purification by flash column chromatography (methylene chloride/methanol, 20:1) gave 0.048 g (77%) pure desired product as an off-white foamy solid.

Step B. Preparation of 2-(2-fluoro-4-methylphenylamino)-1-methyl-6-oxo-1,6-dihydropyridine-3-carboxylic acid (2-hydroxyethoxy)-amide: To a solution of 2-(2-fluoro-4-methylphenylamino)-1-methyl-6-oxo-1,6-dihydropyridine-3-carboxylic acid (2-vinyloxyethoxy)-amide (0.048 g, 0.13 mmol) in ethanol (5 mL) was added aqueous 2 M HCl (0.332 mL, 0.664 mmol). The reaction mixture was stirred for 16 hours at room temperature. The pH of the reaction mixture was adjusted with 1 M NaOH until 7. The reaction mixture was diluted with EtOAc and H₂O. The organic layer was separated and washed with saturated NaCl, dried (Na₂SO₄), and concentrated under reduced pressure to yield 0.044 g (100%) pure desired product as a pale yellow foamy solid. MS ESI (+) m/z 336 (M+1) detected; ¹H NMR (400 MHz, CDCl₃) δ 10.3 (s, 1H), 8.46 (s, 1H), 7.38 (d, 1H), 6.96-6.87 (m, 2H), 6.76 (t, 1H), 6.18 (d, 1H), 4.04 (m, 2H), 3.93 (br s, 1H), 3.75 (br s, 2H), 3.20 (s, 3H), 2.33 (s, 3H).

Any of the hydroxylamines used in the foregoing examples can be coupled as described in Example 154 or Example 155. In some instances, a final deprotection step may be required. These deprotections can be accomplished by standard literature methods. Example 155 is one such example in which a final deprotection step is required.

Example 156

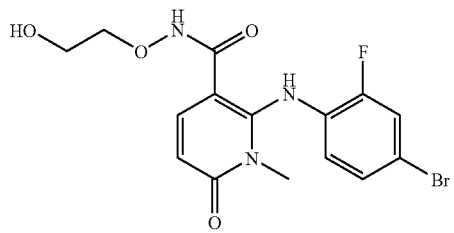

2-(4-Bromo-2-fluorophenylamino)-1-methyl-6-oxo-1,6-dihydropyridine-3-carboxylic acid (2-hydroxyethoxy)-amide Step A. Preparation of 2-(4-bromo-2-fluorophenylamino)-1-methyl-6-oxo-1,6-dihydropyridine-3-carboxylic acid (2-vinyloxyethoxy)-amide: 2-(4-Bromo-2-fluorophenylamino)-1-methyl-6-oxo-1,6-dihydropyridine-3-carboxylic acid (0.020 g, 0.059 mmol) was coupled as described previously in Example 154 using O-(2-vinyloxy-ethyl)-hydroxylamine to yield 0.015 g (60%) pure desired product as a yellow solid.

Step B. Preparation of 2-(4-Bromo-2-fluorophenylamino)-1-methyl-6-oxo-1,6-dihydropyridine-3-carboxylic acid (2-hydroxyethoxy)-amide: 2-(4-Bromo-2-fluorophenylamino)-1-methyl-6-oxo-1,6-dihydropyridine-3-carboxylic acid (2-vinyloxyethoxy)-amide (0.015 g, 0.035 mmol) was deprotected as described previously in Step B of Example 155 to yield 0.010 g (70%) pure desired product as a dark yellow solid. MS ESI (+) m/z 400, 402 (M+, Br pattern) detected; ¹H NMR (400 MHz, CDCl₃) δ 10.3 (s, 1H), 9.11 (s, 1H), 7.47 (d, 1H), 7.32 (d, 1H), 7.23 (d, 1H), 6.70 (t, 1H), 6.22 (d, 1H), 4.04 (br s, 2H), 3.75 (br s, 2H) 3.24 (s, 3H).

Example 157

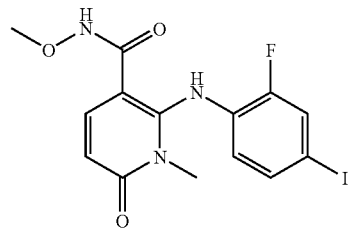

2-(2-Fluoro-4-iodophenylamino)-1-methyl-6-oxo-1,6-dihydropyridine-3-carboxylic acid methoxy-amide 2-(2-Fluoro-4-iodophenylamino)-1-methyl-6-oxo-1,6-dihydropyridine-3-carboxylic acid methyl ester was coupled as described previously in Example 155 using O-methyl-hydroxylamine. MS ESI (+) m/z 418 (M+1) detected.

Example 158

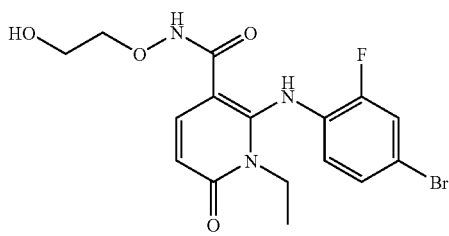

2-(4-Bromo-2-fluorophenylamino)-1-ethyl-6-oxo-1,6-dihydropyridine-3-carboxylic acid (2-hydroxyethoxy)-amide 2-Chloro-6-oxo-1,6-dihydropyridine-3-carboxylic acid was converted to 2-(4-bromo-2-fluorophenylamino)-1-ethyl-6-oxo-1,6-dihydropyridine-3-carboxylic acid methyl ester following the procedures described in Steps B-C of Example 153 using ethyl iodide in Step B of Example 153. 2-(4-Bromo-2-fluorophenylamino)-1-ethyl-6-oxo-1,6-dihydropyridine-3-carboxylic acid methyl ester was then coupled as described in Example 155 to yield the desired product as a tan solid. MS APCI (+) m/z 414, 416 (M+, Br pattern) detected; $^1$H NMR (400 MHz, CD$_3$OD) δ 7.59 (d, 1H), 7.38 (d, 1H), 7.24 (d, 1H), 6.77 (t, 1H), 6.33 (d, 1H), 4.16 (q, 2H), 3.73 (m, 2H), 3.59 (m, 2H), 1.21 (t, 3H).

Example 159

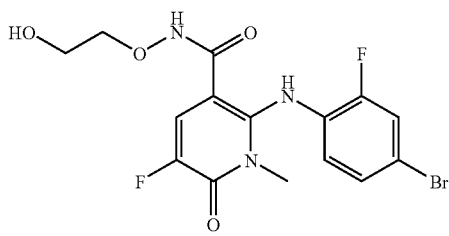

2-(4-Bromo-2-fluorophenylamino)-5-fluoro-1-methyl-6-oxo-1,6-dihydropyridine-3-carboxylic acid (2-hydroxyethoxy)-amide 2,6-Dichloro-5-fluoro-nicotinic acid (Lancaster Synthesis) was converted to 2-(4-bromo-2-fluorophenylamino)-5-fluoro-1-methyl-6-oxo-1,6-dihydropyridine-3-carboxylic acid methyl ester following the procedures described in Steps A-C of Example 153. 2-(4-Bromo-2-fluorophenylamino)-5-fluoro-1-methyl-6-oxo-1,6-dihydropyridine-3-carboxylic acid methyl ester was then coupled as described in Example 155 to yield the desired product as a yellow solid. MS ESI (+) m/z 418, 420 (M+, Br pattern) detected; $^1$H NMR (400 MHz, CDCl$_3$) δ 7.32 (dd, 1H), 7.29–7.19 (m, 2H), 6.61 (t, 1H), 4.06 (m, 2H), 3.76 (m, 2H), 3.33 (s, 3H), 3.32 (s, 3H).

Example 160

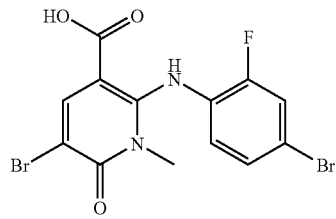

5-Bromo-2-(4-bromo-2-fluorophenylamino)-1-methyl-6-oxo-1,6-dihydropyridine-3-carboxylic acid Step A. Preparation of 5-bromo-2-(4-bromo-2-fluorophenylamino)-1-methyl-6-oxo-1,6-dihydropyridine-3-carboxylic acid methyl ester: To a solution of 2-(4-bromo-2-fluorophenylamino)-1-methyl-6-oxo-1,6-dihydropyridine-3-carboxylic acid methyl ester (0.390 g, 1.34 mmol) in DMF (10 mL) was added N-bromosuccinimide (0.263, 1.48 mmol). The reaction mixture was stirred at room temperature for 25 minutes and then quenched with saturated sodium bisulfite. The reaction mixture was diluted with H$_2$O and partitioned between EtOAc/diethyl ether and saturated NaCl. The layers were separated and the aqueous layer was reextracted with EtOAc (1×). The combined organic layers were dried (Na$_2$SO$_4$) and concentrated under reduced pressure. Purification by flash column chromatography (methylene chloride/EtOAc, 15:1) gave 0.424 g (85%) pure desired product as a lavender foamy solid.

Step B. Preparation of 5-bromo-2-(4-bromo-2-fluorophenylamino)-1-methyl-6-oxo-1,6-dihydropyridine-3-carboxylic acid: To a suspension of 5-bromo-2-(4-bromo-2-fluorophenylamino)-1-methyl-6-oxo-1,6-dihydropyridine-3-carboxylic acid methyl ester (0.030 g, 0.069 mmol) in methanol (1 mL) was added 1 M NaOH (0.346 mL, 0.346 mmol). The reaction mixture was heated to 60° C. for 12 hours. The reaction mixture was diluted with H$_2$O and the pH was adjusted with 1 M HCl until 1-2. Solids precipitated out of solution, which were collected, washed with H$_2$O and dried under vacuum to yield 0.021 g (72%) pure desired product as a pale yellow solid. MS ESI (+) m/z 421, 423 (M+, Br pattern) detected; $^1$H NMR (400 MHz, DMSO-d$_6$) δ 13.3 (br s, 1H), 9.93 (s, 1H), 8.21 (s, 1H), 7.66 (d, 1H), 7.34 (d, 1H), 7.05 (t, 1H), 3.18 (s, 3H).

Example 161

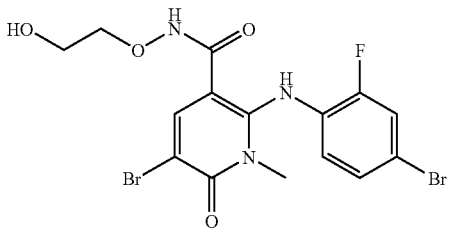

5-Bromo-2-(4-bromo-2-fluorophenylamino)-1-methyl-6-oxo-1,6-dihydropyridine-3-carboxylic acid (2-hydroxyethoxy)-amide 5-Bromo-2-(4-bromo-2-fluorophenylamino)-1-methyl-6-oxo-1,6-dihydropyridine-3-carboxylic acid (0.018 g, 0.043 mmol) was converted to the desired product following the procedures described in Example 156 to yield 0.009 g (45%) pure desired product as a dark yellow solid. MS ESI (+) m/z 480, 482 (M+, Br pattern) detected; $^1$H NMR (400 MHz, CDCl$_3$) δ 8.00 (s, 1H), 7.32 (m, 1H), 7.24 (d, 1H), 6.69 (t, 1H), 3.99 (m, 2H), 3.73 (m, 2H), 3.32 (s, 3H).

Example 162

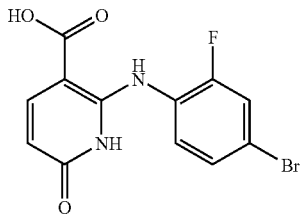

2-(4-Bromo-2-fluorophenylamino)-6-oxo-1,6-dihydropyridine-3-carboxylic acid

Step A. Preparation of 2-(4-bromo-2-fluorophenylamino)-6-chloro-nicotinic acid: To a solution of 4-bromo-2-fluorophenylamine (10.4 g, 54.7 mmol) in THF (25 mL) at −78° C. under N$_2$ was added lithium bis(trimethylsilyl)amide (83.3 mL, 83.3 mmol, 1 M solution in hexanes) dropwise over 15 minutes. The reaction mixture was stirred for one hour at −78° C. 2,6-Dichloro-nicotinic acid (5.00 g, 26.0 mmol) was then added dropwise as a solution in THF (15 mL) and the reaction mixture was allowed to warm from −78° C. to room temperature and stir for 16 hours. The reaction mixture was quenched by the addition of H$_2$O and the pH was adjusted to 0-2 with 6 N HCl and then diluted with EtOAc. The organic layer was separated and washed with H$_2$O, saturated NaCl, dried (Na$_2$SO$_4$), and concentrated under reduced pressure. The crude product was triturated several times with ethyl acetate and the resulting solid was collected, washed with dichloromethane and dried under vacuum to yield 7.50 g (83%) pure desired product as a dark pink solid.

Step B. Preparation of 2-(4-bromo-2-fluorophenylamino)-6-chloro-nicotinic acid methyl ester: To a suspension of 2-(4-bromo-2-fluorophenylamino)-6-chloro-nicotinic acid (5.00 g, 14.5 mmol) in methanol/benzene (1:1, 100 mL) under N$_2$ was added (trimethylsilyl)diazomethane (2.0 M solution in hexanes) dropwise until the bubbling caused by gas evolution ceased. Solids precipitated out of solution. The reaction was allowed to stir for 1 hour. Excess (trimethylsilyl)diazomethane was quenched by the dropwise addition of glacial acetic acid. The precipitated solids were filtered and washed with methanol. The filtrate was concentrated to a smaller volume and additional solids precipitated out of solution that were filtered and washed with methanol. The solids were combined and dried under vacuum to yield 4.82 g (93%) of pure desired product as a dark pink solid.

Step C. Preparation of 2-(4-bromo-2-fluorophenylamino)-6-methoxy-nicotinic acid methyl ester: To a mixture of 2-(4-bromo-2-fluorophenylamino)-6-chloro-nicotinic acid methyl ester (2.00 g, 5.56 mmol) and sodium methoxide (0.791 g, 13.9 mmol) was added MeOH (50 mL) to give a slurry that was stirred at 60-65° C. for 16 hours under N$_2$. Additional sodium methoxide (0.791 g, 13.9 mmol) was added and the reaction mixture was allowed to stir another 3 days at 60-65° C. The reaction mixture was cooled to room temperature and glacial acetic acid was added dropwise until the pH was 7. The resulting suspension was filtered and washed with H$_2$O to yield a pink solid that was collected and dried under vacuum to yield 1.74 g (88%) pure desired product.

Step D. Preparation of 2-(4-bromo-2-fluorophenylamino)-6-oxo-1,6-dihydropyridine-3-carboxylic acid methyl ester: To 2-(4-bromo-2-fluorophenylamino)-6-methoxy-nicotinic acid methyl ester (1.00 g, 2.82 mmol) in a sealed flask was added glacial acetic acid (10 mL) and HBr (10 mL, 48 wt % in H$_2$O). The reaction mixture was stirred at 90-95° C. for 2 hours and then cooled to room temperature. The reaction mixture was diluted with EtOAc and washed with H$_2$O, saturated NaHCO$_3$, and saturated NaCl, dried over Na$_2$SO$_4$ and concentrated under reduced pressure. The crude product was triturated twice with dichloromethane/methanol and the resulting solid was collected and dried under vacuum to yield 0.756 g (79%) pure desired product as a white solid.

Step E. Preparation of 2-(4-bromo-2-fluorophenylamino)-6-oxo-1,6-dihydropyridine-3-carboxylic acid: To a suspension of 2-(4-bromo-2-fluorophenylamino)-6-oxo-1,6-dihydropyridine-3-carboxylic acid methyl ester (0.050 g, 0.147 mmol) in methanol (1.5 mL) was added 1 M NaOH (1.47 mL, 1.47 mmol). The reaction mixture was stirred at 75-80° C. for 2 days. The reaction mixture was diluted with H$_2$O and the pH was adjusted with 1 M HCl until 1-2. The reaction mixture was diluted with EtOAc and washed with saturated NaCl, dried (Na$_2$SO$_4$), and concentrated under reduced pressure. The crude product was triturated with diethyl ether/dichloromethane and the resulting solid was collected and dried under vacuum to yield 0.033 g (69%) pure desired product as a yellow solid. MS ESI (+) m/z 327, 329 (M+, Br pattern) detected; $^1$H NMR (400 mHz, DMSO-d$_6$) δ 13.1 (br s, 1H), 11.5 (s, 1H), 10.9 (s, 1H), 8.77 (br s, 1H), 8.10 (d, 1H), 7.59 (d, 1H), 7.35 (d, 1H) 6.16 (m, 1H).

Example 163

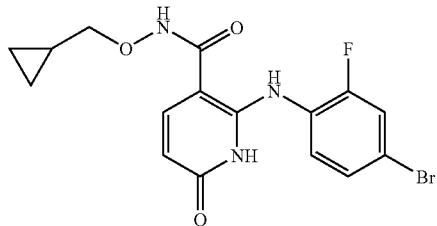

2-(4-Bromo-2-fluorophenylamino)-6-oxo-1,6-dihydropyridine-3-carboxylic acid cyclopropylmethoxy-amide 2-(4-Bromo-2-fluorophenylamino)-6-oxo-1,6-dihydropyridine-3-carboxylic acid (0.025 g, 0.076 mmol) was converted to the desired product following the procedure described in Example 154 to yield 0.023 g (76%) pure desired product as a pale yellow solid. MS ESI (+) m/z 396, 398 (M+, Br pattern) detected; $^1$H NMR (400 mHz, DMSO-d$_6$) δ 11.6 (s, 1H), 11.3 (s, 1H), 11.2 (s, 1H), 9.74 (br s, 1H), 7.90 (d, 1H), 7.56 (d, 1H), 7.32 (d, 1H), 6.13 (d, 1H) 3.70 (d, 2H) 1.10 (m, 1H), 0.54 (m, 2H), 0.27 (m, 2H).

Example 164

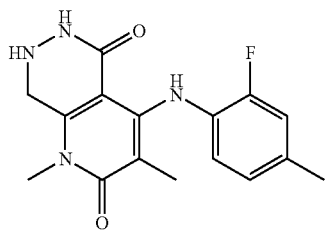

4-(2-Fluoro-4-methylphenylamino)-1,3-dimethyl-7,
8-dihydro-1H,6H-pyrido[2,3-d]pyridazine-2,5-dione To a solution of 2-bromomethyl-4-(2-fluoro-4-methylphenylamino)-1,5-dimethyl-6-oxo-1,6-dihydropyridine-3-carboxylic acid ethyl ester (1 equivalent) in MeOH is added hydrazine (1.10 equivalents). After stirring for 2 hours at room temperature, the reaction mixture is heated to 40° C. for 8 hours. The reaction mixture is diluted with EtOAc and washed with water. The organic layer is dried over MgSO$_4$, filtered, and concentrated in vacuo to give the crude material that is purified by trituration or flash column chromatography to afford the desired product as necessary.

Example 165

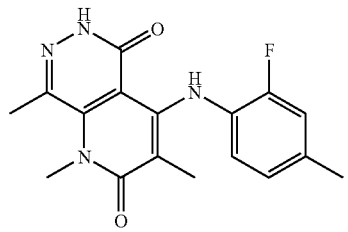

4-(2-Fluoro-4-methylphenylamino)-1,3,8-trimethyl-
1H,6H-pyrido[2,3-d]pyridazine-2,5-dione Step A: Preparation of 2-bromo-4-chloro-1,5-dimethyl-6-oxo-1,6-dihydropyridine-3-carboxylic acid ethyl ester: To a solution of 4-chloro-1,5-dimethyl-6-oxo-1,6-dihydropyridine-3-carboxylic acid ethyl ester (1.00 equivalent) in DMF is added NBS (1.20 equivalents) at room temperature. After stirring for 16 hours at room temperature, the reaction mixture is diluted with EtOAc and washed with water. The organic layer is dried over MgSO$_4$, filtered, and concentrated in vacuo to give the crude material that is purified by trituration or flash column chromatography to afford the desired product as necessary.

Step B: Preparation of 4-chloro-1,5-dimethyl-6-oxo-2-trimethylsilanylethynyl-1,6-dihydropyridine-3-carboxylic acid ethyl ester: To a mixture of 2-bromo-4-chloro-1,5-dimethyl-6-oxo-1,6-dihydropyridine-3-carboxylic acid ethyl ester (1.00 equivalent), trimethylsilylacetylene (1.20 equivalents) and iPr$_2$NH (2.00 equivalents) in THF is added CuI (0.10 equivalents) followed by Pd(PPh$_3$)$_2$Cl$_2$ (0.10 equivalents). After stirring the reaction mixture at reflux for 16 hours, it is cooled to room temperature and diluted with ethyl acetate. The organic layer is washed with saturated NH$_4$Cl solution and brine, dried (MgSO$_4$) and concentrated under reduced pressure. The desired product is obtained by flash column chromatography as necessary.

Step C: Preparation of 2-acetyl-4-chloro-1,5-dimethyl-6-oxo-1,6-dihydropyridine-3-carboxylic acid ethyl ester: A mixture of 4-chloro-1,5-dimethyl-6-oxo-2-trimethylsilanylethynyl-1,6-dihydropyridine-3-carboxylic acid ethyl ester (1.00 equivalent), HgSO$_4$ (1.00 equivalent) and H$_2$SO$_4$ (2.00 equivalents) in ~6:1 acetone:water is refluxed for 3 hours. The reaction mixture is cooled to room temperature and concentrated under reduced pressure. The residue is diluted with a mixture of THF and ethyl acetate and washed with water and brine. The organic layer is dried (MgSO$_4$) and concentrated under reduced pressure. The desired product is obtained by flash column chromatography as necessary.

Step D: Preparation of 2-acetyl-4-chloro-1,5-dimethyl-6-oxo-1,6-dihydropiridine-3-carboxylic acid: To a solution of 2-acetyl-4-chloro-1,5-dimethyl-6-oxo-1,6-dihydropyridine-3-carboxylic acid ethyl ester (1.00 equivalent) in THF:water (4:1) is added 1 M aqueous LiOH solution (2.05 equivalents). After 30 minutes, the reaction mixture is acidified to pH~1 with 1 N HCl solution and extracted with ethyl acetate. The combined organic extracts are dried (MgSO$_4$) and concentrated under reduced pressure to give the desired product which is used directly without further purification.

Step E: Preparation of 4-chloro-1,3,8-trimethyl-1H,6H-pyrido[2,3-d]pyridazine-2,5-dione: To a solution of 2-acetyl-4-chloro-1,5-dimethyl-6-oxo-1,6-dihydropyridine-3-carboxylic acid (1 equivalent) and hydrazine monohydrate (3.30 equivalents) in THF is added 1 N HCl (0.80 equivalents). After 16 hours, the reaction mixture is diluted with ethyl acetate, washed with water and brine, dried (MgSO$_4$) and concentrated under reduced pressure. The desired product purified by trituration or flash column chromatography to afford the desired product as necessary.

Step F: Preparation of 4-(2-fluoro-4-methylphenylamino)-1,3,8-trimethyl-1H,6H-pyrido[2,3-d]pyridazine-2,5-dione: 2-Fluoro-4-methylphenylamine (1.10 equivalents), palladium (II) acetate (0.10 equivalents), rac-2,2-bis(diphenylphosphino)-1,1'-binaphthyl (0.15 equivalents), and cesium carbonate (1.50 equivalents) are added to a solution of 4-chloro-1,3,8-trimethyl-1H,6H-pyrido[2,3-d]pyridazine-2,5-dione (1.00 equivalent) in toluene in a sealed vial. After stirring 10 minutes, the mixture is heated to 80° C. After 24 hours, the reaction mixture is cooled to room temperature and diluted with EtOAc. The resulting precipitate is filtered and washed with EtOAc. The filtrate is diluted with EtOAc and washed with water. The aqueous layer is reextracted with EtOAc. The combined organic layers are washed with brine, dried (Na$_2$SO$_4$) and concentrated. Purification by flash column chromatography gives the desired product.

Example 166

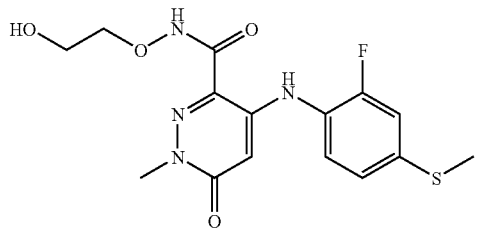

4-(2-Fluoro-4-(methylthio)phenylamino)-N-(2-hydroxyethoxy)-1-methyl-6-oxo-1,6-dihydropyridazine-3-carboxamide Step A: Preparation of ethyl 2-(2-methylhydrazono)propanoate: To a suspension of ethyl pyruvate (37.8 mL, 338 mmol) and $MgSO_4$ (40.8 g, 339 mmol) in $CHCl_3$ (500 mL) was added a solution of methylhydrazine (18.0 mL, 332 mmol) in $CHCl_3$ (100 mL) at 0° C. The reaction mixture was warmed to room temperature. After stirring for 24 hours at room temperature, the reaction mixture was filtered. The filtrate was concentrated under reduced pressure to give 44 g (94%) of the desired product that was used directly without further purification.

Step B: Preparation of methyl 3-(2-(1-ethoxy-1-oxopropan-2-ylidene)-1-methylhydrazinyl)-3-oxopropanoate: To a solution of ethyl 2-(2-methylhydrazono)propanoate (25.0 mL, 186 mmol) in THF (500 mL) at 0° C. was added LiH (2.02 g, 241 mmol). The resulting mixture was stirred for 10 minutes at 0° C., warmed to room temperature, and stirred for 6 hours. Methyl malonyl chloride (26.7 mL, 242 mmol) in THF (20 mL) was added at 0° C. The reaction was warmed to room temperature and stirred for 16 hours. The reaction was carefully quenched with 1N aqueous HCl at 0° C., concentrated under reduced pressure, and diluted with EtOAc. The organic layer was dried over $MgSO_4$, filtered, and concentrated under reduced pressure to give 46 g (99%) of the desired product that was used directly without further purification.

Step C: Preparation of methyl 5-hydroxy-2,6-dimethyl-3-oxo-2,3-dihydropyridazine-4-carboxylate: To a solution of ethyl 2-(2-methyl-2-(methyl 3-oxopropanoyl)hydrazono) propanoate (1.02 g, 4.09 mmol) in MeCN (10 mL) at 0° C. was added DBU (2.0 mL, 13 mmol). The reaction mixture was warmed to room temperature and stirred for 3 hours. The reaction mixture was concentrated under reduced pressure and diluted with EtOAc. The organic layer was washed with 10% aqueous HCl, dried over $MgSO_4$, filtered, and concentrated under reduced pressure to give 0.39 g (48%) of the crude product that was used directly without further purification.

Step D: Preparation of 5-hydroxy-2,6-dimethylpyridazin-3(2H)-one: A mixture of methyl 5-hydroxy-2,6-dimethyl-3-oxo-2,3-dihydropyridazine-4-carboxylate (3.00 g, 15.1 mmol) and 6 N aqueous HCl (25 mL, 150 mmol) in dioxane (25 mL) was refluxed for 48 hours. The reaction mixture was cooled to room temperature and concentrated under reduced pressure to give the crude material that was diluted with EtOAc. The organic layer was washed with water and brine, dried over $MgSO_4$, filtered, and concentrated under reduced pressure to give 0.74 g (35%) of the desired product. The aqueous layer was concentrated under reduced pressure. The resulting solid was diluted with water and EtOAc-THF. The organic layer was separated. The aqueous layer was extracted with EtOAc (2×). The combined organic layers were dried over $MgSO_4$, filtered, and concentrated under reduced pressure to give 0.80 g (37%) of the additional desired product. A total of 1.54 g (72%) of the desired product was obtained, which was used directly without further purification.

Step E: Preparation of 5-chloro-2,6-dimethylpyridazin-3(2H)-one: A mixture of 5-hydroxy-2,6-dimethylpyridazin-3(2H)-one (736 mg, 5.25 mmol) and $POCl_3$ (4.5 mL) was stirred at 85° C. for 2 hours. The reaction mixture was concentrated under reduced pressure to give the crude material that was quenched with saturated aqueous $Na_2CO_3$. The resulting mixture was stirred for 2 hours and extracted with EtOAc (3×). The combined organic layers were dried over $MgSO_4$, filtered, and concentrated under reduced pressure to give 587 mg (70%) of the desired product that was used directly without further purification.

Step F: Preparation of 4-chloro-1-methyl-6-oxo-1,6-dihydropyridazine-3-carboxylic acid: To a solution of 5-chloro-2,6-dimethylpyridazin-3(2H)-one (780 mg, 4.67 mmol) in fuming $H_2SO_4$ (25 mL) at 0° C. was slowly added $K_2Cr_2O_7$ (3.33 g, 11.2 mmol) with stirring. After the addition of $K_2Cr_2O_7$, the ice-bath was removed and the reaction mixture was allowed to warm to room temperature. When the reaction began to progress too rapidly, the ice-bath was replaced and the rest of $K_2Cr_2O_7$ was added. The reaction mixture was stirred at 60° C. for 16 hours. The reaction mixture was cooled to room temperature, poured into ice, and extracted with EtOAc (3×). The combined organic layers were dried over $MgSO_4$, filtered, and concentrated under reduced pressure to give 649 mg (74%) of the desired product that was used directly without further purification.

Step G: Preparation of methyl 4-chloro-1-methyl-6-oxo-1,6-dihydropyridazine-3-carboxylate: A solution of 4-chloro-1-methyl-6-oxo-1,6-dihydropyridazine-3-carboxylic acid (390 mg, 2.07 mmol) and conc. HCl (0.10 mL) in MeOH (6 mL) was refluxed for 8 hours. The reaction mixture was cooled to room temperature and concentrated under reduced pressure to give the crude material that was redissolved into EtOAc. The organic layer was washed with water, dried over $MgSO_4$, filtered, and concentrated under reduced pressure to give the crude material that was purified by silica gel flash column chromatography (100% hexanes to 10 to 20 to 30 to 50% EtOAc in hexanes) to afford 72 mg (17%) of the desired product.

Step H: Preparation of methyl 4-(2-fluoro-4-(methylthio)phenylamino)-1-methyl-6-oxo-1,6-dihydropyridazine-3-carboxylate: A mixture solution of methyl 4-chloro-1-methyl-6-oxo-1,6-dihydropyridazine-3-carboxylate (72 mg, 0.35 mmol), 2-fluoro-4-methylthioaniline (69 mg, 0.44 mmol), $Pd(OAc)_2$ (10 mg, 0.044 mmol), BINAP (40 mg, 0.064 mmol), and $Cs_2CO_3$ (197 mg, 0.60 mmol) in toluene (1.5 mL) was sealed in a vial under $N_2$ atmosphere. It was stirred for 10 minutes at room temperature and then heated at 80° C. for 16 hours with stirring. The reaction mixture was cooled to room temperature and diluted with EtOAc. The precipitate was filtered off and washed with EtOAc. The filtrate was washed with water. The organic layer was separated and the aqueous layer was extracted with EtOAc. The combined organic layers were dried over $MgSO_4$, filtered, concentrated to give the crude material that was purified by silica gel flash column chromatography (100% $CH_2Cl_2$ to 1% MeOH in $CH_2Cl_2$) followed by additional silica gel flash column chromatography (10 to 15 to 20% EtOAc in $CH_2Cl_2$) to afford 48 mg (42%) of the desired product.

Step I: Preparation of 4-(2-fluoro-4-(methylthio)phenylamino)-1-methyl-6-oxo-N-(2-(vinyloxy)ethoxy)-1,6-dihydropyridazine-3-carboxamide: To a solution of methyl 4-(2-fluoro-4-(methylthio)phenylamino)-1-methyl-6-oxo-1,6-dihydropyridazine-3-carboxylate (25 mg, 0.077 mmol) and O-(2-vinyloxy-ethyl)-hydroxylamine (24 mg, 0.23 mmol) in THF (2 mL) at 0° C. was added LiHMDS (0.54 mL, 0.54 mmol, 1 M in THF). The reaction mixture was warmed to room temperature and stirred for 1 hour. The reaction mixture was quenched with saturated aqueous $NaHCO_3$ and diluted with EtOAc. The organic layer was washed with brine, dried over $MgSO_4$, filtered, and concentrated under reduced pressure to give the crude material that was purified by silica gel flash column chromatography (100% CH$_2$Cl$_2$ to 1.5% MeOH in CH$_2$Cl$_2$) to afford 30 mg (99%) of the desired product.

Step J: Preparation of 4-(2-fluoro-4-(methylthio)phenylamino)-N-(2-hydroxyethoxy)-1-methyl-6-oxo-1,6-dihydropyridazine-3-carboxamide: To a solution of 4-(2-fluoro-4-(methylthio)phenylamino)-1-methyl-6-oxo-N-(2-(vinyloxy)ethoxy)-1,6-dihydropyridazine-3-carboxamide (30 mg, 0.077 mmol) in EtOR/THF (2 mL/2 mL) was added 1 N aqueous HCl (0.15 mL, 0.15 mmol, 1 N aqueous solution) at room temperature. The reaction mixture was stirred for 1 hour at room temperature. The reaction mixture was neutralized to pH 7, diluted with EtOAc (3×), washed with water, dried over MgSO$_4$, filtered, and concentrated under reduced pressure to give the crude material that was purified by silica gel flash column chromatography (100% EtOAc to 100% CH$_2$Cl$_2$ to 2.5 to 3 to 5% MeOH in CH$_2$Cl$_2$) to afford 6 mg (22%) of the desired product. MS APCI (−) m/z 367 (M−1) detected; $^1$H NMR (400 MHz, CD$_3$OD) δ 7.35 (t, 1H), 7.18 (dd, 1H), 7.14 (dd, 1H), 5.92 (s, 1H), 4.06 (t, 2H), 3.79 (t, 2H), 3.74 (s, 3H), 2.51 (s, 3H).

Example 167

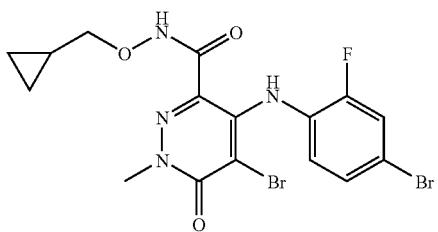

5-Bromo-4-(4-bromo-2-fluorophenylamino)-N-(cyclopropylmethoxy)-1-methyl-6-oxo-1,6-dihydropyridazine-3-carboxamide Step A: Preparation of methyl 4-(2-fluorophenylamino)-1-methyl-6-oxo-1,6-dihydropyridazine-3-carboxylate: The title compound was prepared in 61% yield by the procedure as previously described in Example 166 (step H) using methyl 4-chloro-1-methyl-6-oxo-1,6-dihydropyridazine-3-carboxylate (109 mg, 0.54 mmol, prepared as previously described in Example 1 (steps A-G) and 2-fluoroaniline (0.053 mL, 0.54 mmol).

Step B: Preparation of methyl 5-bromo-4-(4-bromo-2-fluorophenylamino)-1-methyl-6-oxo-1,6-dihydropyridazine-3-carboxylate: A mixture of methyl 4-(2-fluorophenylamino)-1-methyl-6-oxo-1,6-dihydropyridazine-3-carboxylate (88 mg, 0.32 mmol) and NBS (59 mg, 0.33 mmol) in DMF (1.5 mL) was stirred for 2 hours at room temperature. The reaction mixture was diluted with EtOAc and washed with water (2×). The organic layer was dried over MgSO$_4$, filtered, and concentrated under reduced pressure to give the crude material that was purified by silica gel flash column chromatography (100% CH$_2$Cl$_2$ to 0.5% MeOH in CH$_2$Cl$_2$) followed by additional silica gel flash column chromatography (30% EtOAc in CH$_2$Cl$_2$) to give 80 mg of a mixture of methyl 5-bromo-4-(2-fluorophenylamino)-1-methyl-6-oxo-1,6-dihydropyridazine-3-carboxylate and methyl 5-bromo-4-(4-bromo-2-fluorophenylamino)-1-methyl-6-oxo-1,6-dihydropyridazine-3-carboxylate. This mixture was re-submitted for bromination. To this mixture was added DMF (1.5 mL) followed by NBS (29 mg, 0.22 mmol) at room temperature. The reaction mixture was stirred for 2.5 hours at room temperature. Additional 15 mg of NBS was added and the reaction mixture was stirred for additional 20 hours at room temperature. The reaction mixture was diluted with EtOAc and washed with water (2×). The organic layer was dried over MgSO$_4$, filtered, and concentrated under reduced pressure to give the crude material that was purified by silica gel flash column chromatography (30% EtOAc in CH$_2$Cl$_2$) to afford 62 mg (64%) of the desired product.

Step C: Preparation of 5-bromo-4-(4-bromo-2-fluorophenylamino)-N-(cyclopropylmethoxy)-1-methyl-6-oxo-1,6-dihydropyridazine-3-carboxamide: The title compound was prepared in 40% yield by the procedure described in Example 166 (step I) using methyl 5-bromo-4-(4-bromo-2-fluorophenylamino)-1-methyl-6-oxo-1,6-dihydropyridazine-3-carboxylate (31 mg, 0.071 mmol) and O-cyclopropylmethylhydroxylamine (20 mg, 0.23 mmol). MS APCI (−) m/z 487, 489, 491 (M−1, Br pattern) detected; $^1$H NMR (400 MHz, CD$_3$OD) δ 7.38 (dd, 1H), 7.31 (dd, 1H), 7.05 (t, 1H), 3.82 (s, 3H), 3.65 (d, 2H), 1.13 (m, 1H), 0.58 (q, 2H), 0.31 (q, 2H).

Example 168

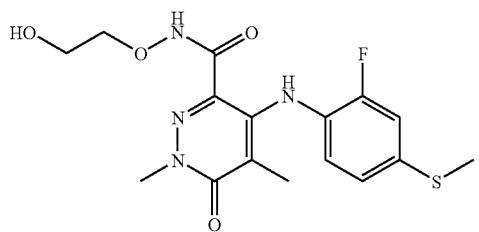

4-(2-Fluoro-4-(methylthio)phenylamino)-N-(2-hydroxyethoxy)-1,5-dimethyl-6-oxo-1,6-dihydropyridazine-3-carboxamide Step A: Preparation of N-methylpropionohydrazide: To a solution of methylhydrazine (27.6 mL, 508 mmol) and catalytic amount of DMAP in CH$_2$Cl$_2$ (130 mL) at 0° C. was added a solution of acetyl chloride (15.0 mL, 169 mmol) in CH$_2$Cl$_2$ (30 mL). The reaction mixture was warmed to room temperature and stirred for 16 hours. The white solids were filtered off and the filtrate was concentrated under reduced pressure to give the crude material that was purified by vacuum distillation to afford 8.25 g (48%) of the desired product (63-66° C. at 0.14 mm Hg).

Step B: Preparation of diethyl 2-(2-methyl-2-propionylhydrazono)malonate: A solution of N-methylpropionohydrazide (18.78 g, 183.9 mmol) and diethyl ketomalonate (56.1 mL, 368 mmol) in toluene (136 mL) was refluxed with a Dean-Stark trap for 4 hours. The reaction mixture was concentrated under reduced pressure to give the crude material that was purified by silica gel flash column chromatography (100% hexanes to 5 to 10% EtOAc in hexanes) to afford 23 g (49%) of the desired product.

Step C: Preparation of ethyl 4-hydroxy-1,5-dimethyl-6-oxo-1,6-dihydropyridazine-3-carboxylate: To a solution of LiHMDS (0.78 mL, 0.78 mmol, 1 M solution in THF) in THF (1 mL) at −78° C. was added a solution of diethyl 2-(2-methyl-2-propionylhydrazono)malonate (50 mg, 0.19 mmol) in THF (1 mL). The resulting mixture was slowly warmed to −40° C. and stirred for 1.5 hours at −40° C. The reaction mixture was quenched with 10% aqueous HCl and diluted with water. The resulting mixture was extracted with EtOAc (2×). The combined organic layers were washed with water, dried over MgSO$_4$, filtered, and concentrated under reduced pressure to give the crude material that was purified by silica gel flash column chromatography (100% hexanes to 20% EtOAc in hexanes) to afford 25 mg (61%) of the desired product.

Step D: Preparation of ethyl 4-chloro-1,5-dimethyl-6-oxo-1,6-dihydropyridazine-3-carboxylate: A mixture of ethyl 4-hydroxy-1,5-dimethyl-6-oxo-1,6-dihydropyridazine-3-carboxylate (1.85 g, 8.72 mmol) and POCl$_3$ (9 mL) was heated for 16 hours at 85° C. POCl$_3$ was removed under reduced pressure. Then the crude material was quenched with ice-water. The mixture was neutralized with saturated aqueous NaHCO$_3$ (pH~6 to 7) and extracted with EtOAc (3×). The combined organic layers were dried over MgSO$_4$, filtered, and concentrated under reduced pressure to give the crude material that was purified by silica gel flash column chromatography (100% hexanes to 5 to 10 to 20% EtOAc in hexanes) to afford 1.72 g (86%) of the desired product.

Step E: Preparation of ethyl 4-(2-fluoro-4-(methylthio)phenylamino)-1,5-dimethyl-6-oxo-1,6-dihydropyridazine-3-carboxylate: The title compound was prepared in 81% yield by the procedure described in Example 166 (step H) using ethyl 4-chloro-1,5-dimethyl-6-oxo-1,6-dihydropyridazine-3-carboxylat (500 mg, 2.17 mmol) and 2-fluoro-4-methylthioaniline (375 mg, 2.38 mmol).

Step F: Preparation of 4-(2-fluoro-4-(methylthio)phenylamino)-N-(2-hydroxyethoxy)-1,5-dimethyl-6-oxo-1,6-dihydropyridazine-3-carboxamide: The title compound was prepared in 78% yield (2 steps) by the procedures described in Example 166 (steps I and J) using ethyl 4-(2-fluoro-4-(methylthio)phenylamino)-1,5-dimethyl-6-oxo-1,6-dihydropyridazine-3-carboxylate (50 mg, 0.14 mmol) and O-(2-vinyloxy-ethyl)-hydroxylamine (44 mg, 0.43 mmol). MS APCI (−) m/z 381 (M−1) detected; $^1$H NMR (400 MHz, CD$_3$OD) δ 7.10 (dd, 1H), 7.03 (dd, 1H), 6.87 (t, 1H), 3.99 (t, 2H), 3.79 (s, 3H), 3.74 (t, 2H), 2.47 (s, 3H), 1.74 (s, 3H).

The following compounds were prepared by the procedure as described in Example 166 (step I) using ethyl 4-(2-fluoro-4-(methylthio)phenylamino)-1,5-dimethyl-6-oxo-1,6-dihydropyridazine-3-carboxylate and the appropriate hydroxylamine.

Example 169

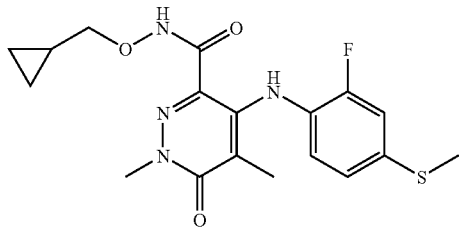

N-(Cyclopropylmethoxy)-4-(2-fluoro-4-(methylthio)phenylamino)-1,5-dimethyl-6-oxo-1,6-dihydropyridazine-3-carboxamide MS APCI (−) m/z 391 (M−1) detected; $^1$H NMR (400 MHz, CD$_3$OD) δ 7.09 (dd, 1H), 7.03 (dd, 1H), 6.86 (t, 1H), 3.78 (s, 3H), 3.71 (d, 2H), 2.47 (s, 3H), 1.75 (s, 3H) 1.16 (m, 1H), 0.58 (m, 2H), 0.31 (m, 2H).

Example 170

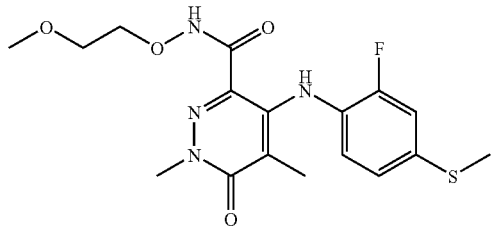

4-(2-Fluoro-4-(methylthio)phenylamino)-N-(2-methoxyethoxy)-1,5-dimethyl-6-oxo-1,6-dihydropyridazine-3-carboxamide MS APCI (−) m/z 395 (M−1) detected; $^1$H NMR (400 MHz, CD$_3$OD) δ 7.10 (dd, 1H), 7.03 (d, 1H), 6.87 (t, 1H), 4.05 (t, 2H), 3.78 (s, 3H), 3.64 (t, 2H), 3.37 (s, 3H), 2.47 (s, 3H), 1.74 (s, 3H).

Example 171

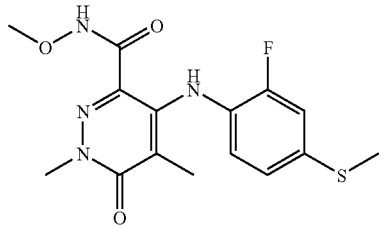

4-(2-Fluoro-4-(methylthio)phenylamino)-N-methoxy-1,5-dimethyl-6-oxo-1,6-dihydropyridazine-3-carboxamide MS APCI (−) m/z 351 (M−1) detected; $^1$H NMR (400 MHz, CD$_3$OD) δ 7.10 (d, 1H), 7.04 (d, 1H), 6.87 (t, 1H), 3.78 (s, 3H), 3.76 (s, 3H), 2.47 (s, 3H), 1.74 (s, 3H).

Example 172

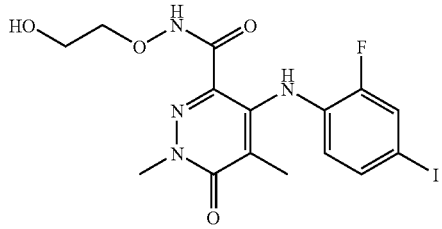

4-(2-Fluoro-4-iodophenylamino)-N-(2-hydroxyethoxy)-1,5-dimethyl-6-oxo-1,6-dihydropyridazine-3-carboxamide Step A: Preparation of 4-hydroxy-1,5-dimethyl-6-oxo-1,6-dihydropyridazine-3-carboxylic acid: To a solution of LiHMDS (331 mL, 331 mmol, 1 M solution in THF) in THF (430 mL) at −78° C. was added a solution of diethyl 2-(2-methyl-2-propionylhydrazono)malonate (21.40 g, 82.86 mmol) prepared by the procedure described in Example 168 (step B) in THF (10 mL). The resulting mixture was slowly warmed to −40° C. over 1 hour and stirred for 1.5 hours at −40° C. To the −40° C. reaction mixture was added water (500 mL). The reaction mixture was warmed to room temperature and stirred for 3 hours. The reaction mixture was concentrated under reduced pressure to remove the THF. The resulting aqueous mixture was quenched with 6 N aqueous HCl at 0° C., and acidified to pH 1 to 2. The resulting mixture was stirred for 16 hours at room temperature. The precipitates were filtered off and triturated with $CH_2Cl_2$ to afford 7.21 g (47%) of the desired product. The filtrate was extracted with EtOAc (3×). The combined organic layers were washed with water, dried over $MgSO_4$, filtered, and concentrated under reduced pressure to give the crude material that was triturated with $CH_2Cl_2$ to afford 3.56 g (23%) of additional desired product. The aqueous layer was extracted again with EtOAc (3×). The combined organic layers were washed with water, dried over $MgSO_4$, filtered, and concentrated under reduced pressure to give the crude material that was triturated with $CH_2Cl_2$ to afford 1.32 g (9%) of additional desired product. A total of 12.09 g (79%) of the desired product was obtained.

Step B: Preparation of 4-chloro-1,5-dimethyl-6-oxo-1,6-dihydropyridazine-3-carboxylic acid: A mixture of 4-hydroxy-1,5-dimethyl-6-oxo-1,6-dihydropyridazine-3-carboxylic acid (876 mg, 4.76 mmol) and $POCl_3$ (4.5 mL) was heated for 24 hours at 85° C. $POCl_3$ was removed under reduced pressure. The crude material was quenched with ice. The reaction mixture was stirred for 1 hour at room temperature. After removing solids by filtration, the aqueous filtrate was extracted with EtOAc (3×). The combined organic layers were dried over $MgSO_4$, filtered, and concentrated under reduced pressure to give. The recovered material was combined with the solids previously isolated and triturated with ether to afford 577 mg (60%) of the desired product.

Step C: Preparation of 4-(2-fluoro-4-iodophenylamino)-1,5-dimethyl-6-oxo-1,6-dihydropyridazine-3-carboxylic acid: To a suspension of 4-chloro-1,5-dimethyl-6-oxo-1,6-dihydropyridazine-3-carboxylic acid (200 mg, 0.99 mmol) and 2-fluoro-4-iodoaniline (478 mg, 1.97 mmol) in THF (6.5 mL) at −78° C. was slowly added a solution of LiHMDS (3.00 mL, 3.00 mmol, 1 M solution in THF). After complete addition, the resulting mixture was slowly warmed to room temperature and stirred for 4 hours. The reaction mixture was quenched with 6 N aqueous HCl (8 mL) at 0° C., warmed to room temperature, and stirred for 1.5 hours. The precipitates were filtered, washed with water and ether, and triturated with ether to afford 158 mg (38%) of the desired product.

Step D: Preparation of 4-(2-fluoro-4-iodophenylamino)-N-(2-hydroxyethoxy)-1,5-dimethyl-6-oxo-1,6-dihydropyridazine-3-carboxamide: To a suspension of 4-(2-fluoro-4-iodophenylamino)-1,5-dimethyl-6-oxo-1,6-dihydropyridazine-3-carboxylic acid (41 mg, 0.10 mmol) and HOBt (28 mg, 0.21 mmol) in DMF (1.5 mL) was added EDCI (40 mg, 0.21 mmol) at room temperature. The resulting mixture was stirred for 1.5 hours. O-(2-Vinyloxy-ethyl)-hydroxylamine (21 mg, 0.20 mmol) and TEA (0.030 mL, 0.22 mmol) was added to the activated ester at room temperature. After stirring for 1.5 hours, the reaction mixture was diluted with EtOAc and washed with saturated aqueous $NH_4Cl$, brine, saturated aqueous $NaHCO_3$ (2×), and brine. The organic layer was separated, dried over $MgSO_4$, filtered, and concentrated under reduced pressure to give 4-(2-fluoro-4-iodophenylamino)-1,5-dimethyl-6-oxo-N-(2-(vinyloxy)ethoxy)-1,6-dihydropyridazine-3-carboxamide that was used directly without further purification. The title compound was prepared by the procedure previously described in Example 1 (step J) using the crude 4-(2-fluoro-4-iodophenylamino)-1,5-dimethyl-6-oxo-N-(2-(vinyloxy)ethoxy)-1,6-dihydropyridazine-3-carboxamide (40% yield over two steps). MS APCI (−) m/z 461 (M−1) detected; $^1$H NMR (400 MHz, $CD_3OD$) δ 7.52 (dd, 1H), 7.44 (d, 1H), 6.63 (t, 1H), 3.98 (t, 2H), 3.80 (s, 3H), 3.74 (t, 2H), 1.78 (s, 3H).

The following compounds were prepared by the procedures as previously described in Example 172 (steps C and D) using the appropriate anilines and hydroxylamine. In some instances, a final deprotection step may be required. These deprotections can be accomplished by standard literature methods Example 173

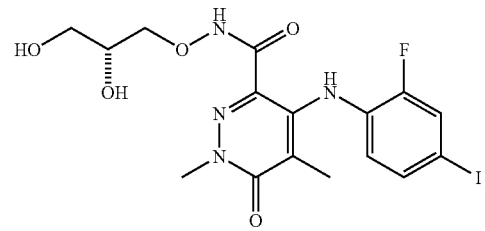

(R)-N-(2,3-Dihydroxypropoxy)-4-(2-fluoro-4-iodophenylamino)-1,5-dimethyl-6-oxo-1,6-dihydropyridazine-3-carboxamide MS APCI (−) m/z 491 (M−1) detected; $^1$H NMR (400 MHz, $CD_3OD$) δ 7.52 (dd, 1H), 7.44 (d, 1H), 6.63 (t, 1H), 4.02 (m, 1H), 3.88 (m, 2H), 3.80 (s, 3H), 3.59 (m, 2H), 1.77 (s, 3H).

Example 174

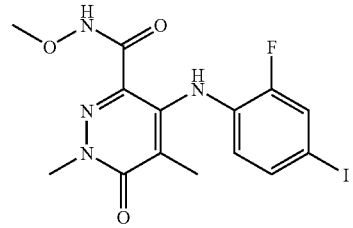

4-(2-Fluoro-4-iodophenylamino)-N-methoxy-1,5-dimethyl-6-oxo-1,6-dihydropyridazine-3-carboxamide MS APCI (−) m/z 431 (M−1) detected; $^1$H NMR (400 MHz, $CD_3OD$) δ 7.52 (dd, 1H), 7.44 (d, 1H), 6.63 (t, 1H), 3.79 (s, 3H), 3.75 (s, 3H), 1.77 (s, 3H).

Example 175

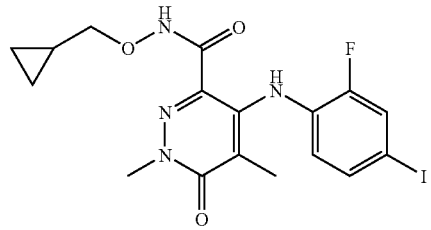

N-(Cyclopropylmethoxy)-4-(2-fluoro-4-iodophenylamino)-1,5-dimethyl-6-oxo-1,6-dihydropyridazine-3-carboxamide MS APCI (−) m/z 471 (M−1) detected; $^1$H NMR (400 MHz, CD$_3$OD) δ 7.51 (dd, 1H), 7.44 (d, 1H), 6.62 (t, 1H), 3.79 (s, 3H), 3.70 (d, 2H), 1.78 (s, 3H), 1.15 (m, 1H), 0.57 (q, 2H), 0.30 (q, 2H).

Example 176

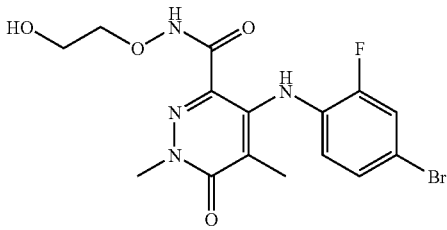

4-(4-Bromo-2-fluorophenylamino)-N-(2-hydroxyethoxy)-1,5-dimethyl-6-oxo-1,6-dihydropyridazine-3-carboxamide MS APCI (−) m/z 413, 415 (M−1, Br pattern) detected; $^1$H NMR (400 MHz, CD$_3$OD) δ 7.38 (dd, 1H), 7.27 (d, 1H), 6.79 (t, 1H), 3.99 (t, 2H), 3.80 (s, 3H), 3.74 (t, 2H), 1.77 (s, 3H).

Example 177

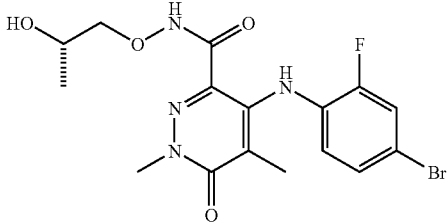

(S)-4-(4-Bromo-2-fluorophenylamino)-N-(2-hydroxypropoxy)-1,5-dimethyl-6-oxo-1,6-dihydropyridazine-3-carboxamide MS APCI (−) m/z 427, 429 (M−1, Br pattern) detected; $^1$H NMR (400 MHz, CD$_3$OD) δ 7.39 (dd, 1H), 7.27 (dd, 1H), 6.79 (t, 1H), 3.98 (m, 1H), 3.84 (dd, 1H), 3.80 (s, 3H), 3.72 (dd, 1H), 1.78 (s, 3H), 1.15 (d, 3H).

Example 178

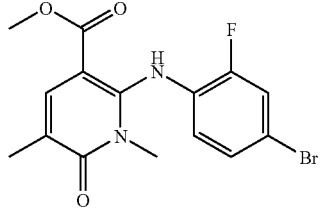

Methyl 2-(4-bromo-2-fluorophenylamino)-1,5-dimethyl-6-oxo-1,6-dihydropyridine-3-carboxylate Step A. Preparation of 2-chloro-6-oxo-1,6-dihydro-pyridine-3-carboxylic acid: 2-Chloro-6-oxo-1,6-dihydro-pyridine-3-carboxylic acid was prepared from dichloro-nicotinic acid (3.00 g, 15.6 mmol, Aldrich) according to the procedure described in U.S. Pat. No. 3,682,932 to yield 1.31 g (48%) of the desired product.

Step B. Preparation of 2-chloro-1-methyl-6-oxo-1,6-dihydro-pyridine-3-carboxylic acid methyl ester: To a solution of 2-chloro-6-oxo-1,6-dihydro-pyridine-3-carboxylic acid (0.644 g, 3.71 mmol) in DMF (20 mL) was added lithium hydride (95%, 0.078 g, 9.28 mmol) and the reaction mixture was stirred for 40 minutes under N$_2$. Methyl iodide (0.508 mL, 1.16 g, 8.16 mmol) was then added and the reaction mixture was stirred for an additional 45 minutes. The reaction mixture was quenched with 2 M HCl until the pH was 6-7. The reaction mixture was diluted with EtOAc and saturated NaCl and the layers separated. The aqueous layer was back extracted with EtOAc (1×). The combined organic layers were dried (Na$_2$SO$_4$) and concentrated under reduced pressure to yield a crude yellow solid. HPLC analysis showed two products in a 4:1 ratio that were separated by flash column chromatography (methylene chloride/EtOAc, 15:1 to 10:1) to give 0.466 g (62%) pure desired product as a white crystalline solid. The minor product was also isolated as a pale yellow crystalline solid and identified as the regioisomer 2-chloro-6-methoxy-nicotinic acid methyl ester.

Step C. Preparation of methyl 5-bromo-2-chloro-1-methyl-6-oxo-1,6-dihydropyridine-3-carboxylate: To a solution of methyl 2-chloro-1-methyl-6-oxo-1,6-dihydropyridine-3-carboxylate (0.100 g, 0.496 mmol) in DMF (5 mL) was added N-bromosuccinimide (0.177 g, 0.992 mmol) and the reaction mixture was stirred for 4 hours at room temperature under N$_2$. The reaction mixture was quenched with saturated sodium bisulfite and then diluted with EtOAc and H$_2$O and the layers separated. The aqueous layer was back extracted with EtOAc (2×). The combined organic layers were dried (Na$_2$SO$_4$) and concentrated under reduced pressure to yield a yellow solid in quantitative yield.

Step D. Preparation of methyl 2-chloro-1,5-dimethyl-6-oxo-1,6-dihydropyridine-3-carboxylate: To a suspension of methyl 5-bromo-2-chloro-1-methyl-6-oxo-1,6-dihydropyridine-3-carboxylate (0.400 g, 1.43 mmol) and 1,1'-bis(diphenylphosphino)ferrocenedichloropalladium(II) (0.0587 g, 0.0713 mmol) in dioxane (8 mL) at 0° C. under N$_2$ was added dimethylzinc (0.713 mL, 1.43 mmol, 2 M solution in toluene). The reaction mixture was immediately heated to 100° C. for 30 minutes. The reaction mixture was cooled to 0° C. and quenched with MeOH (0.800 mL). The reaction mixture was diluted with EtOAc and washed with 1 M HCl. The aqueous layer was back extracted with EtOAc (1×). The combined organic layers were washed with saturated NaCl, dried (Na$_2$SO$_4$) and concentrated under reduced pressure to a dark yellow gum. Purification by flash column chromatography (methylene chloride/EtOAc, 15:1) gave 0.164 g (53%) pure desired product as a yellow crystalline solid.

Step E: Preparation of methyl 2-(4-bromo-2-fluorophenylamino)-1,5-dimethyl-6-oxo-1,6-dihydropyridine-3-carboxylate: To a solution of 4-bromo-2-fluorobenzenamine (0.058 g, 0.31 mmol) in THF (2 mL) at −78° C. under N$_2$ was added lithium bis(trimethylsilyl)amide (0.56 mL, 0.56 mmol, 1 M solution in hexanes) dropwise. The reaction mixture was stirred for one hour at −78° C. Methyl 2-chloro-1,5-dimethyl- 6-oxo-1,6-dihydropyridine-3-carboxylate (0.060 g, 0.28 mmol) was then added dropwise as a solution in THF (1 mL) and the reaction mixture was stirred for 25 minutes at −78° C. The reaction mixture was quenched by the addition of H₂O and the pH was adjusted with 0.1M HCl and then diluted with EtOAc and satutrated NaCl and the layers separated. The aqueous layer was back extracted with EtOAc (1×). The combined EtOAc layers were dried (Na₂SO₄) and concentrated under reduced pressure. Purification by flash column chromatography (methylene chloride/EtOAc, 20:1) gave 0.086 g (84%) pure desired product as a white crystalline solid. MS ESI (+) m/z 371, 373 (M+, Br pattern) detected; ¹H NMR (400 MHz, CDCl₃) δ 9.57 (s, 1H), 7.79 (s, 1H), 7.32 (d, 1H), 7.18 (d, 1H), 6.58 (t, 1H), 3.85 (s, 3H), 3.29 (s, 3H), 2.14 (s, 3H).

Example 179

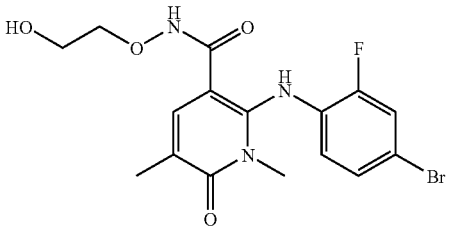

2-(4-Bromo-2-fluorophenylamino)-N-(2-hydroxyethoxy)-1,5-dimethyl-6-oxo-1,6-dihydropyridine-3-carboxamide Step A. Preparation of 2-(4-bromo-2-fluorophenylamino)-1,5-dimethyl-6-oxo-N-(2-(vinyloxy)ethoxy)-1,6-dihydropyridine-3-carboxamide: To a solution of methyl 2-(4-bromo-2-fluorophenylamino)-1,5-dimethyl-6-oxo-1,6-dihydropyridine-3-carboxylate (0.060 g, 0.16 mmol) in THF (2 mL) was added O-(2-vinyloxy-ethyl)-hydroxylamine (0.042 ml, 0.41 mmol). The solution was cooled to 0° C. and lithium bis(trimethylsilyl)amide (0.81 ml, 0.81 mmol, 1 M solution in hexanes) was added dropwise. The reaction mixture was warmed to room temperature. After stirring for 35 minutes the reaction mixture was quenched by the addition of saturated NaHCO₃ and partitioned between EtOAc and saturated NaCl. The layers were separated and the organic layer was dried (Na₂SO₄) and concentrated under reduced pressure. Purification by flash column chromatography (methylene chloride/MeOH, 20:1) gave 0.067 g (94%) pure desired product as an off-white crystalline solid.

Step B. Preparation of 2-(4-bromo-2-fluorophenylamino)-N-(2-hydroxyethoxy)-1,5-dimethyl-6-oxo-1,6-dihydropyridine-3-carboxamide: To a solution of 2-(4-bromo-2-fluorophenylamino)-1,5-dimethyl-6-oxo-N-(2-(vinyloxy)ethoxy)-1,6-dihydropyridine-3-carboxamide (0.067 g, 0.150 mmol) in ethanol (2 mL) was added aqueous 2 M HCl (0.380 mL, 0.760 mmol). The reaction mixture was stirred for 16 hours at room temperature. The pH of the reaction mixture was adjusted with 1 M NaOH. The reaction mixture was diluted with EtOAc and H₂O. The organic layer was separated and washed with saturated NaCl. The combined aqueous layers were back extracted with EtOAc (1×). The combined organic layers were dried (Na₂SO₄) and concentrated under reduced pressure to yield 0.060 g (94%) pure desired product as an off-white crystalline solid. MS ESI (+) m/z 414, 416 (M+, Br pattern detected); ¹H NMR (400 MHz, CDCl₃) δ 9.80 (s, 1H), 8.44 (s, 1H), 7.31 (d, 1H), 7.19 (d, 1H), 6.59 (t, 1H), 4.05 (m, 2H), 3.85 (m, 1H), 3.75 (m, 2H), 3.29 (s, 3H), 2.15 (s, 3H).

The following compounds were prepared using the methods as described in Examples 178 and 179. In some instances, such as Example 179, a final deprotection step may be required. These deprotections can be accomplished by standard literature methods.

Example 180

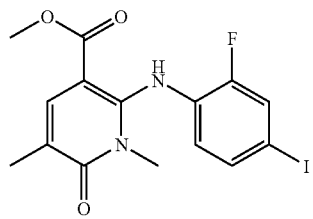

Methyl 2-(2-fluoro-4-iodophenylamino)-1,5-dimethyl-6-oxo-1,6-dihydropyridine-3-carboxylate Methyl 2-chloro-1,5-dimethyl-6-oxo-1,6-dihydropyridine-3-carboxylate was converted to methyl 2-(2-fluoro-4-iodophenylamino)-1,5-dimethyl-6-oxo-1,6-dihydropyridine-3-carboxylate following the procedure described in Step E of Example 178 using 2-fluoro-4-iodobenzenamine to yield the desired product as a white crystalline solid. MS ESI (+) m/z 417 (M+1) detected; ¹H NMR (400 MHz, CDCl₃) δ 9.56 (s, 1H), 7.79 (s, 1H), 7.49 (d, 1H), 7.36 (d, 1H), 6.43 (t, 1H), 3.85 (s, 3H), 3.30 (s, 3H), 2.15 (s, 3H).

Example 181

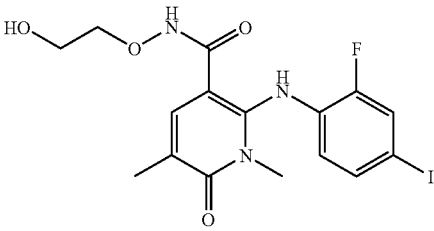

2-(2-fluoro-4-iodophenylamino)-N-(2-hydroxyethoxy)-1,5-dimethyl-6-oxo-1,6-dihydropyridine-3-carboxamide Methyl 2-(2-fluoro-4-iodophenylamino)-1,5-dimethyl-6-oxo-1,6-dihydropyridine-3-carboxylate was coupled and deprotected as described in Example 179 to yield the desired product as a yellow solid. MS ESI (+) m/z 462 (M+1) pattern detected; ¹H NMR (400 MHz, CDCl₃) δ 9.77 (s, 1H), 8.50 (s, 1H), 7.47 (d, 1H), 7.36 (d, 1H), 6.43 (t, 1H), 4.04 (br s, 2H), 3.85 (br s, 1H), 3.74 (br s, 2H), 3.29 (s, 3H), 2.14 (s, 3H).

Example 182

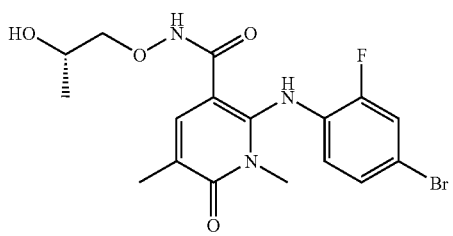

(S)-2-(4-bromo-2-fluorophenylamino)-N-(2-hydroxypropoxy)-1,5-dimethyl-6-oxo-1,6-dihydropyridine-3-carboxamide Step A: Methyl 2-(4-bromo-2-fluorophenylamino)-1,5-dimethyl-6-oxo-1,6-dihydropyridine-3-carboxylate was converted to (S)-2-(4-bromo-2-fluorophenylamino)-N-(2-(tert-butyldimethylsilyloxy)propoxy)-1,5-dimethyl-6-oxo-1,6-dihydropyridine-3-carboxamide following the procedure described in Step A of Example 179.

Step B: To a solution of (S)-2-(4-bromo-2-fluorophenylamino)-N-(2-(tert-butyldimethylsilyloxy)propoxy)-1,5-dimethyl-6-oxo-1,6-dihydropyridine-3-carboxamide (0.037 g, 0.0682 mmol) in THF (1.00 mL) was added 1 M HCl (0.682 mL, 0.682 mmol). The reaction mixture was stirred for one hour at room temperature. The reaction mixture was diluted with EtOAc and washed with saturated NaHCO$_3$ (3×), saturated NaCl (1×), dried (Na$_2$SO$_4$), and concentrated under reduced pressure. Purification by flash column chromatography (methylene chloride/methanol, 30:1) gave 0.020 (69%) pure desired product as a yellow solid. MS ESI (+) m/z 428, 430 (M+, Br pattern) detected; $^1$H NMR (400 MHz, CD$_3$OD) δ 7.55 (s, 1H), 7.40 (d, 1H), 7.24 (d, 1H), 6.68 (t, 1H), 3.86 (m, 1H), 3.71 (m, 1H), 3.58 (m, 1H), 3.40 (s, 3H), 2.12 (s, 3H), 1.10 (d, 3H).

Example 183

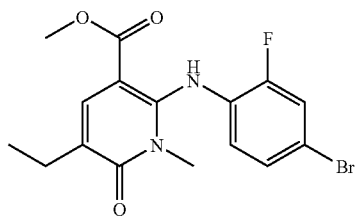

Methyl 2-(4-bromo-2-fluorophenylamino)-5-ethyl-1-methyl-6-oxo-1,6-dihydropyridine-3-carboxylate Step A. Preparation of Methyl 2-chloro-5-ethyl-1-methyl-6-oxo-1,6-dihydropyridine-3-carboxylate: Methyl 5-bromo-2-chloro-1-methyl-6-oxo-1,6-dihydropyridine-3-carboxylate was converted to methyl 2-chloro-5-ethyl-1-methyl-6-oxo-1,6-dihydropyridine-3-carboxylate as described in Step D of Example 178 using diethylzinc (1M in hexanes) to yield the desired product as a yellow crystalline solid.

Step B. Methyl 2-(4-bromo-2-fluorophenylamino)-5-ethyl-1-methyl-6-oxo-1,6-dihydropyridine-3-carboxylate: Methyl 2-chloro-5-ethyl-1-methyl-6-oxo-1,6-dihydropyridine-3-carboxylate was converted to methyl 2-(4-bromo-2-fluorophenylamino)-5-ethyl-1-methyl-6-oxo-1,6-dihydropyridine-3-carboxylate as described in Step E of Example 178. MS ESI (+) m/z 383, 385 (M+, Br pattern) detected; $^1$H NMR (400 MHz, CDCl$_3$) δ 9.59 (s, 1H), 7.76 (s, 1H), 7.32 (d, 1H), 7.18 (d, 1H), 6.59 (t, 1H), 3.86 (s, 3H), 3.28 (s, 3H), 2.56 (q, 2H), 1.22 (t, 3H).

Example 184

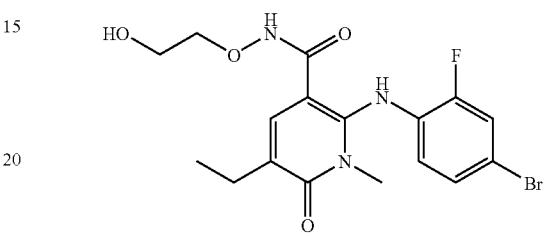

2-(4-Bromo-2-fluorophenylamino)-5-ethyl-N-(2-hydroxyethoxy)-1-methyl-6-oxo-1,6-dihydropyridine-3-carboxamide Methyl 2-(4-bromo-2-fluorophenylamino)-5-ethyl-1-methyl-6-oxo-1,6-dihydropyridine-3-carboxylate was coupled and deprotected as described in Example 179 to yield the desired product as a yellow solid. MS APCI (+) m/z 428, 430 (M+, Br pattern) detected; $^1$H NMR (400 MHz, DMSO-d$_6$) δ 11.51 (br s, 1H), 9.54 (br s, 1H), 7.57 (d, 1H), 7.47 (s, 1H), 7.25 (d, 1H), 6.69 (t, 1H), 4.67 (br s, 1H), 3.74 (m, 2H), 3.50 (m, 2H), 3.24 (s, 3H), 2.43 (q, 2H), 1.14 (t, 3H).

Example 185

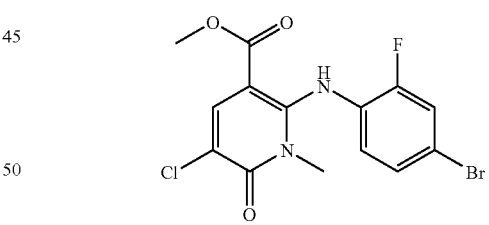

Methyl 2-(4-bromo-2-fluorophenylamino)-5-chloro-1-methyl-6-oxo-1,6-dihydropyridine-3-carboxylate Methyl 2-(4-bromo-2-fluorophenylamino)-1-methyl-6-oxo-1,6-dihydropyridine-3-carboxylate was converted to methyl 2-(4-bromo-2-fluorophenylamino)-5-chloro-1-methyl-6-oxo-1,6-dihydropyridine-3-carboxylate as described in Step A of Example 160 using N-chlorosuccinimide to yield the desired product as a white solid. MS ESI (+) m/z 389, 391, 393 (M+, Cl, Br pattern) detected; $^1$H NMR (400 MHz, CDCl$_3$) δ 9.88 (s, 1H), 8.13 (s, 1H), 7.34 (d, 1H), 7.24 (d, 1H), 6.69 (t, 1H), 3.87 (s, 3H), 3.29 (s, 3H).

Example 186

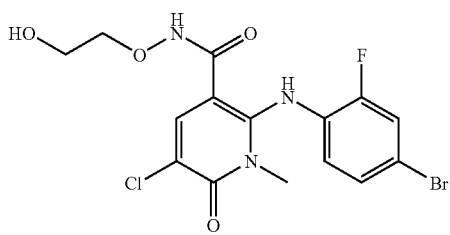

2-(4-bromo-2-fluorophenylamino)-5-chloro-N-(2-hydroxyethoxy)-1-methyl-6-oxo-1,6-dihydropyridine-3-carboxamide Methyl 2-(4-bromo-2-fluorophenylamino)-5-chloro-1-methyl-6-oxo-1,6-dihydropyridine-3-carboxylate was coupled and deprotected as described in Example 179 to yield the desired product as a pale yellow solid. MS APCI (+) m/z 434, 436, 438 (M+, Cl, Br pattern) detected; $^1$H NMR (400 MHz, DMSO-$d_6$) δ 11.56 (br s, 1H), 9.75 (br s, 1H), 7.91 (s, 1H), 7.57 (d, 1H), 7.26 (d, 1H), 6.89 (t, 1H), 4.68 (br s, 1H), 3.70 (m, 2H), 3.50 (m, 2H), 3.28 (s, 3H).

Example 187

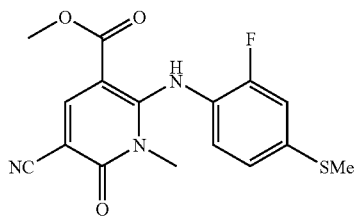

Methyl 5-cyano-2-(2-fluoro-4-(methylthio)phenylamino)-1-methyl-6-oxo-1,6-dihydropyridine-3-carboxylate Step A: Preparation of methyl 2-(2-fluoro-4-(methylthio)phenylamino)-1-methyl-6-oxo-1,6-dihydropyridine-3-carboxylate: Methyl 2-(2-fluoro-4-(methylthio)phenylamino)-1-methyl-6-oxo-1,6-dihydropyridine-3-carboxylate was prepared from methyl 2-chloro-1-methyl-6-oxo-1,6-dihydropyridine-3-carboxylate and 2-fluoro-4-(methylthio)benzenamine as described in Step C of Example 153.

Step B: Preparation of methyl 5-bromo-2-(2-fluoro-4-(methylthio)phenylamino)-1-methyl-6-oxo-1,6-dihydropyridine-3-carboxylate: Methyl 2-(2-fluoro-4-(methylthio)phenylamino)-1-methyl-6-oxo-1,6-dihydropyridine-3-carboxylate was converted to methyl 5-bromo-2-(2-fluoro-4-(methylthio)phenylamino)-1-methyl-6-oxo-1,6-dihydropyridine-3-carboxylate as described in Step A of Example 160.

Step C: Methyl 5-cyano-2-(2-fluoro-4-(methylthio)phenylamino)-1-methyl-6-oxo-1,6-dihydropyridine-3-carboxylate: A mixture of methyl 5-bromo-2-(2-fluoro-4-(methylthio)phenylamino)-1-methyl-6-oxo-1,6-dihydropyridine-3-carboxylate (0.020 g, 0.050 mmol), tris(dibenzylideneacetone)-dipalladium(0) (0.046 g, 0.050 mmol), 1,1'-bis(diphenylphosphine)-ferrocene (0.055 g, 0.100 mmol) and Zn(CN)$_2$ (0.006 g, 0.055 mmol) was heated at 120° C. for 2 hours. The reaction mixture was diluted with EtOAc and H$_2$O and the layers separated. The EtOAc layer was washed with saturated NH$_4$Cl and saturated NaCl, dried (Na$_2$SO$_4$) and concentrated under reduced pressure to a dark yellow gum. Purification by flash column chromatography (methylene chloride/EtOAc, 10:1) gave 0.005 g (29%) pure desired product as a yellow solid. MS APCI (−) m/z 346 (M−1) detected; $^1$H NMR (400 MHz, CDCl$_3$) δ 10.84 (s, 1H), 8.39 (s, 1H), 6.95–7.06 (m, 3H), 3.90 (s, 3H), 3.17 (s, 3H), 2.50 (s, 3H).

Additional compounds of the present invention include compounds of general Formulas Ia as shown in Table 1.

TABLE 1

Ia

| $R^7$ | $R^9$ | $R^1$ | $R^8$ | $R^3$ |
|---|---|---|---|---|
| Me | Me | F | Br | H |
|  |  |  |  | OH |
|  |  |  |  | OMe |
|  |  |  |  | OEt |
|  |  |  |  | HOCH$_2$CH$_2$O |
|  |  |  |  | HOCH$_2$C(Me)$_2$O |
|  |  |  |  | (S)-MeCH(OH)CH$_2$O |
|  |  |  |  | (R)-HOCH$_2$CH(OH)CH$_2$O |
|  |  |  |  | c-PrCH$_2$O |
| Me | Me | F | I | H |
|  |  |  |  | OH |
|  |  |  |  | OMe |
|  |  |  |  | OEt |
|  |  |  |  | HOCH$_2$CH$_2$O |
|  |  |  |  | HOCH$_2$C(Me)$_2$O |
|  |  |  |  | (S)-MeCH(OH)CH$_2$O |
|  |  |  |  | (R)-HOCH$_2$CH(OH)CH$_2$O |
|  |  |  |  | c-PrCH$_2$O |
| Me | Me | F | SMe | H |
|  |  |  |  | OH |
|  |  |  |  | OMe |
|  |  |  |  | OEt |
|  |  |  |  | HOCH$_2$CH$_2$O |
|  |  |  |  | HOCH$_2$C(Me)$_2$O |
|  |  |  |  | (S)-MeCH(OH)CH$_2$O |
|  |  |  |  | (R)-HOCH$_2$CH(OH)CH$_2$O |
|  |  |  |  | c-PrCH$_2$O |
| Me | Me | Cl | Br | H |
|  |  |  |  | OH |
|  |  |  |  | OMe |
|  |  |  |  | OEt |
|  |  |  |  | HOCH$_2$CH$_2$O |
|  |  |  |  | HOCH$_2$C(Me)$_2$O |
|  |  |  |  | (S)-MeCH(OH)CH$_2$O |
|  |  |  |  | (R)-HOCH$_2$CH(OH)CH$_2$O |
|  |  |  |  | c-PrCH$_2$O |
| Me | Me | Cl | I | H |
|  |  |  |  | OH |
|  |  |  |  | OMe |
|  |  |  |  | OEt |
|  |  |  |  | HOCH$_2$CH$_2$O |
|  |  |  |  | HOCH$_2$C(Me)$_2$O |
|  |  |  |  | (S)-MeCH(OH)CH$_2$O |
|  |  |  |  | (R)-HOCH$_2$CH(OH)CH$_2$O |
|  |  |  |  | c-PrCH$_2$O |

TABLE 1-continued

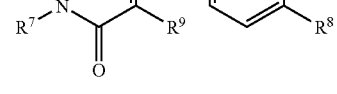

| R7 | R9 | R1 | R8 | R3 |
|---|---|---|---|---|
| Me | Me | Cl | SMe | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | F | F | Br | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | F | F | I | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | F | F | SMe | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | F | Cl | Br | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | F | Cl | I | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | F | Cl | SMe | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | Cl | F | Br | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | Cl | F | I | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | Cl | F | SMe | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | Cl | Cl | Br | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | Cl | Cl | I | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| Me | Cl | Cl | SMe | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |
| c-PrCH2 | Me | F | Br | H |
| | | | | OH |
| | | | | OMe |
| | | | | OEt |
| | | | | HOCH2CH2O |
| | | | | HOCH2C(Me)2O |
| | | | | (S)-MeCH(OH)CH2O |
| | | | | (R)-HOCH2CH(OH)CH2O |
| | | | | c-PrCH2O |

TABLE 1-continued

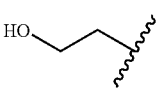

| R⁷ | R⁹ | R¹ | R⁸ | R³ |
|---|---|---|---|---|
| c-PrCH₂ | Me | F | I | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | Me | F | SMe | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | F | F | Br | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | F | F | I | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | F | F | SMe | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |

Additional compounds of the present invention include compounds of general Formulas Va-Vg as shown in Tables 2-8.

TABLE 2

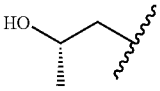

| R⁹ | R³ |
|---|---|
| Me | 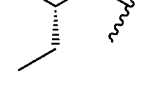 |
| | 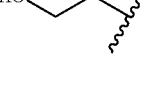 |
| | 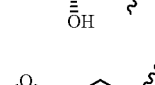 |
| | 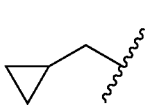 |
| |  |
| | 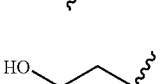 |
| | 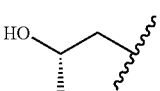 |
| | |
| Et | |

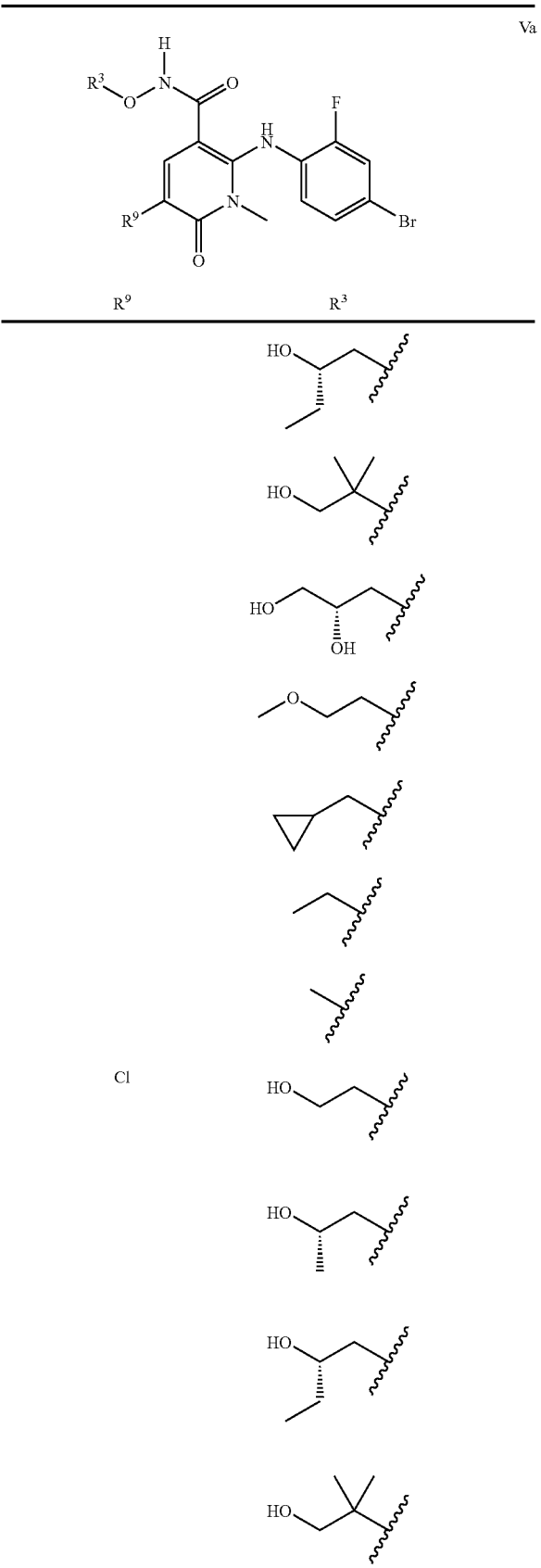
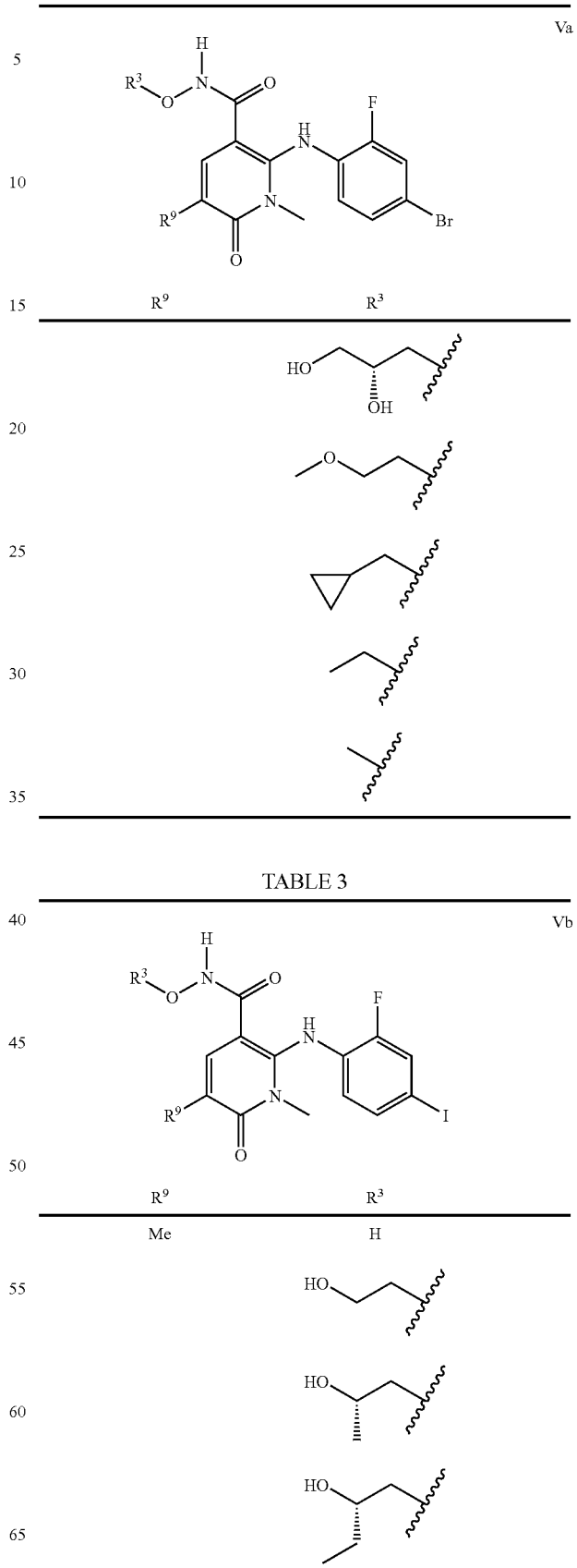

TABLE 3-continued
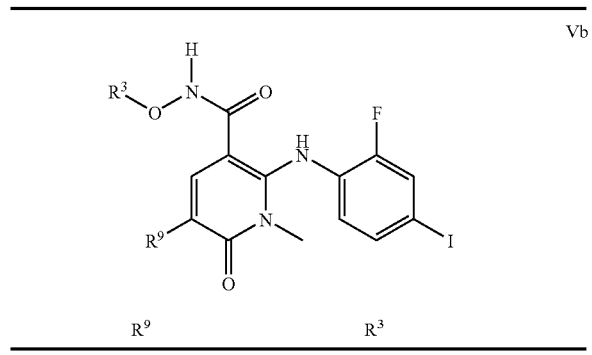
| R⁹ | R³ |
|---|---|
| | 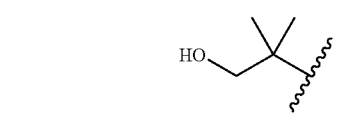 |
| | 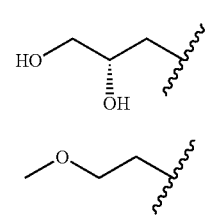 |
| | 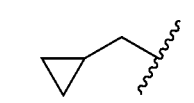 |
| | 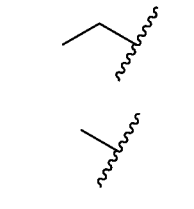 |
| | 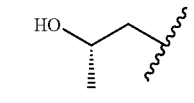 |
| Et | H |
| | 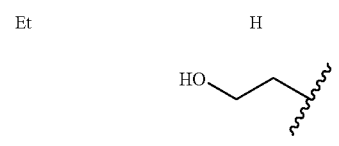 |
| | 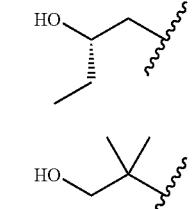 |
| | 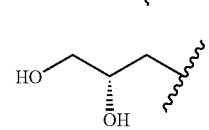 |
TABLE 3-continued
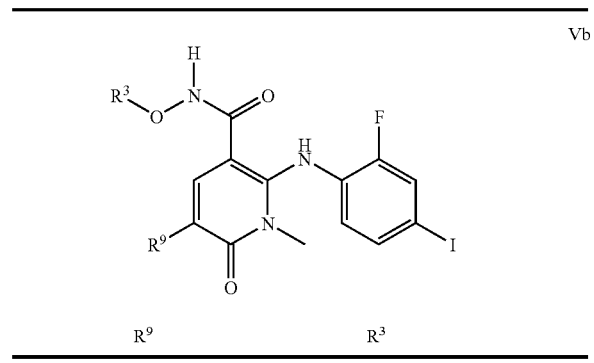
| R⁹ | R³ |
|---|---|
| | 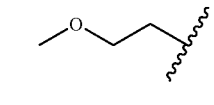 |
| | 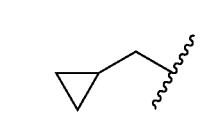 |
| | 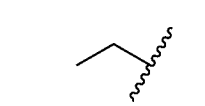 |
| | 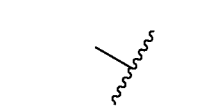 |
| Cl | H |
| | 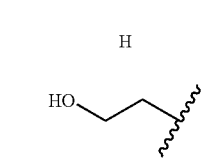 |
| | 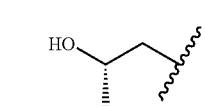 |
| | 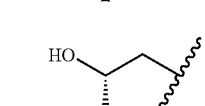 |
| | 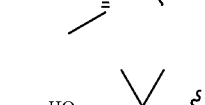 |
| | 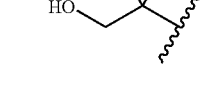 |
| | 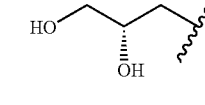 |
| | 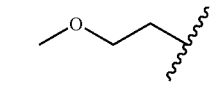 |
| | 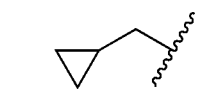 |

TABLE 3-continued
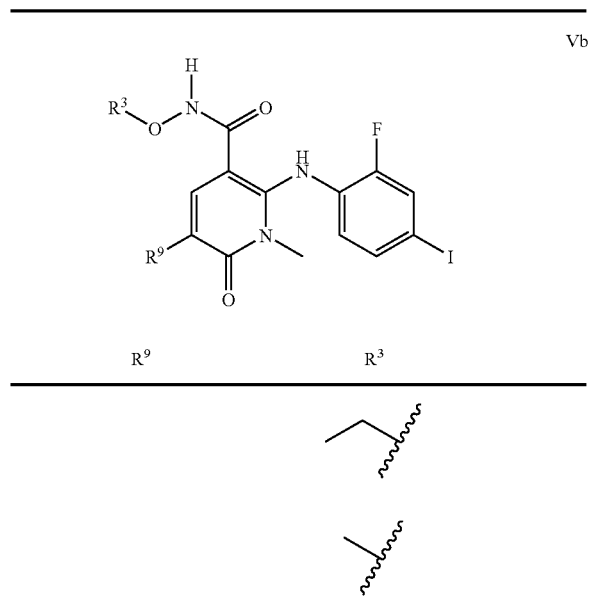
| R⁹ | R³ |
|---|---|
| | (ethyl) |
| | (isopropyl) |
TABLE 4
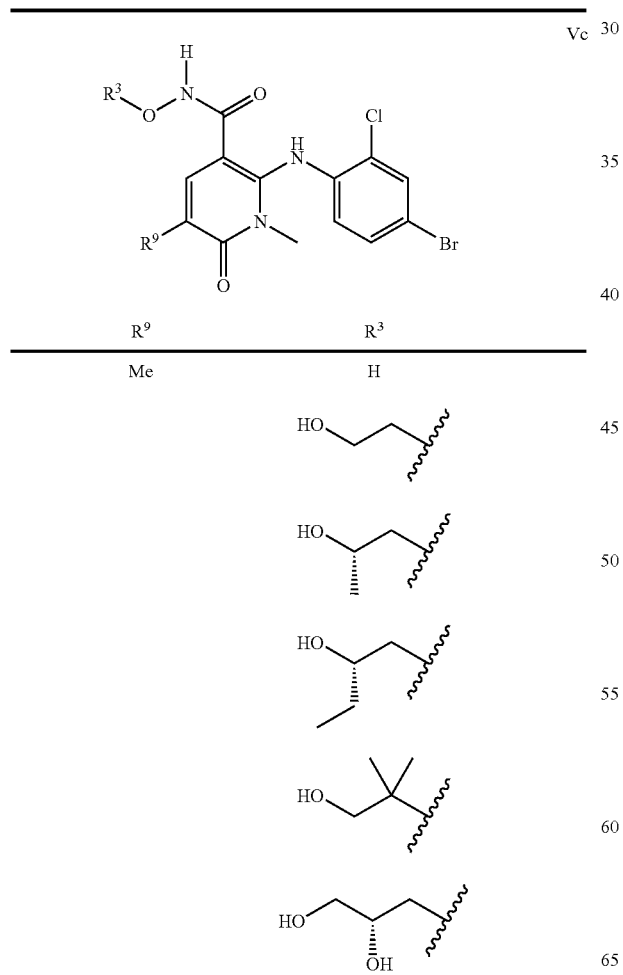
| R⁹ | R³ |
|---|---|
| Me | H |
| | HO—CH₂CH₂CH₂— |
| | (R)-HO-CH(CH₃)-CH₂- |
| | (S)-HO-CH(Et)-CH₂- |
| | HO-CH₂-C(CH₃)₂-CH₂- |
| | (S)-HO-CH₂-CH(OH)-CH₂-CH₂- |
TABLE 4-continued
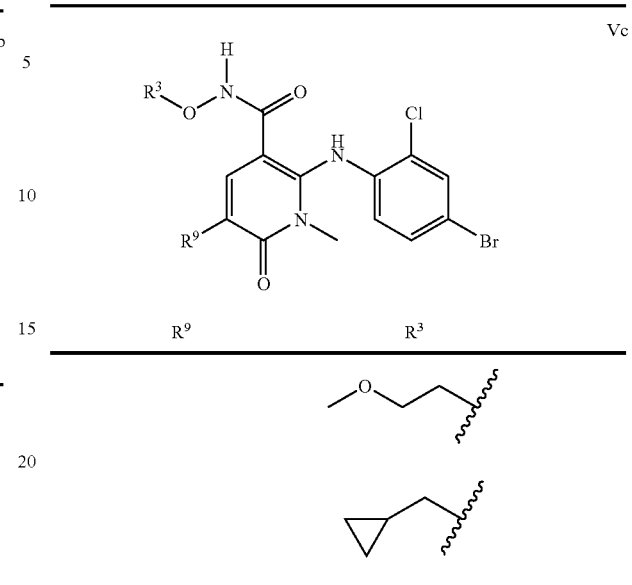
| R⁹ | R³ |
|---|---|
| | MeO-CH₂CH₂CH₂- |
| | cyclopropyl-CH₂- |
| | ethyl |
| | isopropyl |
| Et | H |
| | HO-CH₂CH₂CH₂- |
| | (R)-HO-CH(CH₃)-CH₂- |
| | (S)-HO-CH(Et)-CH₂- |
| | HO-CH₂-C(CH₃)₂-CH₂- |
| | (S)-HO-CH₂-CH(OH)-CH₂-CH₂- |
| | MeO-CH₂CH₂CH₂- |
| | cyclopropyl-CH₂- |

TABLE 4-continued
Vc
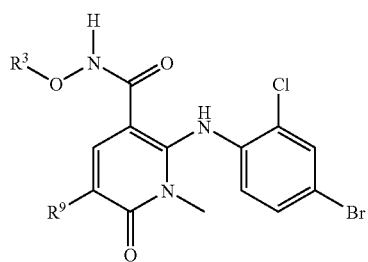
| R⁹ | R³ |
|---|---|
| | (sec-butyl) |
| | (isopropyl) |
| Cl | H |
| | HO~~~ |
| | HO (S)-hydroxybutyl |
| | HO (S)-hydroxypentyl |
| | HO neopentyl diol |
| | HO, OH (R)-dihydroxybutyl |
| | MeO~~~ |
| | cyclopropylmethyl |
| | ethyl |
| | isopropyl |
TABLE 5
Vd
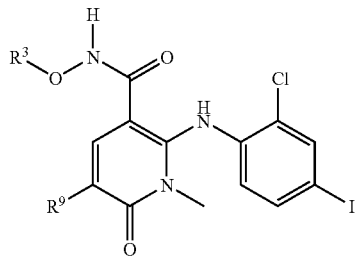
| R⁹ | R³ |
|---|---|
| Me | H |
| | HO~~~ |
| | HO (S)-hydroxybutyl |
| | HO (S)-hydroxypentyl |
| | HO neopentyl |
| | HO, OH (S)-dihydroxybutyl |
| | MeO~~~ |
| | cyclopropylmethyl |
| | sec-butyl |
| | isopropyl |
| Et | H |
| | HO~~~ |
| | HO (S)-hydroxybutyl |

TABLE 5-continued
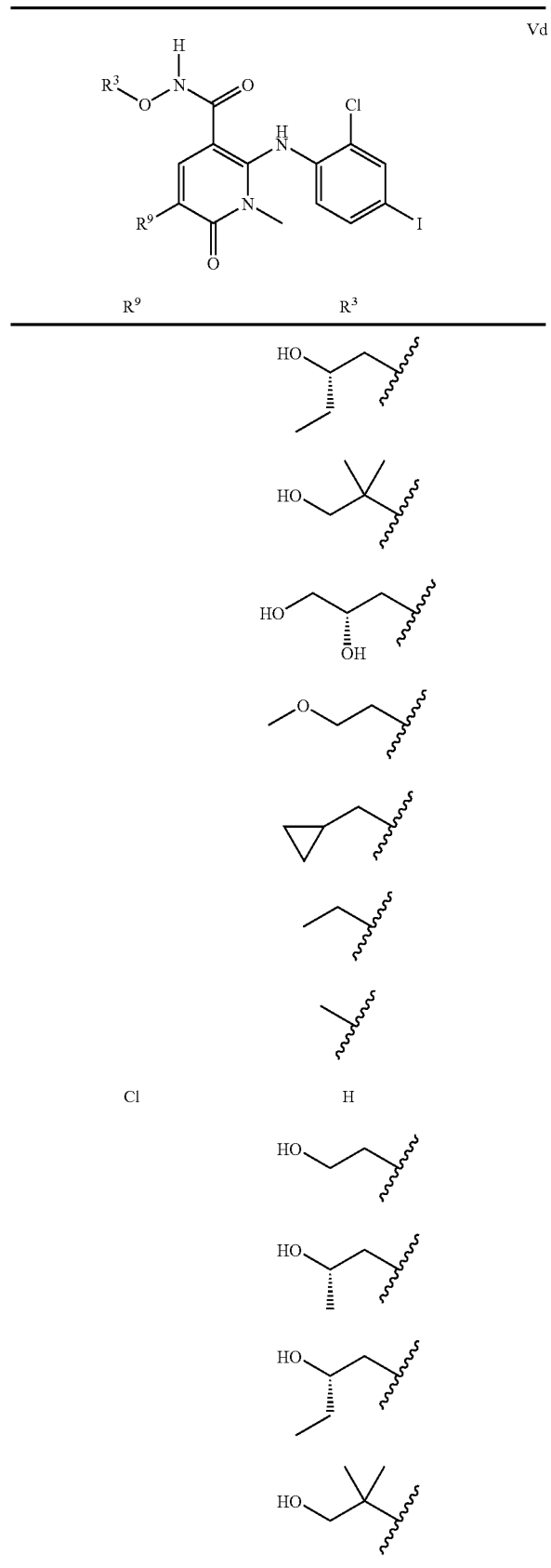
TABLE 5-continued
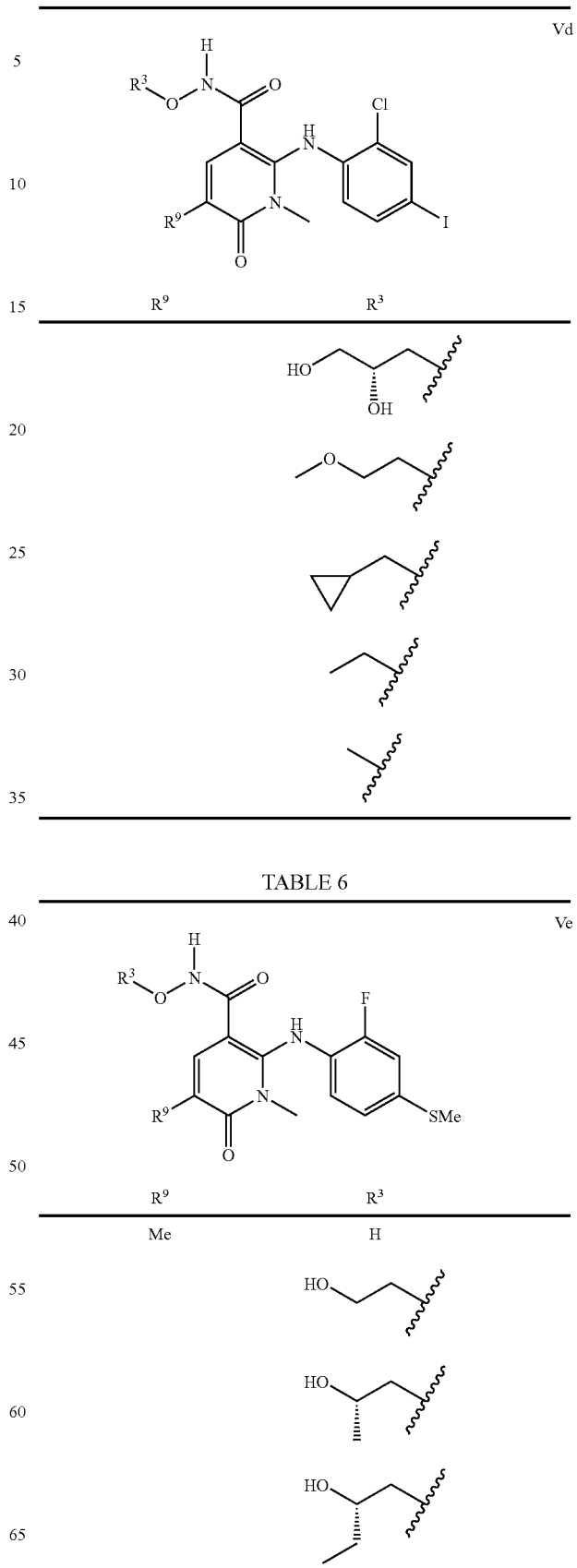

TABLE 6-continued
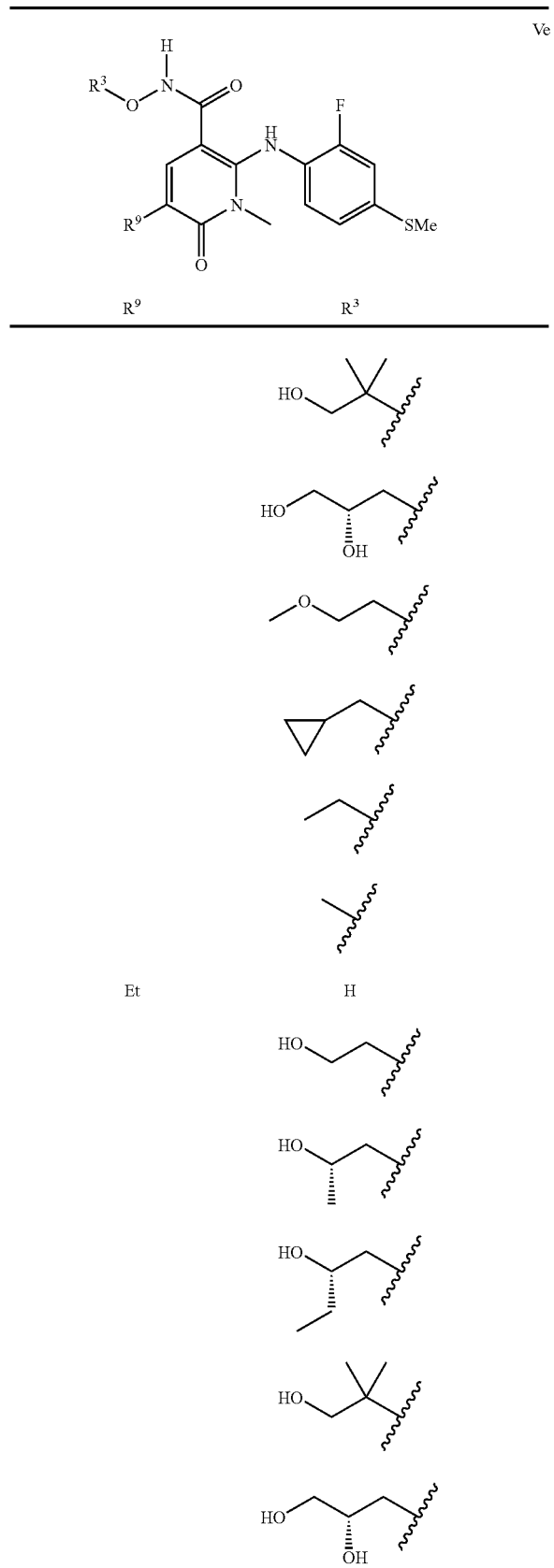
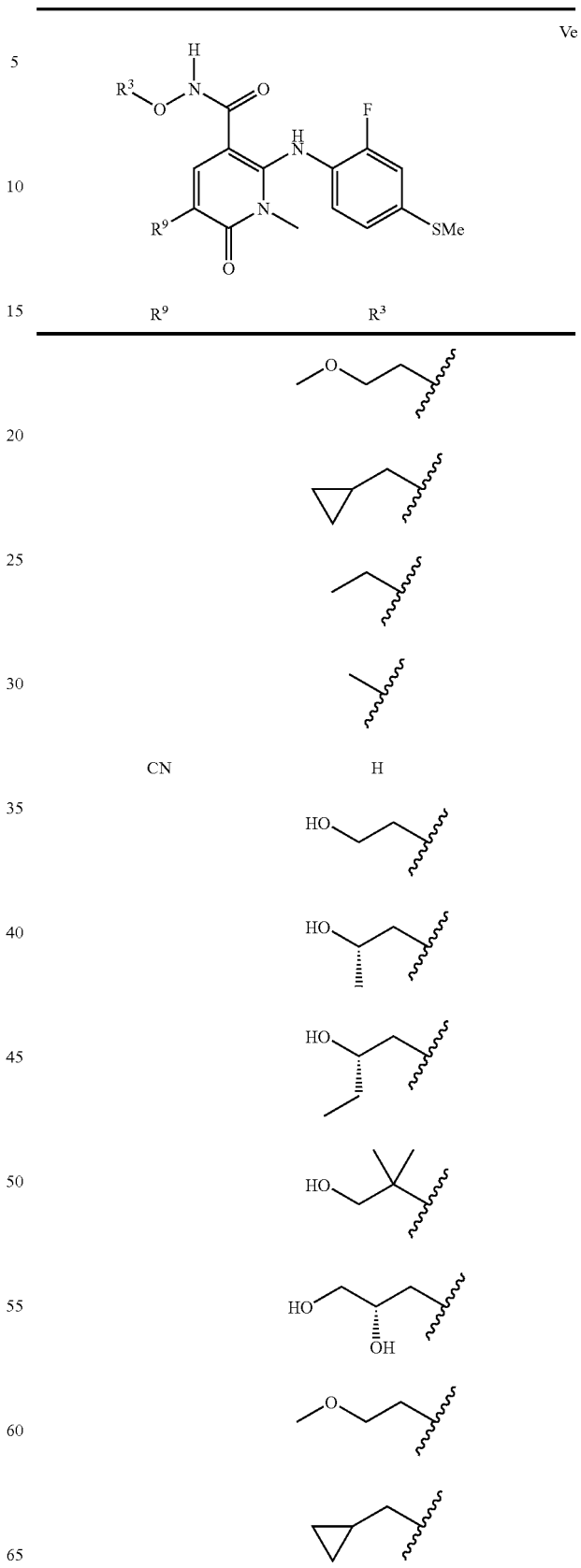

TABLE 6-continued

Ve

[Structure: R³-O-NH-C(=O) attached to N-methyl pyridinone with R⁹ substituent, NH-linked to 2-fluoro-4-(methylthio)phenyl]

| R⁹ | R³ |
|---|---|
| Cl | H |
| | *sec-butyl* |
| | *isopropyl* |
| | HO-CH₂CH₂CH₂- |
| | (R)-HO-CH(CH₃)-CH₂- |
| | (R)-HO-CH(Et)-CH₂- |
| | HO-CH₂-C(CH₃)₂-CH₂- |
| | (S)-HO-CH₂-CH(OH)-CH₂- |
| | MeO-CH₂CH₂CH₂- |
| | cyclopropylmethyl |
| | ethyl |
| | methyl |

TABLE 7

Vf

[Structure: R³-O-NH-C(=O) attached to N-methyl pyridinone with R⁹ substituent, NH-linked to 2-chloro-4-(methylthio)phenyl]

| R⁹ | R³ |
|---|---|
| Me | H |
| | HO-CH₂CH₂CH₂- |
| | (R)-HO-CH(CH₃)-CH₂- |
| | (R)-HO-CH(Et)-CH₂- |
| | HO-CH₂-C(CH₃)₂-CH₂- |
| | (S)-HO-CH₂-CH(OH)-CH₂- |
| | MeO-CH₂CH₂CH₂- |
| | cyclopropylmethyl |
| | ethyl |
| Et | H |
| | HO-CH₂CH₂CH₂- |
| | (R)-HO-CH(CH₃)-CH₂- |

TABLE 7-continued
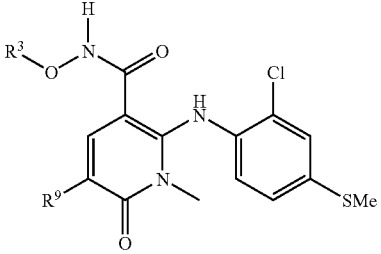
| R⁹ | R³ |
|---|---|
| | 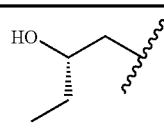 |
| | 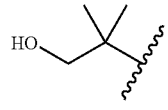 |
| | 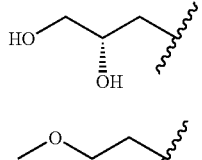 |
| | 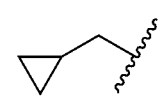 |
| |  |
| | 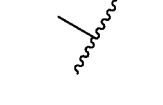 |
| CN | H |
| | 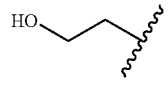 |
| | 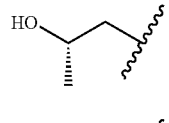 |
| | 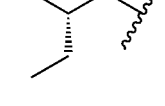 |
| | 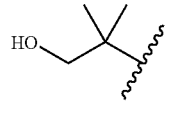 |
TABLE 7-continued
| R⁹ | R³ |
|---|---|
| | 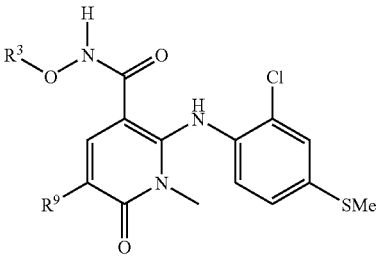 |
| | 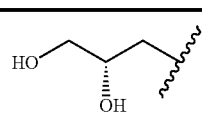 |
| | 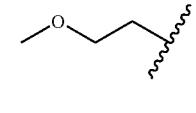 |
| | 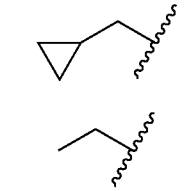 |
| | 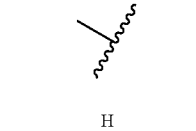 |
| Cl | H |
| | 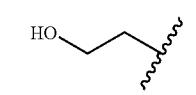 |
| | 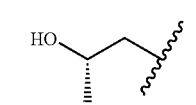 |
| | 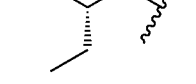 |
| | 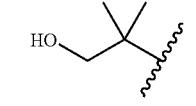 |
| | 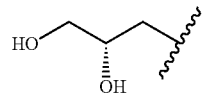 |
| | 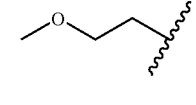 |

TABLE 7-continued

Vf: [structure shown: pyridinone with R³O-NH-C(=O)- at C3, R⁹ at C5, N-methyl, 6-oxo, and 2-(2-chloro-4-methylthio-phenylamino) substituent]

| R⁹ | R³ |
|---|---|
|  | cyclopropylmethyl |
|  | isobutyl |
|  | neopentyl |

TABLE 8

Vg: [structure shown: HO-CH₂-CH(OH)-CH₂-CH₂- with (R) stereochemistry at the hydroxyl carbon]

| R⁹ | R⁸ | R¹ | R³ |
|---|---|---|---|
| Me | I | F | H |
|  |  |  | Me |
|  |  | Cl | H |
|  |  |  | Me |
|  | Br | F | H |
|  |  |  | Me |
|  |  | Cl | H |
|  |  |  | Me |
|  | SMe | F | H |
|  |  |  | Me |
|  |  | Cl | H |
|  |  |  | Me |
| Et | I | F | H |
|  |  |  | Me |
|  |  | Cl | H |
|  |  |  | Me |
|  | Br | F | H |
|  |  |  | Me |
|  |  | Cl | H |
|  |  |  | Me |
|  | SMe | F | H |
|  |  |  | Me |
|  |  | Cl | H |
|  |  |  | Me |
| CN | SMe | F | H |
|  |  |  | Me |
|  |  | Cl | H |
|  |  |  | Me |
| Cl | I | F | H |
|  |  |  | Me |
|  |  | Cl | H |
|  |  |  | Me |
|  | Br | F | H |
|  |  |  | Me |
|  |  | Cl | H |
|  |  |  | Me |
|  | SMe | F | H |
|  |  |  | Me |
|  |  | Cl | H |
|  |  |  | Me |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. 2-(2-fluoro-4-iodophenylamino)-N-(2-hydroxyethoxy)-1,5-dimethyl-6-oxo-1,6-dihydropyridine-3-carboxamide.

* * * * *